United States Patent
Long et al.

(10) Patent No.: US 10,448,639 B2
(45) Date of Patent: Oct. 22, 2019

(54) FUNGICIDAL PYRAZOLES

(71) Applicant: FMC CORPORATION, Philadelphia, PA (US)

(72) Inventors: Jeffrey Keith Long, Wilmington, DE (US); Wonpyo Hong, Clarksville, MD (US); Andrew Edmund Taggi, New Hope, PA (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 16/173,167

(22) Filed: Oct. 29, 2018

(65) Prior Publication Data
US 2019/0059377 A1    Feb. 28, 2019

Related U.S. Application Data

(62) Division of application No. 15/496,048, filed on Apr. 25, 2017, now abandoned, which is a division of (Continued)

(51) Int. Cl.
C07D 231/12    (2006.01)
A01N 43/56    (2006.01)
(Continued)

(52) U.S. Cl.
CPC .......... *A01N 43/56* (2013.01); *C07D 231/12* (2013.01); *C07D 231/20* (2013.01);
(Continued)

(58) Field of Classification Search
None
See application file for complete search history.

(56) References Cited

U.S. PATENT DOCUMENTS 5,470,871 A * 11/1995 Christen .............. C07D 339/04
                                                        514/441
5,523,280 A    6/1996 Chene et al.
(Continued)

FOREIGN PATENT DOCUMENTS

GB    2054555 A    2/1981
JP    8208620 A    8/1996
(Continued)

OTHER PUBLICATIONS

Pfeiffer et al., Synthesis and Reactivity of 6H-1,3,4-Selenadiazines, Pharmazie, 1993, vol. 48, No. 10, pp. 732-735.
(Continued)

*Primary Examiner* — Kamal A Saeed
(74) *Attorney, Agent, or Firm* — Charlene Gross Sternberg

(57) ABSTRACT

Disclosed are compounds of Formula 1, including all geometric and stereoisomers, N-oxides, and salts thereof,

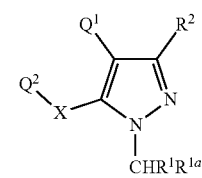

wherein
$Q^1$ is a phenyl ring, naphthalenyl ring system, a 5- to 6-membered fully unsaturated heterocyclic ring or an 8- to 10-membered heteroaromatic bicyclic ring system, each as described with optional substituents as defined in the disclosure;
$Q^2$ is a phenyl ring, a naphthalenyl ring system, a 5- to 6-membered saturated, partially unsaturated or fully unsaturated heterocyclic ring, or an 8- to 10-membered heteroaromatic bicyclic ring system, each as described with optional substituents as defined in the disclosure;
X is O, $S(O)_m$, $NR^4$, $CR^{15}R^{16}$, $C(\!=\!O)$ or $C(\!=\!S)$;
and $R^1$, $R^{1a}$, $R^2$, $R^4$, $R^{15}$, $R^{16}$ and m are as defined in the disclosure.

Also disclosed are compositions containing the compounds of Formula 1 and methods for controlling plant disease caused by a fungal pathogen comprising applying an effective amount of a compound or a composition of the invention. Also disclosed are compounds of Formula 2, including all geometric and stereoisomers, and salts thereof,

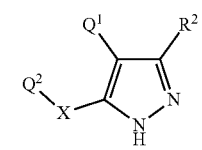

wherein
X is NH; and
$Q^1$, $Q^2$ and $R^2$ are as defined for Formula 1;
which are useful as intermediates for preparing compounds of Formula 1.

3 Claims, No Drawings

Related U.S. Application Data application No. 14/695,689, filed on Apr. 24, 2015, now Pat. No. 9,655,361, which is a division of application No. 13/254,205, filed as application No. PCT/US2010/026003 on Mar. 3, 2010, now Pat. No. 9,062,005.

(60) Provisional application No. 61/304,053, filed on Feb. 12, 2010, provisional application No. 61/157,046, filed on Mar. 3, 2009.

(51) Int. Cl.

| | | |
|---|---|---|
| *C07D 417/12* | (2006.01) | |
| *C07D 409/04* | (2006.01) | |
| *C07D 407/12* | (2006.01) | |
| *C07D 403/12* | (2006.01) | |
| *C07D 401/12* | (2006.01) | |
| *C07D 401/04* | (2006.01) | |
| *C07D 231/38* | (2006.01) | |
| *C07D 231/20* | (2006.01) | |
| *C07D 401/14* | (2006.01) | |

(52) U.S. Cl.
CPC ......... *C07D 231/38* (2013.01); *C07D 401/04* (2013.01); *C07D 401/12* (2013.01); *C07D 401/14* (2013.01); *C07D 403/12* (2013.01); *C07D 407/12* (2013.01); *C07D 409/04* (2013.01); *C07D 417/12* (2013.01)

(56) References Cited

U.S. PATENT DOCUMENTS

| | | |
|---|---|---|
| 5,849,778 A | 12/1998 | Heil et al. |
| 6,087,381 A | 7/2000 | Hanson et al. |
| 2010/0016396 A1 | 1/2010 | Imoto |

FOREIGN PATENT DOCUMENTS

| | | |
|---|---|---|
| WO | 9319054 A1 | 9/1993 |
| WO | 2004050650 A1 | 6/2004 |
| WO | 2004050651 A1 | 6/2004 |
| WO | 2007027842 A1 | 3/2007 |
| WO | 2008093639 A1 | 7/2008 |
| WO | 2009137538 A2 | 11/2009 |
| WO | 2009137651 A2 | 11/2009 |
| WO | 2011051958 A1 | 5/2011 |
| WO | 2011056463 A2 | 5/2011 |
| WO | 2012023143 A1 | 2/2012 |
| WO | 2012030922 A1 | 3/2012 |
| WO | 2012031061 A2 | 3/2012 |
| WO | 2012044650 A1 | 4/2012 |

OTHER PUBLICATIONS

Papageorgiou et al., Pyrazole Bioisosteres of Leflunomide as B-Cell Immunosuppressants for Xenotransplants and Chronic Rejection: Scope and Limitations, J. Med. Chem., 1998, vol. 41, No. 18, pp. 3530-3538.
CAPLUS Abstract of JP8208620, AN 1996:666849.

* cited by examiner

FUNGICIDAL PYRAZOLES

FIELD OF THE INVENTION

This invention relates to certain pyrazoles, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action. JP09208620 discloses N-phenylpyrazolylamine and N-pyridylpyrazolylamine derivatives as insecticides, herbicides and fungicides; however the fungicides of the present invention are not disclosed in this publication.

SUMMARY OF THE INVENTION

This invention is directed to compounds of Formula 1 (including all geometric and stereoisomers), N-oxides, and salts thereof, agricultural compositions containing them and their use as fungicides:

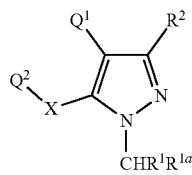

wherein
- $Q^1$ is a phenyl ring or a naphthalenyl ring system, each ring or ring system optionally substituted with up to 5 substituents independently selected from $R^3$; or a 5- to 6-membered fully unsaturated heterocyclic ring or an 8- to 10-membered heteroaromatic bicyclic ring system, each ring or ring system containing ring members selected from carbon atoms and up to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u$ $(=NR^{14})_v$, each ring or ring system optionally substituted with up to 5 substituents independently selected from $R^3$ on carbon atom ring members and selected from cyano, $C_1$-$C_6$ alkyl, $C_2$-$C_6$ alkenyl, $C_2$-$C_6$ alkynyl, $C_3$-$C_6$ cycloalkyl, $C_1$-$C_6$ alkoxy, $C_2$-$C_6$ alkoxyalkyl, $C_2$-$C_6$ alkylcarbonyl, $C_2$-$C_6$ alkoxycarbonyl, $C_2$-$C_6$ alkylaminoalkyl and $C_3$-$C_6$ dialkylaminoalkyl on nitrogen atom ring members;
- $Q^2$ is a phenyl ring or a naphthalenyl ring system, each ring or ring system optionally substituted with up to 5 substituents independently selected from $R^3$; or a 5- to 6-membered saturated, partially unsaturated or fully unsaturated heterocyclic ring or an 8- to 10-membered heteroaromatic bicyclic ring system, each ring or ring system containing ring members selected from carbon atoms and up to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u$ $(=NR^{14})_v$, each ring or ring system optionally substituted with up to 5 substituents independently selected from $R^3$ on carbon atom ring members and selected from cyano, $C_1$-$C_6$ alkyl, $C_2$-$C_6$ alkenyl, $C_2$-$C_6$ alkynyl, $C_3$-$C_6$ cycloalkyl, $C_1$-$C_6$ alkoxy, $C_2$-$C_6$ alkoxyalkyl, $C_2$-$C_6$ alkylcarbonyl, $C_2$-$C_6$ alkoxycarbonyl, $C_2$-$C_6$ alkylaminoalkyl and $C_3$-$C_6$ dialkylaminoalkyl on nitrogen atom ring members; or $C_1$-$C_{12}$ alkyl, $C_2$-$C_{12}$ alkenyl, $C_2$-$C_{12}$ alkynyl, $C_3$-$C_{12}$ cycloalkyl or $C_3$-$C_{12}$ cycloalkenyl, each optionally substituted with up to 5 substituents independently selected from $R^3$;
- X is O, $S(O)_m$, $NR^4$, $CR^{15}R^{16}$, C(=O) or C(=S);
- $R^1$ is H, halogen, $C_1$-$C_6$ alkyl, $C_1$-$C_6$ haloalkyl, $C_2$-$C_4$ alkenyl, $C_2$-$C_4$ alkynyl, $C_3$-$C_7$ cycloalkyl, $CO_2R^5$, C(O)$NR^6R^7$, cyano, $C_1$-$C_6$ alkoxy, $C_1$-$C_6$ haloalkoxy or $C_2$-$C_5$ alkoxyalkyl; or
- $R^1$ is phenyl optionally substituted with up to 3 $R^8$; or a five- or six-membered nitrogen-containing aromatic heterocycle optionally substituted with up to 3 substituents independently selected from $R^{9a}$ on carbon atom ring members and $R^{9b}$ on nitrogen atom ring members;
- $R^{1a}$ is H; or
- $R^{1a}$ and $R^1$ are taken together with the carbon atom to which they are attached to form a cyclopropyl ring optionally substituted with up to 2 substituents independently selected from halogen and methyl;
- $R^2$ is $CH_3$, $CH_2CH_3$, halogen, cyano, cyanomethyl, halomethyl, hydroxymethyl, methoxy or methylthio; or cyclopropyl optionally substituted with up to 2 substituents independently selected from halogen and methyl;
- each $R^3$ is independently selected from halogen, cyano, nitro, amino, methylamino, dimethylamino, formylamino, $C_2$-$C_3$ alkylcarbonylamino, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_2$ alkylsulfonyloxy, $C_1$-$C_2$ haloalkylsulfonyloxy, $C_3$-$C_4$ cycloalkyl, $C_3$-$C_7$ cycloalkoxy, $C_4$-$C_6$ alkylcycloalkyl, $C_4$-$C_6$ cycloalkylalkyl, $C_3$-$C_7$ halocycloalkyl, $C_2$-$C_4$ alkenyl, $C_2$-$C_4$ alkynyl, hydroxy, formyl, $C_2$-$C_3$ alkylcarbonyl, $C_2$-$C_3$ alkylcarbonyloxy, —$SF_5$, —SCN, C(=S)$NR^{19}R^{20}$ or —U—V-T;
- $R^4$ is H, formyl, $C_2$-$C_5$ alkenyl, $C_3$-$C_5$ alkynyl, $C_3$-$C_7$ cycloalkyl, —$SO_3^-M^+$, —$S(=O)_rR^{10}$, —(C=W)$R^{11}$, $NH_2$ or $OR^{21}$; or $C_1$-$C_6$ alkyl or $C_1$-$C_6$ haloalkyl, each optionally substituted with up to 2 $R^{12}$;
- $R^5$ is H, $C_1$-$C_6$ alkyl or $C_1$-$C_6$ haloalkyl;
- $R^6$ and $R^7$ are independently selected from H, $C_1$-$C_6$ alkyl, $C_1$-$C_6$ haloalkyl, $C_3$-$C_7$ cycloalkyl, $C_4$-$C_8$ cycloalkylalkyl and $C_4$-$C_8$ alkylcycloalkyl; or
- $R^6$ and $R^7$ are taken together with the nitrogen atom to which they are connected to form a four- to seven-membered nonaromatic heterocyclic ring containing ring members, in addition to the connecting ring nitrogen atom, selected from carbon atoms and optionally up to one ring member selected from O, $S(O)_n$ and $NR^{13}$;

each $R^8$, $R^{9a}$ and $R^{9b}$ is independently selected from halogen, $C_1$-$C_2$ alkyl, $C_1$-$C_2$ haloalkyl, $C_1$-$C_2$ alkoxy, $C_1$-$C_2$ haloalkoxy, cyano, nitro, $SCH_3$, $S(O)CH_3$ and $S(O)_2CH_3$;

$R^{10}$ is $C_1$-$C_6$ alkyl or $C_1$-$C_6$ haloalkyl;

each $R^{11}$ is independently $C_1$-$C_6$ alkyl, $C_1$-$C_6$ alkoxy, $C_2$-$C_7$ alkoxyalkyl, $C_2$-$C_7$ alkylaminoalkyl, $C_2$-$C_8$ dialkylaminoalkyl, $C_1$-$C_6$ alkylthio or $C_2$-$C_7$ alkylthioalkyl;

each $R^{12}$ is independently $C_3$-$C_7$ cycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl or cyano;

$R^{13}$ is H, $C_1$-$C_3$ alkyl or $C_2$-$C_3$ haloalkyl;

each $R^{14}$ is independently H, cyano, $C_1$-$C_3$ alkyl or $C_1$-$C_3$ haloalkyl;

$R^{15}$ is H, $C_1$-$C_4$ alkyl or $OR^{18}$;

$R^{16}$ is $C_1$-$C_4$ alkyl or $OR^{18}$; or $R^{15}$ and $R^{16}$ are taken together as —$OCH_2CH_2O$—;

each $R^{18}$ is independently H, formyl, $C_3$-$C_7$ cycloalkyl, —$SO_3^-M^+$ or —$(C=W)R^{11}$; or $C_1$-$C_6$ alkyl or $C_1$-$C_6$ haloalkyl, each optionally substituted with up to 2 $R^{12}$;

each $R^{19}$ and $R^{20}$ is independently H or $CH_3$;

$R^{21}$ is H, formyl, $C_3$-$C_7$ cycloalkyl, —$SO_3^-M^+$ or —$(C=W)R^{11}$; or $C_1$-$C_6$ alkyl or $C_1$-$C_6$ haloalkyl, each optionally substituted with up to 2 $R^{12}$;

each U is independently O, $S(=O)_w$, $NR^{22}$ or a direct bond;

each V is independently $C_1$-$C_6$ alkylene, $C_2$-$C_6$ alkenylene, $C_3$-$C_6$ alkynylene, $C_3$-$C_6$ cycloalkylene or $C_3$-$C_6$ cycloalkenylene, wherein up to 3 carbon atoms are independently selected from $C(=O)$, each optionally substituted with up to 5 substituents independently selected from halogen, cyano, nitro, hydroxy, $C_1$-$C_6$ alkyl, $C_1$-$C_6$ haloalkyl, $C_1$-$C_6$ alkoxy and $C_1$-$C_6$ haloalkoxy;

each T is independently cyano, $NR^{23a}R^{23b}$, $OR^{24}$ or $S(=O)_yR^{25}$ each $R^{22}$ is independently H, $C_1$-$C_6$ alkyl, $C_1$-$C_6$ haloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl);

each $R^{23a}$ and $R^{23b}$ is independently H, $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_3$-$C_6$ halocycloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl); or a pair of $R^{23a}$ and $R^{23b}$ attached to the same nitrogen atom are taken together with the nitrogen atom to form a 3- to 6-membered heterocyclic ring, the ring optionally substituted with up to 5 substituents independently selected from $R^{26}$;

each $R^{24}$ and $R^{25}$ is independently H, $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_3$-$C_6$ halocycloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl);

each $R^{26}$ is independently halogen, $C_1$-$C_6$ alkyl, $C_1$-$C_6$ haloalkyl or $C_1$-$C_6$ alkoxy;

each W is independently O or S;

each $M^+$ is independently a cation;

m is 0, 1 or 2;

n is 0, 1 or 2;

t is 0, 1 or 2;

each u and v are independently 0, 1 or 2 in each instance of $S(=O)_u(=NR^{14})_v$, provided that the sum of u and v is 0, 1 or 2;

each w is independently 0, 1 or 2; and each y is independently 0, 1 or 2;

provided that:

when $Q^2$ is a phenyl ring substituted on at least one ortho position with a substituent selected from —U—V-T wherein U is a direct bond, V is $C(=O)$ and T is $NR^{23a}R^{23b}$ or $OR^{24}$, then X is other than $NR^4$.

More particularly, this invention pertains to a compound of Formula 1 (including all geometric and stereoisomers), an N-oxide or a salt thereof.

This invention also relates to a fungicidal composition comprising a compound of Formula 1, an N-oxide, or a salt thereof, and at least one additional component selected from the group consisting of surfactants, solid diluents and liquid diluents.

This invention also relates to a fungicidal composition comprising: (a) a compound of Formula 1, an N-oxide, or a salt thereof, and (b) at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

This invention also relates to a composition comprising a compound of Formula 1, an N-oxide, or a salt thereof, and at least one invertebrate pest control compound or agent.

The invention also relates to compounds of Formula 2 (including all geometric and stereoisomers) and salts thereof

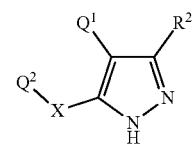

wherein

X is NH; and $Q^1$, $Q^2$ and $R^2$ are as defined above for Formula 1;

provided that:

(a) when $Q^2$ is a phenyl ring substituted on at least one ortho position with a substituent selected from —U—V-T wherein U is a direct bond and T is $NR^{23a}R^{23b}$ or $OR^{24}$, then V is other than $C(=O)$; and (b) when $Q^1$ is phenyl and $Q^2$ is 4-(trifluoromethyl) phenyl, then $R^2$ is other than methyl;

and to use of said compounds as intermediates for preparing compounds of Formula 1. More particularly, the present invention pertains to a compound of Formula 2 or a salt thereof.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

As used herein, the term "alkylating agent" refers to a chemical compound in which a carbon-containing radical is bound through a carbon atom to leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified for $R^1$.

Generally when a molecular fragment (i.e. radical) is denoted by a series of atom symbols (e.g., C, H, N, O, S) the implicit point or points of attachment will be easily recognized by those skilled in the art. In some instances herein, particularly when alternative points of attachment are possible, the point or points of attachment may be explicitly indicated by a hyphen ("-"). For example, "—SCN" indicates that the point of attachment is the sulfur atom (i.e. thiocyanato, not isothiocyanato).

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl isomers. "Alkenyl" also includes polyenes such as 1,2-propadienyl. "Alkynyl" includes straight-chain or branched alkynes such as ethynyl, 1-propynyl, 2-propynyl and the different butynyl isomers. "Alkenylene" denotes a straight-chain or branched alkenediyl containing one olefinic bond. Examples of "alkenylene" include CH=CH, $CH_2CH$=CH, CH=$C(CH_3)$. "Alkynylene" denotes a straight-chain or branched alkynediyl containing one triple bond. Examples of "alkynylene" include $CH_2C$≡C, C≡$CCH_2$ and the different butynylene, pentynylene and hexynylene isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl isomers. Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "(Alkylthio)carbonyl" denotes a straight-chain or branched alkylthio group bonded to a C(=O) moiety. Examples of "(alkylthio)carbonyl" include $CH_3SC$(=O), $CH_3CH_2CH_2SC$(=O) and $(CH_3)_2CHSC$(=O). "Alkoxy(thiocarbonyl)" denotes a straight-chain or branched alkoxy group bonded to a C(=S) moiety. Examples of "alkoxy(thiocarbonyl)" include $CH_3OC$(=S), $CH_3CH_2CH_2OC$(=S) and $(CH_3)_2CHOC$(=S). "Alkylaminoalkyl" denotes a straight-chain or branched alkyl moieties bonded to a nitrogen atom of an amino(straight-chain or branched)alkyl moiety. Examples of "alkylaminoalkyl" include $CH_3NHCH_2$—, $(CH_3)_2CHNHCH_2$— and $CH_3NHCH(CH_3)$—. "Dialkylaminoalkyl" denotes two independent straight-chain or branched alkyl moieties bonded to a nitrogen atom of an amino(straight-chain or branched)alkyl moiety. Examples of "dialkylaminoalkyl" include $(CH_3)_2NCH_2$—, $(CH_3)_2CH(CH_3)NCH_2$— and $(CH_3)_2NCH(CH_3)$—. The term "alkylcarbonylamino" denotes alkyl bonded to a C(=O)NH moiety. Examples of "alkylcarbonylamino" include $CH_3CH_2C$(=O)NH and $CH_3CH_2CH_2C$(=O)NH.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. "Cycloalkenyl" includes carbocyclic rings that contain only one double bond such as cyclopentenyl and cyclohexenyl, as well as carbocyclic rings with more than one double bond such as 1,3- and 1,4-cyclohexadienyl, but are not aromatic. "Cycloalkylcarbonyl" denotes cycloalkyl bonded to a C(=O) group including, for example, cyclopropylcarbonyl and cyclopentylcarbonyl. The term "cycloalkoxycarbonyl" means cycloalkoxy bonded to a C(=O) group, for example, cyclopropyloxycarbonyl and cyclopentyloxycarbonyl. The term"cycloalkylene" denotes a cycloalkanediyl ring. Examples of "cycloalkylene" include cyclopropylene, cyclobutylene, cyclopentylene and cyclohexylene. The term"cycloalkenylene" denotes a cycloalkenediyl ring containing one olefinic bond. Examples of "cycloalkenylene" include cylopropenediyl and cyclpentenediyl.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$—, $ClCH_2$—, $CF_3CH_2$— and $CF_3CCl_2$—. The terms "halocycloalkyl", "haloalkoxy", "haloalkylthio", and the like, are defined analogously to the term "haloalkyl". Examples of "haloalkoxy" include $CH_2FO$—, $CHF_2O$—, $CF_3O$—, $CCl_3CH_2O$—, $HCF_2CH_2CH_2O$— and $CF_3CH_2O$—. Examples of "fluoroalkoxy" include $CH_2FO$—, $CHF_2O$—, $CF_3O$—, $HCF_2CH_2CH_2O$— and $CF_3CH_2O$—. Examples of "fluoromethoxy" include $CH_2FO$—, $CHF_2O$— and $CF_3O$—. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(O)$—, $CCl_3S(O)$—, $CF_3CH_2S(O)$— and $CF_3CF_2S(O)$—. Examples of "haloalkylsulfonyl" include $CF_3S(O)_2$—, $CCl_3S(O)_2$—, $CF_3CH_2S(O)_2$— and $CF_3CF_2S(O)_2$—.

The total number of carbon atoms in a substituent group is indicated by the "$C_i$-$C_j$" prefix where i and j are numbers from 1 to 12. For example, $C_1$-$C_4$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "unsubstituted" in connection with a group such as a ring or ring system means the group does not have any substituents other than its one or more attachments to the remainder of Formula 1. The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. The number of optional substituents may be restricted by an expressed limitation. For example, the phrase "optionally substituted with up to 3 substituents selected from $R^{9a}$ on carbon ring members" means that 0, 1, 2 or 3 substituents can be present (if the number of potential connection points allows). Similarly, the phrase "optionally substituted with up to 5 substituents selected from $R^3$ on carbon ring members" means that 0, 1, 2, 3, 4 or 5 substituents can be present if the number of available connection points allows. When a range specified for the number of substituents (e.g., r being an integer from 0 to 4 or from 0 to 3 for 5- and 6-membered nitrogen-containing heterocycles in Exhibit A) exceeds the number of positions available for substituents on a ring (e.g., 2 positions available for $(R^a)_r$ on U-27 in Exhibit A), the actual higher end of the range is recognized to be the number of available positions.

When a compound is substituted with a substituent bearing a subscript that indicates the number of said substituents can exceed 1, said substituents (when they exceed 1) are independently selected from the group of defined substituents, e.g., $(R^3)_p$ in Table 1 where p is 0, 1, 2, 3, 4 or 5. When a group contains a substituent which can be hydrogen, for example $R^1$, $R^4$, $R^5$, $R^6$, $R^7$ or $R^{13}$, then when this substituent is taken as hydrogen, it is recognized that this is equivalent to said group being unsubstituted. When a variable group is shown to be optionally attached to a position, for example $(R^a)_r$ in H-23 of Exhibit 1, wherein r may be 0, then hydrogen may be at the position even if not recited in the variable group definition. When one or more positions on a group are said to be "not substituted" or "unsubstituted", then hydrogen atoms are attached to take up any free valency.

The variables "m", "n", "t", "u", "v", "w" and "y" in the Summary of the Invention and corresponding parts of the patent specification relate to subscripts appearing to the right of atoms or other molecular fragments within parentheses and denote the integral number of instances present of the atoms or other molecular fragments within the parentheses. "m" relates to "$S(O)_m$", "n" relates to "$S(O)_n$", "t" relates to "—S(=O)$_t R^{10}$", "u" and "v" relate to "$S(=O)_u(=NR^{14})_v$", "w" relates to "$S(=O)_w$", and "y" relates to "$S(=O)_y R^{25}$". For example, "m" being 0, 1 or 2 means that "$S(O)_m$" can be "S", "S(O)" or "$S(O)_2$".

Unless otherwise indicated, a "ring" as a component of Formula 1 is carbocyclic or heterocyclic. The term "ring system" as a component of Formula 1 denotes two fused rings (e.g., a phenyl ring fused to a pyridinyl ring to form quinolinyl). The term "ring member" refers to an atom or other moiety (e.g., O, S(O), $S(O)_2$ or $S(=O)_u(=NR^{14})_v$) forming the backbone of a ring or ring system.

The term "carbocyclic ring" denotes a ring wherein the atoms forming the ring backbone are selected only from carbon. Unless otherwise indicated, a carbocyclic ring can be a saturated, partially unsaturated, or fully unsaturated ring. "Saturated carbocyclic" refers to a ring having a backbone consisting of carbon atoms linked to one another by single bonds; unless otherwise specified, the remaining carbon valences are occupied by hydrogen atoms.

The terms "heterocyclic ring" or "heterocycle" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. The term "saturated heterocyclic ring" refers to a heterocyclic ring containing only single bonds between ring members. In regards to degree of saturation, "a partially unsaturated heterocyclic ring" is intermediate between a saturated heterocyclic ring and a fully unsaturated heterocyclic ring (which may be aromatic). Therefore, as referred to in the present disclosure and claims, the term "partially unsaturated heterocyclic ring" denotes a heterocyclic ring comprising at least one ring member bonded to an adjacent ring member through a double bond and which conceptually potentially accommodates a number of non-cumulated double bonds between adjacent ring members (i.e. in its fully unsaturated counterpart form) greater than the number of double bonds present (i.e. in its partially unsaturated form). When a fully unsaturated heterocyclic ring satisfies Hickel's rule, then said ring is also called a "heteroaromatic ring" or "aromatic heterocyclic ring". The terms "heteroaromatic ring system" and "heteroaromatic bicyclic ring system" denote a ring system in which at least one atom forming the ring backbone is not carbon, e.g., nitrogen, oxygen or sulfur, and at least one ring is aromatic. Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Huickel's rule. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "four- to seven-membered nonaromatic heterocyclic ring" refers to rings containing four to seven ring members and which do not satisfy Hickel's rule. This term (as used where $R^6$ and $R^7$ are taken together) is not limited by carbon atoms only and can include ring members selected from O, $S(O)_n$ and $NR^{13}$.

In the context of the present invention when an instance of $Q^1$, $Q^2$ or $R^1$ comprises a phenyl or a 6-membered fully unsaturated heterocyclic ring, the ortho, meta and para positions of each ring is relative to the connection of the ring to the remainder of Formula 1.

As noted above, $Q^1$, $Q^2$ and $R^1$ can be (among others) phenyl optionally substituted with one or more substituents selected from a group of substituents as defined in the Summary of the Invention. An example of phenyl optionally substituted with one to five substituents is the ring illustrated as U-57 in Exhibit A, wherein $R^8$ is as defined in the Summary of the Invention for $R^8$ and q is an integer from 0 to 5.

As noted above, $Q^1$ is, inter alia, a 5- to 6-membered fully unsaturated heterocyclic ring or an 8- to 10-membered heteroaromatic bicyclic ring system, each ring or ring system containing ring members selected from carbon atoms and up to 4 heteroatoms independently selected from up to 2 O, up to 2 S and up to 4 N atoms, wherein up to 3 carbon atom ring members are independently selected from $C(\!=\!O)$ and $C(\!=\!S)$, the sulfur atom ring members are independently selected from $S(\!=\!O)_u(\!=\!NR^{14})_v$, each ring or ring system optionally substituted with up to 5 substituents independently selected from any substituent defined in the Summary of the Invention for $Q^1$ (e.g., a $Q^1$ ring or ring system is optionally substituted with $R^3$ on carbon ring members and cyano, $C_1$-$C_6$ alkyl, $C_2$-$C_6$ alkenyl, $C_2$-$C_6$ alkynyl, $C_3$-$C_6$ cycloalkyl, $C_1$-$C_6$ alkoxy, $C_2$-$C_6$ alkoxyalkyl, $C_2$-$C_6$ alkylcarbonyl, $C_2$-$C_6$ alkoxycarbonyl, $C_2$-$C_6$ alkylaminoalkyl and $C_3$-$C_6$ dialkylaminoalkyl on nitrogen atom ring members). Similarly, $Q^2$ is, inter alia, a 5- to 6-membered saturated, partially unsaturated or fully unsaturated heterocyclic ring or an 8- to 10-membered heteroaromatic bicyclic ring system, each ring or ring system containing ring members selected from carbon atoms and up to 4 heteroatoms independently selected from up to 2 O, up to 2 S and up to 4 N atoms, wherein up to 3 carbon atom ring members are independently selected from $C(\!=\!O)$ and $C(\!=\!S)$, the sulfur atom ring members are independently selected from $S(\!=\!O)_u$ $(\!=\!NR^{14})_v$, each ring or ring system optionally substituted with up to 5 substituents independently selected from any substituent defined in the Summary of the Invention for $Q^2$. As the substituents on the ring or ring system of $Q^1$ or $Q^2$ are optional, 0 to 5 substituents may be present, limited only by the number of available points of attachment. In these definitions of heterocyclic ring and heteroaromatic ring system, the ring members selected from up to 2 O, up to 2 S and up to 4 N atoms are optional, provided at least one ring member is not carbon (e.g., N, O or S). The definition of $S(\!=\!O)_u(\!=\!NR^{14})_v$ allows the up to 2 sulfur ring members, to be oxidized sulfur moieties (e.g., $S(\!=\!O)$ or $S(\!=\!O)_2$) or unoxidized sulfur atoms (i.e. when u and v are both zero). The nitrogen atom ring members may be oxidized as N-oxides, because compounds relating to Formula 1 also include N-oxide derivatives. The up to 3 carbon atom ring members selected from $C(\!=\!O)$ and $C(\!=\!S)$ are in addition to the up to 4 heteroatoms selected from up to 2 O, up to 2 S and up to 4 N atoms.

Also as noted above, $R^1$ can be (among others) 5- or 6-membered nitrogen-containing aromatic heterocycle, which may be optionally substituted with one or more substituents selected from a group of substituents as defined in the Summary of Invention.

When $R^1$ is phenyl or a 5- or 6-membered nitrogen-containing aromatic heterocycle, it may be attached to the remainder of Formula 1 through any available carbon or nitrogen ring atom, unless otherwise described. Likewise, the ring or ring system of $Q^1$ or $Q^2$ may be attached to the remainder of Formula 1 through any available carbon or nitrogen ring atom, unless otherwise described.

Examples of a 5- to 6-membered fully unsaturated heterocyclic ring include the rings H-1 through H-39 illustrated in Exhibit 1, and examples of an 8- to 10-membered heteroaromatic bicyclic ring system include the ring systems B-1 through B-39 illustrated in Exhibit 2. In Exhibits 1 and 2 the variable $R^a$ is any substituent as defined in the Summary of the Invention for $Q^1$, $Q^2$ or $R^1$ (e.g., a $Q^1$ ring or ring system is optionally substituted with $R^3$ on carbon ring members and cyano, $C_1$-$C_6$ alkyl, $C_2$-$C_6$ alkenyl, $C_2$-$C_6$ alkynyl, $C_3$-$C_6$ cycloalkyl, $C_1$-$C_6$ alkoxy, $C_2$-$C_6$ alkoxyalkyl, $C_2$-$C_6$ alkylcarbonyl, $C_2$-$C_6$ alkoxycarbonyl, $C_2$-$C_6$ alkylaminoalkyl and $C_3$-$C_6$ dialkylaminoalkyl on nitrogen atom ring members) and r is an integer from 0 to 5 for $Q^1$ and $Q^2$ or from 0 to 3 for $R^1$, limited by the number of available positions on each depicted ring or ring system.

Exhibit 1

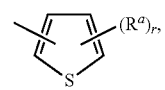

H-1

-continued
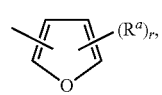 H-2
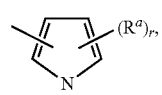 H-3
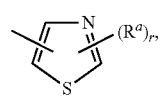 H-4
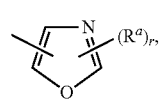 H-5
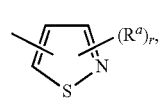 H-6
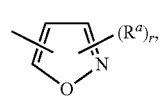 H-7
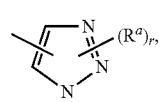 H-8
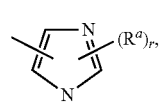 H-9
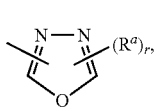 H-10
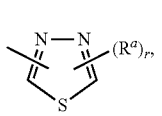 H-11
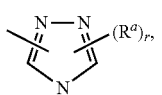 H-12
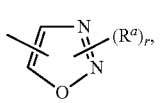 H-13
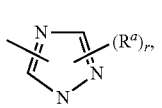 H-14
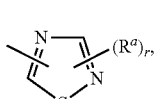 H-15
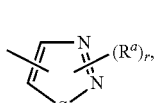 H-16
-continued
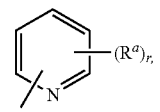 H-17
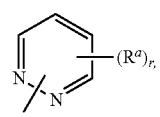 H-18
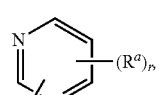 H-19
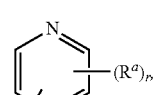 H-20
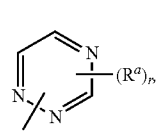 H-21
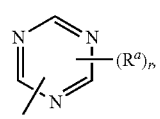 H-22
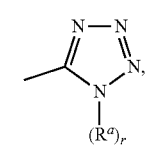 H-23
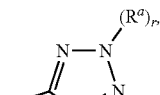 H-24
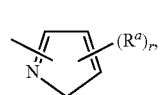 H-25
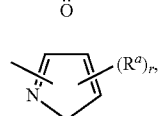 H-26
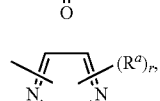 H-27
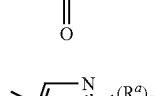 H-28
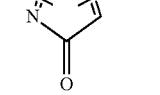

-continued
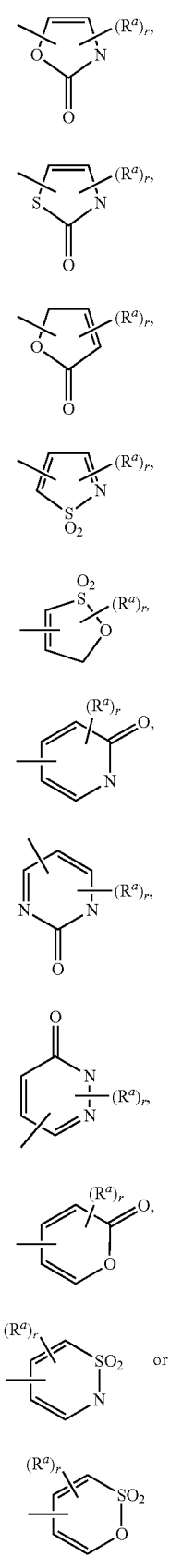
Exhibit 2
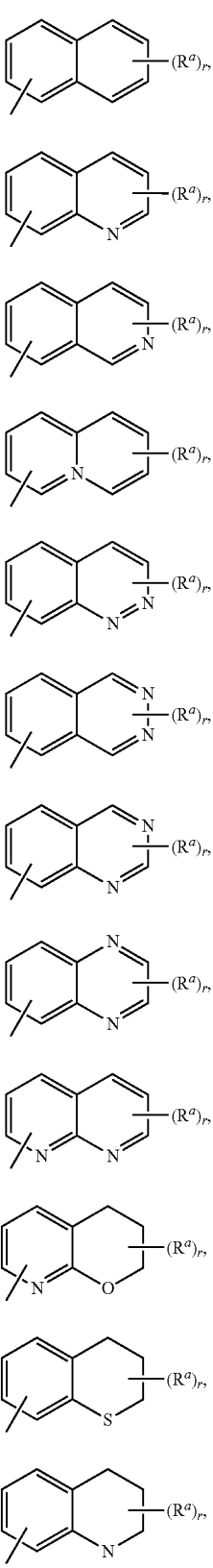

Examples of a saturated or partially unsaturated 5- to 6-membered fully unsaturated heterocyclic ring include the rings P-1 through P-40 illustrated in Exhibit 3. In Exhibit 3 the variable $R^a$ is any substituent as defined in the Summary of the Invention for $Q^2$ (e.g., a $Q^2$ ring is optionally substituted with $R^3$ on carbon ring members and cyano, $C_1$-$C_6$ alkyl, $C_2$-$C_6$ alkenyl, $C_2$-$C_6$ alkynyl, $C_3$-$C_6$ cycloalkyl, $C_1$-$C_6$ alkoxy, $C_2$-$C_6$ alkoxyalkyl, $C_2$-$C_6$ alkylcarbonyl, $C_2$-$C_6$ alkoxycarbonyl, $C_2$-$C_6$ alkylaminoalkyl and $C_3$-$C_6$ dialkylaminoalkyl on nitrogen atom ring members) and r is an integer from 0 to 5, limited by the number of available positions on each depicted ring or ring system.

Exhibit 3

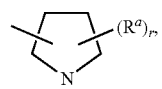
P-1

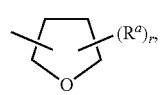
P-2

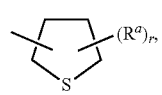
P-3

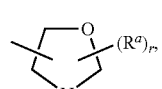
P-4

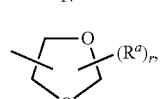
P-5

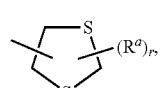
P-6

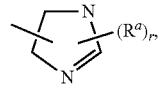
P-7

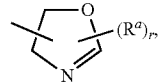
P-8

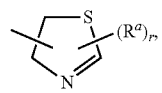
P-9

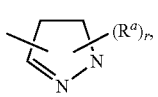
P-10

P-11

P-12

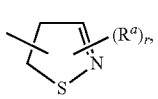
P-13

-continued

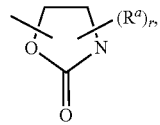
P-14

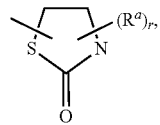
P-15

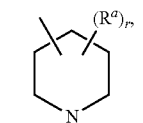
P-16

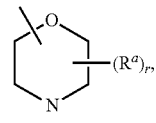
P-17

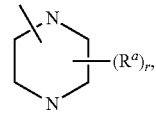
P-18

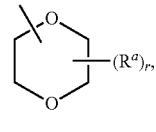
P-19

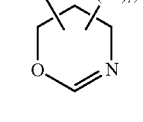
P-20

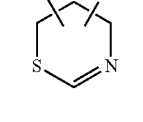
P-21

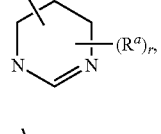
P-22

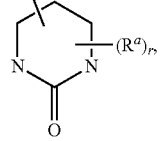
P-23

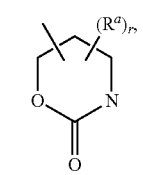
P-24

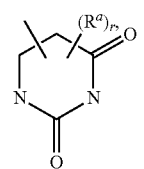 P-25

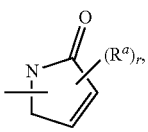 P-26

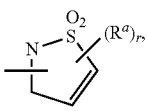 P-27

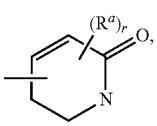 P-28

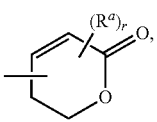 P-29

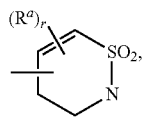 P-30

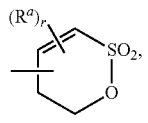 P-31

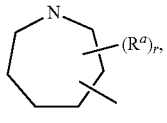 P-32

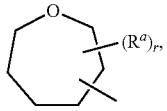 P-33

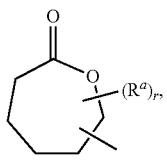 P-34

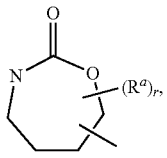 P-35

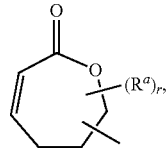 P-36

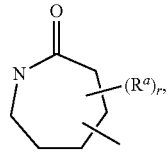 P-37

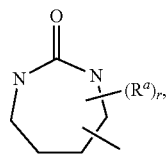 P-38

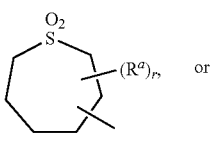 P-39

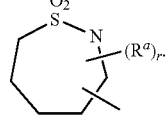 P-40

Examples of a 5- or 6-membered nitrogen-containing heterocycle optionally substituted with from one or more substituents of particular note for $Q^1$, $Q^2$ and $R^1$ include the rings U-1 through U-56 illustrated in Exhibit A wherein $R^a$ is any substituent as defined in the Summary of the Invention for $Q^1$ $Q^2$ and $R^1$, respectively (i.e. for $Q^1$ and $Q^2$: $R^3$ on carbon atom ring members, and the recited list of possible substituents on nitrogen atom ring members; and for $R^1$, $R^{9a}$ on carbon ring members and $R^{9b}$ on nitrogen ring members) and r is an integer ranging from 0 to 4 for $Q^1$ and $Q^2$ and from 0 to 3 for $R^1$, limited by the number of available positions on each U group. Note that some U groups can only be substituted with less than 4 $R^a$ groups (e.g., U-4 through U-43 and U-47 through U-56). As U-24, U-25, U-31, U-32, U-33, U-34, U-35, U-36, U-37 and U-38 have only one available position, for these U groups, r is limited to the integers 0 or 1, and r being 0 means that the U group is unsubstituted and a hydrogen is present at the position indicated by $(R^a)_r$.

Exhibit A

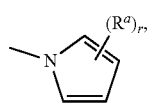 U-1

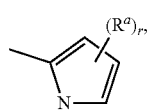 U-2

-continued
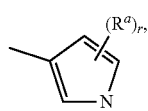 U-3
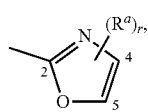 U-4
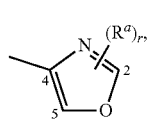 U-5
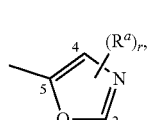 U-6
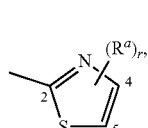 U-7
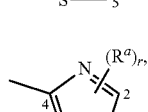 U-8
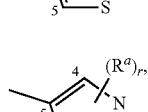 U-9
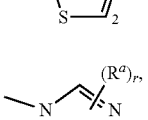 U-10
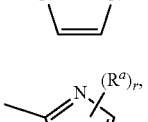 U-11
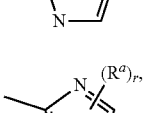 U-12
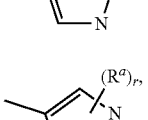 U-13
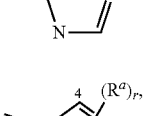 U-14
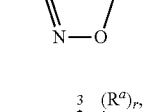 U-15
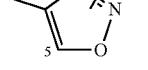
-continued
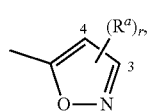 U-16
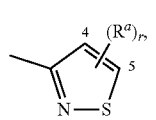 U-17
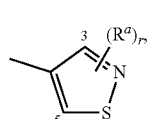 U-18
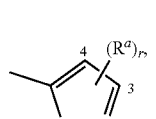 U-19
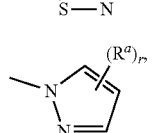 U-20
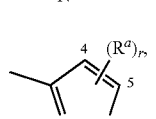 U-21
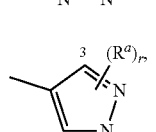 U-22
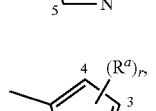 U-23
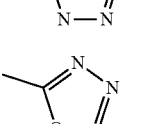 U-24
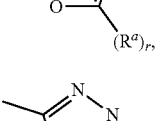 U-25
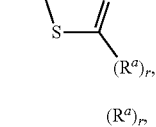 U-26
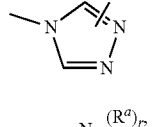 U-27
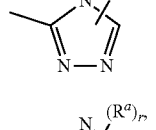 U-28

| | |
|---|---|
| U-29 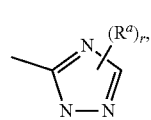 | U-41 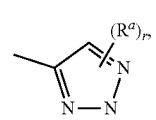 |
| U-30 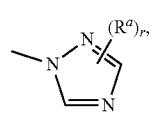 | U-42 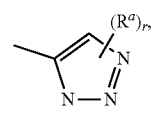 |
| U-31 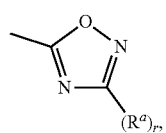 | U-43 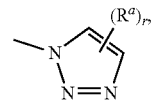 |
| U-32 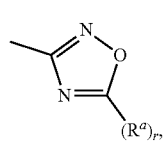 | U-44 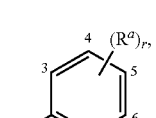 |
| U-33 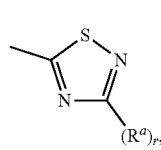 | U-45 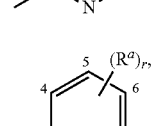 |
| U-34 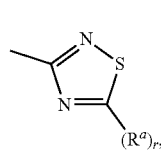 | U-46 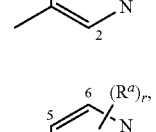 |
| U-35 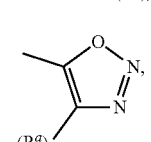 | U-47 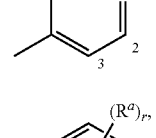 |
| U-36 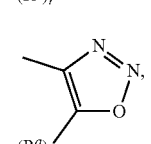 | U-48 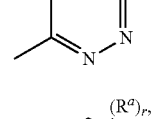 |
| U-37 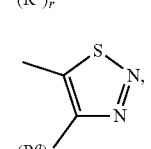 | U-49 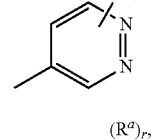 |
| U-38 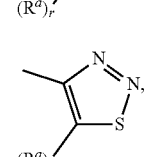 | U-50 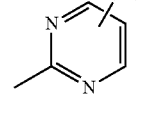 |
| U-39 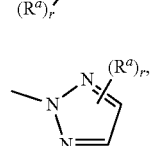 | U-51 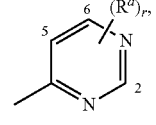 |
| U-40 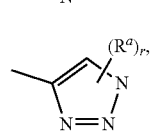 | U-52 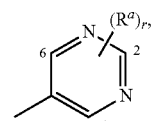 |

25
-continued

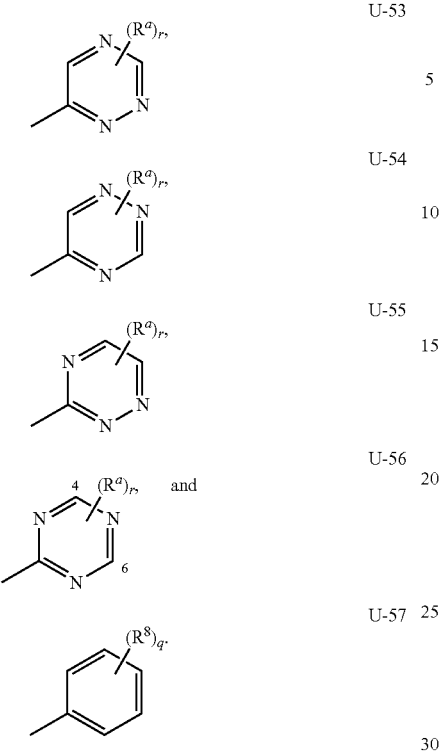

Exhibit 4

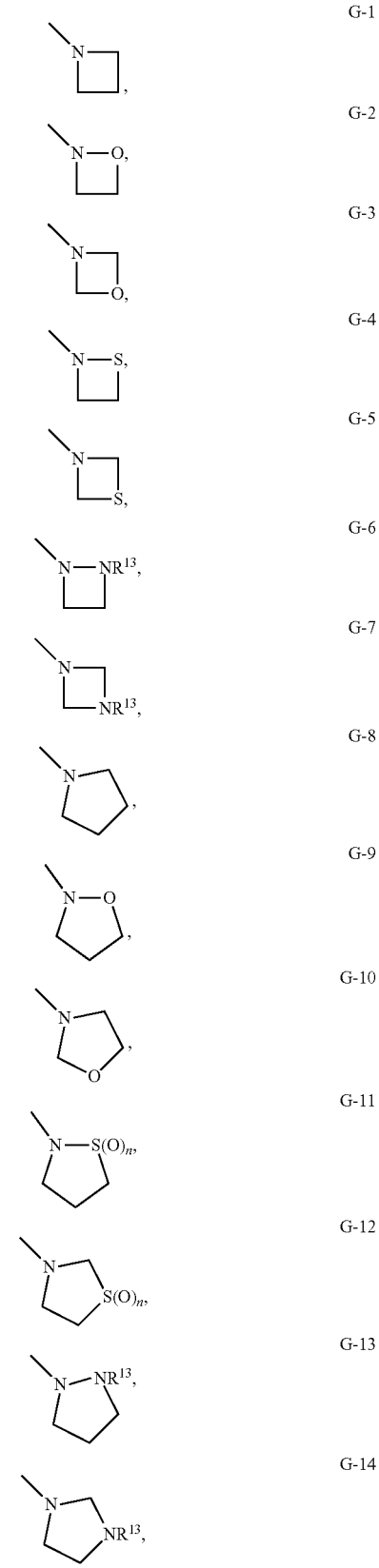

Although R$^a$ groups are shown in the structures H-1 through H-39, B-1 through B-39, P-1 through P-40, and U-1 through U-57 in Exhibits 1 through 3 and Exhibit A, it is noted that they do not need to be present since they are optional substituents. The nitrogen atoms that require substitution to fill their valence are substituted with H or R$^a$. Note that when the attachment point between (R$^a$)$_r$ and the H, B, P or U group in Exhibits 1 through 3 and Exhibit A is illustrated as floating, (R$^a$)$_r$ can be attached to any available carbon atom or nitrogen atom of the H, B, P or U group. Note that when the attachment point on the H, B or P group in Exhibits 1 through 3 is illustrated as floating, the H, B or P group can be attached to the remainder of Formula 1 through any available carbon or nitrogen of the H, B or P group by replacement of a hydrogen atom. Of note are alternative depictions of the chemical structures shown in Exhibits 1 through 3 and Exhibit A in which the "R$^a$" variable substituent is replaced by "R$^v$", wherein the "v" superscript in "R$^v$" does not refer to the subscript variable "v" defined in the Summary of the Invention but instead differentiates "R$^v$" from other substituent variables beginning with "R".

Examples of where R$^6$ and R$^7$ are taken together to form a four- to seven-membered nonaromatic heterocyclic ring include the rings G-1 through G-28 as illustrated in Exhibit 4. Note that when R$^6$ and R$^7$ are taken together to form a ring comprising a ring selected from G-25 through G-28, G$^2$ is selected from O, S(O)$_n$ or NR$^{13}$. Note that when G$^2$ is N, the nitrogen atom can complete its valence by substitution with either H or the substituents corresponding to R$^{13}$ as defined in the Summary of Invention.

-continued

G-15 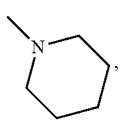

G-16 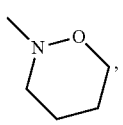

G-17 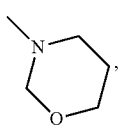

G-18 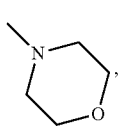

G-19 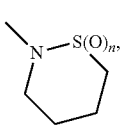

G-20 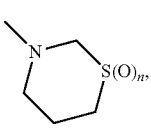

G-21 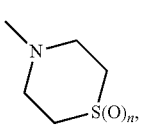

G-22 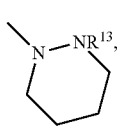

G-23 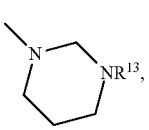

G-24 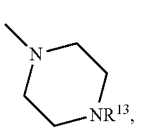

G-25 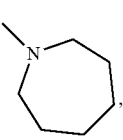

G-26 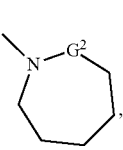

G-27 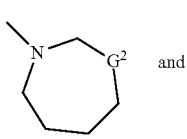 and

G-28 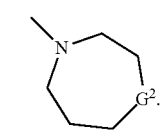

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that some of the compounds disclosed herein can exist in equilibrium with one or more of their respective tautomeric counterparts. Unless otherwise indicated, reference to a compound by one tautomer description is to be considered to include all tautomers. For example, reference to the tautomeric form depicted by Formula 2¹ also includes the tautomic form depicted by Formula 2².

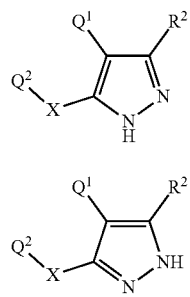

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Compounds selected from Formula 1, geometric and stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

Embodiments of the present invention as described in the Summary of the Invention include (where Formula 1 as used in the following Embodiments includes N-oxides and salts, geometric isomers, stereoisomers and atropisomers thereof):

Embodiment 1

A compound of Formula 1 wherein X is O, $S(O)_m$, $NR^4$, $CR^{15}R^{16}$ or $C(=O)$.

Embodiment 2

A compound of Formula 1 wherein X is O, $S(O)_m$, $NR^4$ or $CR^{15}R^{16}$.

Embodiment 3

A compound of Formula 1 wherein X is O, $NR^4$, $CR^{15}R^{16}$ or $C(=O)$.

Embodiment 4

A compound of Formula 1 wherein X is O, $NR^4$ or $CR^{15}R^{16}$.

Embodiment 5

A compound of Formula 1 wherein X is O, $S(O)_m$ or $NR^4$.

Embodiment 6

A compound of Formula 1 wherein X is O or $S(O)_m$.

Embodiment 7

A compound of Formula 1 wherein X is O.

Embodiment 8

A compound of Formula 1 wherein X is $NR^4$.

Embodiment 9

A compound of Formula 1 wherein X is O or $NR^4$.

Embodiment 10

A compound of Formula 1 wherein X is $CR^{15}R^{16}$, $C(=O)$ or $C(=S)$.

Embodiment 11

A compound of Formula 1 or any one of Embodiments 1 through 10 wherein when $Q^1$ is a six-membered ring (e.g., phenyl, pyridinyl, pyrimidinyl, pyrazinyl or pyridazinyl) and an $R^3$ substituent is located at a meta position (relative to the connection of the $Q^1$ ring to the remainder of Formula 1), then said $R^3$ substituent is selected from F, Cl, Br and cyano (—CN).

Embodiment 11a

A compound of Formula 1 or any one of Embodiments 1 through 11 wherein when $Q^1$ is a six-membered ring and an $R^3$ substituent is located at a meta position (relative to the connection of the $Q^1$ ring to the remainder of Formula 1), then said $R^3$ substituent is F.

Embodiment 12

A compound of Formula 1 or any one of Embodiments 1 through 11a wherein when $Q^1$ is a six-membered ring (e.g., phenyl, pyridinyl, pyrimidinyl, pyrazinyl or pyridazinyl) substituted with only one $R^3$ substituent, then said $R^3$ substituent is attached at an ortho position (relative to the connection of the $Q^1$ ring to the remainder of Formula 1).

Embodiment 13

A compound of Formula 1 or any one of Embodiments 1 through 12 wherein $Q^1$ is phenyl, thienyl, pyridinyl, pyridazinyl, pyrazinyl, pyrimidinyl, naphthalenyl, quinolinyl, isoquinolinyl or quinoxalinyl, each optionally substituted with up to 5 substituents independently selected from $R^3$.

Embodiment 14

A compound of Embodiment 13 wherein $Q^1$ is phenyl, thienyl, pyridinyl, pyridazinyl, pyrazinyl or pyrimidinyl, each optionally substituted with up to 5 substituents independently selected from $R^3$.

Embodiment 15

A compound of Embodiment 14 wherein $Q^1$ is phenyl, pyridinyl, pyrimidinyl, pyrazinyl or pyridazinyl, each substituted with from 1 to 4 substituents independently selected from $R^3$.

Embodiment 16

A compound of Embodiment 15 wherein $Q^1$ is phenyl, pyridinyl, pyrimidinyl, pyrazinyl or pyridazinyl, each substituted with 1, 2 or 3 substituents independently selected from $R^3$.

Embodiment 17

A compound of Embodiment 16 wherein the substituents are located at the ortho and/or para positions (relative to the connection of the $Q^1$ ring to the remainder of Formula 1) of the phenyl, pyridinyl, pyrimidinyl, pyrazinyl or pyridazinyl of $Q^1$.

Embodiment 18

A compound of Embodiment 16 or 17 wherein $Q^1$ is phenyl or pyridinyl, each substituted with 1, 2 or 3 substituents independently selected from $R^3$.

Embodiment 19

A compound of Embodiment 18 wherein $Q^1$ is phenyl or pyridinyl, each substituted with 2 or 3 substituents independently selected from $R^3$.

Embodiment 20

A compound of Embodiment 19 wherein $Q^1$ is phenyl substituted at the 2-, 4- and 6-positions with substituents independently selected from $R^3$; or phenyl substituted at the 2- and 4-positions with substituents independently selected from $R^3$; or phenyl substituted at the 2- and 6-positions with substituents independently selected from $R^3$.

Embodiment 21

A compound of Embodiment 20 wherein $Q^1$ is phenyl substituted at the 2-, 4- and 6-positions with substituents independently selected from $R^3$; or phenyl substituted at the 2- and 4-positions with substituents independently selected from $R^3$.

Embodiment 22

A compound of Embodiment 21 wherein $Q^1$ is phenyl substituted at the 2-, 4- and 6-positions with substituents independently selected from $R^3$.

Embodiment 23

A compound of Embodiment 21 wherein $Q^1$ is phenyl substituted at the 2- and 4-positions with substituents independently selected from $R^3$.

Embodiment 24

A compound of Embodiment 21 wherein $Q^1$ is phenyl substituted at the 2- and 6-positions with substituents independently selected from $R^3$.

Embodiment 25

A compound of Embodiment 18 wherein $Q^1$ is pyridinyl substituted with 1, 2 or 3 substituents independently selected from $R^3$.

Embodiment 26

A compound of Embodiment 25 wherein $Q^1$ is pyridinyl substituted with 1 or 2 substituents independently selected from $R^3$.

Embodiment 27

A compound of Embodiment 26 wherein $Q^1$ is pyridinyl substituted with 1 substituent independently selected from $R^3$.

Embodiment 28

A compound of Formula 1 or any one of Embodiments 1 through 27 wherein when $Q^2$ is a six-membered ring (e.g., phenyl, pyridinyl, pyrimidinyl, pyrazinyl or pyridazinyl) and an $R^3$ substituent is located at a meta position (relative to the connection of the $Q^2$ ring to the remainder of Formula 1), then said $R^3$ substituent is selected from F, Cl, Br and cyano (—CN).

Embodiment 29

A compound of Formula 1 or any one of Embodiments 1 through 28 wherein when $Q^2$ is a six-membered ring and an $R^3$ substituent is located at a meta position (relative to the connection of the $Q^2$ ring to the remainder of Formula 1), then said $R^3$ substituent is F.

Embodiment 30

A compound of Formula 1 or any one of Embodiments 1 through 29 wherein when $Q^2$ is a six-membered ring (e.g., phenyl, pyridinyl, pyrimidinyl, pyrazinyl or pyridazinyl) substituted with only one $R^3$ substituent, then said $R^3$ substituent is attached at an ortho position (relative to the connection of the $Q^2$ ring to the remainder of Formula 1).

Embodiment 31

A compound of Formula 1 or any one of Embodiments 1 through 30 wherein $Q^2$ is phenyl, thienyl, pyridinyl, pyridazinyl, pyrazinyl, pyrimidinyl, naphthalenyl, quinolinyl, isoquinolinyl or quinoxalinyl, each optionally substituted with up to 5 substituents independently selected from $R^3$.

Embodiment 32

A compound of Embodiment 31 wherein $Q^2$ is phenyl, thienyl, pyridinyl, pyridazinyl, pyrazinyl or pyrimidinyl, each optionally substituted with up to 5 substituents independently selected from $R^3$.

Embodiment 33

A compound of Embodiment 32 wherein $Q^2$ is phenyl, pyridinyl, pyrimidinyl, pyrazinyl or pyridazinyl, each substituted with from 1 to 4 substituents independently selected from $R^3$.

Embodiment 34

A compound of any one of Embodiments 31 through 33 wherein $Q^2$ is phenyl, pyridinyl, pyrimidinyl, pyrazinyl or pyridazinyl, each substituted with 1, 2 or 3 substituents independently selected from $R^3$.

Embodiment 35

A compound of Embodiment 34 wherein the substituents are located at the ortho and/or para positions (relative to the connection of the $Q^2$ ring to the remainder of Formula 1) of the phenyl, pyridinyl, pyrimidinyl, pyrazinyl or pyridazinyl of $Q^2$.

Embodiment 36

A compound of any one of Embodiments 34 or 35 wherein $Q^2$ is phenyl or pyridinyl, each substituted with 1, 2 or 3 substituents independently selected from $R^3$.

Embodiment 37

A compound of Embodiment 36 wherein $Q^2$ is phenyl substituted with 1, 2 or 3 substituents independently selected from $R^3$.

Embodiment 38

A compound of Embodiment 37 wherein $Q^2$ is phenyl substituted at the 2-, 4- and 6-positions with substituents independently selected from $R^3$; or phenyl substituted at the 2- and 4-positions with substituents independently selected from $R^3$; or phenyl substituted at the 2- and 6-positions with substituents independently selected from $R^3$.

Embodiment 39

A compound of Embodiment 38 wherein $Q^2$ is phenyl substituted at the 2-, 4- and 6-positions with substituents independently selected from $R^3$.

Embodiment 40

A compound of Embodiment 38 wherein $Q^2$ is phenyl substituted at the 2- and 4-positions with substituents independently selected from $R^3$.

Embodiment 41

A compound of Embodiment 38 wherein $Q^2$ is phenyl substituted at the 2- and 6-positions with substituents independently selected from $R^3$.

Embodiment 42

A compound of Embodiment 36 wherein $Q^2$ is pyridinyl substituted with 1, 2 or 3 substituents independently selected from $R^3$.

Embodiment 43

A compound of Embodiment 42 wherein $Q^2$ is pyridinyl substituted with 1 or 2 substituents independently selected from $R^3$.

Embodiment 44

A compound of Embodiment 43 wherein $Q^2$ is pyridinyl substituted with 1 substituent selected from $R^3$.

Embodiment 45

A compound of Formula 1 or any one of Embodiments 1 through 44 wherein at least one of $Q^1$ and $Q^2$ is phenyl optionally substituted with $R^3$ (e.g., optionally substituted with up to 5 substituents independently selected from $R^3$).

Embodiment 46

A compound of Embodiment 45 wherein at least one of $Q^1$ and $Q^2$ is phenyl substituted with 2, 3 or 4 substituents independently selected from $R^3$.

Embodiment 47

A compound of Embodiment 46 wherein at least one $Q^1$ and $Q^2$ is phenyl substituted with 2 or 3 substituents independently selected from $R^3$.

Embodiment 48

A compound of Embodiment 47 wherein each of $Q^1$ and $Q^2$ is phenyl substituted with 2 or 3 substituents independently selected from $R^3$.

Embodiment 49

A compound of Formula 1 or any one of Embodiments 1 through 48 wherein $R^1$ is H, halogen, $C_1$-$C_6$ alkyl, $C_1$-$C_6$ haloalkyl, $CO_2R^5$, $C(O)NR^6R^7$, cyano, $C_1$-$C_6$ alkoxy, $C_1$-$C_6$ haloalkoxy or $C_2$-$C_5$ alkoxyalkyl; or $R^1$ is a five- or six-membered nitrogen-containing aromatic heterocycle optionally substituted with up to 3 substituents independently selected from $R^{9a}$ on carbon atom ring members and $R^{9b}$ on nitrogen atom ring members.

Embodiment 50

A compound of Embodiment 49 wherein $R^1$ is H, halogen, $C_1$-$C_6$ alkyl, $C_1$-$C_6$ haloalkyl, cyano, $C_1$-$C_6$ alkoxy or $C_1$-$C_6$ haloalkoxy; or $R^1$ is pyridinyl, pyrimidinyl, pyrazolyl or oxazolyl, each optionally substituted with up to 3 substituents independently selected from $R^{9a}$ on carbon atom ring members and $R^{9b}$ on nitrogen atom ring members.

Embodiment 51

A compound of Embodiment 50 wherein $R^1$ is H, halogen, $C_1$-$C_6$ alkyl, $C_1$-$C_6$ haloalkyl, $CO_2R^5$, $C(O)NR^6R^7$, cyano, $C_1$-$C_6$ alkoxy, $C_1$-$C_6$ haloalkoxy or $C_2$-$C_5$ alkoxyalkyl.

Embodiment 52

A compound of Embodiment 51 wherein $R^1$ is H, halogen, $C_1$-$C_6$ alkyl, $C_1$-$C_6$ haloalkyl, $C(O)NR^6R^7$, cyano, $C_1$-$C_6$ alkoxy, $C_1$-$C_6$ haloalkoxy or $C_2$-$C_5$ alkoxyalkyl.

Embodiment 53

A compound of Embodiment 52 wherein $R^1$ is H, halogen, $C_1$-$C_6$ alkyl, $C_1$-$C_6$ haloalkyl, cyano, $C_1$-$C_6$ alkoxy, $C_1$-$C_6$ haloalkoxy or $C_2$-$C_5$ alkoxyalkyl.

Embodiment 54

A compound of Embodiment 53 wherein $R^1$ is H, halogen or $C_1$-$C_6$ alkyl.

Embodiment 55

A compound of Embodiment 54 wherein $R^1$ is H or $CH_3$.

Embodiment 56

A compound of Embodiment 55 wherein $R^1$ is H.

Embodiment 57

A compound of Formula 1 or any one of Embodiments 1 through 56 wherein $R^1$ is other than an optionally substituted phenyl or an optionally substituted five- or six-membered nitrogen-containing aromatic heterocycle.

Embodiment 58

A compound of Formula 1 or any one of Embodiments 1 through 50 wherein $R^1$ is other than H, halogen, $C_1$-$C_6$ alkyl, $C_1$-$C_6$ haloalkyl, $C_2$-$C_4$ alkenyl, $C_2$-$C_4$ alkynyl, $C_3$-$C_7$ cycloalkyl, $CO_2R^5$, $C(O)NR^6R^7$, cyano, $C_1$-$C_6$ alkoxy, $C_1$-$C_6$ haloalkoxy or $C_2$-$C_5$ alkoxyalkyl.

Embodiment 59

A compound of Formula 1 or any one of Embodiments 1 through 58 wherein $R^{1a}$ is H.

Embodiment 60

A compound of Formula 1 or any one of Embodiments 1 through 59 wherein $R^2$ is $CH_3$, $CH_2CH_3$, halogen, cyano, cyanomethyl, monohalomethyl, hydroxymethyl, methoxy or methylthio; or cyclopropyl optionally substituted with up to 2 substituents independently selected from halogen and methyl.

Embodiment 61

A compound of Embodiment 60 wherein $R^2$ is $CH_3$, $CH_2CH_3$, Cl, Br or I.

Embodiment 62

A compound of Embodiment 61 wherein $R^2$ is $CH_3$, $CH_2CH_3$, Cl or Br.

Embodiment 63

A compound of Embodiment 62 wherein $R^2$ is $CH_3$, Cl or Br.

Embodiment 64

A compound of Embodiment 63 wherein $R^2$ is $CH_3$ or Cl.

Embodiment 65

A compound of Embodiment 64 wherein $R^2$ is $CH_3$.

Embodiment 66

A compound of Embodiment 62 wherein $R^2$ is Cl or Br.

Embodiment 67

A compound of Embodiment 66 wherein $R^2$ is Cl.

Embodiment 68

A compound of Formula 1 or any one of Embodiments 1 through 67 wherein $R^5$ is H or $C_1$-$C_6$ alkyl.

Embodiment 69

A compound of Embodiment 68 wherein $R^5$ is H, $CH_3$ or $CH_2CH_3$.

Embodiment 70

A compound of Embodiment 68 wherein $R^5$ is $C_1$-$C_6$ alkyl.

Embodiment 71

A compound of Embodiment 69 or 70 wherein $R^5$ is $CH_3$ or $CH_2CH_3$.

Embodiment 72

A compound of Formula 1 or any one of Embodiments 1 through 71 wherein when $R^6$ is separate (i.e. not taken together with $R^7$ to form a ring), then $R^6$ is H or $C_1$-$C_6$ alkyl.

Embodiment 73

A compound of Embodiment 72 wherein $R^6$ is H.

Embodiment 74

A compound of Formula 1 or any one of Embodiments 1 through 73 wherein when $R^7$ is separate (i.e. not taken together with $R^6$ to form a ring), then $R^7$ is H, $C_1$-$C_6$ alkyl, $C_1$-$C_6$ haloalkyl or $C_4$-$C_8$ alkylcycloalkyl.

Embodiment 75

A compound of Embodiment 74 wherein $R^7$ is H or $C_1$-$C_6$ alkyl.

Embodiment 76

A compound of Embodiment 75 wherein $R^7$ is H.

Embodiment 77

A compound of Formula 1 or any one Embodiments 1 through 76 wherein when $R^6$ and $R^7$ are taken together with the nitrogen atom to which they are connected to form a nonaromatic heterocyclic ring, the ring contains ring members, in addition to the connecting nitrogen atom, selected from carbon atoms and up to one ring member selected from O and $NR^{13}$.

Embodiment 78

A compound of Embodiment 77 wherein when $R^6$ and $R^7$ are taken together with the nitrogen atom to which they are connected to form a nonaromatic heterocyclic ring, the ring is six-membered and contains one ring member selected from O and $NR^{13}$ in addition to the connecting nitrogen atom and ring members selected from carbon atoms.

Embodiment 79

A compound of Embodiment 77 wherein $R^6$ and $R^7$ are taken together with the nitrogen atom to which they are connected to form a piperidine ring.

Embodiment 80

A compound of Embodiment 78 wherein $R^6$ and $R^7$ are taken together with the nitrogen atom to which they are connected to form a piperazine or morpholine ring.

Embodiment 81

A compound of Formula 1 or any one of Embodiments 1 through 80 wherein each $R^8$ is independently selected from halogen, $C_1$-$C_2$ alkyl, $C_1$-$C_2$ haloalkyl, $C_1$-$C_2$ alkoxy, $C_1$-$C_2$ haloalkoxy, cyano and nitro.

Embodiment 82

A compound of Embodiment 81 wherein each $R^8$ is independently selected from halogen, $C_1$-$C_2$ alkyl, $C_1$-$C_2$ alkoxy, cyano and nitro.

Embodiment 83

A compound of Embodiment 82 wherein each $R^8$ is independently Cl or F.

Embodiment 84

A compound of Formula 1 or any one of Embodiments 1 through 83 wherein each $R^{9a}$ is independently selected from halogen, $C_1$-$C_2$ alkyl, $C_1$-$C_2$ haloalkyl, $C_1$-$C_2$ alkoxy, $C_1$-$C_2$ haloalkoxy, cyano and nitro.

Embodiment 85

A compound of Embodiment 84 wherein each $R^{9a}$ is independently selected from halogen, $C_1$-$C_2$ alkyl, $C_1$-$C_2$ alkoxy, cyano and nitro.

Embodiment 86

A compound of Embodiment 85 wherein each $R^{9a}$ is independently selected from Cl, F, $CH_3$, —$OCH_3$ and cyano.

Embodiment 87

A compound of Embodiment 86 wherein each $R^{9a}$ is independently Cl or F.

Embodiment 88

A compound of Formula 1 or any one of Embodiments 1 through 87 wherein each $R^{9b}$ is independently $C_1$-$C_2$ alkyl.

Embodiment 89

A compound of Formula 1 or any one of Embodiments 1 through 88 wherein each $R^3$ is independently selected from halogen, cyano, nitro, amino, methylamino, dimethylamino, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_3$-$C_4$ cycloalkyl, C(=S)$NH_2$ and —U—V-T.

Embodiment 90

A compound of Embodiment 89 wherein each $R^3$ is independently selected from halogen, cyano, nitro, $C_1$-$C_4$ alkyl, $C_1$-$C_4$ haloalkyl, $C_1$-$C_3$ alkoxy, $C_1$-$C_3$ haloalkoxy and —U—V-T.

Embodiment 91

A compound of Embodiment 90 wherein each $R^3$ is independently selected from F, Cl, Br, cyano, nitro, $CH_3$, $CF_3$, —$OCH_3$, —$OCHF_2$ and —U—V-T.

Embodiment 92

A compound of Formula 1 or any one of Embodiments 1 through 91 wherein at least one $R^3$ substituent on the ring or ring system of $Q^1$ or $Q^2$ is —U—V-T.

Embodiment 93

A compound of Formula 1 or any one of Embodiments 1 through 91 wherein each $R^3$ is other than —U—V-T.

Embodiment 94

A compound of Embodiment 89 wherein each $R^3$ is independently selected from halogen, cyano, nitro, amino, methylamino, dimethylamino, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl and $C_3$-$C_4$ cycloalkyl.

Embodiment 95

A compound of Embodiment 94 wherein each $R^3$ is independently selected from halogen, cyano, nitro, $C_1$-$C_4$ alkyl, $C_1$-$C_4$ haloalkyl, $C_1$-$C_3$ alkoxy and $C_1$-$C_3$ haloalkoxy.

Embodiment 96

A compound of Embodiment 95 wherein each $R^3$ is independently selected from halogen, cyano, $C_1$-$C_3$ alkyl, $C_1$-$C_3$ haloalkyl, $C_1$-$C_3$ alkoxy and $C_1$-$C_3$ haloalkoxy.

Embodiment 97

A compound of Embodiment 96 wherein each $R^3$ is independently selected from F, Cl, Br, cyano, $C_1$-$C_2$ alkyl, $C_1$-$C_2$ haloalkyl, $C_1$-$C_2$ alkoxy and $C_1$-$C_2$ haloalkoxy.

Embodiment 98

A compound of Embodiment 97 wherein each $R^3$ is independently selected from F, Cl, Br, cyano, methyl, $C_1$-$C_2$ alkoxy and fluoromethoxy.

Embodiment 99

A compound of Embodiment 98 wherein each $R^3$ is independently selected from F, Cl, cyano, methyl, $C_1$-$C_2$ alkoxy and fluoromethoxy.

Embodiment 100

A compound of Embodiment 95 wherein each $R^3$ is independently selected from F, Cl, Br, cyano, nitro, $CH_3$, $CF_3$, $-OCH_3$ and $-OCHF_2$.

Embodiment 101

A compound of any one of Embodiments 89 through 98 or 100 wherein each $R^3$ is independently selected from F, Cl, Br, cyano and methoxy.

Embodiment 102

A compound of Embodiment 101 wherein each $R^3$ is independently selected from F, Cl, Br and cyano.

Embodiment 103

A compound of Embodiment 101 wherein each $R^3$ is independently selected from F, Cl, cyano and $-OCH_3$.

Embodiment 104

A compound of Formula 1 or any one of Embodiments 1 through 92 wherein each U is independently O or $NR^{22}$.

Embodiment 105

A compound of Embodiment 104 wherein each U is independently O or NH.

Embodiment 106

A compound of Formula 1 or any one of Embodiments 1 through 92 and 104 through 105 wherein each V is $C_2$-$C_4$ alkylene.

Embodiment 107

A compound of Formula 1 or any one of Embodiments 1 through 92 and 104 through 106 wherein each T is independently $NR^{23a}R^{23b}$ or $OR^{24}$.

Embodiment 108

A compound of Formula 1 or any one of Embodiments 1 through 92 and 104 through 107 wherein each $R^{23a}$ and $R^{23b}$ is independently H, $C_1$-$C_6$ alkyl or $C_1$-$C_6$ haloalkyl.

Embodiment 109

A compound of Formula 1 or any one of Embodiments 1 through 92 and 104 through 108 wherein each $R^{24}$ is independently H, $C_1$-$C_6$ alkyl or $C_1$-$C_6$ haloalkyl.

Embodiment 110

A compound of Formula 1 or any one of Embodiments 1 through 109 wherein when an $R^3$ substituent attached to phenyl, pyridinyl, pyrimidinyl, pyrazinyl or pyridazinyl of $Q^1$ or $Q^2$ is other than F, Cl, Br, cyano, methyl, $C_1$-$C_2$ alkoxy and fluoromethoxy, then said $R^3$ substituent is attached at the para position (of the phenyl, pyridinyl, pyrimidinyl, pyrazinyl or pyridazinyl ring).

Embodiment 111

A compound of Formula 1 or any one of Embodiments 1 through 110 wherein $R^4$ is H, formyl, $C_3$-$C_7$ cycloalkyl or $-SR^{10}$; or $C_1$-$C_6$ alkyl or $C_1$-$C_6$ haloalkyl, each optionally substituted with up to 2 $R^{12}$.

Embodiment 112

A compound of Embodiment 111 wherein $R^4$ is H, formyl, $C_3$-$C_7$ cycloalkyl or $-SR^{10}$; or $C_1$-$C_6$ alkyl substituted with one $R^{12}$.

Embodiment 113

A compound of Embodiment 112 wherein $R^4$ is H, formyl, $-CH_2OCH_3$, cyclopropyl, $-SCH_3$, $-SCF_3$ or $-CH_2CN$.

Embodiment 114

A compound of Embodiment 113 wherein $R^4$ is H, formyl, cyclopropyl or $-CH_2CN$.

Embodiment 115

A compound of Embodiment 113 wherein $R^4$ is H, formyl, $-CH_2OCH_3$, cyclopropyl, $-SCH_3$ or $-SCF_3$.

Embodiment 116

A compound of Embodiment 115 wherein $R^4$ is H, formyl or cyclopropyl.

Embodiment 117

A compound of Embodiment 114 or 116 wherein $R^4$ is H.

Embodiment 118

A compound of Formula 1 or any one of Embodiments 1 through 117 wherein $R^{13}$ is H or $CH_3$.

Embodiment 119

A compound of Embodiment 118 wherein $R^{13}$ is $CH_3$.

Embodiment 120

A compound of Formula 1 or any one of Embodiments 1 through 119 wherein each $R^{12}$ is independently $C_3$-$C_7$ cycloalkyl, $C_1$-$C_4$ alkoxy or cyano.

Embodiment 121

A compound of Embodiment 120 wherein each $R^{12}$ is independently cyclopropyl, —$OCH_3$ or cyano.

Embodiment 122

A compound of Embodiment 120 wherein each $R^{12}$ is independently $C_3$-$C_7$ cycloalkyl or $C_1$-$C_4$ alkoxy.

Embodiment 123

A compound of Embodiment 122 wherein each $R^{12}$ is independently cyclopropyl or —$OCH_3$.

Embodiment 124

A compound of Formula 1 or any one of Embodiments 1 through 123 wherein $R^{10}$ is $CH_3$, $CH_2CH_3$, $CF_3$ or $CF_2CF_3$.

Embodiment 125

A compound of Embodiment 124 wherein $R^{10}$ is $CH_3$.

Embodiment 126

A compound of Formula 1 or any one of Embodiments 1 through 125 wherein $R^{11}$ is $C_1$-$C_6$ alkyl, $C_1$-$C_6$ alkoxy or $C_1$-$C_6$ alkylthio.

Embodiment 127

A compound of Embodiment 126 wherein $R^{11}$ is $CH_3$, $CH_2CH_3$, —$OCH_3$, —$OCH_2CH_3$, —$SCH_3$ or —$SCH_2CH_3$.

Embodiment 128

A compound of Embodiment 127 wherein $R^{11}$ is $CH_3$, —$OCH_3$ or —$SCH_3$.

Embodiment 129

A compound of Formula 1 or any one of Embodiments 1 through 128 wherein $R^{15}$ is H or $CH_3$.

Embodiment 130

A compound of Embodiment 129 wherein $R^{15}$ is H.

Embodiment 131

A compound of Formula 1 or any one of Embodiments 1 through 130 wherein $R^{16}$ is $CH_3$ or $OR^{18}$.

Embodiment 132

A compound of Embodiment 131 wherein $R^{16}$ is $OR^{18}$.

Embodiment 133

A compound of Formula 1 or any one of Embodiments 1 through 132 wherein $R^{18}$ is H.

Embodiment 134

A compound of Formula 1 or any one of Embodiments 1 through 133 wherein W is O.

Embodiment 135

A compound of Formula 1 or any one of Embodiments 1 through 134 wherein $M^+$ is a cation selected from sodium, potassium and lithium ions.

Embodiment 136

A compound of Embodiment 135 wherein $M^+$ is a cation selected from sodium and potassium ions.

Embodiment 137

A compound of Embodiment 136 wherein $M^+$ is a sodium ion.

Embodiment 138

A compound of Formula 1 or any one of Embodiments 1 through 137 wherein m is 0.

Embodiment 139

A compound of Formula 1 or any one of Embodiments 1 through 138 wherein n is 0.

Embodiments of this invention, including Embodiments 1-139 above as well as any other embodiments described herein, can be combined in any manner, and the descriptions of variables in the embodiments pertain not only to the compounds of Formula 1 but also to the starting compounds and intermediate compounds (e.g. compounds of Formula 2) useful for preparing the compounds of Formula 1. In addition, embodiments of this invention, including Embodiments 1-139 above as well as any other embodiments described herein, and any combination thereof, pertain to the compositions and methods of the present invention.

Combinations of Embodiments 1-139 are illustrated by:

Embodiment A

A compound of Formula 1 wherein
$Q^1$ is phenyl, pyridinyl, pyrimidinyl, pyrazinyl or pyridazinyl, each substituted with from 1 to 4 substituents independently selected from $R^3$; provided that when an $R^3$ substituent is located at a meta position, then said $R^3$ substituent is selected from F, Cl, Br and cyano;
$Q^2$ is phenyl, pyridinyl, pyrimidinyl, pyrazinyl or pyridazinyl, each substituted with 1, 2 or 3 substituents independently selected from $R^3$, provided that when an $R^3$ substituent is located at a meta position, then said $R^3$ substituent is selected from F, Cl, Br and cyano;
X is O, $NR^4$, C(=O) or $CR^{15}R^{16}$;
$R^1$ is H, halogen, $C_1$-$C_6$ alkyl, $C_1$-$C_6$ haloalkyl, $CO_2R^5$, $C(O)NR^6R^7$, cyano, $C_1$-$C_6$ alkoxy, $C_1$-$C_6$ haloalkoxy or $C_2$-$C_5$ alkoxyalkyl;
$R^{1a}$ is H;
$R^2$ is $CH_3$, $CH_2CH_3$, Cl or Br;
each $R^3$ is independently selected from halogen, cyano, nitro, amino, methylamino, dimethylamino, $C_1$-$C_4$ alkyl, $C_1$-$C_4$ haloalkyl, $C_1$-$C_3$ alkoxy, $C_1$-$C_3$ haloalkoxy $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_3$-$C_4$ cycloalkyl, C(=S)NH$_2$ and —U—V-T;

$R^4$ is H, formyl, $C_3$-$C_7$ cycloalkyl or —SR$^{10}$; or $C_1$-$C_6$ alkyl or $C_1$-$C_6$ haloalkyl, each optionally substituted with up to 2 $R^{12}$;

$R^5$ is $C_1$-$C_6$ alkyl;

$R^6$ is H or $C_1$-$C_6$ alkyl;

$R^7$ is H, $C_1$-$C_6$ alkyl, $C_1$-$C_6$ haloalkyl or $C_4$-$C_8$ alkylcycloalkyl; or $R^6$ and $R^7$ are taken together with the nitrogen atom to which they are connected to form a four- to seven-membered nonaromatic heterocyclic ring containing ring members, in addition to the connecting nitrogen atom, selected from carbon atoms and up to one ring member selected from O and NR$^{13}$;

each $R^{12}$ is independently $C_3$-$C_7$ cycloalkyl, $C_1$-$C_4$ alkoxy or cyano;

$R^{13}$ is H or CH$_3$;

$R^{15}$ is H or CH$_3$; and $R^{16}$ is OR$^{18}$.

Embodiment B

A compound of Embodiment A wherein $Q^1$ is phenyl or pyridinyl, each substituted with 1, 2 or 3 substituents independently selected from $R^3$;

$Q^2$ is phenyl or pyridinyl, each substituted with 1, 2 or 3 substituents independently selected from $R^3$;

$R^1$ is H, halogen or $C_1$-$C_6$ alkyl;

$R^2$ is CH$_3$, Cl or Br;

each $R^3$ is independently selected from halogen, cyano, nitro, $C_1$-$C_4$ alkyl, $C_1$-$C_4$ haloalkyl, $C_1$-$C_3$ alkoxy, $C_1$-$C_3$ haloalkoxy and —U—V-T;

$R^4$ is H, formyl, $C_3$-$C_7$ cycloalkyl or —SR$^{10}$; or $C_1$-$C_6$ alkyl substituted with one $R^{12}$;

each $R^{12}$ is independently cyclopropyl, —OCH$_3$ or cyano;

$R^{15}$ is H;

each U is independently O or NH;

each V is $C_2$-$C_4$ alkylene;

each T is independently NR$^{23a}$R$^{23b}$ or OR$^{24}$;

each $R^{23a}$ and $R^{23b}$ is independently H, $C_1$-$C_6$ alkyl or $C_1$-$C_6$ haloalkyl; and each $R^{24}$ is independently H, $C_1$-$C_6$ alkyl or $C_1$-$C_6$ haloalkyl.

Embodiment C

A compound of Embodiment B wherein at least one of $Q^1$ and $Q^2$ is phenyl substituted with 2 or 3 substituents independently selected from $R^3$;

$R^1$ is H or CH$_3$;

$R^2$ is CH$_3$;

$R^4$ is H;

each $R^3$ is independently selected from halogen, cyano, $C_1$-$C_3$ alkyl, $C_1$-$C_3$ haloalkyl, $C_1$-$C_3$ alkoxy and $C_1$-$C_3$ haloalkoxy; and $R^{18}$ is H.

Embodiment D

A compound of Embodiment C wherein $Q^1$ is phenyl substituted at the 2-, 4- and 6-positions with substituents independently selected from $R^3$; or phenyl substituted at the 2- and 4-positions with substituents independently selected from $R^3$; or phenyl substituted at the 2- and 6-positions with substituents independently selected from $R^3$;

$Q^2$ is phenyl substituted at the 2-, 4- and 6-positions with substituents independently selected from $R^3$; or phenyl substituted at the 2- and 4-positions with substituents independently selected from $R^3$; or phenyl substituted at the 2- and 6-positions with substituents independently selected from $R^3$;

X is O, NR$^4$ or CR$^{15}$R$^{16}$;

$R^1$ is H;

each $R^3$ is independently selected from F, Cl, Br, cyano, $C_1$-$C_2$ alkyl, $C_1$-$C_2$ haloalkyl, $C_1$-$C_2$ alkoxy and $C_1$-$C_2$ haloalkoxy; and $R^4$ is H.

Embodiment E

A compound of Embodiment D wherein each $R^3$ is independently selected from F, Cl, Br, cyano, methyl, $C_1$-$C_2$ alkoxy and fluoromethoxy.

Embodiment F

A compound of Embodiment E wherein

X is O or NH; and each $R^3$ is independently selected from F, Cl, Br, cyano and methoxy.

Specific embodiments include compounds of Formula 1 selected from the group consisting of:

4-(2-chloro-4-fluorophenyl)-1,3-dimethyl-N-(2,4,6-trifluorophenyl)-1H-pyrazol-5-amine (Compound 18), N-(4-chlorophenyl)-4-(2,6-difluoro-4-methoxyphenyl)-1,3-dimethyl-1H-pyrazol-5-amine (Compound 22), 4-(2,6-difluoro-4-methoxyphenyl)-N-(2,4-difluorophenyl)-1,3-dimethyl-1H-pyrazol-5-amine (Compound 23), 4-(2,6-difluoro-4-methoxyphenyl)-1,3-dimethyl-N-(2,4,6-trifluorophenyl)-1H-pyrazol-5-amine (Compound 24), N-(2,6-difluoro-4-methoxyphenyl)-4-(3,4-difluorophenyl)-1,3-dimethyl-1H-pyrazol-5-amine (Compound 36), 4-(2,4-difluorophenyl)-1,3-dimethyl-N-(2,4,6-trifluorophenyl)-1H-pyrazol-5-amine (Compound 41), 4-[[4-(2-chloro-4-fluorophenyl)-1,3-dimethyl-1H-pyrazol-5-yl]oxy]-3,5-difluorobenzonitrile (Compound 45), 4-[[4-(2,6-difluorophenyl)-1,3-dimethyl-1H-pyrazol-5-yl]oxy]-3-fluorobenzonitrile (Compound 361), 4-(2-chloro-4-fluorophenyl)-N-(2,6-difluorophenyl)-1,3-dimethyl-1H-pyrazol-5-amine (Compound 172), 4-[[4-(2-chloro-4-fluorophenyl)-1,3-dimethyl-1H-pyrazol-5-yl]oxy]-3-fluorobenzonitrile (Compound 118), 3-chloro-4-[[4-(2,6-difluorophenyl)-1,3-dimethyl-1H-pyrazol-5-yl]oxy]benzonitrile (Compound 358), 4-(2-chloro-4-fluorophenyl)-α-(2,4-difluorophenyl)-1,3-dimethyl-1H-pyrazole-5-methanol (Compound 351), N,4-bis(2-chloro-4-fluorophenyl)-1,3-dimethyl-1H-pyrazol-5-amine (Compound 175), N-(2-chloro-4-fluorophenyl)-4-(2-chloro-6-fluorophenyl)-1,3-dimethyl-1H-pyrazol-5-amine (Compound 193), N-(2-chloro-4,6-difluorophenyl)-4-(2,6-difluorophenyl)-1,3-dimethyl-1H-pyrazol-5-amine (Compound 297), N-(2-chloro-4,6-difluorophenyl)-4-(2,4-difluorophenyl)-1,3-dimethyl-1H-pyrazol-5-amine (Compound 343), N-(4-chloro-2,6-difluorophenyl)-4-(2,6-difluorophenyl)-1,3-dimethyl-1H-pyrazol-5-amine (Compound 349), N-(4-chloro-2,6-difluorophenyl)-4-(2,4-difluorophenyl)-1,3-dimethyl-1H-pyrazol-5-amine (Compound 357), 3-chloro-4-[[4-(2-chloro-4-fluorophenyl)-1,3-dimethyl-1H-pyrazol-5-yl]oxy]benzonitrile (Compound 139),
4-[[4-(2-chloro-4-fluorophenyl)-1,3-dimethyl-1H-pyrazol-5-yl]amino]-3,5-difluorobenzonitrile (Compound 91),
4-[[4-(2-chloro-4-fluorophenyl)-1,3-dimethyl-1H-pyrazol-5-yl]oxy]-2,5-difluorobenzonitrile (Compound 148),
N-(2-chloro-4-fluorophenyl)-4-(2,6-difluoro-4-methoxyphenyl)-1,3-dimethyl-1H-pyrazol-5-amine (Compound 87),
α,4-bis(2-chloro-4-fluorophenyl)-1,3-dimethyl-1H-pyrazole-5-methanol (Compound 352),
N-(4-chloro-2,6-difluorophenyl)-4-(2-chloro-4-fluorophenyl)-1,3-dimethyl-1H-pyrazole-5-amine (Compound 286),
N-(2-chloro-4,6-difluorophenyl)-4-(2-chloro-4-fluorophenyl)-1,3-dimethyl-1H-pyrazol-5-amine (Compound 287),
N-(2,6-dichloro-4-fluorophenyl)-4-(2,4-difluorophenyl)-1,3-dimethyl-1H-pyrazol-5-amine (Compound 368),
3-chloro-4-[5-[(2-chloro-4,6-difluorophenyl)amino]-1,3-dimethyl-1H-pyrazol-4-yl]-benzonitrile (Compound 332),
3-chloro-4-[5-[(4-chloro-2,6-difluorophenyl)amino]-1,3-dimethyl-1H-pyrazol-4-yl]-benzonitrile (Compound 336),
N-(2-bromo-4-fluorophenyl)-4-(2,4-difluorophenyl)-1,3-dimethyl-1H-pyrazol-5-amine (Compound 346),
4-(2-chloro-4-fluorophenyl)-N-(2,4-dichloro-6-fluorophenyl)-1,3-dimethyl-1H-pyrazol-5-amine (Compound 367),
4-(2-chloro-4-fluorophenyl)-N-(2,6-dichloro-4-fluorophenyl)-1,3-dimethyl-1H-pyrazol-5-amine (Compound 369),
4-[[4-(2-bromo-4-fluorophenyl)-1,3-dimethyl-1H-pyrazol-5-yl]oxy]-3-fluorobenzonitrile (Compound 284),
N-(2-bromo-4-fluorophenyl)-4-(2-chloro-4-fluorophenyl)-1,3-dimethyl-1H-pyrazol-5-amine (Compound 265),
4-(2-bromo-4-fluorophenyl)-1,3-dimethyl-N-(2,4,6-trifluorophenyl)-1H-pyrazol-5-amine (Compound 266),
N-(4-bromo-2,6-difluorophenyl)-4-(2,4-difluorophenyl)-1,3-dimethyl-1H-pyrazol-5-amine (Compound 364),
4-[[4-(2-bromo-4-fluorophenyl)-1,3-dimethyl-1H-pyrazol-5-yl]oxy]-3,5-difluorobenzonitrile (Compound 232),
4-(2-bromo-4-fluorophenyl)-N-(2-chloro-4,6-difluorophenyl)-1,3-dimethyl-1H-pyrazol-5-amine (Compound 292),
4-(2-bromo-4-fluorophenyl)-N-(4-chloro-2,6-difluorophenyl)-1,3-dimethyl-1H-pyrazol-5-amine (Compound 360),
N-(4-bromo-2,6-difluorophenyl)-4-(2-chloro-4-fluorophenyl)-1,3-dimethyl-1H-pyrazol-5-amine (Compound 365),
3-bromo-4-[[4-(2,4-difluorophenyl)-1,3-dimethyl-1H-pyrazol-5-yl]oxy]benzonitrile (Compound 372),
3-chloro-4-[[4-(2,4-difluorophenyl)-1,3-dimethyl-1H-pyrazol-5-yl]oxy]benzonitrile (Compound 373),
N-(2,4-dichloro-6-fluorophenyl)-4-(2,4-difluorophenyl)-1,3-dimethyl-1H-pyrazol-5-amine (Compound 374),
N-(2,6-dichloro-4-fluorophenyl)-4-(2,6-difluorophenyl)-1,3-dimethyl-1H-pyrazol-5-amine (Compound 375),
N-(2-bromo-4,6-difluorophenyl)-4-(2,4-difluorophenyl)-1,3-dimethyl-1H-pyrazol-5-amine (Compound 376),
N-(2-bromo-4,6-difluorophenyl)-4-(2-chloro-4-fluorophenyl)-1,3-dimethyl-1H-pyrazol-5-amine (Compound 377),
N-(4-bromo-2,6-difluorophenyl)-4-(2,6-difluorophenyl)-1,3-dimethyl-1H-pyrazol-5-amine (Compound 378),
N-(2-bromo-4,6-difluorophenyl)-4-(2,6-difluorophenyl)-1,3-dimethyl-1H-pyrazol-5-amine (Compound 379),
N-(2-bromo-4,6-difluorophenyl)-4-(2-chloro-6-fluorophenyl)-1,3-dimethyl-1H-pyrazol-5-amine (Compound 380),
α-(4-chloro-2,6-difluorophenyl)-4-(2-chloro-4-fluorophenyl)-1,3-dimethyl-1H-pyrazole-5-methanol (Compound 381),
4-[5-[(2-chloro-4,6-difluorophenyl)amino]-1,3-dimethyl-1H-pyrazol-4-yl]-3-fluorobenzonitrile (Compound 382),
4-[5-[(4-chloro-2,6-difluorophenyl)amino]-1,3-dimethyl-1H-pyrazol-4-yl]-3-fluorobenzonitrile (Compound 383),
α-(2-chloro-4,6-difluorophenyl)-4-(2-chloro-4-fluorophenyl)-1,3-dimethyl-1H-pyrazole-5-methanol (Compound 384),
α-(2-bromo-4-fluorophenyl)-4-(2,4-difluorophenyl)-1,3-dimethyl-1H-pyrazole-5-methanol (Compound 385), and
α-(2-bromo-4-fluorophenyl)-4-(2-chloro-4-fluorophenyl)-1,3-dimethyl-1H-pyrazole-5-methanol (Compound 386).

This invention provides a fungicidal composition comprising a compound of Formula 1 (including all geometric and stereoisomers, N-oxides, and salts thereof), and at least one other fungicide. Of note as embodiments of such compositions are compositions comprising a compound corresponding to any of the compound embodiments described above.

This invention provides a fungicidal composition comprising a fungicidally effective amount of a compound of Formula 1 (including all geometric and stereoisomers, N-oxides, and salts thereof), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 (including all geometric and stereoisomers, N-oxides, and salts thereof). Of note as embodiment of such methods are methods comprising applying a fungicidally effective amount of a compound corresponding to any of the compound embodiments describe above. Of particular note are embodiments where the compounds are applied as compositions of this invention.

Of note are compounds of Formula 1 that are compounds of Formula 1P (including all geometric and stereoisomers), N-oxides, and salts thereof, and also agricultural compositions containing them and their use as fungicides:

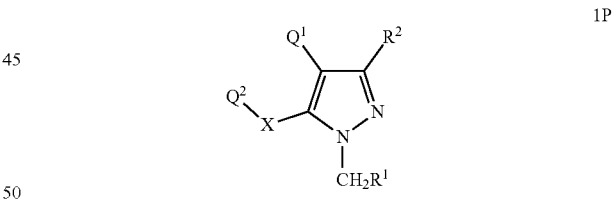

1P wherein
Q$^1$ and Q$^2$ are independently phenyl, thienyl, pyridinyl, pyridazinyl, pyrazinyl or pyrimidinyl, each optionally substituted with up to 5 substituents independently selected from R$^3$;
X is O, S(O)$_m$ or NR$^4$;
R$^1$ is H, halogen, C$_1$-C$_6$ alkyl, C$_1$-C$_6$ haloalkyl, C$_2$-C$_4$ alkenyl, C$_2$-C$_4$ alkynyl, C$_3$-C$_7$ cycloalkyl, CO$_2$R$^5$, C(O)NR$^6$R$^7$, cyano, C$_1$-C$_6$ alkoxy, C$_1$-C$_6$ haloalkoxy or C$_2$-C$_5$ alkoxyalkyl; or
R$^1$ is phenyl optionally substituted with up to 3 R$^8$; or a five- or six-membered nitrogen-containing aromatic heterocycle optionally substituted with up to 3 substituents independently selected from R$^{9a}$ on carbon atom ring members and R$^{9b}$ on nitrogen atom ring members;
R$^2$ is CH$_3$, CH$_2$CH$_3$, cyclopropyl or halogen;

each $R^3$ is independently selected from halogen, cyano, nitro, amino, methylamino, dimethylamino, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_3$-$C_4$ cycloalkyl, $C_3$-$C_7$ cycloalkoxy, $C_4$-$C_6$ alkylcycloalkyl, $C_4$-$C_6$ cycloalkylalkyl, $C_3$-$C_7$ halocycloalkyl, $C_2$-$C_4$ alkenyl and $C_2$-$C_4$ alkynyl;

$R^4$ is H, formyl, $C_3$-$C_7$ cycloalkyl, —$SO_3$-$M^+$, —$SR^{10}$ or —(C=W)$R^{11}$; or $C_1$-$C_6$ alkyl or $C_1$-$C_6$ haloalkyl, each optionally substituted with up to 2 $R^{12}$;

$R^5$ is H, $C_1$-$C_6$ alkyl or $C_1$-$C_6$ haloalkyl;

$R^6$ and $R^7$ are independently selected from H, $C_1$-$C_6$ alkyl, $C_1$-$C_6$ haloalkyl, $C_3$-$C_7$ cycloalkyl, $C_4$-$C_8$ cycloalkylalkyl and $C_4$-$C_8$ alkylcycloalkyl; or $R^6$ and $R^7$ are taken together with the nitrogen atom to which they are connected to form a four- to seven-membered nonaromatic heterocyclic ring containing ring members, in addition to the connecting ring nitrogen atom, selected from carbon atoms and optionally up to one ring member selected from O, S(O)$_n$ and $NR^{13}$;

each $R^8$, $R^{9a}$ and $R^{9b}$ is independently selected from halogen, $C_1$-$C_2$ alkyl, $C_1$-$C_2$ haloalkyl, $C_1$-$C_2$ alkoxy, $C_1$-$C_2$ haloalkoxy, cyano, nitro, $SCH_3$, $S(O)CH_3$ and $S(O)_2CH_3$;

$R^{10}$ is $C_1$-$C_6$ alkyl or $C_1$-$C_6$ haloalkyl;

$R^{11}$ is $C_1$-$C_6$ alkyl, $C_1$-$C_6$ alkoxy, $C_2$-$C_7$ alkoxyalkyl, $C_2$-$C_7$ alkylaminoalkyl, $C_2$-$C_8$ dialkylaminoalkyl, $C_1$-$C_6$ alkylthio or $C_2$-$C_7$ alkylthioalkyl;

each $R^{12}$ is independently $C_3$-$C_7$ cycloalkyl, $C_1$-$C_4$ alkoxy, $C_1$-$C_4$ haloalkoxy, $C_1$-$C_4$ alkylthio, $C_1$-$C_4$ alkylsulfinyl or $C_1$-$C_4$ alkylsulfonyl;

$R^{13}$ is H, $C_1$-$C_3$ alkyl or $C_2$-$C_3$ haloalkyl;

W is O or S;

$M^+$ is a cation;

m is 0, 1 or 2; and n is 0, 1 or 2.

Accordingly of note is a compound selected from Formula 1P (including all geometric and stereoisomers), N-oxides, and salts thereof, as defined above. Also of note are counterpart embodiments that are embodiment counterparts to Embodiments 1 through 139 and Embodiments A through F wherein in said counterpart embodiments "Formula 1" is replaced by "Formula 1P" and the scope of said counterpart embodiments does not exceed the scope defined above for Formula 1P. Examples of combinations of Embodiments 1 through 139 as applied to Formula 1P are Embodiments AP, BP, CP, DP and EP:

Embodiment AP

A compound of Formula 1P wherein $Q^1$ is phenyl, pyridinyl, pyrimidinyl, pyrazinyl or pyridazinyl, each substituted with from 1 to 4 substituents independently selected from $R^3$;

$Q^2$ is phenyl, pyridinyl, pyrimidinyl, pyrazinyl or pyridazinyl, each substituted with 1, 2 or 3 substituents independently selected from $R^3$;

X is O or $NR^4$;

$R^1$ is H, halogen, $C_1$-$C_6$ alkyl, $C_1$-$C_6$ haloalkyl, $CO_2R^5$, $C(O)NR^6R^7$, cyano, $C_1$-$C_6$ alkoxy, $C_1$-$C_6$ haloalkoxy or $C_2$-$C_5$ alkoxyalkyl; or $R^1$ is a five- or six-membered nitrogen-containing aromatic heterocycle optionally substituted with up to 3 substituents independently selected from $R^{9a}$ on carbon atom ring members and $R^{9b}$ on nitrogen atom ring members;

$R^2$ is $CH_3$, $CH_2CH_3$, Cl or Br;

each $R^3$ is independently selected from halogen, cyano, nitro, amino, methylamino, dimethylamino, $C_1$-$C_4$ alkyl, $C_1$-$C_4$ haloalkyl, $C_1$-$C_3$ alkoxy, $C_1$-$C_3$ haloalkoxy $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl and $C_3$-$C_4$ cycloalkyl;

$R^4$ is H, formyl, $C_3$-$C_7$ cycloalkyl or —$SR^{10}$; or $C_1$-$C_6$ alkyl or $C_1$-$C_6$ haloalkyl, each optionally substituted with up to 2 $R^{12}$;

$R^5$ is H or $C_1$-$C_6$ alkyl;

$R^6$ is H or $C_1$-$C_6$ alkyl;

$R^7$ is H, $C_1$-$C_6$ alkyl, $C_1$-$C_6$ haloalkyl or $C_4$-$C_8$ alkylcycloalkyl; or $R^6$ and $R^7$ are taken together with the nitrogen atom to which they are connected to form a four- to seven-membered nonaromatic heterocyclic ring containing ring members, in addition to the connecting nitrogen atom, selected from carbon atoms and up to one ring member selected from O and $NR^{13}$;

each $R^8$ is independently selected from halogen, $C_1$-$C_2$ alkyl, $C_1$-$C_2$ haloalkyl, $C_1$-$C_2$ alkoxy, $C_1$-$C_2$ haloalkoxy, cyano and nitro;

each $R^{9a}$ is independently selected from halogen, $C_1$-$C_2$ alkyl, $C_1$-$C_2$ haloalkyl, $C_1$-$C_2$ alkoxy, $C_1$-$C_2$ haloalkoxy, cyano and nitro;

each $R^{9b}$ is $C_1$-$C_2$ alkyl;

$R^{10}$ is $CH_3$, $CH_2CH_3$, $CF_3$ or $CF_2CF_3$;

each $R^{12}$ is independently $C_3$-$C_7$ cycloalkyl or $C_1$-$C_4$ alkoxy; and $R^{13}$ is H or $CH_3$.

Embodiment BP

A compound of Embodiment AP wherein $Q^1$ is phenyl or pyridinyl, each substituted with 1, 2 or 3 substituents independently selected from $R^3$;

$Q^2$ is phenyl or pyridinyl, each substituted with 1, 2 or 3 substituents independently selected from $R^3$;

X is $NR^4$;

$R^1$ is H, halogen, $C_1$-$C_6$ alkyl, $C_1$-$C_6$ haloalkyl, cyano, $C_1$-$C_6$ alkoxy or $C_1$-$C_6$ haloalkoxy;

$R^2$ is $CH_3$;

each $R^3$ is independently selected from halogen, cyano, nitro, $C_1$-$C_4$ alkyl, $C_1$-$C_4$ haloalkyl, $C_1$-$C_3$ alkoxy and $C_1$-$C_3$ haloalkoxy;

$R^4$ is H, formyl, $C_3$-$C_7$ cycloalkyl or —$SR^{10}$; or $C_1$-$C_6$ alkyl substituted with one $R^{12}$;

$R^{10}$ is $CH_3$; and each $R^{12}$ is independently cyclopropyl or —$OCH_3$.

Embodiment CP

A compound of Embodiment AP wherein $Q^1$ is phenyl substituted at the 2-, 4- and 6-positions with substituents independently selected from $R^3$; or $Q^1$ is phenyl substituted at the 2- and 4-positions with substituents independently selected from $R^3$;

$Q^2$ is phenyl substituted at the 2-, 4- and 6-positions with substituents independently selected from $R^3$;

X is O;

$R^2$ is $CH_3$;

each $R^3$ is independently selected from F, Cl, Br, cyano, nitro, $CH_3$, $CF_3$, —$OCH_3$, and —$OCHF_2$; and $R^4$ is H, formyl or cyclopropyl.

Embodiment DP

A compound of Embodiment CP wherein
$Q^1$ is phenyl substituted at the 2- and 4-positions with substituents independently selected from $R^3$;
$Q^2$ is phenyl substituted at the 2-, 4- and 6-positions with substituents independently selected from $R^3$;
each $R^3$ is independently selected from F, Cl, cyano and —OCH$_3$; and
$R^4$ is H.

Embodiment EP

A compound of Embodiment BP wherein
$Q^1$ is phenyl substituted at the 2- and 4-positions with substituents independently selected from $R^3$;
$Q^2$ is phenyl substituted at the 2-, 4- and 6-positions with substituents independently selected from $R^3$;
each $R^3$ is independently selected from F, Cl, CN and —OCH$_3$; and
$R^4$ is H.

Also of note is a fungicidal composition comprising a fungicidally effective amount of a compound of Formula 1P (including all geometric and stereoisomers, N-oxides, and salts thereof) or any one of counterpart embodiments that are embodiment counterparts to Embodiments 1 through 139 and Embodiments A through F (e.g., Embodiment AP, BP, CP, DP or EP), and at least one additional component selected from the group consisting of surfactants, solid diluents and liquid diluents. Also of note is a method for controlling plant diseases caused by fungal plant pathogens comprising applying to the plant or portion thereof, or to the plant seed, a fungicidally effective amount of a compound of Formula 1P (including all geometric and stereoisomers, N-oxides, and salts thereof) or any one of said counterpart embodiments. Of particular note are embodiments where the compounds of Formula 1P are applied as compositions of this invention.

One or more of the following methods and variations as described in Schemes 1-24 can be used to prepare the compounds of Formula 1 (including Formula 1P). The definitions of $Q^1$, $Q^2$, $R^1$, $R^2$ and m in the compounds of Formulae 1-33 below are as defined above in the Summary of the Invention unless otherwise noted. Formulae 1a, 1b, 1c, 1d, 1e, 1f, 1g and 1h are various subsets of Formula 1; Formulae 4a, 4b and 4c are various subsets of Formula 4; Formulae 6a and 6b are various subsets of Formula 6; Formula 11a is a subset of Formula 11; Formula 13a is a subset or analog of Formula 13; and Formula 17a is a subset of Formula 17. Substituents for each subset formula are as defined for its parent formula unless otherwise noted.

As illustrated in Scheme 1, sulfoxides and sulfones of Formula 1b (i.e. Formula 1 wherein X is S(O)$_m$ and m is 1 or 2) can be made via oxidation of the linking sulfur atom on sulfides of Formula 1a (i.e. Formula 1 wherein X is S(O)$_m$ and m is 0). In this method a compound of Formula 1b wherein m is 1 (i.e. sulfoxides) or m is 2 (i.e. sulfones) is prepared by oxidizing a corresponding sulfide of Formula 1a with a suitable oxidizing agent. In a typical procedure, an oxidizing agent in an amount from 1 to 4 equivalents depending on the oxidation state of the product desired is added to a solution of the compound of Formula 1a in a solvent. Useful oxidizing agents include Oxone® (potassium peroxymonosulfate), hydrogen peroxide, sodium periodate, peracetic acid and 3-chloroperbenzoic acid. The solvent is selected with regard to the oxidizing agent employed. Aqueous ethanol or aqueous acetone is preferably used with potassium peroxymonosulfate, and dichloromethane is generally preferable with 3-chloroperbenzoic acid. Useful reaction temperatures typically range from −78 to 90° C. Particular procedures useful for oxidizing sulfides to sulfoxides and sulfones are described by Brand et al., *J. Agric. Food Chem.* 1984, 32, 221-226 and references cited therein.

Scheme 1

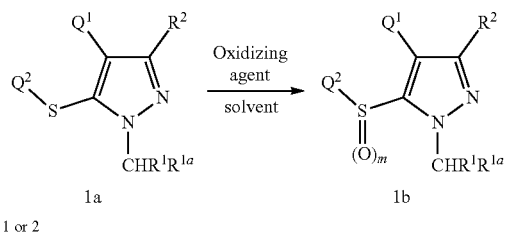

m is 1 or 2

As shown in Scheme 2, compounds of Formula 1 in which X is NH and $R^{1a}$ is H can be prepared by the reaction of 1H-pyrazole compounds of Formula 2 with various alkylating agents (e.g., Formula 3), such as iodoalkanes, alkylsulfonates (e.g., mesylate (OMs) or tosylate (OTs)) or trialkyl phosphates, preferably in the presence of an organic or inorganic base such as 1,8-diazabicyclo[5.4.0]undec-7-ene, potassium carbonate or potassium hydroxide, and in a solvent such as N,N-dimethylformamide, tetrahydrofuran, toluene or water.

Scheme 2

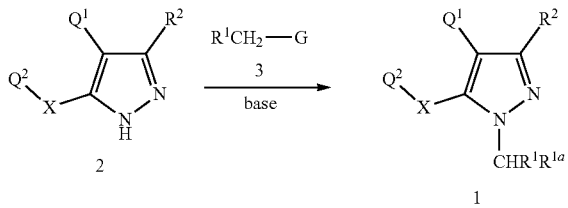

$R^{1a}$ is H
X is NH
G is, e.g., Cl, Br, I, OMs, OTs or phosphate

Compounds of Formula 1 wherein CHR$^1$R$^{1a}$ forms an optionally substituted cyclopropyl ring can likewise be prepared by reaction of a pyrazole of Formula 2 with an organometallic reagent, such as tricyclopropylbismuth, in the presence of a catalyst, such as copper acetate, under conditions known in the art. See, for example, *J. Am. Chem. Soc.* 2007, 129(1), 44-45. Of note as starting materials in the method of Scheme 2 are compounds of Formula 2 specifically disclosed in Tables 588 through 671 below.

As is shown in Scheme 3, compounds of Formula 1 can be prepared by the reaction of compounds of Formula 4 (i.e. 5-aminopyrazoles for X being NR$^4$, 5-hydroxypyrazoles (5-pyrazolones) for X being O, or 5-mercaptopyrazoles for X being S) with aromatic compounds of Formula 5 containing a leaving group G (i.e. halogen or (halo)alkylsulfonate), optionally in the presence of a metal catalyst, and generally in the presence of a base and a polar aprotic solvent such as N,N-dimethylformamide or dimethyl sulfoxide. For example, compounds of Formula 5 in which $Q^2$ is an electron-deficient heteroaromatic ring, or a benzene ring with electron-withdrawing substituents, react by direct displacement of the leaving group G from the ring to provide compounds of Formula 1. For compounds of Formula 5 wherein $Q^2$ is attached through a $sp^3$-hybridized carbon atom, G is typically Cl, Br, I or a sulfonate (e.g., $OS(O)_2CH_3$). Compounds of Formula 5 are commercially available or their preparation is known in the art. Of note are embodiments of the method of Scheme 3 wherein a compound of Formula 4 is used to prepare a corresponding compound of Formula 1 specifically disclosed in Tables 85 through 252 below.

Scheme 3

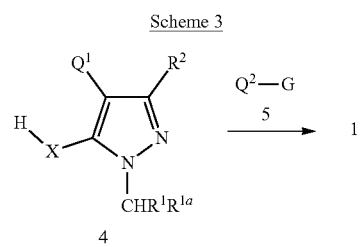

G is F, Cl, Br, I, $NO_2$, $OSO_2CF_3$, etc.

For reactions according to the method of Scheme 3 of a compound of Formula 4 wherein X is O or $NR^4$ with a compound of Formula 5 ($Q^2$-G) wherein Q is an aromatic or heteroaromatic ring Q lacking sufficiently electron-withdrawing substituents, or to improve reaction rate, yield or product purity, the use of a metal catalyst (e.g., metal or metal salt) in amounts ranging from catalytic up to superstoichiometric can facilitate the desired reaction. Typically for these conditions, G is Br or I or a sulfonate such as $OS(O)_2CF_3$ or $OS(O)_2(CF_2)_3CF_3$. For example, copper salt complexes (e.g., CuI with N,N'-dimethyl-ethylenediamine, proline or bipyridyl), palladium complexes (e.g., tris(dibenzylidene-acetone)dipalladium(0)) or palladium salts (e.g., palladium acetate) with ligands such as 4,5-bis(diphenylphosphino)-9,9-dimethylxanthene (i.e. "Xantphos"), 2-dicyclohexyl-phosphino-2',4',6'-triisopropylbiphenyl (i.e. "Xphos") or 2,2'-bis(diphenylphosphino)-1,1'-binaphthalene (i.e. "BINAP"), in the presence of a base such as potassium carbonate, cesium carbonate, sodium phenoxide or sodium tert-butoxide, in a solvent such as N,N-dimethylformamide, 1,2-dimethoxyethane, dimethyl sulfoxide, 1,4-dioxane or toluene, optionally mixed with alcohols such as ethanol, can be used. Alternatively as illustrated in Scheme 4, compounds of Formula 1c (i.e. Formula 1 in which X is $NR^4$ and $R^4$ is H) can be prepared by reaction of compounds of Formula 6 (i.e. 5-bromopyrazoles or other pyrazoles substituted at the 5-position with a leaving group) with compounds of Formula 7 under metal-catalyzed conditions similar to those described above for Scheme 3. Compounds of Formula 7 are commercially available or their preparation is known in the art.

Scheme 4

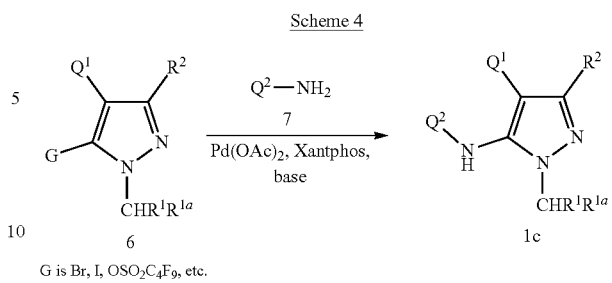

G is Br, I, $OSO_2C_4F_9$, etc.

As shown in Scheme 5, compounds of Formula 6 wherein G is Br or I can be prepared by reaction of 5-aminopyrazoles of Formula 4a (i.e. Formula 4 wherein X is NH) under diazotization conditions either in the presence of, or followed by combination with, copper salts containing bromide or iodide. For example, addition of tert-butyl nitrite to a solution of a 5-aminopyrazole of Formula 4a in the presence of $CuBr_2$ in a solvent such as acetonitrile provides the corresponding 5-bromopyrazole of Formula 6. Likewise, a 5-aminopyrazole of Formula 4a can be converted to a diazonium salt and then to a corresponding 5-halopyrazole of Formula 6 by treatment with sodium nitrite in solvents such as water, acetic acid or trifluoroacetic acid, in the presence of a mineral acid typically containing the same halide atom (such as aqueous HI solution for G being I), followed by treatment with the corresponding copper(I) or copper(II) salt according to general procedures well known to those skilled in the art.

Scheme 5

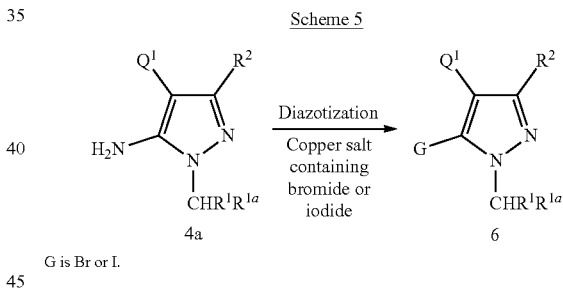

G is Br or I.

As shown in Scheme 6, 5-bromopyrazoles of Formula 6a (i.e. Formula 6 wherein G is Br) can be prepared by reacting 5-hydroxypyrazoles of Formula 4b (i.e. Formula 4 wherein X is O) with phosphorus tribromide as described in *Tetrahedron Lett.* 2000, 41(24), 4713.

Scheme 6

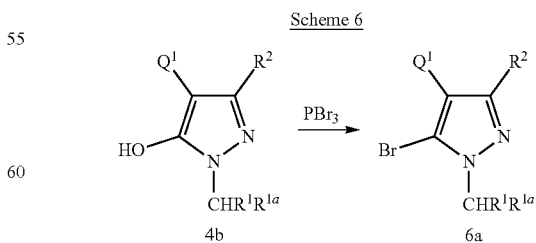

As shown in Scheme 7, 5-hydroxypyrazoles of Formula 4b can also be used to prepare 5-fluoroalkylsulfonyl (e.g, 5-trifluoromethanesulfonyl, 5-nonafluorobutylsulfonyl)

pyrazoles of Formula 6b (i.e. Formula 6 wherein G is fluoroalkylsulfonyl) as described in *Synlett* 2004, 5, 795.

Scheme 7

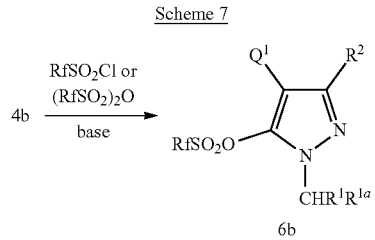

wherein Rf is fluoroalkyl such as $CF_3$ or $(CF_2)_2CF_3$

As shown in Scheme 8, compounds of Formula 1 can be prepared by reaction of 4-bromo or iodo pyrazoles of Formula 10 wherein X is O, $NR^4$, C(=O) or $S(O)_m$ in which m is 2 with organometallic compounds of formula $Q^1$-M (Formula 11) under transition-metal-catalyzed cross-coupling reaction conditions. Reaction of a 4-bromo or iodo pyrazole of Formula 10 with a boronic acid, trialkyltin, zinc or organomagnesium reagent of Formula 11 in the presence of a palladium or nickel catalyst having appropriate ligands (e.g., triphenylphosphine ($PPh_3$), dibenzylideneacetone (dba), dicyclohexyl(2',6'-dimethoxy-[1,1'-biphenyl]-2-yl) phosphine (SPhos)) and a base, if needed, affords the corresponding compound of Formula 1. For example, a substituted aryl boronic acid or derivative (e.g., Formula 11 wherein $Q^1$ is optionally substituted phenyl or heterocyclyl and M is $B(OH)_2$, $B(OC(CH_3)_2C(CH_3)_2O)$ or $B(O-i-Pr)_3$/Li— reacts with a 4-bromo- or 4-iodopyrazole of Formula 10 in the presence of dichlorobis(triphenylphosphine) palladium(II) and aqueous base such as sodium carbonate or potassium hydroxide, in solvents such as 1,4-dioxane, 1,2-dimethoxyethane, toluene or ethyl alcohol, or under anhydrous conditions with a ligand such as phosphine oxide or phosphite ligand (e.g., diphenylphosphine oxide) and potassium fluoride in a solvent such as 1,4-dioxane (see *Angewandte Chemie, International Edition* 2008, 47(25), 4695-4698) to provide the corresponding compound of Formula 1.

Scheme 8

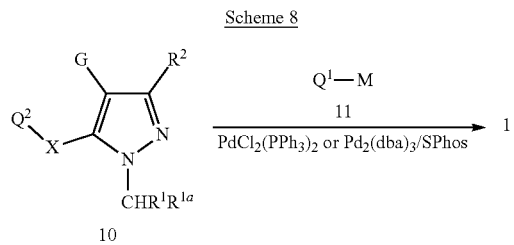

G is Br, I
M is, e.g., B(OH)₂, B(OC(CH₃)₂C(CH₃)₂O), Sn(Me)₃, Sn(Bu)₃, ZNCl, MgBr, MgCl or

As illustrated in Scheme 9, compounds of Formula 4a (i.e. Formula 4 wherein X is NH) can be prepared by reacting compounds of Formula 12 with compounds of Formula 11 (such as $Q^1$-$B(OH)_2$ (Formula 11a)) using transition-metal-catalyzed cross-coupling reaction conditions as described for the method of Scheme 8.

Scheme 9

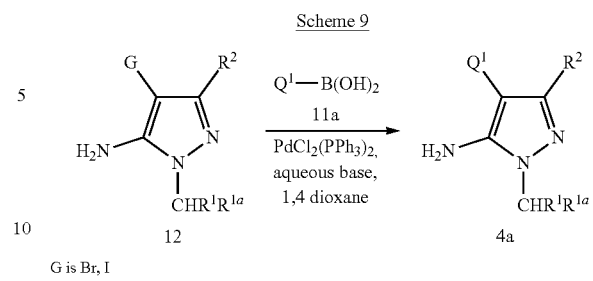

G is Br, I

As illustrated in Scheme 10, pyrazoles of Formula 10 wherein X is O, $S(O)_2$, $NR^4$ or C(=O) and G is Br or I are readily prepared by the reaction of pyrazoles unsubstituted at the 4-position (Formula 13) with halogenating reagents such as bromine, sodium bromite, N-bromosuccinimide (NBS) or N-iodosuccinimide (NIS), in solvents such as acetic acid, acetonitrile, N,N-dimethylformamide, N,N-dimethylacetamide or 1,4-dioxane, or a mixture of water with the aforementioned solvents, at temperatures ranging from ambient to the boiling point of the solvent.

Scheme 10

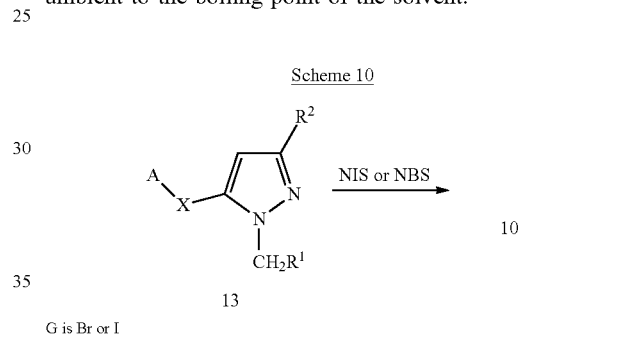

G is Br or I
X is O, $S(O)_2$, $NR^4$ or C(=O)
A is $Q^2$

Furthermore, using reaction conditions similar to those for the method of Scheme 10, compounds of Formula 13 wherein A is H or a protecting group can be converted into intermediates corresponding to Formula 10 wherein $Q^2$ is replaced by A or a protecting group, respectively, which are useful for preparing compounds of Formula 1. Compounds of Formula 13 wherein A is H can be prepared by methods known in the art; see, for example, *Synlett* 2004, 5, 795-798, U.S. Pat. No. 4,256,902 and references cited therein. Furthermore, some compounds of Formula 13 wherein A is H, particularly those in which $R^2$ is methyl, ethyl or halogen, are commercially available.

As shown in Scheme 11, compounds of Formula 13 wherein X is O, $S(O)_m$ or $NR^4$, m is 0, and A is $Q^2$ can be prepared from corresponding compounds of Formula 13a (i.e. Formula 13 wherein A is H) by procedures analogous those used for the method of Scheme 3. Compounds of Formula 13 wherein X is S (i.e. $S(O)_m$ wherein m is 0) can then be oxidized using procedures such as those used for the method of Scheme 1 to provide corresponding compounds of Formula 13 wherein X is $S(O)_2$ for use in the method of Scheme 10. Compounds of Formula 13a are commercially available or can be prepared by methods known in the art.

Scheme 11

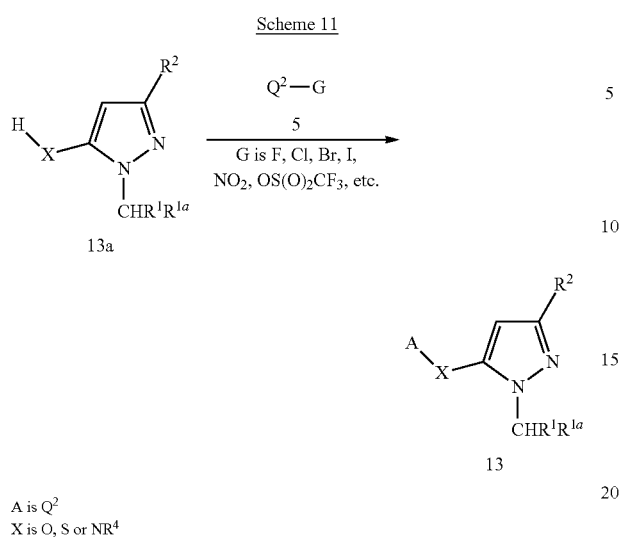

A is $Q^2$
X is O, S or $NR^4$

As shown in Scheme 12, compounds of Formula 1a (i.e. Formula 1 wherein X is $S(O)_m$ and m is 0), Formula 1d (i.e. Formula 1 wherein X is $CR^{15}R^{16}$, $R^{15}$ is H, $R^{16}$ is $OR^{18}$ and $R^{18}$ is H) and Formula 1e (i.e. Formula 1 wherein X is C(=O)) can be prepared by treatment of compounds of Formula 6 with an organometallic reagent (i.e. Formula 26) such as an alkyllithium, preferably n-butyllithium, or an alkylmagnesium reagent, preferably isopropylmagnesium chloride (optionally complexed with lithium chloride), followed by the addition of a sulfur electrophile (i.e. Formula 27) or carbonyl electrophile (i.e. Formula 28, 29 or 30). Reaction temperatures can range from −90° C. to the boiling point of the reaction solvent; temperatures of −78° C. to ambient temperature are generally preferred, with temperatures of −78 to −10° C. preferred when an alkyllithium reagent is used, and −20° C. to ambient temperature preferred with use of alkylmagnesium reagents. A variety of solvents are useful, such as toluene, ethyl ether, tetrahydrofuran or dimethoxymethane; anhydrous tetrahydrofuran is preferred. A second metallic component, such as zinc chloride, zinc bromide or a monovalent copper salt, such as copper(I) iodide or copper(I) cyanide, can advantageously be added before the electrophile in cases in which the electrophile is $Q^2C(O)Cl$ (i.e. Formula 30). The $Q^2$-containing sulfur and carbonyl intermediates of Formulae 27, 28, 29 and 30 are commercially available or can be prepared by methods known in the art.

Scheme 12

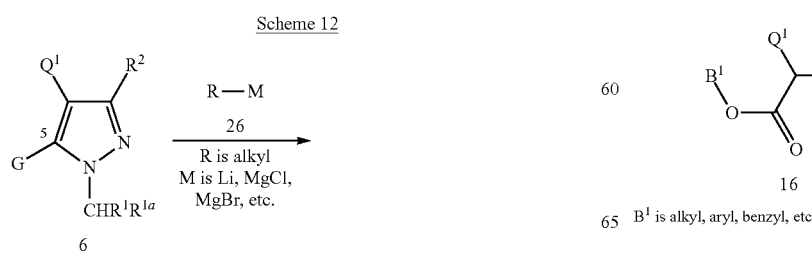

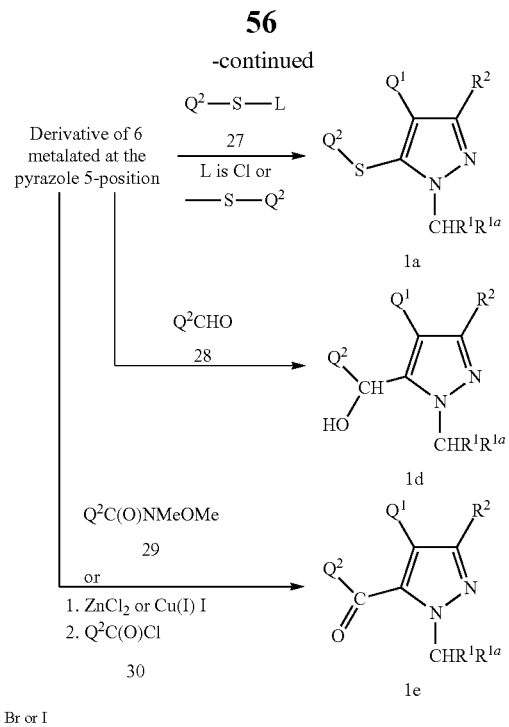

G is Br or I

It will be recognized by one skilled in the art that reactions analogous to those shown in Scheme 12 can also be utilized with pyrazoles lacking a $Q^1$ substituent, thus affording certain compounds of Formula 13 that are useful in the method outlined in Scheme 10.

General methods useful for preparing 5-aminopyrazoles of Formula 4a are well known in the art; see, for example, *Journal für Praktische Chemie* (Leipzig) 1911, 83, 171 and *J. Am. Chem. Soc.* 1954, 76, 501. Such a method is illustrated in Scheme 13 in which $R^2$ is alkyl or cycloalkyl.

Scheme 13

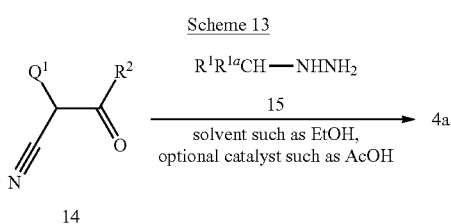

Similarly, general methods useful for preparing 5-hydroxypyrazoles of Formula 4b are well known in the art; see, for example, *Annalen der Chemie* 1924, 436, 88. Such a method is illustrated in Scheme 14 in which $R^2$ is alkyl or cycloalkyl.

Scheme 14

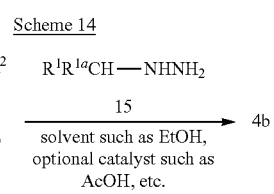

$B^1$ is alkyl, aryl, benzyl, etc

As shown in Scheme 15, 5-thiopyrazole compounds of Formula 4c (i.e. Formula 4 wherein X is S) can be prepared by reaction of corresponding 5-hydroxypyrazole compounds of Formula 4b with $P_2S_5$ (see, for example, *Justus Liebigs Annalen der Chemie* 1908, 361, 251) or with Lawesson's Reagent (2,4-bis-(4-methoxyphenyl)-1,3-dithia-2,4-diphosphetane 2,4-disulfide; see, for example, International Patent Publication WO 2005/118575) in solvents such as toluene, xylene or tetrahydrofuran.

Scheme 15

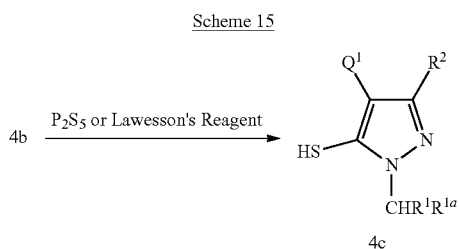

As shown in Scheme 16, compounds of Formula 1c (i.e. Formula 1 wherein X is $NR^4$ and $R^4$ is H) can be prepared by condensing compounds of Formula 17 with alkylhydrazines of Formula 15 in a solvent such as ethanol or methanol and optionally in the presence of an acid or base catalyst such as acetic acid, piperidine or sodium methoxide, according to general procedures known in the art.

Scheme 16

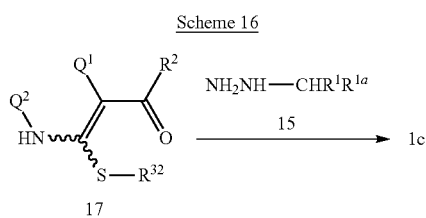

wherein $R^{32}$ is H or lower alkyl (e.g., $CH_3$, $CH_2CH_3$ or $(CH_2)_2CH_3$)

In a manner analogous to the method of Scheme 16, compounds of Formula 2 wherein X is NH can be similarly prepared by condensing compounds of Formula 17 with hydrazine. This method is described in *Chemistry of Heterocyclic Compounds* 2005, 41(1), 105-110.

As shown in Scheme 17, compounds of Formula 17 (wherein, e.g., $R^2$ is methyl, ethyl or optionally substituted cyclopropyl and $R^{33}$ is H or lower alkyl such as $CH_3$, $CH_2CH_3$ or $(CH_2)_2CH_3$) can be prepared by reaction of corresponding ketene dithioacetal compounds of Formula 18 with compounds of formula $Q^2-NH_2$ (i.e. Formula 7) optionally in the presence of a base, such as sodium hydride or ethylmagnesium chloride, in solvents such as toluene, tetrahydrofuran or dimethoxymethane, at temperatures ranging from −10° C. to the boiling point of the solvent. See, for example, *J. Heterocycl. Chem.* 1975, 12(1), 139. Methods useful for preparing compounds of Formula 18 are known in the art.

Scheme 17

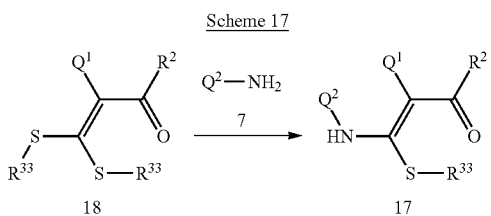

wherein $R^{33}$ is H or lower alkyl (e.g., $CH_3$, $CH_2CH_3$ or $(CH_2)_2CH_3$)

It is also known in the art (see, for example, Synthesis 1989, 398) that compounds of Formula 18 in which the two $R^{33}$ groups are taken together as a single $CH_2$ group (thus forming a dithietane ring) react with an stoichiometric excess amount of hydrazines of Formula 15 to afford compounds of Formula 4c, which are useful for preparation of compounds of Formula 1 in which X is S according to the method of Scheme 3.

As shown in Scheme 18, compounds of Formula 17a (i.e. tautomer of Formula 17 wherein $R^{33}$ is H) can be prepared by reaction of corresponding isothiocyanate compounds of Formula 19 with arylacetone compounds of Formula 20 wherein $R^2$ is methyl, ethyl or optionally substituted cyclopropyl; see, for example, *Zhurnal Organicheskoi Khimii* 1982, 18(12), 2501. Bases useful for this reaction include sodium hydride, alkoxide bases (e.g., potassium tert-butoxide or sodium ethoxide), potassium hydroxide, sodium hydroxide, potassium carbonate, or amine bases (e.g., triethylamine or N,N-diisopropylethylamine). A variety of solvents are useful, such as tetrahydrofuran, ether, toluene, N,N-dimethylformamide, alcohols (e.g., ethanol), esters (e.g., ethyl acetate or isopropyl acetate), or mixtures thereof. Solvents are chosen for compatibility with the base selected, as is well-known in the art. Reaction temperatures can range from −78° C. to the boiling point of the solvent. One useful mixture of base and solvent is potassium tert-butoxide in tetrahydrofuran, to which at −70 to 0° C. is added a combined solution of an isothiocyanate of Formula 19 and a carbonyl compound of Formula 20.

Scheme 18

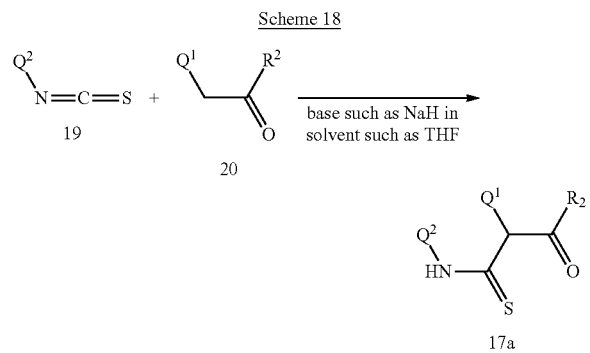

Ketothioamides of Formula 17 can be also be prepared by allowing the corresponding ketoamides to react with sulfurizing agents such as Lawesson's reagent or $P_2S_5$; see, for example, *Helv. Chim. Act.* 1998, 81(7), 1207.

Compounds of Formula 2 wherein X is NH and $R^2$ is Cl or Br, which are useful for preparing compounds of Formula 1 according to the method of Scheme 2, can be prepared by reaction of corresponding compounds of Formula 31 with POCl$_3$ or POBr$_3$ using general procedures known in the art, as shown in Scheme 19.

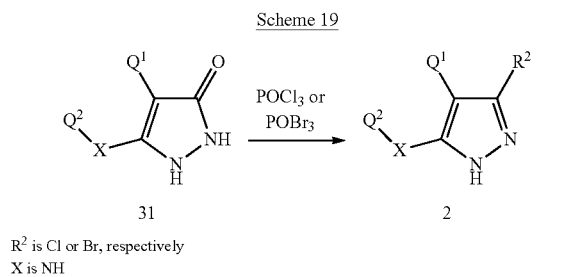

Scheme 19

R$^2$ is Cl or Br, respectively
X is NH

As shown in Scheme 20, compounds of Formula 1f (i.e. Formula 1 wherein R$^1$ and R$^{1a}$ are H and R$^2$ is OCH$_3$) can be prepared by reacting corresponding compounds of Formula 31 with diazomethane or iodomethane in the presence of base using general procedures known in the art, such as those described in *J. Heterocyclic Chem.* 1988, 1307-1310.

Scheme 20

Compounds of Formula 1g (i.e. Formula 1 wherein R$^1$ and R$^{1a}$ are H and R$^2$ is SCH$_3$) can be prepared by treating corresponding compounds of Formula 31 with P$_2$S$_5$ or Lawesson's Reagent to prepare compounds of Formula 32, which are then reacted with diazomethane or iodomethane in the presence of base using general procedures known in the art, as shown in Scheme 21.

Scheme 21

As shown in Scheme 22, compounds of Formula 31 wherein X is NH can be prepared by condensation of corresponding isothiocyanates of Formula 19 with esters of Formula 33 wherein R$^{33}$ is lower alkyl (e.g., methyl, ethyl, propyl) in the presence of a strong, non-nucleophilic base such as sodium hydride or lithium hexamethyldisilazide, in an inert solvent such as tetrahydrofuran (analogous to the method of Scheme 18), followed by reaction of the intermediate with hydrazine or an acid salt of hydrazine, such as, for example, an acetate or hydrochloride salt (analogous to the method of Scheme 16).

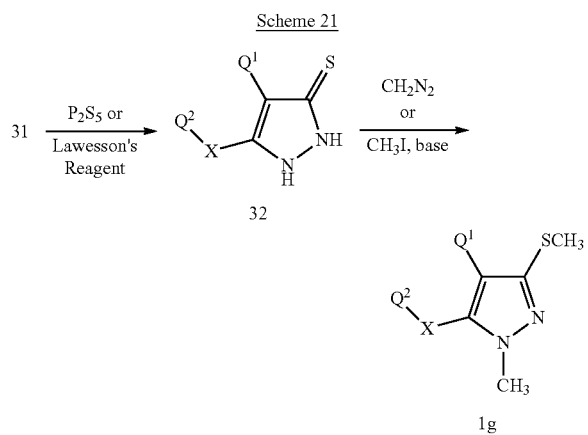

Scheme 22

X is NH

R$^{33}$ is lower alkyl

One skilled in the art will recognize that use of a substituted hydrazine of formula H$_2$NNHCHR$^1$R$^{1a}$ instead of unsubstituted hydrazine in the method of Scheme 22, followed by the further manipulations described for Schemes 19, 20 and 21 will also afford compounds of Formula 1.

Compounds of Formula 1c (i.e. Formula 1 wherein X is NR$^4$ and R$^4$ is H) in which R$^2$ is halogen can also be prepared as shown in Scheme 23. In this method an acetonitrile compound of Formula 21 is condensed with an isothiocyanate compound of Formula 22 in the presence of a base such as sodium hydride or potassium tert-butoxide, in a solvent such as N,N-dimethylformamide or tetrahydrofuran, to afford a cyano ketoamide intermediate compound, which is then reacted with a methylating agent such as iodomethane or dimethyl sulfate, in the presence of a base to provide the corresponding compound of Formula 23. Alternatively, the methylating agent can be included in the reaction mixture with the compounds of Formulae 21 and 22 without isolation of the cyano ketoamide intermediate. One skilled in the art will recognize that compounds of Formula 23 can also be prepared by a method analogous to Scheme 17 wherein the C(O)R$^2$ of the compound of Formula 18 is replaced by cyano. According to the method of Scheme 23, the resultant compound of Formula 23 is then reacted with an alkylhydrazine of Formula 15 to form the corresponding 3-aminopyrazole compound of Formula 24 using general procedures known in the art; see, for example, *J. Chem. Soc. Perkin* 1 1988, 2, 169-173 and *J. Med. Chem.* 2003, 46(7), 1229-1241. The amino group of the compound of Formula 24 can then be converted to R$^2$ being halogen in Formula 1c by a diazotization reaction using conditions known in the art, such as those previously described for Scheme 5.

Scheme 23

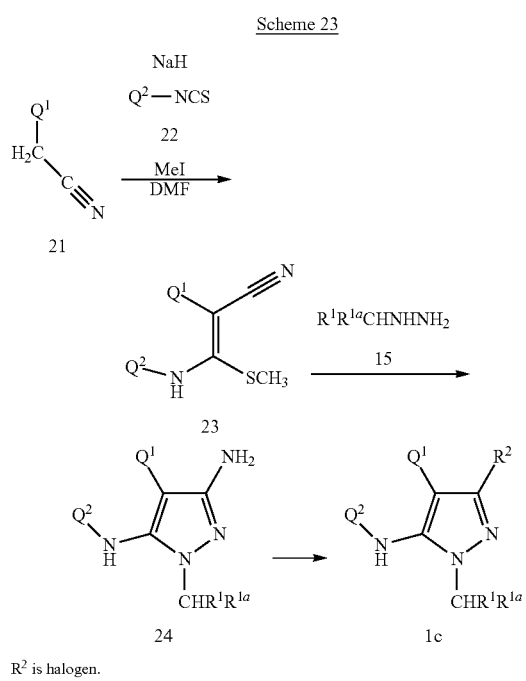

$R^2$ is halogen.

Analogous to the method of Scheme 23, compounds of Formula 2 wherein X is NH and $R^2$ is halogen can be similarly prepared by condensing compounds of Formula 23 with hydrazine instead of an alkylhydrazine of Formula 15.

As shown in Scheme 24, compounds of Formula 1h (i.e. Formula 1 wherein X in $NR^4$) can be prepared by reacting corresponding compounds of Formula 1c (i.e. Formula 1 wherein X is NH) with an electrophile comprising $R^4$ (i.e. Formula 25) typically in the presence of a base such as NaH and a polar solvent such as N,N-dimethylformamide. In this context the expression "electrophile comprising $R^4$" means a chemical compound capable of transferring an $R^4$ moiety to a nucleophile (such as the nitrogen atom attached to $Q^2$ in Formula 1c). Often electrophiles comprising $R^4$ have the formula $R^4Lg$ wherein Lg is a nucleofuge (i.e. leaving group in nucleophilic reactions). Typical nucleofuges include halogens (e.g., Cl, Br, I) and sulfonates (e.g., $OS(O)_2CH_3$, $OS(O)_2CF_3$, $OS(O)_2$-(4-$CH_3$-Ph)). However, some electrophiles comprising $R^4$ do not comprise a nucleofuge; an example is sulfur trioxide ($SO_3$), which after deprotonation (such as by a base of the formulae $M^+H^-$ wherein $M^+$ is a cation) of the nitrogen atom attached to $Q^2$ in Formula 1c, can bond to the nitrogen atom as a $—SO_3^-M^+$ substituent.

Scheme 24

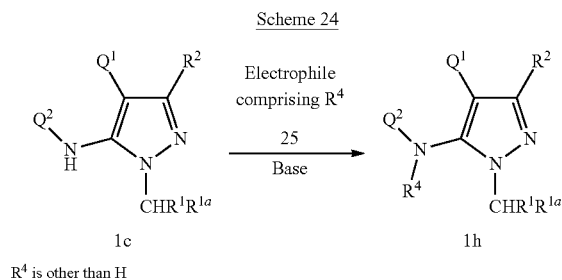

$R^4$ is other than H

It is recognized by one skilled in the art that various functional groups can be converted into others to provide different compounds of Formula 1. For example, compounds of Formula 1 in which $R^2$ is methyl, ethyl or cyclopropyl can be modified by free-radical halogenation to form compounds of Formula 1 wherein $R^2$ is halomethyl, haloethyl or halocyclopropyl. The halomethyl compounds can be used as intermediates to prepare compounds of Formula 1 wherein $R^2$ is hydroxymethyl or cyanomethyl. Compounds of Formula 1 or intermediates for their preparation may contain aromatic nitro groups, which can be reduced to amino groups, and then be converted via reactions well known in the art such as the Sandmeyer reaction, to various halides, providing other compounds of Formula 1. By similar known reactions, aromatic amines (anilines) can be converted via diazonium salts to phenols, which can then be alkylated to prepare compounds of Formula 1 with alkoxy substituents. Likewise, aromatic halides such as bromides or iodides prepared via the Sandmeyer reaction can react with alcohols under copper-catalyzed conditions, such as the Ullmann reaction or known modifications thereof, to provide compounds of Formula 1 that contain alkoxy substituents. Additionally, some halogen groups, such as fluorine or chlorine, can be displaced with alcohols under basic conditions to provide compounds of Formula 1 containing the corresponding alkoxy substituents. The resultant alkoxy compounds can themselves be used in further reactions to prepare compounds of Formula 1 wherein $R^3$ is —U—V-T (see, for example, PCT Publication WO 2007/149448 A2). Compounds of Formula 1 or precursors thereof in which $R^2$ or $R^3$ is halide, preferably bromide or iodide, are particularly useful intermediates for transition metal-catalyzed cross-coupling reactions to prepare compounds of Formula 1. These types of reactions are well documented in the literature; see, for example, Tsuji in *Transition Metal Reagents and Catalysts: Innovations in Organic Synthesis*, John Wiley and Sons, Chichester, 2002; Tsuji in *Palladium in Organic Synthesis*, Springer, 2005; and Miyaura and Buchwald in *Cross Coupling Reactions: A Practical Guide*, 2002; and references cited therein.

One skilled in the art will recognize that sulfide groups can be oxidized to the corresponding sulfoxides or sulfones by conditions well-known in the art. Likewise, compounds of Formula 1 wherein X is $CR^{15}R^{16}$, $R^{15}$ is H, $R^{16}$ is $OR^{18}$ and $R^{18}$ is H can be readily interconverted with corresponding compounds of Formula 1 wherein X is C(=O) by alcohol oxidation and ketone reduction reactions well known in the art. Compounds of Formula 1 wherein X is C(=O) (i.e. ketones) can be readily converted to ketals using general methods known in the art, thus providing compounds of Formula 1 wherein X is $CR^{15}R^{16}$ and $R^{15}$ and $R^{16}$ are taken together as $—OCH_2CH_2O—$. Compounds of Formula 1 wherein X is C(=O) can also be converted by the use of Lawesson's Reagent to prepare corresponding compounds of Formula 1 wherein X is C(=S). Furthermore, compounds of Formula 1 wherein X is $CR^{15}R^{16}$, $R^{15}$ is $C_1$-$C_4$ alkyl, $R^{16}$ is $OR^{18}$, and $R^{18}$ is H can be prepared by adding an alkyl Grignard reagent to the corresponding compounds of Formula 1 wherein X is C(=O).

The above reactions can also in many cases be performed in alternate sequence, such as the preparation of 1H pyrazoles for use in the reaction in Scheme 2 by reactions illustrated later for the general preparation of substituted pyrazoles. The presence of certain functional groups may not be compatible with all of these reaction conditions, and the use of protecting groups may be desirable for obtaining the desired products with improved yields and or purity.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1. One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in CDCl$_3$ unless otherwise noted; "s" means singlet, "m" means multiplet, "br s" means broad singlet. Mass spectra are reported as the molecular weight of the highest isotopic abundance parent ion (M+1) formed by addition of H$^+$ (molecular weight of 1) to the molecule, observed by mass spectrometry using atmospheric pressure chemical ionization (AP$^+$) where "amu" stands for atomic mass units.

Synthesis Example 1

Preparation of N-(3-Chlorophenyl)-4-(2,4-difluorophenyl)-1,3-dimethyl-1H-pyrazol-5-amine (Compound 1)

Step A: Preparation of α-Acetyl-2,4-difluorobenzeneacetonitrile (Alternatively Named methyl α-cyano-2,4-difluorobenzeneacetate)

Sodium hydride (60% in mineral oil) (1.5 g, 38 mmol) was stirred in xylenes (7 mL) under a nitrogen atmosphere at ambient temperature. A solution of anhydrous ethanol (6.3 mL, 64 mmol) in xylenes (2 mL) was added dropwise over about 20 minutes at a temperature of about 40° C. The reaction mixture was heated to 70° C., and a solution of 2,4-difluorophenylacetonitrile (3.9 g, 25 mmol), ethyl acetate (3.8 mL, 38 mmol) and xylenes (1 mL) was added dropwise over 15 min. Additional xylenes (5 mL) was added to aid stirring. The reaction mixture was heated for 2 h, then allowed to cool. Water (50 mL) was added, and the mixture was extracted with hexanes (50 mL). The aqueous phase was then acidified to pH 3-4 with 1 N aqueous HCl solution. The aqueous phase was extracted with ether (50 mL), and the ethereal extract was washed with water (25 mL) and brine, then dried over MgSO$_4$, and concentrated to give the title compound as a viscous residue (3.3 g). $^1$H NMR δ 7.42 (m, 1H), 6.8-7.0 (m, 2H), 4.95 (s, 1H), 2.36 (s, 3H).

Step B: Preparation of 4-(2,4-Difluorophenyl)-1,3-dimethyl-1H-pyrazol-5-amine

Acetic acid (0.5 mL, 8.3 mmol) and methylhydrazine (534 μL, 10.0 mmol) were added to a solution of the residue obtained in Step A (1.6 g, 8.5 mmol) in ethyl alcohol (8 mL). The reaction mixture was then heated at reflux for 16 h under a nitrogen atmosphere. While the reaction mixture was still warm, water was added in small portions (1 mL at a time) until a precipitate formed (about 12 mL of water total). The mixture was reheated to dissolve the solids and then allowed cooled to room temperature. The resulting precipitate was collected on a glass frit, washed with 2 to 3 mL of 50% aqueous ethyl alcohol, and dried under vacuum to obtain the compound as a white solid (0.99 g).

$^1$H NMR δ 7.20 (m, 1H), 6.92 (m, 2H), 3.68 (s, 3H), 3.47 (br s, 2H), 2.14 (s, 3H).

Step C: Preparation of N-(3-Chlorophenyl)-4-(2,4-difluorophenyl)-1,3-dimethyl-1H-pyrazol-5-amine Palladium(II) acetate (90 mg, 0.40 mmol), 4,5-bis(diphenylphosphino)-9,9-dimethylxanthene (460 mg, 0.80 mmol) and powdered potassium carbonate (5.5 g, 40 mmol) were combined in anhydrous 1,4-dioxane (20 mL), and the mixture was sparged with a subsurface stream of N$_2$ gas for 10 min. 4-(2,4-Difluorophenyl)-1,3-dimethyl-1H-pyrazol-5-amine (i.e. the product of Step B) (0.89 g, 4.0 mmol) was added in one portion, and 1-bromo-3-chlorobenzene (0.47 mL, 4.0 mmol) was added via a syringe. The reaction mixture was heated at reflux under a nitrogen atmosphere for 3 h. Additional 1-bromo-3-chlorobenzene (0.09 mL, 0.8 mmol) was added, and heating was continued for 1 h. The reaction mixture was allowed to cool to room temperature, and then partitioned between water (40 mL) and ethyl acetate (40 mL). The organic phase was washed with additional water (40 mL), brine (40 mL), dried over MgSO$_4$ and concentrated under reduced pressure. The residue was purified by column chromatography through 10 g of silica gel eluted with hexanes/ethyl acetate (1:1) to give the title compound, a compound of the present invention, as a solid (0.41 g).

$^1$H NMR δ 7.2-7.3 (m, 2H), 7.10 (m, 1H), 6.9-7.0 (m, 2H), 6.70 (m, 1H), 6.58 (m, 1H), 6.52 (m, 1H), 3.64 (s, 3H), 2.14 (s, 3H). MS: 334 amu.

Synthesis Example 2

Preparation of 4-(2-Chloro-4-fluorophenyl)-N-(2,6-difluoro-4-methoxyphenyl)-1,3-dimethyl-1H-pyrazol-5-amine (Compound 17)

Step A: Preparation of 5-Bromo-4-(2-chloro-4-fluorophenyl)-1,3-dimethyl-1H-pyrazole Copper(II) bromide (3.94 g, 17.7 mmol) was added to a solution of 4-[2-chloro-4-fluorophenyl]-1,3-dimethyl-1H- pyrazol-5-amine (prepared similarly to the preparation of 4-(2,4-Difluorophenyl)-1,3-dimethyl-1H-pyrazol-5-amine in Steps A and B of Synthesis Example 1) (2.4 g, 10 mmol) in acetonitrile (50 mL), and the mixture was stirred and cooled in an ice-water bath while tert-butyl nitrite (90% technical grade, 2.33 mL, 17.7 mmol) was added dropwise over 5 min. The reaction mixture was allowed to warm slowly to ambient temperature. Aqueous HCl solution (20 mL) was added, and then ethyl acetate was added (20 mL). This mixture was filtered through a 2-cm pad of Celite® diatomaceous filter aid. The filter pad was washed with ethyl acetate (20 mL), and the phases were separated. The organic phase was washed with 1.0 N aqueous hydrochloric acid solution and brine, dried over $MgSO_4$, and concentrated to leave the title compound as an orange-brown semisolid (2.8 g).

$^1$H NMR δ 7.18-7.25 (m, 2H), 7.04 (m, 1H), 3.89 (s, 3H), 2.14 (s, 3H).

Step B: Preparation of 4-(2-Chloro-4-fluorophenyl)-N-(2,6-difluoro-4-methoxyphenyl)-1,3-dimethyl-1H-pyrazol-5-amine 5-Bromo-4-(2-chloro-4-fluorophenyl)-1,3-dimethyl-1H-pyrazole (i.e. the product of Step A) (0.20 g, 0.66 mmol), palladium(II) acetate (15 mg, 0.066 mmol), 4,5-bis(diphenylphosphino)-9,9-dimethylxanthene (76 mg, 0.13 mmol) and powdered potassium carbonate (1.8 g, 13 mmol) were combined in anhydrous 1,4-dioxane (3 mL), and the mixture was sparged with a subsurface stream of $N_2$ gas for 10 min. 2,6-Difluoro-4-methoxyaniline (0.22 g, 1.3 mmol) was added in one portion, and the reaction mixture was heated at reflux for 22 h. The reaction mixture was filtered through Celite® diatomaceous filter aid, and the filter pad was washed with ethyl acetate (20 mL). The filtrate was washed with water (10 mL) and brine (10 mL), dried over $MgSO_4$, and concentrated to leave a semisolid residue. This residue was purified by column chromatography through 5 g of silica gel eluted with a gradient of hexanes/ethyl acetate (20:1 to 1:3) to give the title compound, a compound of the present invention, as a light-brown solid (48 mg).

$^1$H NMR δ 7.0-7.1 (m, 2H), 6.85 (m, 1H), 6.26 (m, 2H), 4.84 (br s, 1H), 3.78 (s, 3H), 3.66 (s, 3H), 2.08 (s 3H). MS: 382 amu.

Synthesis Example 3

Preparation of 4-(2,6-Difluoro-4-methoxyphenyl)-1,3-dimethyl-N-(2,4,6-trifluorophenyl)-1H-pyrazol-5-amine (Compound 24)

Step A: Preparation of 2,6-Difluoro-4-methoxybenzeneacetonitrile

A solution of KCN (0.88 g, 13 mmol) dissolved in water (2 mL) was added dropwise to a water-bath-cooled solution of 2,6-difluoro-4-methoxybenzyl bromide (2.50 g, 10.5 mmol) in N,N-dimethylformamide (10 mL). The reaction mixture was stirred for 20 min. Water was added (20 mL) and then the reaction mixture was poured into saturated aqueous $NaHCO_3$ solution (20 mL) and extracted with ether (50 mL). The organic phase was washed with water (5×25 mL), dried over $MgSO_4$, and concentrated to give an oil, which crystallized on standing to provide the title compound as a white solid (1.9 g).

$^1$H NMR δ 6.50 (m, 2H), 3.80 (s, 3H), 3.65 (s, 2H).

Step B: Preparation of ca-Acetyl-2,6-difluoro-4-methoxybenzeneacetonitrile

Solid sodium ethoxide (4.7 g, 66 mmol) was stirred in a mixture of xylene (20 mL) and ethanol (10 mL) and heated to 50° C. A solution of 2,6-difluoro-4-methoxybenzeneacetonitrile (i.e. the product of Step A) (8.0 g, 44 mmol) in ethyl acetate (10.4 mL) was added dropwise. The reaction mixture was heated at 50° C. for 4 h and then allowed to cool to ambient temperature. The reaction mixture was poured into water (100 mL) and extracted with ethyl acetate (25 mL). The aqueous phase was acidified with 3 N aqueous HCl to pH 4 and extracted with ethyl acetate (100 mL). This organic phase was washed with water (50 mL), brine (50 mL), then dried over $MgSO_4$, and concentrated to leave the title compound as a tan semisolid (8.0 g).

$^1$H NMR δ 6.56 (m, 2H), 4.86 (s, 1H), 3.83 (s, 3H), 2.40 (s, 3H).

Step C: Preparation of 4-(2,6-Difluoro-4-methoxyphenyl)-1,3-dimethyl-1H-pyrazole-5-amine α-Acetyl-2,6-difluoro-4-methoxybenzeneacetonitrile (i.e. the product of Step B) (8.03 g, 35.7 mmol) and acetic acid (5 mL) were stirred in ethanol (35 mL), and methylhydrazine (1.91 mL, 35.7 mmol) was added. The reaction mixture was heated at reflux for 16 h, cooled, and then poured into water (100 mL). The resulting mixture was extracted with ethyl acetate (100 mL). The organic phase was washed with 1 N aqueous NaOH (50 mL) and then brine (50 mL), dried over $MgSO_4$, and concentrated to leave a solid. The solid was dissolved in methanol, and the resulting solution was warmed to 45° C.

Water (25 mL) was added dropwise, and the mixture was allowed to cool. The precipitate was collected on a glass frit to give the title compound as a white solid (3.88 g).

$^1$H NMR δ 6.55 (m, 2H), 3.81 (s, 3H), 3.67 (s, 3H), 3.43 (br s, 2H), 2.09 (s, 3H).

Step D: Preparation of 5-Bromo-4-(2,6-difluoro-4-methoxyphenyl)-1,3-dimethyl-1H-pyrazole Copper(II) bromide (3.81 g, 16.9 mmol) was added to a solution of 4-(2,6-difluoro-4-methoxyphenyl)-1,3-dimethyl-1H-pyrazole (i.e. the product of Step C) (3.88 g, 15.4 mmol) in acetonitrile (50 mL), and the mixture was stirred and cooled in an ice-water bath while tert-butyl nitrite (90% technical grade, 3.54 mL, 26.9 mmol) was added dropwise over 5 min. The reaction mixture was allowed to warm slowly to ambient temperature. Aqueous hydrochloric acid solution (25 mL) was added, then ethyl acetate (25 mL) was added, and the resulting mixture was filtered through a 2-cm pad of Celite® diatomaceous filter aid. The filter pad was washed with ethyl acetate (50 mL), and the phases were separated. The organic phase was washed with 1 N aqueous HCl solution (25 mL) and brine (25 mL), dried over $MgSO_4$, and concentrated. The residue was purified by column chromatography through 24 g of silica gel eluted with a gradient of hexanes/ethyl acetate (9:1 to 1:1) to give the title compound as a white solid (3.25 g).

$^1$H NMR δ 6.54 (m, 2H), 3.88 (s, 3H), 3.83 (s, 3H), 2.16 (s, 3H).

Step E: Preparation of 4-(2,6-Difluoro-4-methoxyphenyl)-1,3-dimethyl-N-(2,4,6-trifluorophenyl)-1H-pyrazol-5-amine 5-Bromo-4-(2,6-difluoro-4-methoxyphenyl)-1,3-dimethyl-1H-pyrazole (i.e. the product of Step D) (0.30 g, 0.94 mmol), palladium(II) acetate (20 mg, 0.090 mmol), 4,5-bis(diphenylphosphino)-9,9-dimethylxanthene (0.11 g, 0.19 mmol) and powdered potassium carbonate (2.6 g, 19 mmol) were combined in anhydrous 1,4-dioxane (4 mL), and the resulting mixture was sparged with a subsurface stream of $N_2$ gas for 10 min. 2,4,6-Trifluoroaniline (0.28 g, 1.9 mmol) was added in one portion, and the reaction mixture was heated at reflux under nitrogen for 22 h. The reaction mixture was cooled, then filtered through Celite® diatomaceous filter aid. The filter pad was washed with ethyl acetate (20 mL), and the filtrate was washed with water (10 mL) and brine (10 mL), dried over $MgSO_4$, and concentrated to leave a semisolid residue. The residue was purified by column chromatography through 12 g of silica gel eluted with a gradient of hexanes/ethyl acetate (20:1 to 1:3) to give the title compound, a compound of the present invention, as a semisolid (73 mg).

$^1$H NMR (acetone-$d_6$) δ 6.84 (br s, 1H), 6.68 (m, 2H), 6.43 (m, 2H), 3.77 (s, 3H), 3.75 (s, 3H), 1.99 (s, 3H). MS: 384 amu ($AP^+$).

Synthesis Example 4

Preparation of 4-[[4-(2-Chloro-4-fluorophenyl)-1,3-dimethyl-1H-pyrazol-5-yl]oxy]-3,5-difluorobenzonitrile (Compound 45)

Step A: Preparation of 4-[(1,3-Dimethyl-1H-pyrazol-5-yl)oxy]-3,5-difluorobenzonitrile Potassium carbonate (1.38 g, 10 mmol) was added to a solution of 2,4-dihydro-2,5-dimethyl-3H-pyrazol-3-one (0.70 g, 6.3 mmol) in N,N-dimethylformamide (15 mL). 3,4,5-Trifluorobenzonitrile (0.94 g, 6.0 mmol) was added, and the reaction mixture was heated at 75° C. under a nitrogen atmosphere for 16 h, then allowed to cool. The reaction mixture was partitioned between water (60 mL) and ethyl acetate (30 mL). The organic phase was washed with water (2×30 mL) and brine (30 mL), dried over $MgSO_4$, and concentrated to give the title compound as a yellow oil (1.38 g).

$^1$H NMR δ 7.36 (m, 2H), 5.24 (s, 1H), 3.78 (s, 3H), 2.16 (s, 3H).

Step B: Preparation of 3,5-Difluoro-4-[(4-iodo-1,3-dimethyl-1H-pyrazol-5-yl)oxy]benzonitrile A solution of 4-[(1,3-dimethyl-1H-pyrazol-5-yl)oxy]-3,5-difluorobenzonitrile (i.e. the product of Step A) (1.38 g, 5.5 mmol) in acetonitrile (20 mL) was stirred at ambient temperature, and N-iodosuccinimide (1.35 g, 6.0 mmol) was added in one portion. The reaction mixture was heated at reflux for 2 h, cooled, and then poured into water (40 mL). The resulting mixture was extracted with ethyl acetate (40 mL). The organic phase was washed with water (20 mL) and saturated aqueous $NaHCO_3$ solution (20 mL), dried over $MgSO_4$, and concentrated under reduced pressure to give the title compound as a tan solid (2.1 g).

$^1$H NMR (acetone-$d_6$) δ 7.80 (m, 2H), 3.82 (s, 3H), 2.09 (s, 3H). MS: 376 amu ($AP^+$).

Step C: Preparation of 4-[[4-(2-Chloro-4-fluorophenyl)-1,3-dimethyl-1H-pyrazol-5-yl]oxy]-3,5-difluorobenzonitrile To a solution of 3,5-difluoro-4-[(4-iodo-1,3-dimethyl-1H-pyrazol-5-yl)oxy]-benzonitrile (i.e. the product of Step B) (1.0 g, 2.67 mmol) in 1,4-dioxane (6 mL) was added 2-chloro-4-fluorobenzeneboronic acid (alternatively named B-(2-chloro-4-fluorophenyl)-boronic acid) (0.93 g, 5.33 mmol), dichloro(bis)triphenylphosphine palladium(II) (alternatively named bis(triphenylphosphine)palladium(II) dichloride) (93 mg, 0.13 mmol), potassium carbonate (0.74 g, 5.33 mmol), and water (4 mL). The resulting mixture was heated at reflux for 5 h, allowed to cool, and partitioned between water (20 mL) and ethyl acetate (20 mL). The organic layer was dried over $MgSO_4$ and concentrated. The residue was purified by chromatography on silica gel with a gradient of hexanes/ethyl acetate to obtain the title compound, a compound of the present invention, as an off-white solid (110 mg).

$^1$H NMR δ 7.00-7.09 (m, 3H), 6.97 (m, 1H), 6.86 (m, 1H), 3.85 (s, 3H), 2.02 (s, 3H).

Synthesis Example 5

Preparation of 4-(2,4-Dichlorophenyl)-N-(2,4-difluorophenyl)-1,3-dimethyl-1H-pyrazol-5-amine (Compound 69)

Step A: Preparation of α-Acetyl-2,4-dichloro-N-(2,4-difluorophenyl)benzeneethanethioamide 2,4-Difluorophenyl isothiocyanate (0.27 mL, 2.0 mmol) was added to a stirred suspension of sodium hydride (60% in mineral oil) (112 mg, 2.8 mmol) in anhydrous tetrahydrofuran (4 mL) cooled in an ice-water bath under a nitrogen atmosphere. A solution of (2,4-dichlorophenyl)-2-propanone (570 mg, 2.8 mmol) in tetrahydrofuran (4 mL) was added dropwise over 5 min. The resultant yellow solution was stirred at 5-10° C. for 1 h. Water (10 mL) was carefully added, and the reaction mixture was extracted with ethyl acetate (10 mL). The aqueous phase was acidified to pH 3 with 1 N aqueous HCl, then extracted with ethyl acetate (20 mL). The organic extract was washed with water (10 mL) and brine (10 mL), dried over $MgSO_4$, and concentrated to leave a solid. The solid was triturated with hexanes/ethyl acetate (2:1), collected on a glass frit, and air-dried to give the title compound as a white solid (240 mg). MS: 373 amu ($AP^+$).

Step B: Preparation of 4-(2,4-Dichlorophenyl)-N-(2,4-difluorophenyl)-1,3-dimethyl-1H-pyrazol-5-amine Acetic acid (50 μL) and methylhydrazine (41 μL) were added to a stirred suspension of α-acetyl-2,4-dichloro-N-(2,4-difluorophenyl)benzeneethanethioamide (238 mg, 0.64 mmol) in ethanol (4 mL). The reaction mixture was heated at reflux for 2 h and allowed to cool. Then the reaction mixture was diluted with ethyl acetate (10 mL) and washed with 1 N aqueous NaOH (10 mL), water (10 mL) and brine (10 mL), dried over $MgSO_4$, and concentrated to leave a solid residue. The residue was purified by column chromatography on 5 g of silica gel with a gradient of hexanes/ethyl acetate (2:1 to 1:1) to give the title compound as a solid (170 mg).

$^1$H NMR δ 7.43 (s, 1H), 7.19 (m, 1H), 7.07 (m, 1H), 6.78 (m, 1H), 6.62 (m, 1H), 6.37 (m, 1H), 5.22 (br s, 1H), 3.70 (s, 3H), 2.18 (s, 3H). MS: 368 amu (AP$^+$).

Synthesis Example 6

Preparation of 4-(2-Chloro-4-fluorophenyl)-α-(2,4-difluorophenyl)-1,3-dimethyl-1H-pyrazole-5-methanol (Compound 351)

5-Bromo-4-(2-chloro-4-fluorophenyl)-1,3-dimethyl-1H-pyrazole (i.e. the product of Synthesis Example 2, Step A) (0.25 g, 0.82 mmol) was dissolved in anhydrous tetrahydrofuran (12 mL), and the mixture was cooled in a dry ice/acetone bath under a nitrogen atmosphere. A cyclohexane solution of n-butyllithium (2.0 M, 0.49 mL, 0.98 mmol) was added dropwise over 5 minutes. After 15 minutes, a solution of 2,4-difluorobenzaldehyde (0.09 mL, 0.82 mmol) in anhydrous tetrahydrofuran (3 mL) was added slowly dropwise, causing the dark red-colored solution to lighten to a yellow color. After 45 minutes, the reaction mixture was quenched by the addition of saturated aqueous NH$_4$Cl solution (~20 mL) and allowed to warm to ambient temperature. This mixture was extracted with ethyl acetate, and the organic phase was washed with saturated aqueous NH$_4$Cl solution (25 mL) and with brine, dried over Na$_2$SO$_4$, and concentrated to leave a viscous residue. This residue was purified by column chromatography through silica gel eluted with a gradient of ethyl acetate in hexane (7% to 10%) to give the title product, a compound of the present invention, as a white semi-solid (109 mg).

$^1$H NMR δ 7.5 (m, 1H), 7.1 (m, 2H), 7.0 (m, 1H), 6.85 (m, 2H), 6.0 (br s, 1H), 5.9 (s, 1H), 3.8 (s, 3H), 2.1 (s, 3H). MS: 367 amu (AP$^+$).

Synthesis Example 7

Preparation of [4-(2-Chloro-4-fluorophenyl)-1,3-dimethyl-1H-pyrazol-5-yl](2,4-difluorophenyl) methanone (Compound 370)

4-(2-Chloro-4-fluorophenyl)-α-(2,4-difluorophenyl)-1,3-dimethyl-1H-pyrazole-5-methanol (i.e. the product of Synthesis Example 6) (90 mg, 0.25 mmol) was dissolved in dichloromethane (8 mL), and pyridinium dichromate (113 mg, 0.3 mmol) was added in one portion. The reaction mixture was stirred at ambient temperature for 16 h, and then the reaction mixture was partitioned between water (5 mL) and dichloromethane (5 mL). The organic phase was washed with additional water (5 mL) and with brine (5 mL), dried over Na$_2$SO$_4$ and concentrated under reduced pressure to give a viscous residue. This residue was purified by column chromatography through silica gel eluted with a gradient of ethyl acetate in hexane (25% to 30%) to give the title product, a compound of the present invention, as a pale yellow viscous oil (29 mg).

$^1$H NMR δ 7.94 (m, 1H), 7.32 (s, 1H), 7.27 (m, 1H), 7.03 (m, 1H), 6.95 (m, 1H), 6.78 (m, 1H), 3.82 (s, 3H), 2.13 (s, 3H). MS: 365 amu (AP$^+$).

Synthesis Example 8

Preparation of 5-(2,6-Difluoro-4-nitrophenoxy)-1,3-dimethyl-4-(2,4,6-trifluorophenyl)-1H-pyrazole (Compound 54)

Step A: Preparation of Methyl 2,4,6-trifluorobenzeneacetate

A solution of 2,4,6-trifluorobenzeneacetic acid (5.00 g, 26.3 mmol) in methanol (25 mL) was stirred at ambient temperature, and thionyl chloride (6 mL, ~3 eq.) was added dropwise, causing the temperature of the reaction mixture to reach 60° C. The reaction mixture was allowed to cool to ambient temperature and was stirred for 3 h. Water (25 mL) was added with ice cooling. The mixture was extracted with ethyl acetate (2×100 mL). The combined organic phases were washed with water (2×), with saturated aqueous sodium bicarbonate solution and with brine, and dried over MgSO$_4$. Concentration provided the title product as a clear oil (5.38 g).

$^1$H NMR δ 6.68 (m, 2H), 3.72 (s, 3H), 3.66 (s, 2H).

Step B: Preparation of Methyl α-acetyl-2,4,6-trifluorobenzeneacetate

To a commercially obtained tetrahydrofuran solution of lithium bis(trimethyl-silyl)amide (1.0 M, 21.0 mL), stirred under a nitrogen atmosphere and cooled to an internal temperature of −65° C., was added dropwise over 30 minutes a solution of methyl 2,4,6-trifluorobenzeneacetate (i.e. the product of Step A) (2.04 g, 10.0 mmol) dissolved in dry tetrahydrofuran (10 mL). The reaction mixture was stirred for an additional 30 minutes, and then while maintaining the −65° C. temperature, a solution of freshly distilled acetyl chloride (0.80 mL, 11 mmol) in dry tetrahydrofuran (3 mL) was added dropwise. The reaction mixture was allowed to warm slowly to ambient temperature, and then water (30 mL) was added. The resultant mixture was extracted with ethyl acetate (60 mL). The aqueous phase was acidified with 1 N hydrochloric acid and extracted with ethyl acetate (60 mL). Only the first extract was retained, because thin layer chromatographic analysis showed the second extract to contain apparent polar impurities besides additional desired product. The initial organic phase was further washed with 1 N hydrochloric acid, water and brine, dried over MgSO$_4$, and concentrated to provide the title product as a clear oil (1.86 g).

$^1$H NMR δ 6.69 (m, 2H), 3.7 (m, 1H and s, 3H), 1.87 (s, 3H); minor resonances at 13.2 ppm and 4.9 ppm indicated presence of enolic tautomer.

Step C: Preparation of 1,3-Dimethyl-4-(2,4,6-trifluorophenyl)-1H-pyrazol-5-ol

To a solution of methyl α-acetyl-2,4,6-trifluorobenzeneacetate (i.e. the product of Step B) (2.46 g, 10.0 mmol) in methanol (15 mL) was added methylhydrazine (0.665 mL, 12.5 mmol), and the mixture was stirred at ambient temperature over 3 days. Aqueous citric acid solution (1 M, 10 mL) was added, and then water (50 mL) was added. The mixture was extracted with ethyl acetate (2×50 mL). The combined organic extracts were washed with water and with brine, dried over MgSO$_4$, and concentrated to leave a yellow solid. This solid was suspended in a small volume of ethyl acetate (about 5 mL), an equal volume of hexanes was gradually added, and the suspension was stirred for 30 minutes. The solid component was collected on a glass frit, washed with small portions of ethyl acetate/hexanes (1:1 and 1:2 v:v), and allowed to dry in air to provide a white solid (1.02 g). Evaporation of the mother liquor and treatment of the resultant residue with small volumes of ethyl acetate and hexanes as already described provided an additional 0.13 g of solid containing the title product (1.15 g total). Analysis of the combined solids by LC/MS showed a primary component of mass 242 (AP+) and a minor component, eluting later by reverse-phase LC, also having a mass of 242 (AP+). The apparent ratio of components was 94:6.

¹H NMR (acetone-d₆) δ 6.95 (m, 2H), 3.52 (s, 3H), 1.98 (s, 3H); 5-hydroxy resonance was not observed in this solvent.

Step D: Preparation of 5-(2,6-Difluoro-4-nitrophenoxy)-1,3-dimethyl-4-(2,4,6-trifluorophenyl)-1H-pyrazole 1,3-Dimethyl-4-(2,4,6-trifluorophenyl)-1H-pyrazol-5-ol (i.e. the product of Step C) (0.310 g, 1.28 mmol), was combined with 3,4,5-trifluoronitrobenzene (157 μL, 1.35 mmol) and potassium carbonate powder (0.27 g, 2 mmol) in dry N,N-dimethylformamide (4 mL). This mixture was stirred and heated at 80° C. for 45 minutes and then allowed to cool. The reaction mixture was diluted with water (10 mL) and extracted with ethyl acetate (2×10 mL). The organic phase was washed with water and with brine, dried over MgSO₄, and concentrated to leave a viscous residue. This residue was purified by column chromatography through silica gel eluted with a gradient of ethyl acetate (30% to 100%) in hexane to give the title product, a compound of the present invention, as an off-white solid (209 mg).
¹H NMR δ 7.71 (m, 2H), 6.54 (m, 2H), 3.86 (s, 3H), 2.07 (s, 3H); 400 amu (AP⁺).

Synthesis Example 9

Preparation of 4-[[1,3-Dimethyl-4-(2,4,6-trifluorophenyl)-1H-pyrazol-5-yl]oxy]-3,5-difluorobenzenamine (Compound 371)

5-(2,6-Difluoro-4-nitrophenoxy)-1,3-dimethyl-4-(2,4,6-trifluorophenyl)-1H-pyrazole (i.e. the product of Synthesis Example 8) (0.780 g, 1.95 mmol) was combined with iron powder (325 mesh, 0.58 g, 10 mmol) and ammonium chloride (64 mg, 1.2 mmol) in ethanol (27 mL) to which water (3 mL) had been added. The mixture was heated at reflux for 1.25 h and then allowed to cool. The reaction mixture was diluted with an equal volume of ethyl acetate and filtered through Celite filter aid. The filtrate was dried with MgSO₄ and concentrated. Analysis by LC/MS showed the major component (93%) to have mass 370 amu (AP+). The residue was dissolved in anhydrous dimethyl sulfoxide (8 mL), and a commercial solution of sodium methoxide in methanol (0.45 mL of 25% solution) was added. This solution was stirred under nitrogen and heated at reflux for 1 h. Additional sodium methoxide/methanol solution (0.20 mL) was added, and heating was continued for an additional 30 minutes. The reaction mixture was allowed to cool, and it was then treated with aqueous citric acid solution (1 M, 5 mL), diluted with water (50 mL) and extracted with ethyl acetate (2×25 mL). The organic phase was washed with water (3×) and with brine, dried over MgSO₄, and concentrated to leave the title product, a compound of the present invention, as a viscous oil (0.52 g).
¹H NMR δ 6.29 (m, 2H), 5.95 (m, 2H), 3.80 (s, 3H), 3.75 (s, 3H), 3.55-3.75 (br s, NH₂), 2.01 (s, 3H); 382 amu (AP+).

Synthesis Example 10

Preparation of 5-(4-Chloro-2,6-difluorophenoxy)-4-(2,6-difluoro-4-methoxyphenyl)-1,3-dimethyl-1H-pyrazole (Compound 58)

Copper(I) chloride (56 mg, 0.42 mmol) was added to a solution of 4-[[4-(2,6-difluoro-4-methoxyphenyl)-1,3-dimethyl-1H-pyrazol-5-yl]oxy]-3,5-difluorobenzenamine (prepared analogous to Synthesis Example 9) (132 mg, 0.346 mmol) in acetonitrile (5 mL). The stirred mixture was cooled using an ice-water bath, and tert-butyl nitrite (90% technical grade, 72 μL) was added dropwise. The reaction mixture was allowed to warm slowly to ambient temperature and stirred at room temperature overnight, and then it was heated at reflux for 1 h. Hydrochloric acid (1 N, 5 mL) was added, and the mixture was extracted with ethyl acetate (~20 mL). The organic phase was washed with brine, dried over MgSO₄, and concentrated. The residue was purified by column chromatography through silica gel eluted with 20% ethyl acetate in hexane to give the title product, a compound of the present invention, as a viscous oil (45 mg).
¹H NMR δ 6.74 (m, 2H), 6.30 (m, 2H), 3.83 (s, 3H), 3.75 (s, 3H), 2.03 (s, 3H); 401 amu (AP+).

By the procedures described herein together with methods known in the art, the compounds disclosed in the Tables that follow can be prepared. The following abbreviations are used in the Table which follows: Me means methyl, Et means ethyl, n-Pr means n-propyl, c-Pr means cyclopropyl, Ph means phenyl, OMe (or MeO) means methoxy, OEt (or EtO) means ethoxy, —CN means cyano, and —NO₂ means nitro.

TABLE 1

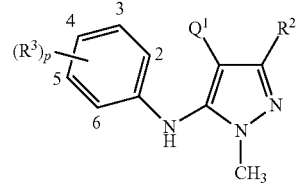

Q¹ is 2,6-di-F-Ph, and R² is Me.

| $(R^3)_p$ |
|---|
| 2-F |
| 3-F |
| 4-F |
| 2-Cl |
| 3-Cl |
| 4-Cl |
| 2-Br |
| 3-Br |
| 4-Br |
| 2,4-di-F |
| 2,6-di-F |
| 2,4,6-tri-F |
| 2,4,5-tri-F |
| 2,3,5-tri-F |
| 2,3,6-tri-F |
| 2-Cl-4-F |
| 2-F-4-Cl |
| 2,4-di-Cl |
| 2,6-di-Cl |
| 2,4,6-tri-Cl |
| 2-Br-4-F |
| 2-I-4-F |
| 2-Me-4-F |
| 2-F-4-MeO |
| 2-Cl-4-MeO |
| 2-Br-4-MeO |
| 2,6-di-F-4-MeO |
| 2-F-4-CN |
| 2-Cl-4-CN |
| 2-Br-4-CN |
| 2,6-di-F-4-CN |
| 2-Cl-4,5-di-F |
| 2-Cl-4,6-di-F |
| 2-Br-4,5-di-F |
| 2-Br-4,6-di-F |
| 4-Cl-2,5-di-F |

TABLE 1-continued

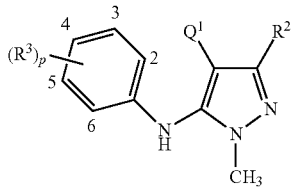

$Q^1$ is 2,6-di-F-Ph, and $R^2$ is Me.

$(R^3)_p$

4-Cl-2,6-di-F
4-Br-2,5-di-F
4-Br-2,6-di-F
2,4-di-Cl-6-F
2,6-di-Cl-4-F
2,6-di-Cl-4-MeO
2-CF$_3$-4-F
4-Me
2,4-di-Me
2-F-4-Br
2-Cl-4-Br
2-Br-4-Cl
2-Br-4-F-6-Cl
2-Cl-4-Br-6-F

The present disclosure also includes Tables 2 through 84, each of which is constructed the same as Table 1 above, except that the row heading in Table 1 (i.e. "$Q^1$ is 2,6-di-F-Ph, and $R^2$ is Me.") is replaced with the respective row heading shown below. For Example, in Table 2 the row heading is "$Q^1$ is 2,6-di-F-Ph, and $R^2$ is Cl.", and $(R^3)_p$ is as defined in Table 1 above. Thus, the first entry in Table 2 specifically discloses 2-chloro-4-(2,6-difluorophenyl)-N-(2-fluorophenyl)-1-methyl-1H-pyrazol-5-amine. Tables 3 through 84 are constructed similarly.

| Table | Row Heading |
|---|---|
| 2 | $Q^1$ is 2,6-di-F—Ph, and $R^2$ is Cl. |
| 3 | $Q^1$ is 2,6-di-F—Ph, and $R^2$ is Br. |
| 4 | $Q^1$ is 2,4-di-F—Ph, and $R^2$ is Me. |
| 5 | $Q^1$ is 2,4-di-F—Ph, and $R^2$ is Cl. |
| 6 | $Q^1$ is 2,4-di-F—Ph, and $R^2$ is Br. |
| 7 | $Q^1$ is 2,4,6-tri-F—Ph, and $R^2$ is Me. |
| 8 | $Q^1$ is 2,4,6-tri-F—Ph, and $R^2$ is Cl. |
| 9 | $Q^1$ is 2,4,6-tri-F—Ph, and $R^2$ is Br. |
| 10 | $Q^1$ is 2,6-di-F-4-OMe—Ph, and $R^2$ is Me. |
| 11 | $Q^1$ is 2,6-di-F-4-OMe—Ph, and $R^2$ is Cl. |
| 12 | $Q^1$ is 2,6-di-F-4-OMe—Ph, and $R^2$ is Br. |
| 12A | $Q^1$ is 2,6-di-F-4-OEt—Ph, and $R^2$ is Me. |
| 12B | $Q^1$ is 2,6-di-F-4-OEt—Ph, and $R^2$ is Cl. |
| 12C | $Q^1$ is 2,6-di-F-4-OEt—Ph, and $R^2$ is Br. |
| 13 | $Q^1$ is 2,6-di-F-4-CN—Ph, and $R^2$ is Me. |
| 14 | $Q^1$ is 2,6-di-F-4-CN—Ph, and $R^2$ is Cl. |
| 15 | $Q^1$ is 2,6-di-F-4-CN—Ph, and $R^2$ is Br. |
| 16 | $Q^1$ is 2-Cl-4-F—Ph, and $R^2$ is Me. |
| 17 | $Q^1$ is 2-Cl-4-F—Ph, and $R^2$ is Cl. |
| 18 | $Q^1$ is 2-Cl-4-F—Ph, and $R^2$ is Br. |
| 19 | $Q^1$ is 2-Cl-6-F—Ph, and $R^2$ is Me. |
| 20 | $Q^1$ is 2-Cl-6-F—Ph, and $R^2$ is Cl. |
| 21 | $Q^1$ is 2-Cl-6-F-Ph, and $R^2$ is Br. |
| 22 | $Q^1$ is 2-Cl-4,6-di-F—Ph, and $R^2$ is Me. |
| 23 | $Q^1$ is 2-Cl-4,6-di-F—Ph, and $R^2$ is Cl. |
| 24 | $Q^1$ is 2-Cl-4,6-di-F—Ph, and $R^2$ is Br. |
| 25 | $Q^1$ is 4-Cl-2,6-di-F—Ph, and $R^2$ is Me. |
| 26 | $Q^1$ is 4-Cl-2,6-di-F—Ph, and $R^2$ is Cl. |
| 27 | $Q^1$ is 4-Cl-2,6-di-F—Ph, and $R^2$ is Br. |
| 28 | $Q^1$ is 2-Br-4-F—Ph, and $R^2$ is Me. |
| 29 | $Q^1$ is 2-Br-4-F—Ph, and $R^2$ is Cl. |
| 30 | $Q^1$ is 2-Br-4-F—Ph, and $R^2$ is Br. |
| 31 | $Q^1$ is 2-Br-6-F—Ph, and $R^2$ is Me. |
| 32 | $Q^1$ is 2-Br-6-F—Ph, and $R^2$ is Cl. |
| 33 | $Q^1$ is 2-Br-6-F—Ph, and $R^2$ is Br. |
| 34 | $Q^1$ is 2-Me-4-F—Ph, and $R^2$ is Me. |
| 35 | $Q^1$ is 2-Me-4-F—Ph, and $R^2$ is Cl. |
| 36 | $Q^1$ is 2-Me-4-F—Ph, and $R^2$ is Br. |
| 37 | $Q^1$ is 2-I-4-F—Ph, and $R^2$ is Me. |
| 38 | $Q^1$ is 2-I-4-F—Ph, and $R^2$ is Cl. |
| 39 | $Q^1$ is 2-I-4-F—Ph, and $R^2$ is Br. |
| 40 | $Q^1$ is 2-F—Ph, and $R^2$ is Me. |
| 41 | $Q^1$ is 2-F—Ph, and $R^2$ is Cl. |
| 42 | $Q^1$ is 2-F—Ph, and $R^2$ is Br. |
| 43 | $Q^1$ is 2-Cl—Ph, and $R^2$ is Me. |
| 44 | $Q^1$ is 2-Cl—Ph, and $R^2$ is Cl. |
| 45 | $Q^1$ is 2-Cl—Ph, and $R^2$ is Br. |
| 46 | $Q^1$ is 2-Br—Ph, and $R^2$ is Me. |
| 47 | $Q^1$ is 2-Br—Ph, and $R^2$ is Cl. |
| 48 | $Q^1$ is 2-Br—Ph, and $R^2$ is Br. |
| 49 | $Q^1$ is 2-F-4-Cl—Ph, and $R^2$ is Me. |
| 50 | $Q^1$ is 2-F-4-Cl—Ph, and $R^2$ is Cl. |
| 51 | $Q^1$ is 2-F-4-Cl—Ph, and $R^2$ is Br. |
| 52 | $Q^1$ is 2,4-di-Cl—Ph, and $R^2$ is Me. |
| 53 | $Q^1$ is 2,4-di-Cl—Ph, and $R^2$ is Cl. |
| 54 | $Q^1$ is 2,4-di-Cl—Ph, and $R^2$ is Br. |
| 55 | $Q^1$ is 2,6-di-Cl—Ph, and $R^2$ is Me. |
| 56 | $Q^1$ is 2,6-di-Cl—Ph, and $R^2$ is Cl. |
| 57 | $Q^1$ is 2,6-di-Cl—Ph, and $R^2$ is Br. |
| 58 | $Q^1$ is 2-F-4-MeO—Ph, and $R^2$ is Me. |
| 59 | $Q^1$ is 2-F-4-MeO—Ph, and $R^2$ is Cl. |
| 60 | $Q^1$ is 2-F-4-MeO—Ph, and $R^2$ is Br. |
| 60A | $Q^1$ is 2-F-4-EtO—Ph, and $R^2$ is Me. |
| 60B | $Q^1$ is 2-F-4-EtO—Ph, and $R^2$ is Cl. |
| 60C | $Q^1$ is 2-F-4-EtO—Ph, and $R^2$ is Br. |
| 61 | $Q^1$ is 2-Cl-4-MeO—Ph, and $R^2$ is Me. |
| 62 | $Q^1$ is 2-Cl-4-MeO—Ph, and $R^2$ is Cl. |
| 63 | $Q^1$ is 2-Cl-4-MeO—Ph, and $R^2$ is Br. |
| 63A | $Q^1$ is 2-Cl-4-EtO—Ph, and $R^2$ is Me. |
| 63B | $Q^1$ is 2-Cl-4-EtO—Ph, and $R^2$ is Cl. |
| 63C | $Q^1$ is 2-Cl-4-EtO—Ph, and $R^2$ is Br. |
| 64 | $Q^1$ is 2-Br-4-MeO—Ph, and $R^2$ is Me. |
| 65 | Q1 is 2-Br-4-MeO—Ph, and $R^2$ is Cl. |
| 66 | $Q^1$ is 2-Br-4-MeO—Ph, and $R^2$ is Br. |
| 66A | $Q^1$ is 2-Br-4-EtO—Ph, and $R^2$ is Me. |
| 66B | $Q^1$ is 2-Br-4-EtO—Ph, and $R^2$ is Cl. |
| 66C | $Q^1$ is 2-Br-4-EtO—Ph, and $R^2$ is Br. |
| 67 | $Q^1$ is 2-F-4-CN—Ph, and $R^2$ is Me. |
| 68 | $Q^1$ is 2-F-4-CN—Ph, and $R^2$ is Cl. |
| 69 | $Q^1$ is 2-F-4-CN—Ph, and $R^2$ is Br. |
| 70 | $Q^1$ is 2-Cl-4-CN—Ph, and $R^2$ is Me. |
| 71 | $Q^1$ is 2-Cl-4-CN—Ph, and $R^2$ is Cl. |
| 72 | $Q^1$ is 2-Cl-4-CN—Ph, and $R^2$ is Br. |
| 73 | $Q^1$ is 2-Br-4-CN—Ph, and $R^2$ is Me. |
| 74 | $Q^1$ is 2-Br-4-CN—Ph, and $R^2$ is Cl. |
| 75 | $Q^1$ is 2-Br-4-CN—Ph, and $R^2$ is Br. |
| 76 | $Q^1$ is 2,5-di-Cl-3-pyridinyl, and $R^2$ is Me. |
| 77 | $Q^1$ is 2,5-di-Cl-3-pyridinyl, and $R^2$ is Cl. |
| 78 | $Q^1$ is 2,5-di-Cl-3-pyridinyl, and $R^2$ is Br. |
| 79 | $Q^1$ is 2-Cl-3-thienyl, and $R^2$ is Me. |
| 80 | $Q^1$ is 2-Cl-3-thienyl, and $R^2$ is Cl. |
| 81 | $Q^1$ is 2-Cl-3-thienyl, and $R^2$ is Br. |
| 82 | $Q^1$ is 2,5-di-Cl-3-thienyl, and $R^2$ is Me. |
| 83 | $Q^1$ is 2,5-di-Cl-3-thienyl, and $R^2$ is Cl. |
| 84 | $Q^1$ is 2,5-di-Cl-3-thienyl, and $R^2$ is Br. |

TABLE 85

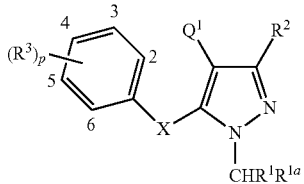

Q$^1$ is 2,6-di-F-Ph, X is O, R$^1$ and R$^{1a}$ are both H, and R$^2$ is Me.

| (R$^3$)$_p$ |
|---|
| 4-F |
| 4-Cl |
| 4-Br |
| 2,4-di-F |
| 2-Br-4-F |
| 2,6-di-F |
| 2,4-di-Cl |
| 2,6-di-Cl |
| 2-Cl-4-F |
| 2-F-4-Cl |
| 2-F-4-Br |
| 2-Br-6-F |
| 2-Cl-4-Br |
| 2-Br-4-Cl |
| 2-I-4-F |
| 2-F-4-I |
| 2-Cl-4,6-di-F |
| 4-Cl-2,6-di-F |
| 2-Br-4,6-di-F |
| 4-Br-2,6-di-F |
| 2-F-4-MeO |
| 2-Cl-4-MeO |
| 2,6-di-F-4-MeO |
| 2-F-4-CN |
| 2-Cl-4-CN |
| 2-Br-4-CN |
| 2,6-di-F-4-CN |
| 2-F-4-NO$_2$ |
| 2-Cl-4-NO$_2$ |
| 2-Br-4-NO$_2$ |
| 2,5-di-F-4-CN |
| 4-Cl-2,5-di-F |
| 2-Br-4,5-di-F |
| 4-Br-2,5-di-F |
| 2-Cl-4,5-di-F |

The present disclosure also includes Tables 86 through 280, each of which is constructed the same as Table 85 above, except that the row heading in Table 85 (i.e. "Q$^1$ is 2,6-di-F-Ph, X is O, R$^1$ and R$^{1a}$ are both H, and R$^2$ is Me.") is replaced with the respective row heading shown below. For Example, in Table 86 the row heading is "Q$^1$ is 2,6-di-F-Ph, X is O, R$^1$ and R$^{1a}$ are both H, and R$^2$ is Cl." and (R$^3$)$_p$ is as defined in Table 85 above. Thus, the first entry in Table 86 specifically discloses 3-chloro-4-(2,6-difluorophenyl)-5-(4-fluorophenoxy)-1-methyl-1H-pyrazole. Tables 87 through 280 are constructed similarly.

| Table | Row Heading |
|---|---|
| 86 | Q$^1$ is 2,6-di-F-Ph, X is O, R$^1$ and R$^{1a}$ are both H, and R$^2$ is Cl. |
| 87 | Q$^1$ is 2,6-di-F—Ph, X is O, R$^1$ and R$^{1a}$ are both H, and R$^2$ is Br. |
| 88 | Q$^1$ is 2,4-di-F—Ph, X is O, R$^1$ and R$^{1a}$ are both H, and R$^2$ is Me. |
| 89 | Q$^1$ is 2,4-di-F—Ph, X is O, R$^1$ and R$^{1a}$ are both H, and R$^2$ is Cl. |
| 90 | Q$^1$ is 2,4-di-F—Ph, X is O, R$^1$ and R$^{1a}$ are both H, and R$^2$ is Br. |
| 91 | Q$^1$ is 2,4,6-tri-F—Ph, X is O, R$^1$ and R$^{1a}$ are both H, and R$^2$ is Me. |
| 92 | Q$^1$ is 2,4,6-tri-F—Ph, X is O, R$^1$ and R$^{1a}$ are both H, and R$^2$ is Cl. |
| 93 | Q$^1$ is 2,4,6-tri-F—Ph, X is O, R$^1$ and R$^{1a}$ are both H, and R$^2$ is Br. |
| 94 | Q$^1$ is 2,6-di-F-4-OMe—Ph, X is O, R$^1$ and R$^{1a}$ are both H, and R$^2$ is Me. |
| 95 | Q$^1$ is 2,6-di-F-4-OMe—Ph, X is O, R$^1$ and R$^{1a}$ are both H, and R$^2$ is Cl. |
| 96 | Q$^1$ is 2,6-di-F-4-OMe—Ph, X is O, R$^1$ and R$^{1a}$ are both H, and R$^2$ is Br. |
| 96A | Q$^1$ is 2,6-di-F-4-OEt—Ph, X is O, R$^1$ and R$^{1a}$ are both H, and R$^2$ is Me. |
| 96B | Q$^1$ is 2,6-di-F-4-OEt—Ph, X is O, R$^1$ and R$^{1a}$ are both H, and R$^2$ is Cl. |
| 96C | Q$^1$ is 2,6-di-F-4-OEt—Ph, X is O, R$^1$ and R$^{1a}$ are both H, and R$^2$ is Br. |
| 97 | Q$^1$ is 2,6-di-F-4-CN—Ph, X is O, R$^1$ and R$^{1a}$ are both H, and R$^2$ is Me. |
| 98 | Q$^1$ is 2,6-di-F-4-CN—Ph, X is O, R$^1$ and R$^{1a}$ are both H, and R$^2$ is Cl. |
| 99 | Q$^1$ is 2,6-di-F-4-CN—Ph, X is O, R$^1$ and R$^{1a}$ are both H, and R$^2$ is Br. |
| 100 | Q$^1$ is 2-Cl-4-F—Ph, X is O, R$^1$ and R$^{1a}$ are both H, and R$^2$ is Me. |
| 101 | Q$^1$ is 2-Cl-4-F—Ph, X is O, R$^1$ and R$^{1a}$ are both H, and R$^2$ is Cl. |
| 102 | Q$^1$ is 2-Cl-4-F—Ph, X is O, R$^1$ and R$^{1a}$ are both H, and R$^2$ is Br. |
| 103 | Q$^1$ is 2-Cl-6-F—Ph, X is O, R$^1$ and R$^{1a}$ are both H, and R$^2$ is Me. |
| 104 | Q$^1$ is 2-Cl-6-F—Ph, X is O, R$^1$ and R$^{1a}$ are both H, and R$^2$ is Cl. |
| 105 | Q$^1$ is 2-Cl-6-F—Ph, X is O, R$^1$ and R$^{1a}$ are both H, and R$^2$ is Br. |
| 106 | Q$^1$ is 2-Cl-4,6-di-F—Ph, X is O, R$^1$ and R$^{1a}$ are both H, and R$^2$ is Me. |
| 107 | Q$^1$ is 2-Cl-4,6-di-F—Ph, X is O, R$^1$ and R$^{1a}$ are both H, and R$^2$ is Cl. |
| 108 | Q$^1$ is 2-Cl-4,6-di-F—Ph, X is O, R$^1$ and R$^{1a}$ are both H, and R$^2$ is Br. |
| 109 | Q$^1$ is 4-Cl-2,6-di-F—Ph, X is O, R$^1$ and R$^{1a}$ are both H, and R$^2$ is Me. |
| 110 | Q$^1$ is 4-Cl-2,6-di-F—Ph, X is O, R$^1$ and R$^{1a}$ are both H, and R$^2$ is Cl. |
| 111 | Q$^1$ is 4-Cl-2,6-di-F—Ph, X is O, R$^1$ and R$^{1a}$ are both H, and R$^2$ is Br. |
| 112 | Q$^1$ is 2-Br-4-F—Ph, X is O, R$^1$ and R$^{1a}$ are both H, and R$^2$ is Me. |
| 113 | Q$^1$ is 2-Br-4-F—Ph, X is O, R$^1$ and R$^{1a}$ are both H, and R$^2$ is Cl. |
| 114 | Q$^1$ is 2-Br-4-F—Ph, X is O, R$^1$ and R$^{1a}$ are both H, and R$^2$ is Br. |
| 115 | Q$^1$ is 2-Br-6-F—Ph, X is O, R$^1$ and R$^{1a}$ are both H, and R$^2$ is Me. |
| 116 | Q$^1$ is 2-Br-6-F—Ph, X is O, R$^1$ and R$^{1a}$ are both H, and R$^2$ is Cl. |
| 117 | Q$^1$ is 2-Br-6-F—Ph, X is O, R$^1$ and R$^{1a}$ are both H, and R$^2$ is Br. |
| 118 | Q$^1$ is 2-Me-4-F—Ph, X is O, R$^1$ and R$^{1a}$ are both H, and R$^2$ is Me. |
| 119 | Q$^1$ is 2-Me-4-F—Ph, X is O, R$^1$ and R$^{1a}$ are both H, and R$^2$ is Cl. |
| 120 | Q$^1$ is 2-Me-4-F—Ph, X is O, R$^1$ and R$^{1a}$ are both H, and R$^2$ is Br. |
| 121 | Q$^1$ is 2-I-4-F—Ph, X is O, R$^1$ and R$^{1a}$ are both H, and R$^2$ is Me. |
| 122 | Q$^1$ is 2-I-4-F—Ph, X is O, R$^1$ and R$^{1a}$ are both H, and R$^2$ is Cl. |
| 123 | Q$^1$ is 2-I-4-F—Ph, X is O, R$^1$ and R$^{1a}$ are both H, and R$^2$ is Br. |
| 124 | Q$^1$ is 2-F—Ph, X is O, R$^1$ and R$^{1a}$ are both H, and R$^2$ is Me. |
| 125 | Q$^1$ is 2-F—Ph, X is O, R$^1$ and R$^{1a}$ are both H, and R$^2$ is Cl. |
| 126 | Q$^1$ is 2-F—Ph, X is O, R$^1$ and R$^{1a}$ are both H, and R$^2$ is Br. |

| Table | Row Heading |
|---|---|
| 127 | $Q^1$ is 2-Cl—Ph, X is O, $R^1$ and $R^{1a}$ are both H, and $R^2$ is Me. |
| 128 | $Q^1$ is 2-Cl—Ph, X is O, $R^1$ and $R^{1a}$ are both H, and $R^2$ is Cl. |
| 129 | $Q^1$ is 2-Cl—Ph, X is O, $R^1$ and $R^{1a}$ are both H, and $R^2$ is Br. |
| 130 | $Q^1$ is 2-Br—Ph, X is O, $R^1$ and $R^{1a}$ are both H, and $R^2$ is Me. |
| 131 | $Q^1$ is 2-Br—Ph, X is O, $R^1$ and $R^{1a}$ are both H, and $R^2$ is Cl. |
| 132 | $Q^1$ is 2-Br—Ph, X is O, $R^1$ and $R^{1a}$ are both H, and $R^2$ is Br. |
| 133 | $Q^1$ is 2-F-4-Cl—Ph, X is O, $R^1$ and $R^{1a}$ are both H, and $R^2$ is Me. |
| 134 | $Q^1$ is 2-F-4-Cl—Ph, X is O, $R^1$ and $R^{1a}$ are both H, and $R^2$ is Cl. |
| 135 | $Q^1$ is 2-F-4-Cl—Ph, X is O, $R^1$ and $R^{1a}$ are both H, and $R^2$ is Br. |
| 136 | $Q^1$ is 2,4-di-Cl—Ph, X is O, $R^1$ and $R^{1a}$ are both H, and $R^2$ is Me. |
| 137 | $Q^1$ is 2,4-di-Cl—Ph, X is O, $R^1$ and $R^{1a}$ are both H, and $R^2$ is Cl. |
| 138 | $Q^1$ is 2,4-di-Cl—Ph, X is O, $R^1$ and $R^{1a}$ are both H, and $R^2$ is Br. |
| 139 | $Q^1$ is 2,6-di-Cl—Ph, X is O, $R^1$ and $R^{1a}$ are both H, and $R^2$ is Me. |
| 140 | $Q^1$ is 2,6-di-Cl—Ph, X is O, $R^1$ and $R^{1a}$ are both H, and $R^2$ is Cl. |
| 141 | $Q^1$ is 2,6-di-Cl—Ph, X is O, $R^1$ and $R^{1a}$ are both H, and $R^2$ is Br. |
| 142 | $Q^1$ is 2-F-4-MeO—Ph, X is O, $R^1$ and $R^{1a}$ are both H, and $R^2$ is Me. |
| 143 | $Q^1$ is 2-F-4-MeO—Ph, X is O, $R^1$ and $R^{1a}$ are both H, and $R^2$ is Cl. |
| 144 | $Q^1$ is 2-F-4-MeO—Ph, X is O, $R^1$ and $R^{1a}$ are both H, and $R^2$ is Br. |
| 144A | $Q^1$ is 2-F-4-EtO—Ph, X is O, $R^1$ and $R^{1a}$ are both H, and $R^2$ is Me. |
| 144B | $Q^1$ is 2-F-4-EtO—Ph, X is O, $R^1$ and $R^{1a}$ are both H, and $R^2$ is Cl. |
| 144C | $Q^1$ is 2-F-4-EtO—Ph, X is O, $R^1$ and $R^{1a}$ are both H, and $R^2$ is Br. |
| 145 | $Q^1$ is 2-Cl-4-MeO—Ph, X is O, $R^1$ and $R^{1a}$ are both H, and $R^2$ is Me. |
| 146 | $Q^1$ is 2-Cl-4-MeO—Ph, X is O, $R^1$ and $R^{1a}$ are both H, and $R^2$ is Cl. |
| 147 | $Q^1$ is 2-Cl-4-MeO—Ph, X is O, $R^1$ and $R^{1a}$ are both H, and $R^2$ is Br. |
| 147A | $Q^1$ is 2-Cl-4-EtO—Ph, X is O, $R^1$ and $R^{1a}$ are both H, and $R^2$ is Me. |
| 147B | $Q^1$ is 2-Cl-4-EtO—Ph, X is O, $R^1$ and $R^{1a}$ are both H, and $R^2$ is Cl. |
| 147C | $Q^1$ is 2-Cl-4-EtO—Ph, X is O, $R^1$ and $R^{1a}$ are both H, and $R^2$ is Br. |
| 148 | $Q^1$ is 2-Br-4-MeO—Ph, X is O, $R^1$ and $R^{1a}$ are both H, and $R^2$ is Me. |
| 149 | $Q^1$ is 2-Br-4-MeO—Ph, X is O, $R^1$ and $R^{1a}$ are both H, and $R^2$ is Cl. |
| 150 | $Q^1$ is 2-Br-4-MeO—Ph, X is O, $R^1$ and $R^{1a}$ are both H, and $R^2$ is Br. |
| 150A | $Q^1$ is 2-Br-4-EtO—Ph, X is O, $R^1$ and $R^{1a}$ are both H, and $R^2$ is Me. |
| 150B | $Q^1$ is 2-Br-4-EtO—Ph, X is O, $R^1$ and $R^{1a}$ are both H, and $R^2$ is Cl. |
| 150C | $Q^1$ is 2-Br-4-EtO—Ph, X is O, $R^1$ and $R^{1a}$ are both H, and $R^2$ is Br. |
| 151 | $Q^1$ is 2-F-4-CN—Ph, X is O, $R^1$ and $R^{1a}$ are both H, and $R^2$ is Me. |
| 152 | $Q^1$ is 2-F-4-CN—Ph, X is O, $R^1$ and $R^{1a}$ are both H, and $R^2$ is Cl. |
| 153 | $Q^1$ is 2-F-4-CN—Ph, X is O, $R^1$ and $R^{1a}$ are both H, and $R^2$ is Br. |
| 154 | $Q^1$ is 2-Cl-4-CN—Ph, X is O, $R^1$ and $R^{1a}$ are both H, and $R^2$ is Me. |
| 155 | $Q^1$ is 2-Cl-4-CN—Ph, X is O, $R^1$ and $R^{1a}$ are both H, and $R^2$ is Cl. |
| 156 | $Q^1$ is 2-Cl-4-CN—Ph, X is O, $R^1$ and $R^{1a}$ are both H, and $R^2$ is Br. |
| 157 | $Q^1$ is 2-Br-4-CN—Ph, X is O, $R^1$ and $R^{1a}$ are both H, and $R^2$ is Me. |
| 158 | $Q^1$ is 2-Br-4-CN—Ph, X is O, $R^1$ and $R^{1a}$ are both H, and $R^2$ is Cl. |
| 159 | $Q^1$ is 2-Br-4-CN—Ph, X is O, $R^1$ and $R^{1a}$ are both H, and $R^2$ is Br. |
| 160 | $Q^1$ is 2,5-di-Cl-3-pyridinyl, X is O, $R^1$ and $R^{1a}$ are both H, and $R^2$ is Me. |
| 161 | $Q^1$ is 2,5-di-Cl-3-pyridinyl, X is O, $R^1$ and $R^{1a}$ are both H, and $R^2$ is Cl. |
| 162 | $Q^1$ is 2,5-di-Cl-3-pyridinyl, X is O, $R^1$ and $R^{1a}$ are both H, and $R^2$ is Br. |
| 163 | $Q^1$ is 2-Cl-3-thienyl, X is O, $R^1$ and $R^{1a}$ are both H, and $R^2$ is Me. |
| 164 | $Q^1$ is 2-Cl-3-thienyl, X is O, $R^1$ and $R^{1a}$ are both H, and $R^2$ is Cl. |
| 165 | $Q^1$ is 2-Cl-3-thienyl, X is O, $R^1$ and $R^{1a}$ are both H, and $R^2$ is Br. |
| 166 | $Q^1$ is 2,5-di-Cl-3-thienyl, X is O, $R^1$ and $R^{1a}$ are both H, and $R^2$ is Me. |
| 167 | $Q^1$ is 2,5-di-Cl-3-thienyl, X is O, $R^1$ and $R^{1a}$ are both H, and $R^2$ is Cl. |
| 168 | $Q^1$ is 2,5-di-Cl-3-thienyl, X is O, $R^1$ and $R^{1a}$ are both H, and $R^2$ is Br. |
| 169 | $Q^1$ is 2,6-di-F—Ph, X is S, $R^1$ and $R^{1a}$ are both H, and $R^2$ is Me. |
| 170 | $Q^1$ is 2,6-di-F—Ph, X is S, $R^1$ and $R^{1a}$ are both H, and $R^2$ is Cl. |
| 171 | $Q^1$ is 2,6-di-F—Ph, X is S, $R^1$ and $R^{1a}$ are both H, and $R^2$ is Br. |
| 172 | $Q^1$ is 2,4-di-F—Ph, X is S, $R^1$ and $R^{1a}$ are both H, and $R^2$ is Me. |
| 173 | $Q^1$ is 2,4-di-F—Ph, X is S, $R^1$ and $R^{1a}$ are both H, and $R^2$ is Cl. |
| 174 | $Q^1$ is 2,4-di-F—Ph, X is S, $R^1$ and $R^{1a}$ are both H, and $R^2$ is Br. |
| 175 | $Q^1$ is 2,4,6-tri-F—Ph, X is S, $R^1$ and $R^{1a}$ are both H, and $R^2$ is Me. |
| 176 | $Q^1$ is 2,4,6-tri-F—Ph, X is S, $R^1$ and $R^{1a}$ are both H, and $R^2$ is Cl. |
| 177 | $Q^1$ is 2,4,6-tri-F—Ph, X is S, $R^1$ and $R^{1a}$ are both H, and $R^2$ is Br. |
| 178 | $Q^1$ is 2,6-di-F-4-OMe—Ph, X is S, $R^1$ and $R^{1a}$ are both H, and $R^2$ is Me. |
| 179 | $Q^1$ is 2,6-di-F-4-OMe—Ph, X is S, $R^1$ and $R^{1a}$ are both H, and $R^2$ is Cl. |
| 180 | $Q^1$ is 2,6-di-F-4-OMe—Ph, X is S, $R^1$ and $R^{1a}$ are both H, and $R^2$ is Br. |
| 180A | $Q^1$ is 2,6-di-F-4-OEt—Ph, X is S, $R^1$ and $R^{1a}$ are both H, and $R^2$ is Me. |
| 180B | $Q^1$ is 2,6-di-F-4-OEt—Ph, X is S, $R^1$ and $R^{1a}$ are both H, and $R^2$ is Cl. |
| 180C | $Q^1$ is 2,6-di-F-4-OEt—Ph, X is S, $R^1$ and $R^{1a}$ are both H, and $R^2$ is Br. |
| 181 | $Q^1$ is 2,6-di-F-4-CN—Ph, X is S, $R^1$ and $R^{1a}$ are both H, and $R^2$ is Me. |
| 182 | $Q^1$ is 2,6-di-F-4-CN—Ph, X is S, $R^1$ and $R^{1a}$ are both H, and $R^2$ is Cl. |
| 183 | $Q^1$ is 2,6-di-F-4-CN—Ph, X is S, $R^1$ and $R^{1a}$ are both H, and $R^2$ is Br. |
| 184 | $Q^1$ is 2-Cl-4-F—Ph, X is S, $R^1$ and $R^{1a}$ are both H, and $R^2$ is Me. |
| 185 | $Q^1$ is 2-Cl-4-F—Ph, X is S, $R^1$ and $R^{1a}$ are both H, and $R^2$ is Cl. |
| 186 | $Q^1$ is 2-Cl-4-F—Ph, X is S, $R^1$ and $R^{1a}$ are both H, and $R^2$ is Br. |
| 187 | $Q^1$ is 2-Cl-6-F—Ph, X is S, $R^1$ and $R^{1a}$ are both H, and $R^2$ is Me. |
| 188 | $Q^1$ is 2-Cl-6-F—Ph, X is S, $R^1$ and $R^{1a}$ are both H, and $R^2$ is Cl. |
| 189 | $Q^1$ is 2-Cl-6-F—Ph, X is S, $R^1$ and $R^{1a}$ are both H, and $R^2$ is Br. |
| 190 | $Q^1$ is 2-Cl-4,6-di-F—Ph, X is S, $R^1$ and $R^{1a}$ are both H, and $R^2$ is Me. |
| 191 | $Q^1$ is 2-Cl-4,6-di-F—Ph, X is S, $R^1$ and $R^{1a}$ are both H, and $R^2$ is Cl. |

| Table | Row Heading |
|---|---|
| 192 | Q¹ is 2-Cl-4,6-di-F—Ph, X is S, R¹ and R^{1a} are both H, and R² is Br. |
| 193 | Q¹ is 4-Cl-2,6-di-F—Ph, X is S, R¹ and R^{1a} are both H, and R² is Me. |
| 194 | Q¹ is 4-Cl-2,6-di-F—Ph, X is S, R¹ and R^{1a} are both H, and R² is Cl. |
| 195 | Q¹ is 4-Cl-2,6-di-F—Ph, X is S, R¹ and R^{1a} are both H, and R² is Br. |
| 196 | Q¹ is 2-Br-4-F—Ph, X is S, R¹ and R^{1a} are both H, and R² is Me. |
| 197 | Q¹ is 2-Br-4-F—Ph, X is S, R¹ and R^{1a} are both H, and R² is Cl. |
| 198 | Q¹ is 2-Br-4-F—Ph, X is S, R¹ and R^{1a} are both H, and R² is Br. |
| 199 | Q¹ is 2-Br-6-F—Ph, X is S, R¹ and R^{1a} are both H, and R² is Me. |
| 200 | Q¹ is 2-Br-6-F—Ph, X is S, R¹ and R^{1a} are both H, and R² is Cl. |
| 201 | Q¹ is 2-Br-6-F—Ph, X is S, R¹ and R^{1a} are both H, and R² is Br. |
| 202 | Q¹ is 2-Me-4-F—Ph, X is S, R¹ and R^{1a} are both H, and R² is Me. |
| 203 | Q¹ is 2-Me-4-F—Ph, X is S, R¹ and R^{1a} are both H, and R² is Cl. |
| 204 | Q¹ is 2-Me-4-F—Ph, X is S, R¹ and R^{1a} are both H, and R² is Br. |
| 205 | Q¹ is 2-I-4-F—Ph, X is S, R¹ and R^{1a} are both H, and R² is Me. |
| 206 | Q¹ is 2-I-4-F—Ph, X is S, R¹ and R^{1a} are both H, and R² is Cl. |
| 207 | Q¹ is 2-I-4-F—Ph, X is S, R¹ and R^{1a} are both H, and R² is Br. |
| 208 | Q¹ is 2-F—Ph, X is S, R¹ and R^{1a} are both H, and R² is Me. |
| 209 | Q¹ is 2-F—Ph, X is S, R¹ and R^{1a} are both H, and R² is Cl. |
| 210 | Q¹ is 2-F—Ph, X is S, R¹ and R^{1a} are both H, and R² is Br. |
| 211 | Q¹ is 2-Cl—Ph, X is S, R¹ and R^{1a} are both H, and R² is Me. |
| 212 | Q¹ is 2-Cl—Ph, X is S, R¹ and R^{1a} are both H, and R² is Cl. |
| 213 | Q¹ is 2-Cl—Ph, X is S, R¹ and R^{1a} are both H, and R² is Br. |
| 214 | Q¹ is 2-Br—Ph, X is S, R¹ and R^{1a} are both H, and R² is Me. |
| 215 | Q¹ is 2-Br—Ph, X is S, R¹ and R^{1a} are both H, and R² is Cl. |
| 216 | Q¹ is 2-Br—Ph, X is S, R¹ and R^{1a} are both H, and R² is Br. |
| 217 | Q¹ is 2-F-4-Cl—Ph, X is S, R¹ and R^{1a} are both H, and R² is Me. |
| 218 | Q¹ is 2-F-4-Cl—Ph, X is S, R¹ and R^{1a} are both H, and R² is Cl. |
| 219 | Q¹ is 2-F-4-Cl—Ph, X is S, R¹ and R^{1a} are both H, and R² is Br. |
| 220 | Q¹ is 2,4-di-Cl—Ph, X is S, R¹ and R^{1a} are both H, and R² is Me. |
| 221 | Q¹ is 2,4-di-Cl—Ph, X is S, R¹ and R^{1a} are both H, and R² is Cl. |
| 222 | Q¹ is 2,4-di-Cl—Ph, X is S, R¹ and R^{1a} are both H, and R² is Br. |
| 223 | Q¹ is 2,6-di-Cl—Ph, X is S, R¹ and R^{1a} are both H, and R² is Me. |
| 224 | Q¹ is 2,6-di-Cl—Ph, X is S, R¹ and R^{1a} are both H, and R² is Cl. |
| 225 | Q¹ is 2,6-di-Cl—Ph, X is S, R¹ and R^{1a} are both H, and R² is Br. |
| 226 | Q¹ is 2-F-4-MeO—Ph, X is S, R¹ and R^{1a} are both H, and R² is Me. |
| 227 | Q¹ is 2-F-4-MeO—Ph, X is S, R¹ and R^{1a} are both H, and R² is Cl. |
| 228 | Q¹ is 2-F-4-MeO—Ph, X is S, R¹ and R^{1a} are both H, and R² is Br. |
| 228A | Q¹ is 2-F-4-EtO—Ph, X is S, R¹ and R^{1a} are both H, and R² is Me. |
| 228B | Q¹ is 2-F-4-EtO—Ph, X is S, R¹ and R^{1a} are both H, and R² is Cl. |
| 228C | Q¹ is 2-F-4-EtO—Ph, X is S, R¹ and R^{1a} are both H, and R² is Br. |
| 229 | Q¹ is 2-Cl-4-MeO—Ph, X is S, R¹ and R^{1a} are both H, and R² is Me. |
| 230 | Q¹ is 2-Cl-4-MeO—Ph, X is S, R¹ and R^{1a} are both H, and R² is Cl. |
| 231 | Q¹ is 2-Cl-4-MeO—Ph, X is S, R¹ and R^{1a} are both H, and R² is Br. |
| 231A | Q¹ is 2-Cl-4-EtO—Ph, X is S, R¹ and R^{1a} are both H, and R² is Me. |
| 231B | Q¹ is 2-Cl-4-EtO—Ph, X is S, R¹ and R^{1a} are both H, and R² is Cl. |
| 231C | Q¹ is 2-Cl-4-EtO—Ph, X is S, R¹ and R^{1a} are both H, and R² is Br. |
| 232 | Q¹ is 2-Br-4-MeO—Ph, X is S, R¹ and R^{1a} are both H, and R² is Me. |
| 233 | Q¹ is 2-Br-4-MeO—Ph, X is S, R¹ and R^{1a} are both H, and R² is Cl. |
| 234 | Q¹ is 2-Br-4-MeO—Ph, X is S, R¹ and R^{1a} are both H, and R² is Br. |
| 234A | Q¹ is 2-Br-4-EtO—Ph, X is S, R¹ and R^{1a} are both H, and R² is Me. |
| 234B | Q¹ is 2-Br-4-EtO—Ph, X is S, R¹ and R^{1a} are both H, and R² is Cl. |
| 234C | Q¹ is 2-Br-4-EtO—Ph, X is S, R¹ and R^{1a} are both H, and R² is Br. |
| 235 | Q¹ is 2-F-4-CN—Ph, X is S, R¹ and R^{1a} are both H, and R² is Me. |
| 236 | Q¹ is 2-F-4-CN—Ph, X is S, R¹ and R^{1a} are both H, and R² is Cl. |
| 237 | Q¹ is 2-F-4-CN—Ph, X is S, R¹ and R^{1a} are both H, and R² is Br. |
| 238 | Q¹ is 2-Cl-4-CN—Ph, X is S, R¹ and R^{1a} are both H, and R² is Me. |
| 239 | Q¹ is 2-Cl-4-CN—Ph, X is S, R¹ and R^{1a} are both H, and R² is Cl. |
| 240 | Q¹ is 2-Cl-4-CN—Ph, X is S, R¹ and R^{1a} are both H, and R² is Br. |
| 241 | Q¹ is 2-Br-4-CN—Ph, X is S, R¹ and R^{1a} are both H, and R² is Me. |
| 242 | Q¹ is 2-Br-4-CN—Ph, X is S, R¹ and R^{1a} are both H, and R² is Cl. |
| 243 | Q¹ is 2-Br-4-CN—Ph, X is S, R¹ and R^{1a} are both H, and R² is Br. |
| 244 | Q¹ is 2,5-di-Cl-3-pyridinyl, X is S, R¹ and R^{1a} are both H, and R² is Me. |
| 245 | Q¹ is 2,5-di-Cl-3-pyridinyl, X is S, R¹ and R^{1a} are both H, and R² is Cl. |
| 246 | Q¹ is 2,5-di-Cl-3-pyridinyl, X is S, R¹ and R^{1a} are both H, and R² is Br. |
| 247 | Q¹ is 2-Cl-3-thienyl, X is S, R¹ and R^{1a} are both H, and R² is Me. |
| 248 | Q¹ is 2-Cl-3-thienyl, X is S, R¹ and R^{1a} are both H, and R² is Cl. |
| 249 | Q¹ is 2-Cl-3-thienyl, X is S, R¹ and R^{1a} are both H, and R² is Br. |
| 250 | Q¹ is 2,5-di-Cl-3-thienyl, X is S, R¹ and R^{1a} are both H, and R² is Me. |
| 251 | Q¹ is 2,5-di-Cl-3-thienyl, X is S, R¹ and R^{1a} are both H, and R² is Cl. |
| 252 | Q¹ is 2,5-di-Cl-3-thienyl, X is S, R¹ and R^{1a} are both H, and R² is Br. |
| 253 | Q¹ is 2,6-di-F—Ph, X is NH, R¹ and R^{1a} form c-Pr, and R² is Me. |
| 254 | Q¹ is is 2,4-di-F—Ph, X is O, R¹ is Et, R^{1a} is H, and R² is Cl. |
| 255 | Q¹ is 2,4,6-tri-F—Ph, X is S, R¹ and R^{1a} are both H, and R² is Et. |
| 256 | Q¹ is is 2,6-di-F-4-OMe—Ph, X is CHOH, R¹ |
| 257 | Q¹ is is 2,6-di-F-4-CN—Ph, X is NH, R¹ is CH=CH2, R^{1a} is H, and R² is Cl. |
| 258 | Q¹ is 2-Cl-4-F—Ph, X is CHOH, X is O, R¹ is c-Pr, R^{1a} is H, and R² is Br. |
| 259 | Q¹ is 2-Cl-6-F—Ph, X is S, R¹ and R^{1a} form c-Pr, and R² is Me. |

| Table | Row Heading |
|---|---|
| 260 | Q$^1$ is 2-Cl-4,6-di-F—Ph, X is CHOH, R$^1$ is c-Pr, R$^{1a}$ is H, and R$^2$ is Cl. |
| 261 | Q$^1$ is 4-Cl-2,6-di-F—Ph, X is NH, X is NH, R$^1$ is Et, R$^{1a}$ is H, and R$^2$ is Br. |
| 262 | Q$^1$ is 2-Br-4-F—Ph, X is O, R$^1$ and R$^{1a}$ both H, and R$^2$ is Et. |
| 263 | Q$^1$ is 2-Br-6-F—Ph, X is S, R$^1$ is CH$_2$CH=CH$_2$, R$^{1a}$ is H, and R$^2$ is Cl. |
| 264 | Q$^1$ is 2-Me-4-F—Ph, X is CHOH, R$^1$ and R$^{1a}$ are both H, and R$^2$ is c-Pr. |
| 265 | Q$^1$ is 2-I-4-F—Ph, X is NH, R$^1$ is CH$_2$CF$_3$, R$^{1a}$ is H, and R$^2$ is Me. |
| 266 | Q$^1$ is 2-F—Ph, X is O, R$^1$ is CH$_2$F, R$^{1a}$ is H, and R$^2$ is Cl. |
| 267 | Q$^1$ is 2-Cl—Ph, X is S, R$^1$ and R$^{1a}$ are both H, and R$^2$ is CH$_2$Cl. |
| 268 | Q$^1$ is 2-Br—Ph, X is CHCH$_3$, R$^1$ and R$^{1a}$ are both H, and R$^2$ is Me. |
| 269 | Q$^1$ is 2-F-4-Cl—Ph, X is C(CH$_3$)OH, R$^1$ and R$^{1a}$ are both H, and R$^2$ is Me. |
| 270 | Q$^1$ is 2,4-di-Cl—Ph, X is O, R$^1$ is Et, R$^{1a}$ is H, and R$^2$ is Br. |
| 271 | Q$^1$ is 2,6-di-Cl—Ph, X is S, R$^1$ and R$^{1a}$ are both H, and R$^2$ is OMe. |
| 272 | Q$^1$ is 2-F-4-MeO—Ph, X is CHOCH$_3$, R$^1$ and R$^{1a}$ are both H, and R$^2$ is Cl. |
| 273 | Q$^1$ is 2-Cl-4-MeO—Ph, X is NH, R$^1$ and R$^{1a}$ form c-Pr, and R$^2$ is Br. |
| 274 | Q$^1$ is 2-Br-4-MeO—Ph, X is O, R$^1$ is n-Pr, R$^{1a}$ is H, and R$^2$ is Me. |
| 275 | Q$^1$ is 2-F-4-CN—Ph, X is NH, R$^1$ is CH$_2$CCH, R$^{1a}$ is H, and R$^2$ is Cl. |
| 276 | Q$^1$ is 2-Cl-4-CN—Ph, X is C(OCH$_3$)$_2$, R$^1$ and R$^{1a}$ are both H, and R$^2$ is Br. |
| 277 | Q$^1$ is 2-Br-4-CN—Ph, X is NH, R$^1$ and R$^{1a}$ form c-Pr, and R$^2$ is Me. |
| 278 | Q$^1$ is 2,5-di-Cl-3-pyridinyl, X is O, R$^1$ is c-Pr, R$^{1a}$ is H, and R$^2$ is Cl. |
| 279 | Q$^1$ is 2-Cl-3-thienyl, X is S, R$^1$ and R$^{1a}$ are both H, and R$^2$ is Et. |
| 280 | Q$^1$ is 2,5-di-Cl-3-thienyl, X is CHOH, R$^1$ is Et, R$^{1a}$ is H, and R$^2$ is Me. |

TABLE 281

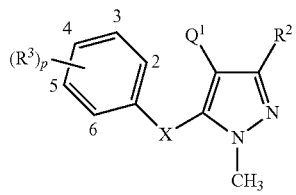

Q$^1$ is 2,6-di-F-Ph, X is CHOH, and R$^2$ is Me.

(R$^3$)$_p$

4-F
4-Cl
4-Br
4-Me
2,4-di-F
2,6-di-F
2,4-di-Cl
2,6-di-Cl
2-Cl-4-F
2-F-4-Cl
2-F-4-Br
2-Br-6-F
2-Cl-4-Br
2-Br-4-Cl
2-I-4-F
2-F-4-I
2-Cl-4,6-di-F
4-Cl-2,6-di-F
2-Br-4,6-di-F
4-Br-2,6-di-F
2-Br-4-F
2-Me-4-F
2,4,6-tri-F
2-Cl-4,5-di-F
4-Cl-2,5-di-F
2-F-4-CN
2-Cl-4-CN
2-Br-4-CN
2,6-diF-4-CN
2-F-4-MeO
2-Cl-4-MeO
2-Br-4-MeO
2,6-di-F-4-MeO
4-Br-2,5-di-F
2-Br-4,5-di-F The present disclosure also includes Tables 282 through 448, each of which is constructed the same as Table 281 above, except that the row heading in Table 281 (i.e. "Q$^1$ is 2,6-di-F-Ph, X is CHOH, and R$^2$ is Me.") is replaced with the respective row heading shown below. For Example, in Table 282 the row heading is "Q$^1$ is 2,6-di-F-Ph, X is CHOH, and R$^2$ is Cl." and (R$^3$)$_p$ is as defined in Table 281 above. Thus, the first entry in Table 282 specifically discloses 3-chloro-4-(2,6-difluorophenyl)-α-(4-fluorophenyl)-1-methyl-1H-pyrazole-5-methanol. Tables 283 through 448 are constructed similarly.

| Table | Row Heading |
|---|---|
| 282 | Q$^1$ is 2,6-di-F—Ph, X is CHOH, and R$^2$ is Cl. |
| 283 | Q$^1$ is 2,6-di-F—Ph, X is CHOH, and R$^2$ is Br. |
| 284 | Q$^1$ is 2,4-di-F—Ph, X is CHOH, and R$^2$ is Me. |
| 285 | Q$^1$ is 2,4-di-F—Ph, X is CHOH, and R$^2$ is Cl. |
| 286 | Q$^1$ is 2,4-di-F—Ph, X is CHOH, and R$^2$ is Br. |
| 287 | Q$^1$ is 2,4,6-tri-F—Ph, X is CHOH, and R$^2$ is Me. |
| 288 | Q$^1$ is 2,4,6-tri-F—Ph, X is CHOH, and R$^2$ is Cl. |
| 289 | Q$^1$ is 2,4,6-tri-F—Ph, X is CHOH, and R$^2$ is Br. |
| 290 | Q$^1$ is 2,6-di-F-4-OMe—Ph, X is CHOH, and R$^2$ is Me. |
| 291 | Q$^1$ is 2,6-di-F-4-OMe—Ph, X is CHOH, and R$^2$ is Cl. |
| 292 | Q$^1$ is 2,6-di-F-4-OMe—Ph, X is CHOH, and R$^2$ is Br. |
| 292A | Q$^1$ is 2,6-di-F-4-OEt—Ph, X is CHOH, and R$^2$ is Me. |
| 292B | Q$^1$ is 2,6-di-F-4-OEt—Ph, X is CHOH, and R$^2$ is Cl. |
| 292C | Q$^1$ is 2,6-di-F-4-OEt—Ph, X is CHOH, and R$^2$ is Br. |
| 293 | Q$^1$ is 2,6-di-F-4-CN—Ph, X is CHOH, and R$^2$ is Me. |
| 294 | Q$^1$ is 2,6-di-F-4-CN—Ph, X is CHOH, and R$^2$ is Cl. |
| 295 | Q$^1$ is 2,6-di-F-4-CN—Ph, X is CHOH, and R$^2$ is Br. |
| 296 | Q$^1$ is 2-Cl-4-F—Ph, X is CHOH, and R$^2$ is Me. |
| 297 | Q$^1$ is 2-Cl-4-F—Ph, X is CHOH, and R$^2$ is Cl. |
| 298 | Q$^1$ is 2-Cl-4-F—Ph, X is CHOH, and R$^2$ is Br. |
| 299 | Q$^1$ is 2-Cl-6-F—Ph, X is CHOH, and R$^2$ is Me. |
| 300 | Q$^1$ is 2-Cl-6-F—Ph, X is CHOH, and R$^2$ is Cl. |
| 301 | Q$^1$ is 2-Cl-6-F—Ph, X is CHOH, and R$^2$ is Br. |
| 302 | Q$^1$ is 2-Cl-4,6-di-F—Ph, X is CHOH, and R$^2$ is Me. |
| 303 | Q$^1$ is 2-Cl-4,6-di-F—Ph, X is CHOH, and R$^2$ is Cl. |
| 304 | Q$^1$ is 2-Cl-4,6-di-F—Ph, X is CHOH, and R$^2$ is Br. |
| 305 | Q$^1$ is 4-Cl-2,6-di-F—Ph, X is CHOH, and R$^2$ is Me. |

| Table | Row Heading |
|---|---|
| 306 | $Q^1$ is 4-Cl-2,6-di-F—Ph, X is CHOH, and $R^2$ is Cl. |
| 307 | $Q^1$ is 4-Cl-2,6-di-F—Ph, X is CHOH, and $R^2$ is Br. |
| 308 | $Q^1$ is 2-Br-4-F—Ph, X is CHOH, and $R^2$ is Me. |
| 309 | $Q^1$ is 2-Br-4-F—Ph, X is CHOH, and $R^2$ is Cl. |
| 310 | $Q^1$ is 2-Br-4-F—Ph, X is CHOH, and $R^2$ is Br. |
| 311 | $Q^1$ is 2-Br-6-F—Ph, X is CHOH, and $R^2$ is Me. |
| 312 | $Q^1$ is 2-Br-6-F—Ph, X is CHOH, and $R^2$ is Cl. |
| 313 | $Q^1$ is 2-Br-6-F—Ph, X is CHOH, and $R^2$ is Br. |
| 314 | $Q^1$ is 2-Me-4-F—Ph, X is CHOH, and $R^2$ is Me. |
| 315 | $Q^1$ is 2-Me-4-F—Ph, X is CHOH, and $R^2$ is Cl. |
| 316 | $Q^1$ is 2-Me-4-F—Ph, X is CHOH, and $R^2$ is Br. |
| 317 | $Q^1$ is 2-I-4-F—Ph, X is CHOH, and $R^2$ is Me. |
| 318 | $Q^1$ is 2-I-4-F—Ph, X is CHOH, and $R^2$ is Cl. |
| 319 | $Q^1$ is 2-I-4-F—Ph, X is CHOH, and $R^2$ is Br. |
| 320 | $Q^1$ is 2-F—Ph, X is CHOH, and $R^2$ is Me. |
| 321 | $Q^1$ is 2-F—Ph, X is CHOH, and $R^2$ is Cl. |
| 322 | $Q^1$ is 2-F—Ph, X is CHOH, and $R^2$ is Br. |
| 323 | $Q^1$ is 2-Cl—Ph, X is CHOH, and $R^2$ is Me. |
| 324 | $Q^1$ is 2-Cl—Ph, X is CHOH, and $R^2$ is Cl. |
| 325 | $Q^1$ is 2-Cl—Ph, X is CHOH, and $R^2$ is Br. |
| 326 | $Q^1$ is 2-Br—Ph, X is CHOH, and $R^2$ is Me. |
| 327 | $Q^1$ is 2-Br—Ph, X is CHOH, and $R^2$ is Cl. |
| 328 | $Q^1$ is 2-Br—Ph, X is CHOH, and $R^2$ is Br. |
| 329 | $Q^1$ is 2-F-4-Cl—Ph, X is CHOH, and $R^2$ is Me. |
| 330 | $Q^1$ is 2-F-4-Cl—Ph, X is CHOH, and $R^2$ is Cl. |
| 331 | $Q^1$ is 2-F-4-Cl—Ph, X is CHOH, and $R^2$ is Br. |
| 332 | $Q^1$ is 2,4-di-Cl—Ph, X is CHOH, and $R^2$ is Me. |
| 333 | $Q^1$ is 2,4-di-Cl—Ph, X is CHOH, and $R^2$ is Cl. |
| 334 | $Q^1$ is 2,4-di-Cl—Ph, X is CHOH, and $R^2$ is Br. |
| 335 | $Q^1$ is 2,6-di-Cl—Ph, X is CHOH, and $R^2$ is Me. |
| 336 | $Q^1$ is 2,6-di-Cl—Ph, X is CHOH, and $R^2$ is Cl. |
| 337 | $Q^1$ is 2,6-di-Cl—Ph, X is CHOH, and $R^2$ is Br. |
| 338 | $Q^1$ is 2-F-4-MeO—Ph, X is CHOH, and $R^2$ is Me. |
| 339 | $Q^1$ is 2-F-4-MeO—Ph, X is CHOH, and $R^2$ is Cl. |
| 340 | $Q^1$ is 2-F-4-MeO—Ph, X is CHOH, and $R^2$ is Br. |
| 340A | $Q^1$ is 2-F-4-EtO—Ph, X is CHOH, and $R^2$ is Me. |
| 340B | $Q^1$ is 2-F-4-EtO—Ph, X is CHOH, and $R^2$ is Cl. |
| 340C | $Q^1$ is 2-F-4-EtO—Ph, X is CHOH, and $R^2$ is Br. |
| 341 | $Q^1$ is 2-Cl-4-MeO—Ph, X is CHOH, and $R^2$ is Me. |
| 342 | $Q^1$ is 2-Cl-4-MeO—Ph, X is CHOH, and $R^2$ is Cl. |
| 343 | $Q^1$ is 2-Cl-4-MeO—Ph, X is CHOH, and $R^2$ is Br. |
| 343A | $Q^1$ is 2-Cl-4-EtO—Ph, X is CHOH, and $R^2$ is Me. |
| 343B | $Q^1$ is 2-Cl-4-EtO—Ph, X is CHOH, and $R^2$ is Cl. |
| 343C | $Q^1$ is 2-Cl-4-EtO—Ph, X is CHOH, and $R^2$ is Br. |
| 344 | $Q^1$ is 2-Br-4-MeO—Ph, X is CHOH, and $R^2$ is Me. |
| 345 | $Q^1$ is 2-Br-4-MeO—Ph, X is CHOH, and $R^2$ is Cl. |
| 346 | $Q^1$ is 2-Br-4-MeO—Ph, X is CHOH, and $R^2$ is Br. |
| 346A | $Q^1$ is 2-Br-4-EtO—Ph, X is CHOH, and $R^2$ is Me. |
| 346B | $Q^1$ is 2-Br-4-EtO—Ph, X is CHOH, and $R^2$ is Cl. |
| 346C | $Q^1$ is 2-Br-4-EtO—Ph, X is CHOH, and $R^2$ is Br. |
| 347 | $Q^1$ is 2-F-4-CN—Ph, X is CHOH, and $R^2$ is Me. |
| 348 | $Q^1$ is 2-F-4-CN—Ph, X is CHOH, and $R^2$ is Cl. |
| 349 | $Q^1$ is 2-F-4-CN—Ph, X is CHOH, and $R^2$ is Br. |
| 350 | $Q^1$ is 2-Cl-4-CN—Ph, X is CHOH, and $R^2$ is Me. |
| 351 | $Q^1$ is 2-Cl-4-CN—Ph, X is CHOH, and $R^2$ is Cl. |
| 352 | $Q^1$ is 2-Cl-4-CN—Ph, X is CHOH, and $R^2$ is Br. |
| 353 | $Q^1$ is 2-Br-4-CN—Ph, X is CHOH, and $R^2$ is Me. |
| 354 | $Q^1$ is 2-Br-4-CN—Ph, X is CHOH, and $R^2$ is Cl. |
| 355 | $Q^1$ is 2-Br-4-CN—Ph, X is CHOH, and $R^2$ is Br. |
| 356 | $Q^1$ is 2,5-di-Cl-3-pyridinyl, X is CHOH, and $R^2$ is Me. |
| 357 | $Q^1$ is 2,5-di-Cl-3-pyridinyl, X is CHOH, and $R^2$ is Cl. |
| 358 | $Q^1$ is 2,5-di-Cl-3-pyridinyl, X is CHOH, and $R^2$ is Br. |
| 359 | $Q^1$ is 2-Cl-3-thienyl, X is CHOH, and $R^2$ is Me. |
| 360 | $Q^1$ is 2-Cl-3-thienyl, X is CHOH, and $R^2$ is Cl. |
| 361 | $Q^1$ is 2-Cl-3-thienyl, X is CHOH, and $R^2$ is Br. |
| 362 | $Q^1$ is 2,5-di-Cl-3-thienyl, X is CHOH, and $R^2$ is Me. |
| 363 | $Q^1$ is 2,5-di-Cl-3-thienyl, X is CHOH, and $R^2$ is Cl. |
| 364 | $Q^1$ is 2,5-di-Cl-3-thienyl, X is CHOH, and $R^2$ is Br. |
| 365 | $Q^1$ is 2,6-di-F—Ph, X is C(O), and $R^2$ is Cl. |
| 366 | $Q^1$ is 2,6-di-F—Ph, X is C(O), and $R^2$ is Cl. |
| 367 | $Q^1$ is 2,6-di-F—Ph, X is C(O), and $R^2$ is Br. |
| 368 | $Q^1$ is 2,4-di-F—Ph, X is C(O), and $R^2$ is Me. |
| 369 | $Q^1$ is 2,4-di-F—Ph, X is C(O), and $R^2$ is Cl. |
| 370 | $Q^1$ is 2,4-di-F—Ph, X is C(O), and $R^2$ is Br. |
| 371 | $Q^1$ is 2,4,6-tri-F—Ph, X is C(O), and $R^2$ is Me. |
| 372 | $Q^1$ is 2,4,6-tri-F—Ph, X is C(O), and $R^2$ is Cl. |
| 373 | $Q^1$ is 2,4,6-tri-F—Ph, X is C(O), and $R^2$ is Br. |
| 374 | $Q^1$ is 2,6-di-F-4-OMe—Ph, X is C(O), and $R^2$ is Me. |
| 375 | $Q^1$ is 2,6-di-F-4-OMe—Ph, X is C(O), and $R^2$ is Cl. |
| 376 | $Q^1$ is 2,6-di-F-4-OMe—Ph, X is C(O), and $R^2$ is Br. |
| 376A | $Q^1$ is 2,6-di-F-4-OEt—Ph, X is C(O), and $R^2$ is Me. |
| 376B | $Q^1$ is 2,6-di-F-4-OEt—Ph, X is C(O), and $R^2$ is Cl. |
| 376C | $Q^1$ is 2,6-di-F-4-OEt—Ph, X is C(O), and $R^2$ is Br. |
| 377 | $Q^1$ is 2,6-di-F-4-CN—Ph, X is C(O), and $R^2$ is Me. |
| 378 | $Q^1$ is 2,6-di-F-4-CN—Ph, X is C(O), and $R^2$ is Cl. |
| 379 | $Q^1$ is 2,6-di-F-4-CN—Ph, X is C(O), and $R^2$ is Br. |
| 380 | $Q^1$ is 2-Cl-4-F—Ph, X is C(O), and $R^2$ is Me. |
| 381 | $Q^1$ is 2-Cl-4-F—Ph, X is C(O), and $R^2$ is Cl. |
| 382 | $Q^1$ is 2-Cl-4-F—Ph, X is C(O), and $R^2$ is Br. |
| 383 | $Q^1$ is 2-Cl-6-F—Ph, X is C(O), and $R^2$ is Me. |
| 384 | $Q^1$ is 2-Cl-6-F—Ph, X is C(O), and $R^2$ is Cl. |
| 385 | $Q^1$ is 2-Cl-6-F—Ph, X is C(O), and $R^2$ is Br. |
| 386 | $Q^1$ is 2-Cl-4,6-di-F—Ph, X is C(O), and $R^2$ is Me. |
| 387 | $Q^1$ is 2-Cl-4,6-di-F—Ph, X is C(O), and $R^2$ is Cl. |
| 388 | $Q^1$ is 2-Cl-4,6-di-F—Ph, X is C(O), and $R^2$ is Br. |
| 389 | $Q^1$ is 4-Cl-2,6-di-F—Ph, X is C(O), and $R^2$ is Me. |
| 390 | $Q^1$ is 4-Cl-2,6-di-F—Ph, X is C(O), and $R^2$ is Cl. |
| 391 | $Q^1$ is 4-Cl-2,6-di-F—Ph, X is C(O), and $R^2$ is Br. |
| 392 | $Q^1$ is 2-Br-4-F—Ph, X is C(O), and $R^2$ is Me. |
| 393 | $Q^1$ is 2-Br-4-F—Ph, X is C(O), and $R^2$ is Cl. |
| 394 | $Q^1$ is 2-Br-4-F—Ph, X is C(O), and $R^2$ is Br. |
| 395 | $Q^1$ is 2-Br-6-F—Ph, X is C(O), and $R^2$ is Me. |
| 396 | $Q^1$ is 2-Br-6-F—Ph, X is C(O), and $R^2$ is Cl. |
| 397 | $Q^1$ is 2-Br-6-F—Ph, X is C(O), and $R^2$ is Br. |
| 398 | $Q^1$ is 2-Me-4-F—Ph, X is C(O), and $R^2$ is Me. |
| 399 | $Q^1$ is 2-Me-4-F—Ph, X is C(O), and $R^2$ is Cl. |
| 400 | $Q^1$ is 2-Me-4-F—Ph, X is C(O), and $R^2$ is Br. |
| 401 | $Q^1$ is 2-I-4-F—Ph, X is C(O), and $R^2$ is Me. |
| 402 | $Q^1$ is 2-I-4-F—Ph-Ph, X is C(O), and $R^2$ is Cl. |
| 403 | $Q^1$ is 2-I-4-F—Ph, X is C(O), and $R^2$ is Br. |
| 404 | $Q^1$ is 2-F—Ph, X is C(O), and $R^2$ is Me. |
| 405 | $Q^1$ is 2-F—Ph, X is C(O), and $R^2$ is Cl. |
| 406 | $Q^1$ is 2-F—Ph, X is C(O), and $R^2$ is Br. |
| 407 | $Q^1$ is 2-Cl—Ph, X is C(O), and $R^2$ is Me. |
| 408 | $Q^1$ is 2-Cl—Ph, X is C(O), and $R^2$ is Cl. |
| 409 | $Q^1$ is 2-Cl—Ph, X is C(O), and $R^2$ is Br. |
| 410 | $Q^1$ is 2-Br—Ph, X is C(O), and $R^2$ is Me. |
| 411 | $Q^1$ is 2-Br—Ph, X is C(O), and $R^2$ is Cl. |
| 412 | $Q^1$ is 2-Br—Ph, X is C(O), and $R^2$ is Br. |
| 413 | $Q^1$ is 2-F-4-Cl—Ph, X is C(O), and $R^2$ is Me. |
| 414 | $Q^1$ is 2-F-4-Cl—Ph, X is C(O), and $R^2$ is Cl. |
| 415 | $Q^1$ is 2-F-4-Cl—Ph, X is C(O), and $R^2$ is Br. |
| 416 | $Q^1$ is 2,4-di-Cl—Ph, X is C(O), and $R^2$ is Me. |
| 417 | $Q^1$ is 2,4-di-Cl—Ph, X is C(O), and $R^2$ is Cl. |
| 418 | $Q^1$ is 2,4-di-Cl—Ph, X is C(O), and $R^2$ is Br. |
| 419 | $Q^1$ is 2,6-di-Cl—Ph, X is C(O), and $R^2$ is Me. |
| 420 | $Q^1$ is 2,6-di-Cl—Ph, X is C(O), and $R^2$ is Cl. |
| 421 | $Q^1$ is 2,6-di-Cl—Ph, X is C(O), and $R^2$ is Br. |
| 422 | $Q^1$ is 2-F-4-MeO—Ph, X is C(O), and $R^2$ is Me. |
| 423 | $Q^1$ is 2-F-4-MeO—Ph, X is C(O), and $R^2$ is Cl. |
| 424 | $Q^1$ is 2-F-4-MeO—Ph, X is C(O), and $R^2$ is Br. |
| 424A | $Q^1$ is 2-F-4-EtO—Ph, X is C(O), and $R^2$ is Me. |
| 424B | $Q^1$ is 2-F-4-EtO—Ph, X is C(O), and $R^2$ is Cl. |
| 424C | $Q^1$ is 2-F-4-EtO—Ph, X is C(O), and $R^2$ is Br. |
| 425 | $Q^1$ is 2-Cl-4-MeO—Ph, X is C(O), and $R^2$ is Me. |
| 426 | $Q^1$ is 2-Cl-4-MeO—Ph, X is C(O), and $R^2$ is Cl. |
| 427 | $Q^1$ is 2-Cl-4-MeO—Ph, X is C(O), and $R^2$ is Br. |
| 427A | $Q^1$ is 2-Cl-4-EtO—Ph, X is C(O), and $R^2$ is Me. |
| 427B | $Q^1$ is 2-Cl-4-EtO—Ph, X is C(O), and $R^2$ is Cl. |
| 427C | $Q^1$ is 2-Cl-4-EtO—Ph, X is C(O), and $R^2$ is Br. |
| 428 | $Q^1$ is 2-Br-4-MeO—Ph, X is C(O), and $R^2$ is Me. |
| 429 | $Q^1$ is 2-Br-4-MeO—Ph, X is C(O), and $R^2$ is Cl. |
| 430 | $Q^1$ is 2-Br-4-MeO—Ph, X is C(O), and $R^2$ is Br. |
| 430A | $Q^1$ is 2-Br-4-EtO—Ph, X is C(O), and $R^2$ is Me. |
| 430B | $Q^1$ is 2-Br-4-EtO—Ph, X is C(O), and $R^2$ is Cl. |
| 430C | $Q^1$ is 2-Br-4-EtO—Ph, X is C(O), and $R^2$ is Br. |
| 431 | $Q^1$ is 2-F-4-CN—Ph, X is C(O), and $R^2$ is Me. |
| 432 | $Q^1$ is 2-F-4-CN—Ph, X is C(O), and $R^2$ is Cl. |
| 433 | $Q^1$ is 2-F-4-CN—Ph, X is C(O), and $R^2$ is Br. |
| 434 | $Q^1$ is 2-Cl-4-CN—Ph, X is C(O), and $R^2$ is Me. |
| 435 | $Q^1$ is 2-Cl-4-CN—Ph, X is C(O), and $R^2$ is Cl. |
| 436 | $Q^1$ is 2-Cl-4-CN—Ph, X is C(O), and $R^2$ is Br. |
| 437 | $Q^1$ is 2-Br-4-CN—Ph, X is C(O), and $R^2$ is Me. |
| 438 | $Q^1$ is 2-Br-4-CN—Ph, X is C(O), and $R^2$ is Cl. |

| Table | Row Heading |
|---|---|
| 439 | $Q^1$ is 2-Br-4-CN—Ph, X is C(O), and $R^2$ is Br. |
| 440 | $Q^1$ is 2,5-di-Cl-3-pyridinyl, X is C(O), and $R^2$ is Me. |
| 441 | $Q^1$ is 2,5-di-Cl-3-pyridinyl, X is C(O), and $R^2$ is Cl. |
| 442 | $Q^1$ is 2,5-di-Cl-3-pyridinyl, X is C(O), and $R^2$ is Br. |
| 443 | $Q^1$ is 2-Cl-3-thienyl, X is C(O), and $R^2$ is Me. |
| 444 | $Q^1$ is 2-Cl-3-thienyl, X is C(O), and $R^2$ is Cl. |
| 445 | $Q^1$ is 2-Cl-3-thienyl, X is C(O), and $R^2$ is Br. |
| 446 | $Q^1$ is 2,5-di-Cl-3-thienyl, X is C(O), and $R^2$ is Me. |
| 447 | $Q^1$ is 2,5-di-Cl-3-thienyl, X is C(O), and $R^2$ is Cl. |
| 448 | $Q^1$ is 2,5-di-Cl-3-thienyl, X is C(O), and $R^2$ is Br. |

TABLE 449

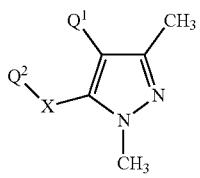

| $Q^2$ | $Q^2$ | $Q^2$ | $Q^2$ |
|---|---|---|---|
| 2-Cl-3-pyridinyl | 6-Cl-3-pyridinyl | 2,6-di-Cl-3-pyridinyl | 3-Cl-2-pyridinyl |
| 3,5-di-Cl-2-pyridinyl | 3,5-di-F-2-pyridinyl | 5-Me-2-pyridinyl | 5-CN-2-pyridinyl |
| 5-pyrimidinyl | 2-Cl-5-pyrimidinyl | 1,3-di-Me-5-pyrazolyl | 5-Me-2-thiazolyl |
| 5-Cl-2-pyridinyl | 3,5-di-Cl-4-pyridinyl | tetrahydro-2H-pyran-4-yl | quinolin-2-yl |

$Q^1$ is 2,6-di-F—Ph, and X is NH.

The present disclosure also includes Tables 450 through 587, each of which is constructed the same as Table 449 above, except that the row heading in Table 449 (i.e. "$Q^1$ is 2,6-di-F-Ph, and X is NH.") is replaced with the respective row heading shown below. For Example, in Table 450 the row heading is "$Q^1$ is 2,4-di-F-Ph, and X is NH." and $Q^2$ is as defined in Table 449 above. Thus, the first entry in Table 450 specifically discloses 2-chloro-N-[4-(2,4-difluorophenyl)-1,3-dimethyl-1H-pyrazol-5-yl]-3-pyridinamine. Tables 451 through 587 are constructed similarly.

| Table | Row Heading |
|---|---|
| 450 | $Q^1$ is 2,4-di-F-Ph, and X is NH. |
| 451 | $Q^1$ is 2,4,6-tri-F-Ph, and X is NH. |
| 452 | $Q^1$ is 2,6-di-F-4-OMe-Ph, and X is NH. |
| 453 | $Q^1$ is 2,6-di-F-4-CN-Ph, and X is NH. |
| 454 | $Q^1$ is 2-Cl-4-F-Ph, and X is NH. |
| 455 | $Q^1$ is 2-Cl-6-F-Ph, and X is NH. |
| 456 | $Q^1$ is 2-Cl-4,6-di-F-Ph, and X is NH. |
| 457 | $Q^1$ is 4-Cl-2,6-di-F-Ph, and X is NH. |
| 458 | $Q^1$ is 2-Br-4-F-Ph, and X is NH. |
| 459 | $Q^1$ is 2-Br-6-F-Ph, and X is NH. |
| 460 | $Q^1$ is 2-Me-4-F-Ph, and X is NH. |
| 461 | $Q^1$ is 2-I-4-F-Ph, and X is NH. |
| 462 | $Q^1$ is 2-F-Ph, and X is NH. |
| 463 | $Q^1$ is 2-Cl-Ph, and X is NH. |
| 464 | $Q^1$ is 2-Br-Ph, and X is NH. |
| 465 | $Q^1$ is 2-F-4-Cl-Ph, and X is NH. |
| 466 | $Q^1$ is 2,4-di-Cl-Ph, and X is NH. |
| 467 | $Q^1$ is 2,6-di-Cl-Ph, and X is NH. |
| 468 | $Q^1$ is 2-F-4-MeO-Ph, and X is NH. |
| 469 | $Q^1$ is 2-Cl-4-MeO-Ph, and X is NH. |
| 470 | $Q^1$ is 2-Br-4-MeO-Ph, and X is NH. |
| 471 | $Q^1$ is 2-F-4-CN-Ph, and X is NH. |
| 472 | $Q^1$ is 2-Cl-4-CN-Ph, and X is NH. |
| 473 | $Q^11$ is 2-Br-4-CN-Ph, and X is NH. |
| 474 | $Q^1$ is 2,5-di-Cl-3-pyridinyl, and X is NH. |
| 475 | $Q^1$ is 2-Cl-3-thienyl, and X is NH. |
| 476 | $Q^1$ is 2,5-di-Cl-3-thienyl, and X is NH. |
| 477 | $Q^1$ is 2,6-di-F-Ph, and X is O. |
| 478 | $Q^1$ is 2,4-di-F-Ph, and X is O. |
| 479 | $Q^1$ is 2,4,6-tri-F-Ph, and X is O. |
| 480 | $Q^1$ is 2,6-di-F-4-OMe-Ph, and X is O. |
| 481 | $Q^1$ is 2,6-di-F-4-CN-Ph, and X is O. |
| 482 | $Q^1$ is 2-Cl-4-F-Ph, and X is O. |
| 483 | $Q^1$ is 2-Cl-6-F-Ph, and X is O. |
| 484 | $Q^1$ is 2-Cl-4,6-di-F-Ph, and X is O. |
| 485 | $Q^1$ is 4-Cl-2,6-di-F-Ph, and X is O. |
| 486 | $Q^1$ is 2-Br-4-F-Ph, and X is O. |
| 487 | $Q^1$ is 2-Br-6-F-Ph, and X is O. |
| 488 | $Q^1$ is 2-Me-4-F-Ph, and X is O. |
| 489 | $Q^1$ is 2-I-4-F-Ph, and X is O. |
| 490 | $Q^1$ is 2-F-Ph, and X is O. |
| 491 | $Q^1$ is 2-Cl-Ph, and X is O. |
| 492 | $Q^1$ is 2-Br-Ph, and X is O. |
| 493 | $Q^1$ is 2-F-4-Cl-Ph, and X is O. |
| 494 | $Q^1$ is 2,4-di-Cl-Ph, and X is O. |
| 495 | $Q^1$ is 2,6-di-Cl-Ph, and X is O. |
| 496 | $Q^1$ is 2-F-4-MeO-Ph, and X is O. |
| 497 | $Q^1$ is 2-Cl-4-MeO-Ph, and X is O. |
| 498 | $Q^1$ is 2-Br-4-MeO-Ph, and X is O. |
| 499 | $Q^1$ is 2-F-4-CN-Ph, and X is O. |
| 500 | $Q^1$ is 2-Cl-4-CN-Ph, and X is O. |
| 501 | $Q^1$ is 2-Br-4-CN-Ph, and X is O. |
| 502 | $Q^1$ is 2,5-di-Cl-pyridin-3-yl, and X is O. |
| 503 | $Q^1$ is 2-Cl-thien-3-yl, and X is O. |
| 504 | $Q^1$ is 2,5-di-Cl-thien-3-yl, and X is O. |
| 505 | $Q^1$ is 2,6-di-F-Ph, and X is S. |
| 506 | $Q^1$ is 2,4-di-F-Ph, and X is S. |
| 507 | $Q^1$ is 2,4,6-tri-F-Ph, and X is S. |
| 508 | $Q^1$ is 2,6-di-F-4-OMe-Ph, and X is S. |
| 509 | $Q^1$ is 2,6-di-F-4-CN-Ph, and X is S. |
| 510 | $Q^1$ is 2-Cl-4-F-Ph, and X is S. |
| 511 | $Q^1$ is 2-Cl-6-F-Ph, and X is S. |
| 512 | $Q^1$ is 2-Cl-4,6-di-F-Ph, and X is S. |
| 513 | $Q^1$ is 4-Cl-2,6-di-F-Ph, and X is S. |
| 514 | $Q^1$ is 2-Br-4-F-Ph, and X is S. |
| 515 | $Q^1$ is 2-Br-6-F-Ph, and X is S. |
| 516 | $Q^1$ is 2-Me-4-F-Ph, and X is S. |
| 517 | $Q^1$ is 2-I-4-F-Ph, and X is S. |
| 518 | $Q^1$ is 2-F-Ph, and X is S. |
| 519 | $Q^1$ is 2-Cl-Ph, and X is S. |
| 520 | $Q^1$ is 2-Br-Ph, and X is S. |
| 521 | $Q^1$ is 2-F-4-Cl-Ph, and X is S. |

| Table | Row Heading |
|---|---|
| 522 | $Q^1$ is 2,4-di-Cl-Ph, and X is S. |
| 523 | $Q^1$ is 2,6-di-Cl-Ph, and X is S. |
| 524 | $Q^1$ is 2-F-4-MeO-Ph, and X is S. |
| 525 | $Q^1$ is 2-Cl-4-MeO-Ph, and X is S. |
| 526 | $Q^1$ is 2-Br-4-MeO-Ph, and X is S. |
| 527 | $Q^1$ is 2-F-4-CN-Ph, and X is S. |
| 528 | $Q^1$ is 2-Cl-4-CN-Ph, and X is S. |
| 529 | $Q^1$ is 2-Br-4-CN-Ph, and X is S. |
| 530 | $Q^1$ is 2,5-di-Cl-3-pyridinyl, and X is S. |
| 531 | $Q^1$ is 2-Cl-3-thienyl, and X is S. |
| 532 | $Q^1$ is 2,5-di-Cl-3-thienyl, and X is S. |
| 533 | $Q^1$ is 2,6-di-F-Ph, and X is CHOH. |
| 534 | $Q^1$ is 2,4-di-F-Ph, and X is CHOH. |
| 535 | $Q^1$ is 2,4,6-tri-F-Ph, and X is CHOH. |
| 536 | $Q^1$ is 2,6-di-F-4-OMe-Ph, and X is CHOH. |
| 537 | $Q^1$ is 2,6-di-F-4-CN-Ph, and X is CHOH. |
| 538 | $Q^1$ is 2-Cl-4-F-Ph, and X is CHOH. |
| 539 | $Q^1$ is 2-Cl-6-F-Ph, and X is CHOH. |
| 540 | $Q^1$ is 2-Cl-4,6-di-F-Ph, and X is CHOH. |
| 541 | $Q^1$ is 4-Cl-2,6-di-F-Ph, and X is CHOH. |
| 542 | $Q^1$ is 2-Br-4-F-Ph, and X is CHOH. |
| 543 | $Q^1$ is 2-Br-6-F-Ph, and X is CHOH. |
| 544 | $Q^1$ is 2-Me-4-F-Ph, and X is CHOH. |
| 545 | $Q^1$ is 2-I-4-F-Ph, and X is CHOH. |
| 546 | $Q^1$ is 2-F-Ph, and X is CHOH. |
| 547 | $Q^1$ is 2-Cl-Ph, and X is CHOH. |
| 548 | $Q^1$ is 2-Br-Ph, and X is CHOH. |
| 549 | $Q^1$ is 2-F-4-Cl-Ph, and X is CHOH. |
| 550 | $Q^1$ is 2,4-di-Cl-Ph, and X is CHOH. |
| 551 | $Q^1$ is 2,6-di-Cl-Ph, and X is CHOH. |
| 552 | $Q^1$ is 2-F-4-MeO-Ph, and X is CHOH. |
| 553 | $Q^1$ is 2-Cl-4-MeO-Ph, and X is CHOH. |
| 554 | $Q^1$ is 2-Br-4-MeO-Ph, and X is CHOH. |
| 555 | $Q^1$ is 2-F-4-CN-Ph, and X is CHOH. |
| 556 | $Q^1$ is 2-Cl-4-CN-Ph, and X is CHOH. |
| 557 | $Q^1$ is 2-Br-4-CN-Ph, and X is CHOH. |
| 558 | $Q^1$ is 2,5-di-Cl-pyridin-3-yl, and X is CHOH. |
| 559 | $Q^1$ is 2,5-di-Cl-thien-3-yl, and X is CHOH. |
| 560 | $Q^1$ is 2,6-di-F-Ph, and X is C(O). |
| 561 | $Q^1$ is 2,4-di-F-Ph, and X is C(O). |
| 562 | $Q^1$ is 2,4,6-tri-F-Ph, and X is C(O). |
| 563 | $Q^1$ is 2,6-di-F-4-OM-Ph e, and X is C(O). |
| 564 | $Q^1$ is 2,6-di-F-4-CN-Ph, and X is C(O). |
| 565 | $Q^1$ is 2-Cl-4-F-Ph, and X is C(O). |
| 566 | $Q^1$ is 2-Cl-6-F-Ph, and X is C(O). |
| 567 | $Q^1$ is 2-Cl-4,6-di-F-Ph, and X is C(O). |
| 568 | $Q^1$ is 4-Cl-2,6-di-F-Ph, and X is C(O). |
| 569 | $Q^1$ is 2-Br-4-F-Ph, and X is C(O). |
| 570 | $Q^1$ is 2-Br-6-F-Ph, and X is C(O). |
| 571 | $Q^1$ is 2-Me-4-F-Ph, and X is C(O). |
| 572 | $Q^1$ is 2-I-4-F-Ph, and X is C(O). |
| 573 | $Q^1$ is 2-F-Ph, and X is C(O). |
| 574 | $Q^1$ is 2-Cl-Ph, and X is C(O). |
| 575 | $Q^1$ is 2-Br-Ph, and X is C(O). |
| 576 | $Q^1$ is 2-F-4-Cl-Ph, and X is C(O). |
| 577 | $Q^1$ is 2,4-di-Cl-Ph, and X is C(O). |
| 578 | $Q^1$ is 2,6-di-Cl-Ph, and X is C(O). |
| 579 | $Q^1$ is 2-F-4-MeO-Ph, and X is C(O). |
| 580 | $Q^1$ is 2-Cl-4-MeO-Ph, and X is C(O). |
| 581 | $Q^1$ is 2-Br-4-MeO-Ph, and X is C(O). |
| 582 | $Q^1$ is 2-F-4-CN-Ph, and X is C(O). |
| 583 | $Q^1$ is 2-Cl-4-CN-Ph, and X is C(O). |
| 584 | $Q^1$ is 2-Br-4-CN-Ph, and X is C(O). |
| 585 | $Q^1$ is 2,5-di-Cl-3-pyridinyl, and X is C(O). |
| 586 | $Q^1$ is 2-Cl-3-thienyl, and X is C(O). |
| 587 | $Q^1$ is 2,5-di-Cl-3-thienyl, and X is C(O). |

TABLE 588

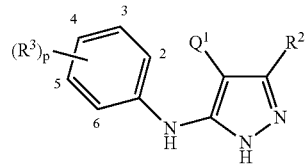

| $(R^3)_p$ | $(R^3)_p$ | $(R^3)_p$ | $(R^3)_p$ | $(R^3)_p$ |
|---|---|---|---|---|
| 2-F | 3-F | 4-F | 2-Cl | 3-Cl |
| 4-Cl | 2-Br | 3-Br | 4-Br | 2,4-di-F |
| 2,6-di-F | 2,4,6-tri-F | 2,4,5-tri-F | 2,3,5-tri-F | 2,3,6-tri-F |
| 2-Cl-4-F | 2-F-4-Cl | 2,4-di-Cl | 2,6-di-Cl | 2,4,6-tri-Cl |
| 2-Br-4-F | 2-I-4-F | 2-Me-4-F | 2-F-4-MeO | 2-Cl-4-MeO |
| 2-Br-4-MeO | 2,6-di-F-4-MeO | 2-F-4-CN | 2-Cl-4-CN | 2-Br-4-CN |
| 2,6-di-F-4-CN | 2-Cl-4,5-di-F | 2-Cl-4,6-di-F | 2-Br-4,5-di-F | 2-Br-4,6-di-F |
| 4-Cl-2,5-di-F | 4-Cl-2,6-di-F | 4-Br-2,5-di-F | 4-Br-2,6-di-F | 2,4-di-Cl-6-F |
| 2,6-di-Cl-4-F | 2,6-di-Cl-4-MeO | 2-$CF_3$-4-F | 4-Me | 2,4-di-Me |
| 2-F-4-Br | 2-Cl-4-Br | 2-Br-4-Cl | 2-Br-4-F-6-Cl | 2-Cl-4-Br-6-F |

$Q^1$ is 2,6-di-F—Ph, and $R^2$ is Me.

The present disclosure also includes Tables 589 through 671, each of which is constructed the same as Table 588 above, except that the row heading in Table 588 (i.e. "$Q^1$ is 2,6-di-F-Ph, and $R^2$ is Me.") is replaced with the respective row heading shown below. For Example, in Table 589 the row heading is "$Q^1$ is 2,6-di-F-Ph, and $R^2$ is Cl.", and $(R^3)_p$ is as defined in Table 588 above. Thus, the first entry in Table 589 specifically discloses 5-chloro-4-(2,6-difluorophenyl)-N-(2-fluorophenyl)-1H-pyrazol-3-amine. Tables 589 through 671 are constructed similarly.

| Table | Row Heading |
| --- | --- |
| 589 | $Q^1$ is 2,6-di-F-Ph, and $R^2$ is Cl. |
| 590 | $Q^1$ is 2,6-di-F-Ph, and $R^2$ is Br. |
| 591 | $Q^1$ is 2,4-di-F-Ph, and $R^2$ is Me. |
| 592 | $Q^1$ is 2,4-di-F-Ph, and $R^2$ is Cl. |
| 593 | $Q^1$ is 2,4-di-F-Ph, and $R^2$ is Br. |
| 594 | $Q^1$ is 2,4,6-tri-F-Ph, and $R^2$ is Me. |
| 595 | $Q^1$ is 2,4,6-tri-F-Ph, and $R^2$ is Cl. |
| 596 | $Q^1$ is 2,4,6-tri-F-Ph, and $R^2$ is Br. |
| 597 | $Q^1$ is 2,6-di-F-4-OMe-Ph, and $R^2$ is Me. |
| 598 | $Q^1$ is 2,6-di-F-4-OMe-Ph, and $R^2$ is Cl. |
| 599 | $Q^1$ is 2,6-di-F-4-OMe-Ph, and $R^2$ is Br. |
| 599A | $Q^1$ is 2,6-di-F-4-OEt-Ph, and $R^2$ is Me. |
| 599B | $Q^1$ is 2,6-di-F-4-OEt-Ph, and $R^2$ is Cl. |
| 599C | $Q^1$ is 2,6-di-F-4-OEt-Ph, and $R^2$ is Br. |
| 600 | $Q^1$ is 2,6-di-F-4-CN-Ph, and $R^2$ is Me. |
| 601 | $Q^1$ is 2,6-di-F-4-CN-Ph, and $R^2$ is Cl. |
| 602 | $Q^1$ is 2,6-di-F-4-CN-Ph, and $R^2$ is Br. |
| 603 | $Q^1$ is 2-Cl-4-F-Ph, and $R^2$ is Me. |
| 604 | $Q^1$ is 2-Cl-4-F-Ph, and $R^2$ is Cl. |
| 605 | $Q^1$ is 2-Cl-4-F-Ph, and $R^2$ is Br. |
| 606 | $Q^1$ is 2-Cl-6-F-Ph, and $R^2$ is Me. |
| 607 | $Q^1$ is 2-Cl-6-F-Ph, and $R^2$ is Cl. |
| 608 | $Q^1$ is 2-Cl-6-F-Ph, and $R^2$ is Br. |
| 609 | $Q^1$ is 2-Cl-4,6-di-F-Ph, and $R^2$ is Me. |
| 610 | $Q^1$ is 2-Cl-4,6-di-F-Ph, and $R^2$ is Cl. |
| 611 | $Q^1$ is 2-Cl-4,6-di-F-Ph, and $R^2$ is Br. |
| 612 | $Q^1$ is 4-Cl-2,6-di-F-Ph, and $R^2$ is Me. |
| 613 | $Q^1$ is 4-Cl-2,6-di-F-Ph, and $R^2$ is Cl. |
| 614 | $Q^1$ is 4-Cl-2,6-di-F-Ph, and $R^2$ is Br. |
| 615 | $Q^1$ is 2-Br-4-F-Ph, and $R^2$ is Me. |
| 616 | $Q^1$ is 2-Br-4-F-Ph, and $R^2$ is Cl. |
| 617 | $Q^1$ is 2-Br-4-F-Ph, and $R^2$ is Br. |
| 618 | $Q^1$ is 2-Br-6-F-Ph, and $R^2$ is Me. |
| 619 | $Q^1$ is 2-Br-6-F-Ph, and $R^2$ is Cl. |
| 620 | $Q^1$ is 2-Br-6-F-Ph, and $R^2$ is Br. |
| 621 | $Q^1$ is 2-Me-4-F-Ph, and $R^2$ is Me. |
| 622 | $Q^1$ is 2-Me-4-F-Ph, and $R^2$ is Cl. |
| 623 | $Q^1$ is 2-Me-4-F-Ph, and $R^2$ is Br. |
| 624 | $Q^1$ is 2-I-4-F-Ph, and $R^2$ is Me. |
| 625 | $Q^1$ is 2-I-4-F-Ph, and $R^2$ is Cl. |
| 626 | $Q^1$ is 2-I-4-F-Ph, and $R^2$ is Br. |
| 627 | $Q^1$ is 2-F-Ph, and $R^2$ is Me. |
| 628 | $Q^1$ is 2-F-Ph, and $R^2$ is Cl. |
| 629 | $Q^1$ is 2-F-Ph, and $R^2$ is Br. |
| 630 | $Q^1$ is 2-Cl-Ph, and $R^2$ is Me. |
| 631 | $Q^1$ is 2-Cl-Ph, and $R^2$ is Cl. |
| 632 | $Q^1$ is 2-Cl-Ph, and $R^2$ is Br. |
| 633 | $Q^1$ is 2-Br-Ph, and $R^2$ is Me. |
| 634 | $Q^1$ is 2-Br-Ph, and $R^2$ is Cl. |
| 635 | $Q^1$ is 2-Br-Ph, and $R^2$ is Br. |
| 636 | $Q^1$ is 2-F-4-Cl-Ph, and $R^2$ is Me. |
| 637 | $Q^1$ is 2-F-4-Cl-Ph, and $R^2$ is Cl. |
| 638 | $Q^1$ is 2-F-4-Cl-Ph, and $R^2$ is Br. |
| 639 | $Q^1$ is 2,4-di-Cl-Ph, and $R^2$ is Me. |
| 640 | $Q^1$ is 2,4-di-Cl-Ph, and $R^2$ is Cl. |
| 641 | $Q^1$ is 2,4-di-Cl-Ph, and $R^2$ is Br. |
| 642 | $Q^1$ is 2,6-di-Cl-Ph, and $R^2$ is Me. |
| 643 | $Q^1$ is 2,6-di-Cl-Ph, and $R^2$ is Cl. |
| 644 | $Q^1$ is 2,6-di-Cl-Ph, and $R^2$ is Br. |
| 645 | $Q^1$ is 2-F-4-MeO-Ph, and $R^2$ is Me. |
| 646 | $Q^1$ is 2-F-4-MeO-Ph, and $R^2$ is Cl. |
| 647 | $Q^1$ is 2-F-4-MeO-Ph, and $R^2$ is Br. |
| 647A | $Q^1$ is 2-F-4-EtO-Ph, and $R^2$ is Me. |
| 647B | $Q^1$ is 2-F-4-EtO-Ph, and $R^2$ is Cl. |
| 647C | $Q^1$ is 2-F-4-EtO-Ph, and $R^2$ is Br. |
| 648 | $Q^1$ is 2-Cl-4-MeO-Ph, and $R^2$ is Me. |
| 649 | $Q^1$ is 2-Cl-4-MeO-Ph, and $R^2$ is Cl. |
| 650 | $Q^1$ is 2-Cl-4-MeO-Ph, and $R^2$ is Br. |
| 650A | $Q^1$ is 2-Cl-4-EtO-Ph, and $R^2$ is Me. |
| 650B | $Q^1$ is 2-Cl-4-EtO-Ph, and $R^2$ is Cl. |
| 650C | $Q^1$ is 2-Cl-4-EtO-Ph, and $R^2$ is Br. |
| 651 | $Q^1$ is 2-Br-4-MeO-Ph, and $R^2$ is Me. |
| 652 | $Q^1$ is 2-Br-4-MeO-Ph, and $R^2$ is Cl. |
| 653 | $Q^1$ is 2-Br-4-MeO-Ph, and $R^2$ is Br. |
| 653A | $Q^1$ is 2-Br-4-EtO-Ph, and $R^2$ is Me. |
| 653B | $Q^1$ is 2-Br-4-EtO-Ph, and $R^2$ is Cl. |
| 653C | $Q^1$ is 2-Br-4-EtO-Ph, and $R^2$ is Br. |
| 654 | $Q^1$ is 2-F-4-CN-Ph, and $R^2$ is Me. |
| 655 | $Q^1$ is 2-F-4-CN-Ph, and $R^2$ is Cl. |
| 656 | $Q^1$ is 2-F-4-CN-Ph, and $R^2$ is Br. |
| 657 | $Q^1$ is 2-Cl-4-CN-Ph, and $R^2$ is Me. |
| 658 | $Q^1$ is 2-Cl-4-CN-Ph, and $R^2$ is Cl. |
| 659 | $Q^1$ is 2-Cl-4-CN-Ph, and $R^2$ is Br. |
| 660 | $Q^1$ is 2-Br-4-CN-Ph, and $R^2$ is Me. |
| 661 | $Q^1$ is 2-Br-4-CN-Ph, and $R^2$ is Cl. |
| 662 | $Q^1$ is 2-Br-4-CN-Ph, and $R^2$ is Br. |
| 663 | $Q^1$ is 2,5-di-Cl-3-pyridinyl, and $R^2$ is Me. |
| 664 | $Q^1$ is 2,5-di-Cl-3-pyridinyl, and $R^2$ is Cl. |
| 665 | $Q^1$ is 2,5-di-Cl-3-pyridinyl, and $R^2$ is Br. |
| 666 | $Q^1$ is 2-Cl-3-thienyl, and $R^2$ is Me. |
| 667 | $Q^1$ is 2-Cl-3-thienyl, and $R^2$ is Cl. |
| 668 | $Q^1$ is 2-Cl-3-thienyl, and $R^2$ is Br. |
| 669 | $Q^1$ is 2,5-di-Cl-3-thienyl, and $R^2$ is Me. |
| 670 | $Q^1$ is 2,5-di-Cl-3-thienyl, and $R^2$ is Cl. |
| 671 | $Q^1$ is 2,5-di-Cl-3-thienyl, and $R^2$ is Br. |

The compounds of Tables 588 through 671 illustrate compounds of Formula 2 wherein X is NH, which are useful intermediates to prepare compounds of Formula 1 using the method of Scheme 2.

TABLE 672

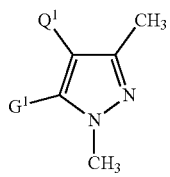

| $Q^1$ | $Q^1$ | $Q^1$ | $Q^1$ |
| --- | --- | --- | --- |
| 2,6-di-F—Ph | 2-Cl-4,6-di-F—Ph | 2-Cl—Ph | 2-Br-4-MeO—Ph |
| 2,4-di-F—Ph | 4-Cl-2,6-di-F—Ph | 2-Br—Ph | 2-F-4-CN—Ph |
| 2,4,6-tri-F—Ph | 2-Br-4-F—Ph | 2-F-4-Cl—Ph | 2-Cl-4-CN—Ph |
| 2,6-di-F-4-OMe—Ph | 2-Br-6-F—Ph | 2,4-di-Cl—Ph | 2-Br-4-CN—Ph |
| 2,6-di-F-4-CN—Ph | 2-Me-4-F—Ph | 2,6-di-Cl—Ph | 2,5-di-Cl-3-pyridinyl |
| 2-Cl-4-F—Ph | 2-I-4-F—Ph | 2-F-4-MeO—Ph | 2-Cl-3-thienyl |

TABLE 672-continued

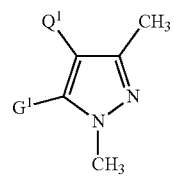

| Q¹ | Q¹ | Q¹ | Q¹ |
|---|---|---|---|
| 2-Cl-6-F—Ph | 2-F—Ph | 2-Cl-4-MeO—Ph | 2,5-di-Cl-3-thienyl |
| 2,6-di-F-4-EtO—Ph | 2-F-4-EtO—Ph | 2-Cl-4-EtO—Ph | 2-Br-4-EtO—Ph |

G¹ is —OH.

The present disclosure also includes Tables 673 through 676, each of which is constructed the same as Table 672 above, except that the row heading in Table 672 (i.e. "G¹ is —OH.") is replaced with the respective row heading shown below. For Example, in Table 673 the row heading is "G¹ is —SH.", and Q¹ is as defined in Table 672 above. Thus, the first entry in Table 673 specifically discloses 4-(2,6-difluorophenyl)-1,3-dimethyl-1H-pyrazol-5-thiol. Tables 674 through 676 are constructed similarly.

| Table | Row Heading |
|---|---|
| 673 | G¹ is —SH. |
| 674 | G¹ is Cl. |
| 675 | G¹ is Br. |
| 675A | G¹ is I. |
| 676 | G¹ is —NH₂. |

The compounds of Tables 672 and 673 illustrate compounds of Formula 4 wherein X is O or S, $R^1$ and $R^{1a}$ are each H, and $R^2$ is $CH_3$, which are useful intermediates to prepare compounds of Formula 1 using the method of Scheme 3. The compounds of Table 672 further illustrate compounds of Formula 4b wherein $R^1$ and $R^{1a}$ are each H, and $R^2$ is $CH_3$, which are useful intermediates to prepare intermediate compounds of Formula 6a using the method of Scheme 6 and to prepare intermediate compounds of Formula 6b using the method of Scheme 7. Tables 674 and 675 illustrate compounds of Formula 6 wherein G is Cl or Br, and $R^{1a}$ are each H, and $R^2$ is $CH_3$ which are useful intermediates to prepare compounds of Formula 1c using the method of Scheme 4. Table 676 illustrates compounds of Formula 4a wherein $R^1$ and $R^{1a}$ are each H, and $R^2$ is $CH_3$, which are useful intermediates to prepare intermediate compounds of Formula 6 using the method of Scheme 5.

TABLE 677

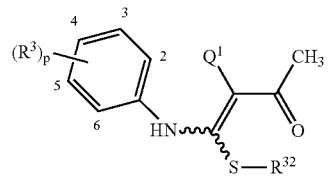

| $(R^3)_p$ | $(R^3)_p$ | $(R^3)_p$ | $(R^3)_p$ | $(R^3)_p$ |
|---|---|---|---|---|
| 2-F | 3-F | 4-F | 2-Cl | 3-Cl |
| 4-Cl | 2-Br | 3-Br | 4-Br | 2,4-di-F |
| 2,6-di-F | 2,4,6-tri-F | 2,4,5-tri-F | 2,3,5-tri-F | 2,3,6-tri-F |
| 2-Cl-4-F | 2-F-4-Cl | 2,4-di-Cl | 2,6-di-Cl | 2,4,6-tri-Cl |
| 2-Br-4-F | 2-I-4-F | 2-Me-4-F | 2-F-4-MeO | 2-Cl-4-MeO |
| 2-Br-4-MeO | 2,6-di-F-4-MeO | 2-F-4-CN | 2-Cl-4-CN | 2-Br-4-CN |
| 2,6-di-F-4-CN | 2-Cl-4,5-di-F | 2-Cl-4,6-di-F | 2-Br-4,5-di-F | 2-Br-4,6-di-F |
| 4-Cl-2,5-di-F | 4-Cl-2,6-di-F | 4-Br-2,5-di-F | 4-Br-2,6-di-F | 2,4-di-Cl-6-F |
| 2,6-di-Cl-4-F | 2,6-di-Cl-4-MeO | 2-CF₃-4-F | 4-Me | 2,4-di-Me |
| 2-F-4-Br | 2-Cl-4-Br | 2-Br-4-Cl | 2-Br-4-F-6-Cl | 2-Cl-4-Br-6-F |

Q¹ is 2,6-di-F—Ph, and $R^{32}$ is Me.

The present disclosure also includes Tables 678 through 704, each of which is constructed the same as Table 677 above, except that the row heading in Table 677 (i.e. "$Q^1$ is 2,6-di-F-Ph.") is replaced with the respective row heading shown below. For Example, in Table 2 the row heading is "$Q^1$ is 2,4-di-F-Ph.", and $(R^3)_p$ is as defined in Table 677 above. Thus, the first entry in Table 678 specifically discloses 3-(2,6-difluorophenyl)-4-[(2,4-difluorophenyl)amino]-4-(methylthio)-3-buten-2-one. Tables 679 through 704 are constructed similarly.

| Table | Row Heading |
| --- | --- |
| 678 | $Q^1$ is 2,4-di-F-Ph, and $R^{32}$ is Me. |
| 679 | $Q^1$ is 2,4,6-tri-F-Ph, and $R^{32}$ is Me. |
| 680 | $Q^1$ is 2,6-di-F-4-OMe-Ph, and $R^{32}$ is Me. |
| 680A | $Q^1$ is 2,6-di-F-4-OEt-Ph, and $R^{32}$ is Me. |
| 681 | $Q^1$ is 2,6-di-F-4-CN-Ph, and $R^{32}$ is Me. |
| 682 | $Q^1$ is 2-Cl-4-F-Ph, and $R^{32}$ is Me. |
| 683 | $Q^1$ is 2-Cl-6-F-Ph, and $R^{32}$ is Me. |
| 684 | $Q^1$ is 2-Cl-4,6-di-F-Ph, and $R^{32}$ is Me. |
| 685 | $Q^1$ is 4-Cl-2,6-di-F-Ph, and $R^{32}$ is Me. |
| 686 | $Q^1$ is 2-Br-4-F-Ph, and $R^{32}$ is Me. |
| 687 | $Q^1$ is 2-Br-6-F-Ph, and $R^{32}$ is Me. |
| 688 | $Q^1$ is 2-Me-4-F-Ph, and $R^{32}$ is Me. |
| 689 | $Q^1$ is 2-I-4-F-Ph, and $R^{32}$ is Me. |
| 690 | $Q^1$ is 2-F-Ph, and $R^{32}$ is Me. |
| 691 | $Q^1$ is 2-Cl-Ph, and $R^{32}$ is Me. |
| 692 | $Q^1$ is 2-Br-Ph, and $R^{32}$ is Me. |
| 693 | $Q^1$ is 2-F-4-Cl-Ph, and $R^{32}$ is Me. |
| 694 | $Q^1$ is 2,4-di-Cl-Ph, and $R^{32}$ is Me. |
| 695 | $Q^1$ is 2,6-di-Cl-Ph, and $R^{32}$ is Me. |
| 696 | $Q^1$ is 2-F-4-MeO-Ph, and $R^{32}$ is Me. |
| 696A | $Q^1$ is 2-F-4-EtO-Ph, and $R^{32}$ is Me. |
| 697 | $Q^1$ is 2-Cl-4-MeO-Ph, and $R^{32}$ is Me. |
| 697A | $Q^1$ is 2-Cl-4-EtO-Ph, and $R^{32}$ is Me. |
| 698 | $Q^1$ is 2-Br-4-MeO-Ph, and $R^{32}$ is Me. |
| 698A | $Q^1$ is 2-Br-4-EtO-Ph, and $R^{32}$ is Me. |
| 699 | $Q^1$ is 2-F-4-CN-Ph, and $R^{32}$ is Me. |
| 700 | $Q^1$ is 2-Cl-4-CN-Ph, and $R^{32}$ is Me. |
| 701 | $Q^1$ is 2-Br-4-CN-Ph, and $R^{32}$ is Me. |
| 702 | $Q^1$ is 2,5-di-Cl-3-pyridinyl, and $R^{32}$ is Me. |
| 703 | $Q^1$ is 2-Cl-3-thienyl, and $R^{32}$ is Me. |
| 704 | $Q^1$ is 2,5-di-Cl-3-thienyl, and $R^{32}$ is Me. |
| 705 | $Q^1$ is 2,6-di-F-Ph, and $R^{32}$ is Et. |
| 706 | $Q^1$ is 2,4-di-F-Ph, and $R^{32}$ is Et. |
| 707 | $Q^1$ is 2,4,6-tri-F-Ph, and $R^{32}$ is Et. |
| 708 | $Q^1$ is 2,6-di-F-4-OMe-Ph, and $R^{32}$ is Et. |
| 708A | $Q^1$ is 2,6-di-F-4-OEt-Ph, and $R^{32}$ is Et. |
| 709 | $Q^1$ is 2,6-di-F-4-CN-Ph, and $R^{32}$ is Et. |
| 710 | $Q^1$ is 2-Cl-4-F-Ph, and $R^{32}$ is Et. |
| 711 | $Q^1$ is 2-Cl-6-F-Ph, and $R^{32}$ is Et. |
| 712 | $Q^1$ is 2-Cl-4,6-di-F-Ph, and $R^{32}$ is Et. |
| 713 | $Q^1$ is 4-Cl-2,6-di-F-Ph, and $R^{32}$ is Et. |
| 714 | $Q^1$ is 2-Br-4-F-Ph, and $R^{32}$ is Et. |
| 715 | $Q^1$ is 2-Br-6-F-Ph, and $R^{32}$ is Et. |
| 716 | $Q^1$ is 2-Me-4-F-Ph, and $R^{32}$ is Et. |
| 717 | $Q^1$ is 2-I-4-F-Ph, and $R^{32}$ is Et. |
| 718 | $Q^1$ is 2-F-Ph, and $R^{32}$ is Et. |
| 719 | $Q^1$ is 2-Cl-Ph, and $R^{32}$ is Et. |
| 720 | $Q^1$ is 2-Br-Ph, and $R^{32}$ is Et. |
| 721 | $Q^1$ is 2-F-4-Cl-Ph, and $R^{32}$ is Et. |
| 722 | $Q^1$ is 2,4-di-Cl-Ph, and $R^{32}$ is Et. |
| 723 | $Q^1$ is 2,6-di-Cl-Ph, and $R^{32}$ is Et. |
| 724 | $Q^1$ is 2-F-4-MeO-Ph, and $R^{32}$ is Et. |
| 724A | $Q^1$ is 2-F-4-EtO-Ph, and $R^{32}$ is Et. |
| 725 | $Q^1$ is 2-Cl-4-MeO-Ph, and $R^{32}$ is Et. |
| 725A | $Q^1$ is 2-Cl-4-EtO-Ph, and $R^{32}$ is Et. |
| 726 | $Q^1$ is 2-Br-4-MeO-Ph, and $R^{32}$ is Et. |
| 726A | $Q^1$ is 2-Br-4-EtO-Ph, and $R^{32}$ is Et. |
| 727 | $Q^1$ is 2-F-4-CN-Ph, and $R^{32}$ is Et. |
| 728 | $Q^1$ is 2-Cl-4-CN-Ph, and $R^{32}$ is Et. |
| 729 | $Q^1$ is 2-Br-4-CN-Ph, and $R^{32}$ is Et. |
| 730 | $Q^1$ is 2,5-di-Cl-3-pyridinyl, and $R^{32}$ is Et. |
| 731 | $Q^1$ is 2-Cl-3-thienyl, and $R^{32}$ is Et. |
| 732 | $Q^1$ is 2,5-di-Cl-3-thienyl, and $R^{32}$ is Et. |
| 733 | $Q^1$ is 2,6-di-F-Ph, and $R^{32}$ is n-Pr. |
| 734 | $Q^1$ is 2,4-di-F-Ph, and $R^{32}$ is n-Pr. |
| 735 | $Q^1$ is 2,4,6-tri-F-Ph, and $R^{32}$ is n-Pr. |
| 736 | $Q^1$ is 2,6-di-F-4-OMe-Ph, and $R^{32}$ is n-Pr. |
| 736A | $Q^1$ is 2,6-di-F-4-OEt-Ph, and $R^{32}$ is n-Pr. |
| 737 | $Q^1$ is 2,6-di-F-4-CN-Ph, and $R^{32}$ is n-Pr. |
| 738 | $Q^1$ is 2-Cl-4-F-Ph, and $R^{32}$ is n-Pr. |
| 739 | $Q^1$ is 2-Cl-6-F-Ph, and $R^{32}$ is n-Pr. |
| 740 | $Q^1$ is 2-Cl-4,6-di-F-Ph, and $R^{32}$ is n-Pr. |
| 741 | $Q^1$ is 4-Cl-2,6-di-F-Ph, and $R^{32}$ is n-Pr. |
| 742 | $Q^1$ is 2-Br-4-F-Ph, and $R^{32}$ is n-Pr. |
| 743 | $Q^1$ is 2-Br-6-F-Ph, and $R^{32}$ is n-Pr. |
| 744 | $Q^1$ is 2-Me-4-F-Ph, and $R^{32}$ is n-Pr. |
| 745 | $Q^1$ is 2-I-4-F-Ph, and $R^{32}$ is n-Pr. |
| 746 | $Q^1$ is 2-F-Ph, and $R^{32}$ is n-Pr. |
| 747 | $Q^1$ is 2-Cl-Ph, and $R^{32}$ is n-Pr. |
| 748 | $Q^1$ is 2-Br-Ph, and $R^{32}$ is n-Pr. |
| 749 | $Q^1$ is 2-F-4-Cl-Ph, and $R^{32}$ is n-Pr. |
| 750 | $Q^1$ is 2,4-di-Cl-Ph, and $R^{32}$ is n-Pr. |
| 751 | $Q^1$ is 2,6-di-Cl-Ph, and $R^{32}$ is n-Pr. |
| 752 | $Q^1$ is 2-F-4-MeO-Ph, and $R^{32}$ is n-Pr. |
| 752A | $Q^1$ is 2-F-4-EtO-Ph, and $R^{32}$ is n-Pr. |
| 753 | $Q^1$ is 2-Cl-4-MeO-Ph, and $R^{32}$ is n-Pr. |
| 753A | $Q^1$ is 2-Cl-4-EtO-Ph, and $R^{32}$ is n-Pr. |
| 754 | $Q^1$ is 2-Br-4-MeO-Ph, and $R^{32}$ is n-Pr. |
| 754A | $Q^1$ is 2-Br-4-EtO-Ph, and $R^{32}$ is n-Pr. |
| 755 | $Q^1$ is 2-F-4-CN-Ph, and $R^{32}$ is n-Pr. |
| 756 | $Q^1$ is 2-Cl-4-CN-Ph, and $R^{32}$ is n-Pr. |
| 757 | $Q^1$ is 2-Br-4-CN-Ph, and $R^{32}$ is n-Pr. |
| 758 | $Q^1$ is 2,5-di-Cl-3-pyridinyl, and $R^{32}$ is n-Pr. |
| 759 | $Q^1$ is 2-Cl-3-thienyl, and $R^{32}$ is n-Pr. |
| 760 | $Q^1$ is 2,5-di-Cl-3-thienyl, and $R^{32}$ is n-Pr. |

The compounds of Tables 677 through 760 illustrate compounds of Formula 17 wherein $R^2$ is $CH_3$, which are useful intermediates to prepare compounds of Formula 1c using the method of Scheme 16.

TABLE 761

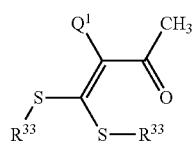

| $Q^1$ | $Q^1$ | $Q^1$ | $Q^1$ |
| --- | --- | --- | --- |
| 2,6-di-F—Ph | 2-Cl-4,6-di-F—Ph | 2-Cl—Ph | 2-Br-4-MeO—Ph |
| 2,4-di-F—Ph | 4-Cl-2,6-di-F—Ph | 2-Br—Ph | 2-F-4-CN—Ph |
| 2,4,6-tri-F—Ph | 2-Br-4-F—Ph | 2-F-4-Cl—Ph | 2-Cl-4-CN—Ph |
| 2,6-di-F-4-OMe—Ph | 2-Br-6-F—Ph | 2,4-di-Cl—Ph | 2-Br-4-CN—Ph |
| 2,6-di-F-4-CN—Ph | 2-Me-4-F—Ph | 2,6-di-Cl—Ph | 2,5-di-Cl-3-pyridinyl |
| 2-Cl-4-F—Ph | 2-I-4-F—Ph | 2-F-4-MeO—Ph | 2-Cl-3-thienyl |

TABLE 761-continued $$\underset{R^{33}}{\overset{Q^1}{\underset{S}{\bigvee}}}\overset{CH_3}{\underset{S-R^{33}}{\bigvee}}\overset{}{\underset{O}{\parallel}}$$

| Q$^1$ | Q$^1$ | Q$^1$ | Q$^1$ |
|---|---|---|---|
| 2-Cl-6-F—Ph | 2-F—Ph | 2-Cl-4-MeO—Ph | 2,5-di-Cl-3-thienyl |
| 2,6-di-F-4-EtO—Ph | 2-F-4-EtO—Ph | 2-Cl-4-EtO—Ph | 2-Br-4-EtO—Ph |

Each R$^{33}$ is Me.

The present disclosure also includes Tables 762 through 764, each of which is constructed the same as Table 761 above, except that the row heading in Table 761 (i.e. "Each R$^{33}$ is Me.") is replaced with the respective row heading shown below. For Example, in Table 762 the row heading is "Each R$^{33}$ is Et.", and Q$^1$ is as defined in Table 761 above. Thus, the first entry in Table 762 specifically discloses 3-(2,6-difluorophenyl)-4,4-bis(ethylthio)-3-buten-2-one. Tables 763 and 764 are constructed similarly.

| Table | Row Heading |
|---|---|
| 762 | Each R$^{33}$ is Et. |
| 763 | Each R$^{33}$ is n-Pr. |
| 764 | The two R$^{33}$ are taken together as —CH$_2$—. |

The compounds of Tables 761 through 763 illustrate compounds of Formula 18 wherein R$^2$ is CH$_3$, which are useful intermediates to prepare intermediate compounds of Formula 17 using the method of Scheme 17. The compounds of Table 764 illustrate compounds of Formula 18 wherein R$^2$ is CH$_3$, which are useful intermediates to prepare intermediate compounds of Formula 4c using the method described below Scheme 17.

TABLE 765

$$\underset{B^1}{\overset{Q^1}{\underset{O}{\bigvee}}}\overset{CH_3}{\underset{O}{\bigvee}}\overset{}{\underset{O}{\parallel}}$$

| Q$^1$ | Q$^1$ | Q$^1$ | Q$^1$ |
|---|---|---|---|
| 2,6-di-F—Ph | 2-Cl-4,6-di-F—Ph | 2-Cl—Ph | 2-Br-4-MeO—Ph |
| 2,4-di-F—Ph | 4-Cl-2,6-di-F—Ph | 2-Br—Ph | 2-F-4-CN—Ph |
| 2,4,6-tri-F—Ph | 2-Br-4-F—Ph | 2-F-4-Cl—Ph | 2-Cl-4-CN—Ph |
| 2,6-di-F-4-OMe—Ph | 2-Br-6-F—Ph | 2,4-di-Cl—Ph | 2-Br-4-CN—Ph |
| 2,6-di-F-4-CN—Ph | 2-Me-4-F—Ph | 2,6-di-Cl—Ph | 2,5-di-Cl-3-pyridinyl |
| 2-Cl-4-F—Ph | 2-I-4-F—Ph | 2-F-4-MeO—Ph | 2-Cl-3-thienyl |
| 2-Cl-6-F—Ph | 2-F—Ph | 2-Cl-4-MeO—Ph | 2,5-di-Cl-3-thienyl |
| 2,6-di-F-4-EtO—Ph | 2-F-4-EtO—Ph | 2-Cl-4-EtO—Ph | 2-Br-4-EtO—Ph |

B$^1$ is Me.

The present disclosure also includes Tables 766 through 769, each of which is constructed the same as Table 765 above, except that the row heading in Table 765 (i.e. "B$^1$ is Me.") is replaced with the respective row heading shown below. For Example, in Table 766 the row heading is "B$^1$ is Et.", and Q$^1$ is as defined in Table 765 above. Thus, the first entry in Table 766 specifically discloses ethyl α-acetyl-2,6-difluorobenzeneacetate. Tables 767 through 769 are constructed similarly

| Table | Row Heading |
|---|---|
| 766 | B$^1$ is Et. |
| 767 | B$^1$ is is n-Pr. |
| 768 | B$^1$ is Ph. |
| 769 | B$^1$ is CH$_2$Ph. |

The compounds of Tables 765 through 769 illustrate compounds of Formula 16 wherein R$^2$ is CH$_3$, which are useful intermediates to prepare intermediate compounds of Formula 4b using the method of Scheme 14.

Formulation/Utility

A compound of this invention will generally be used as a fungicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g, oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 m range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| Compound 18 | 98.5% |
| silica aerogel | 0.5% |
| synthetic amorphous fine silica | 1.0% |

Example B

| Wettable Powder | |
|---|---|
| Compound 22 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 23 | 10.0% |
| attapulgite granules (low volatile matter, 0.71/0.30 mm; U.S.S. No. 25-50 sieves) | 90.0% |

Example D

| Extruded Pellet | |
|---|---|
| Compound 24 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 36 | 10.0% |
| polyoxyethylene sorbitol hexoleate | 20.0% |
| $C_6$—$C_{10}$ fatty acid methyl ester | 70.0% |

Example F

| Microemulsion | |
|---|---|
| Compound 41 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
|---|---|
| Compound 45 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Formulations such as those in the Formulation Table are typically diluted with water to form aqueous compositions before application. Aqueous compositions for direct applications to the plant or portion thereof (e.g., spray tank compositions) typically at least about 1 ppm or more (e.g., from 1 ppm to 100 ppm) of the compound(s) of this invention.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans*, *Phytophthora megasperma*, *Phytophthora parasitica*, *Phytophthora cinnamomi* and *Phytophthora capsici*, *Pythium* diseases such as *Pythium aphanidermatum*, and diseases in the Peronosporaceae family such as *Plasmopara viticola*, *Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae*, *Guignardia* diseases such as *Guignardia bidwell*, *Venturia* diseases such as *Venturia inaequalis*, *Septoria* diseases such as *Septoria nodorum* and *Septoria tritici*, powdery mildew diseases such as *Erysiphe* spp. (including *Erysiphe graminis* and *Erysiphe polygoni*), *Uncinula necatur*, *Sphaerotheca fuligena* and *Podosphaera leucotricha*, *Pseudocercosporella herpotrichoides*, *Botrytis* diseases such as *Botrytis cinerea*, *Monilinia fructicola*, *Sclerotinia* diseases such as *Sclerotinia sclerotiorum*, *Magnaporthe grisea*, *Phomopsis viticola*, *Helminthosporium* diseases such as *Helminthosporium tritici* repentis, *Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondita*, *Puccinia striiformis*, *Puccinia hordei*, *Puccinia graminis* and *Puccinia arachidis*), *Hemileia vastatrix* and *Phakopsora pachyrhizi*; other pathogens including *Rutstroemia floccosum* (also known as *Sclerontina homoeocarpa*); *Rhizoctonia* spp. (such as *Rhizoctonia solani*); *Fusarium* diseases such as *Fusarium roseum*, *Fusarium graminearum* and *Fusarium oxysporum*; *Verticillium dahliae*; *Sclerotium rolfsii*; *Rynchosporium secalis*; *Cercosporidium personatum*, *Cercospora arachidicola* and *Cercospora beticola*; and other genera and species closely related to these pathogens. In addition to their fungicidal activity, the compositions or combinations also have activity against bacteria such as *Erwinia amylovora, Xanthomonas campestris, Pseudomonas syringae*, and other related species.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Accordingly, this aspect of the present invention can also be described as a method for protecting a plant or plant seed from diseases caused by fungal pathogens comprising applying a fungicidally effective amount of a compound of Formula 1, an N-oxide, or salt thereof to the plant (or portion thereof) or plant seed (directly or through the environment (e.g., growing medium) of the plant or plant seed).

Rates of application for these compounds can be influenced by many factors of the environment and should be determined under actual use conditions. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a fungicidally effective amount of a compound of Formula 1 and a biologically effective amount of at least one additional biologically active compound or agent and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

As mentioned in the Summary of the Invention, one aspect of the present invention is a fungicidal composition comprising (i.e. a mixture or combination of) a compound of Formula 1, an N-oxide, or a salt thereof (i.e. component a), and at least one other fungicide (i.e. component b).

Of note is a composition which, in addition to the Formula 1 compound of component (a), includes as component (b) at least one fungicidal compound selected from the group consisting of the classes (b1) methyl benzimidazole carbamate (MBC) fungicides; (b2) dicarboximide fungicides; (b3) demethylation inhibitor (DMI) fungicides; (b4) phenylamide fungicides; (b5) amine/morpholine fungicides; (b6) phospholipid biosynthesis inhibitor fungicides; (b7) carboxamide fungicides; (b8) hydroxy(2-amino-)pyrimidine fungicides; (b9) anilinopyrimidine fungicides; (b10) N-phenyl carbamate fungicides; (b11) quinone outside inhibitor (QoI) fungicides; (b12) phenylpyrrole fungicides; (b13) quinoline fungicides; (b14) lipid peroxidation inhibitor fungicides; (b15) melanin biosynthesis inhibitors-reductase (MBI-R) fungicides; (b16) melanin biosynthesis inhibitors-dehydratase (MBI-D) fungicides; (b17) hydroxyanilide fungicides; (b18) squalene-epoxidase inhibitor fungicides; (b19) polyoxin fungicides; (b20) phenylurea fungicides; (b21) quinone inside inhibitor (QiI) fungicides; (b22) benzamide fungicides; (b23) enopyranuronic acid antibiotic fungicides; (b24) hexopyranosyl antibiotic fungicides; (b25) glucopyranosyl antibiotic: protein synthesis fungicides; (b26) glucopyranosyl antibiotic: trehalase and inositol biosynthesis fungicides; (b27) cyanoacetamideoxime fungicides; (b28) carbamate fungicides; (b29) oxidative phosphorylation uncoupling fungicides; (b30) organo tin fungicides; (b31) carboxylic acid fungicides; (b32) heteroaromatic fungicides; (b33) phosphonate fungicides; (b34) phthalamic acid fungicides; (b35) benzotriazine fungicides; (b36) benzene-sulfonamide fungicides; (b37) pyridazinone fungicides; (b38) thiophene-carboxamide fungicides; (b39) pyrimidinamide fungicides; (b40) carboxylic acid amide (CAA) fungicides; (b41) tetracycline antibiotic fungicides; (b42) thiocarbamate fungicides; (b43) benzamide fungicides; (b44) host plant defense induction fungicides; (b45) multi-site contact activity fungicides; (b46) fungicides other than classes (b1) through (b45); and salts of compounds of classes (b1) through (b46).

Further descriptions of these classes of fungicidal compounds are provided below.

(b1) "Methyl benzimidazole carbamate (MBC) fungicides" (FRAC (Fungicide Resistance Action Committee) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(b2) "Dicarboximide fungicides" (FRAC code 2) are proposed to inhibit a lipid peroxidation in fungi through interference with NADH cytochrome c reductase. Examples include chlozolinate, iprodione, procymidone and vinclozolin.

(b3) "Demethylation inhibitor (DMI) fungicides" (FRAC code 3) inhibit C14-demethylase which plays a role in sterol production. Sterols, such as ergosterol, are needed for membrane structure and function, making them essential for the development of functional cell walls. Therefore, exposure to these fungicides result in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz, pefurazoate and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(b4) "Phenylamide fungicides" (FRAC code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl, metalaxyl-M (also known as mefenoxam). The oxazolidinones include oxadixyl. The butyrolactones include ofurace.

(b5) "Amine/morpholine fungicides" (FRAC code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(b6) "Phospholipid biosynthesis inhibitor fungicides" (FRAC code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

(b7) "Carboxamide fungicides" (FRAC code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamide, furan carboxamide, oxathiin carboxamide, thiazole carboxamide, pyrazole carboxamide and pyridine carboxamide. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include bixafen, furametpyr, isopyrazam, fluxapyroxad, sedaxane (N-[2-(1S,2R)-[1,1'-bicyclopropyl]-2-ylphenyl]-3-(difluoromethyl)-1-methyl-1H-pyrazole-4-carboxamide) and penflufen (N-[2-(1,3-dimethylbutyl)phenyl]-5-fluoro-1,3-dimethyl-1H-pyrazole-4-carboxamide (PCT Patent Publication WO 2003/010149)). The pyridine carboxamides include boscalid.

(b8) "Hydroxy(2-amino-)pyrimidine fungicides" (FRAC code 8) inhibit nucleic acid synthesis by interfering with adenosine deaminase. Examples include bupirimate, dimethirimol and ethirimol.

(b9) "Anilinopyrimidine fungicides" (FRAC code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(b10) "N-Phenyl carbamate fungicides" (FRAC code 10) inhibit mitosis by binding to β-tubulin and disrupting microtubule assembly. Inhibition of microtubule assembly can disrupt cell division, transport within the cell and cell structure. Examples include diethofencarb.

(b11) "Quinone outside inhibitor (QoI) fungicides" (FRAC code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylate, methoxycarbamate, oximinoacetate, oximinoacetamide, oxazolidinedione, dihydrodioxazine, imidazolinone and benzylcarbamate fungicides. The methoxyacrylates include azoxystrobin, enestroburin (SYP-Z071) and picoxystrobin. The methoxycarbamates include pyraclostrobin and pyrametostrobin. The oximinoacetates include kresoxim-methyl, pyraoxystrobin and trifloxystrobin. The oximinoacetamides include dimoxystrobin, metominostrobin, orysastrobin, α-[methoxyimino]-N-methyl-2-[[[1-[3-(trifluoromethyl) phenyl]ethoxy]imino]-methyl]benzeneacetamide and 2-[[[3-(2,6-dichlorophenyl)-1-methyl-2-propen-1-ylidene]-amino]oxy]methyl]-α-(methoxyimino)-N-methylbenzeneacetamide. The oxazolidinediones include famoxadone. The dihydrodioxazines include fluoxastrobin. The imidazolinones include fenamidone. The benzylcarbamates include pyribencarb.

(b12) "Phenylpyrrole fungicides" (FRAC code 12) inhibit a MAP protein kinase associated with osmotic signal transduction in fungi. Fenpiclonil and fludioxonil are examples of this fungicide class.

(b13) "Quinoline fungicides" (FRAC code 13) are proposed to inhibit signal transduction by affecting G-proteins in early cell signaling. They have been shown to interfere with germination and/or appressorium formation in fungi that cause powder mildew diseases. Quinoxyfen is an example of this class of fungicide.

(b14) "Lipid peroxidation inhibitor fungicides" (FRAC code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbon fungicides include biphenyl, chloroneb, dicloran, quintozene, tecnazene and tolclofos-methyl. The 1,2,4-thiadiazole fungicides include etridiazole.

(b15) "Melanin biosynthesis inhibitors-reductase (MBI-R) fungicides" (FRAC code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(b16) "Melanin biosynthesis inhibitors-dehydratase (MBI-D) fungicides" (FRAC code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(b17) "Hydroxyanilide fungicides (FRAC code 17) inhibit C4-demethylase which plays a role in sterol production. Examples include fenhexamid.

(b18) "Squalene-epoxidase inhibitor fungicides" (FRAC code 18) inhibit squalene-epoxidase in ergosterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(b19) "Polyoxin fungicides" (FRAC code 19) inhibit chitin synthase. Examples include polyoxin.

(b20) "Phenylurea fungicides" (FRAC code 20) are proposed to affect cell division. Examples include pencycuron.

(b21) "Quinone inside inhibitor (QiI) fungicides" (FRAC code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(b22) "Benzamide fungicides" (FRAC code 22) inhibit mitosis by binding to β-tubulin and disrupting microtubule assembly. Inhibition of microtubule assembly can disrupt cell division, transport within the cell and cell structure. Examples include zoxamide.

(b23) "Enopyranuronic acid antibiotic fungicides" (FRAC code 23) inhibit growth of fungi by affecting protein biosynthesis. Examples include blasticidin-S.

(b24) "Hexopyranosyl antibiotic fungicides" (FRAC code 24) inhibit growth of fungi by affecting protein biosynthesis. Examples include kasugamycin.

(b25) "Glucopyranosyl antibiotic: protein synthesis fungicides" (FRAC code 25) inhibit growth of fungi by affecting protein biosynthesis. Examples include streptomycin.

(b26) "Glucopyranosyl antibiotic: trehalase and inositol biosynthesis fungicides" (FRAC code 26) inhibit trehalase in inositol biosynthesis pathway. Examples include validamycin.

(b27) "Cyanoacetamideoxime fungicides (FRAC code 27) include cymoxanil.

(b28) "Carbamate fungicides" (FRAC code 28) are considered multi-site inhibitors of fungal growth. They are proposed to interfere with the synthesis of fatty acids in cell membranes, which then disrupts cell membrane permeability. Propamacarb, propamacarb-hydrochloride, iodocarb, and prothiocarb are examples of this fungicide class.

(b29) "Oxidative phosphorylation uncoupling fungicides" (FRAC code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

(b30) "Organo tin fungicides" (FRAC code 30) inhibit adenosine triphosphate (ATP) synthase in oxidative phosphorylation pathway. Examples include fentin acetate, fentin chloride and fentin hydroxide.

(b31) "Carboxylic acid fungicides" (FRAC code 31) inhibit growth of fungi by affecting deoxyribonucleic acid (DNA) topoisomerase type II (gyrase). Examples include oxolinic acid.

(b32) "Heteroaromatic fungicides" (FRAC code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

(b33) "Phosphonate fungicides" (FRAC code 33) include phosphorous acid and its various salts, including fosetyl-aluminum.

(b34) "Phthalamic acid fungicides" (FRAC code 34) include teclofthalam.

(b35) "Benzotriazine fungicides" (FRAC code 35) include triazoxide.

(b36) "Benzene-sulfonamide fungicides" (FRAC code 36) include flusulfamide.

(b37) "Pyridazinone fungicides" (Fungicide Resistance Action Committee (FRAC) code 37) include diclomezine.

(b38) "Thiophene-carboxamide fungicides" (FRAC code 38) are proposed to affect ATP production. Examples include silthiofam.

(b39) "Pyrimidinamide fungicides" (FRAC code 39) inhibit growth of fungi by affecting phospholipid biosynthesis and include diflumetorim.

(b40) "Carboxylic acid amide (CAA) fungicides" (FRAC code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb and valifenalate (valiphenal). The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)-amino]butanamide and N-[2-[4-[[3-(4-chlorophenyl)-2-propyn-1-yl]oxy]-3-methoxyphenyl]-ethyl]-3-methyl-2-[(ethyl sulfonyl)amino]butanamide.

(b41) "Tetracycline antibiotic fungicides" (FRAC code 41) inhibit growth of fungi by affecting complex 1 nicotinamide adenine dinucleotide (NADH) oxidoreductase. Examples include oxytetracycline.

(b42) "Thiocarbamate fungicides (b42)" (FRAC code 42) include methasulfocarb.

(b43) "Benzamide fungicides" (FRAC code 43) inhibit growth of fungi by delocalization of spectrin-like proteins. Examples include acylpicolide fungicides such as fluopicolide and fluopyram.

(b44) "Host plant defense induction fungicides" (FRAC code P) induce host plant defense mechanisms. Host plant defense induction fungicides include benzo-thiadiazole, benzisothiazole and thiadiazole-carboxamide fungicides. The benzo-thiadiazoles include acibenzolar-S-methyl. The benzisothiazoles include probenazole. The thiadiazole-carboxamides include tiadinil and isotianil.

(b45) "Multi-site contact fungicides" inhibit fungal growth through multiple sites of action and have contact/preventive activity. This class of fungicides includes: (b45.1) "copper fungicides" (FRAC code M1)", (b45.2) "sulfur fungicides" (FRAC code M2), (b45.3) "dithiocarbamate fungicides" (FRAC code M3), (b45.4) "phthalimide fungicides" (FRAC code M4), (b45.5) "chloronitrile fungicides" (FRAC code M5), (b45.6) "sulfamide fungicides" (FRAC code M6), (b45.7) "guanidine fungicides" (FRAC code M7), (b45.8) "triazine fungicides" (FRAC code M8) and (b45.9) "quinone fungicides" (FRAC code M9). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine and imoctadine, including iminoctadine albesilate and iminoctadine triacetate. "Triazine fungicides" include anilazine. "Quinone fungicides" include dithianon.

(b46) "Fungicides other than fungicides of classes (b1) through (b45)" include certain fungicides whose mode of action may be unknown. These include: (b46.1) "thiazole carboxamide fungicides" (FRAC code US), (b46.2) "phenyl-acetamide fungicides" (FRAC code U6), (b46.3) "quinazolinone fungicides" (FRAC code U7) and (b46.4) "benzophenone fungicides" (FRAC code U8). The thiazole carboxamides include ethaboxam. The phenyl-acetamides include cyflufenamid and N-[[(cyclopropylmethoxy)amino][6-(difluoromethoxy)-2,3-difluorophenyl]-methylene]benzeneacetamide. The quinazolinones include proquinazid and 2-butoxy-6-iodo-3-propyl-4H-1-benzopyran-4-one. The benzophenones include metrafenone and pyriofenone. The (b46) class also includes bethoxazin, neo-asozin (ferric methanearsonate), fenpyrazamine, pyrrolnitrin, quinomethionate, tebufloquin, N-[2-[4-[[3-(4-chlorophenyl)-2-propyn-1-yl]oxy]-3-methoxyphenyl]ethyl]-3-methyl-2-[(methyl sulfonyl)amino]butanamide, N-[2-[4-[[3-(4-chlorophenyl)-2-propyn-1-yl]oxy]-3-methoxyphenyl] ethyl]-3-methyl-2-[(ethylsulfonyl)amino]-butanamide, 2-[[2-fluoro-5-(trifluoromethyl)phenyl]thio]-2-[3-(2-methoxyphenyl)-2-thiazolidinylidene]acetonitrile, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, 5-chloro-6-(2,4,6-trifluorophenyl)-7-(4-methylpiperidin-1-yl)[1,2,4]triazolo[1,5-a]pyrimidine, N-(4-chloro-2-nitrophenyl)-N-ethyl-4-methylbenzenesulfonamide, N-[[(cyclopropylmethoxy)amino][6-(difluoromethoxy)-2,3-difluorophenyl] methylene]benzeneacetamide, N-[4-[4-chloro-3-(trifluoromethyl)phenoxy]-2,5-dimethylphenyl]-N-ethyl-N-methylmethanimidamide and 1-[(2-propenylthio)carbonyl]-2-(1-methylethyl)-4-(2-methylphenyl)-5-amino-1H-pyrazol-3-one.

Therefore of note is a mixture (i.e. composition) comprising as component (a) a compound of Formula 1 (or an N-oxide or salt thereof) and as component (b) at least one fungicidal compound selected from the group consisting of the aforedescribed classes (b1) through (b46). Also of note are embodiments wherein component (b) comprises at least one fungicide from each of two different groups selected from (b1) through (b46). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 and at least one fungicidal compound selected from the group of specific compounds listed above in connection with classes (b1) through (b46). Also of particular note is a composition comprising said mixture (in fungicidally effective amount) and further comprising at least one additional surfactant selected from the group consisting of surfactants, solid diluents and liquid diluents.

Examples of other biologically active compounds or agents with which compounds of this invention can be formulated are: insecticides such as abamectin, acephate, acetamiprid, acetoprole, aldicarb, amidoflumet (S-1955), amitraz, avermectin, azadirachtin, azinphos-methyl, bifenthrin, bifenazate, bistrifluron, buprofezin, carbofuran, cartap, chinomethionat, chlorfenapyr, chlorfluazuron, chlorantraniliprole (DPX-E2Y45), chlorpyrifos, chlorpyrifos-methyl, chlorobenzilate, chromafenozide, clothianidin, cyantraniliprole (3-bromo-1-(3-chloro-2-pyridinyl)-N-[4-cyano-2-methyl-6-[(methylamino)-carbonyl]phenyl]-1H-pyrazole-5-carboxamide), cyflumetofen, cyfluthrin, beta-cyfluthrin, cyhalothrin, gamma-cyhalothrin, lambda-cyhalothrin, cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, fipronil, flonicamid, flubendiamide, flucythrinate, tau-fluvalinate, flufenerim (UR-50701), flufenoxuron, fonophos, halofenozide, hexaflumuron, hexythiazox, hydramethylnon, imicyafos, imidacloprid, indoxacarb, isofenphos, lufenuron, malathion, metaflumizone, metaldehyde, methamidophos, methidathion, methomyl, methoprene, methoxychlor, methoxyfenozide, metofluthrin, monocrotophos, nitenpyram, nithiazine, novaluron (XDE-007), noviflumuron, oxamyl, parathion, parathion-methyl, permethrin, phorate, phosalone, phosmet, phosphamidon, pirimicarb, profenofos, profluthrin, propargite, prothiocarb, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spiridiclofen, spiromesifen (BSN 2060), spirotetramat, sulprofos, tebufenozide, tebufenpyrad, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon, triflumuron; nematocides such as aldicarb, imicyafos, oxamyl and fenamiphos; bactericides such as streptomycin; acaricides such as amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

General references for agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U. K., 2003 and *The BioPesticide Manual*, 2nd Edition, L. G. Copping, Ed., British Crop Protection Council, Farnham, Surrey, U. K., 2001.

For embodiments where one or more of these various mixing partners are used, the weight ratio of these various mixing partners (in total) to the compound of Formula 1 (or an N-oxide or salt thereof) is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

Of note is a combination of a compound of Formula 1 (or an N-oxide or salt thereof) with at least one other fungicidal active ingredient. Of particular note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a biologically effective amount of at least one additional fungicidal active ingredient having a similar spectrum of control but a different site of action.

Of particular note are compositions which in addition to a compound of Formula 1 include at least one compound selected from the group consisting of (1) alkylenebis(dithiocarbamate) fungicides; (2) cymoxanil; (3) phenylamide fungicides; (4) pyrimidinone fungicides; (5) chlorothalonil; (6) carboxamides acting at complex II of the fungal mitochondrial respiratory electron transfer site; (7) quinoxyfen; (8) metrafenone or pyriofenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) $bc_1$ complex fungicides; and salts of compounds of (1) through (28).

Further descriptions of classes of fungicidal compounds are provided below.

Pyrimidinone fungicides (group (4)) include compounds of Formula A1

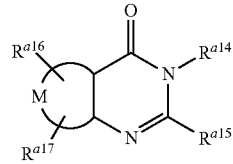

wherein M forms a fused phenyl, thiophene or pyridine ring; $R^{a14}$ is $C_1$-$C_6$ alkyl; $R^{a15}$ is $C_1$-$C_6$ alkyl or $C_1$-$C_6$ alkoxy; $R^{a16}$ is halogen; and $R^{a17}$ is hydrogen or halogen.

Pyrimidinone fungicides are described in PCT Patent Application Publication WO 94/26722 and U.S. Pat. Nos. 6,066,638, 6,245,770, 6,262,058 and 6,277,858. Of note are pyrimidinone fungicides selected from the group: 6-bromo-3-propyl-2-propyloxy-4(3H)-quinazolinone, 6,8-diiodo-3-propyl-2-propyloxy-4(3H)-quinazolinone, 6-iodo-3-propyl-2-propyloxy-4(3H)-quinazolinone (proquinazid), 6-chloro-2-propoxy-3-propylthieno[2,3-d]pyrimidin-4(3H)-one, 6-bromo-2-propoxy-3-propylthieno[2,3-d]pyrimidin-4(3H)-one, 7-bromo-2-propoxy-3-propylthieno[3,2-d]pyrimidin-4(3H)-one, 6-bromo-2-propoxy-3-propylpyrido[2,3-d]pyrimidin-4(3H)-one, 6,7-dibromo-2-propoxy-3-propylthieno[3,2-d]pyrimidin-4(3H)-one, and 3-(cyclopropylmethyl)-6-iodo-2-(propylthio)pyrido-[2,3-d]pyrimidin-4(3H)-one.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

$bc_1$ Complex Fungicides (group 28) have a fungicidal mode of action which inhibits the $bc_1$ complex in the mitochondrial respiration chain. The $bc_1$ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The $bc_1$ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin and trifloxystrobin are known to have this mode of action (H. Sauter et al., *Angew. Chem. Int. Ed.* 1999, 38, 1328-1349). Other fungicidal compounds that inhibit the $bc_1$ complex in the mitochondrial respiration chain include famoxadone and fenamidone.

Alkylenebis(dithiocarbamate)s (group (1)) include compounds such as mancozeb, maneb, propineb and zineb. Phenylamides (group (3)) include compounds such as metalaxyl, benalaxyl, furalaxyl and oxadixyl. Carboxamides (group (6)) include compounds such as boscalid, carboxin, fenfuram, flutolanil, fluxapyroxad, furametpyr, mepronil, oxycarboxin, thifluzamide, penthiopyrad and penflufen (N-[2-(1,3-dimethylbutyl)phenyl]-5-fluoro-1,3-dimethyl-1H-pyrazole-4-carboxamide (PCT Patent Publication WO 2003/010149)), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin.

Examples of component (b) fungicides include acibenzolar-S-methyl, aldimorph, ametoctradin, amisulbrom, anilazine, azaconazole, azoxystrobin, benalaxyl, benalaxyl-M, benodanil, benomyl, benthiavalicarb, benthiavalicarb-isopropyl, bethoxazin, binapacryl, biphenyl, bitertanol, bixafen, blasticidin-S, boscalid, bromuconazole, bupirimate, carboxin, carpropamid, captafol, captan, carbendazim, chloroneb, chlorothalonil, chlozolinate, clotrimazole, copper salts such as Bordeaux mixture (tribasic copper sulfate), copper hydroxide and copper oxychloride, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, diniconazole-M, dinocap, dithianon, dodemorph, dodine, edifenphos, enestroburin, epoxiconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fenpyrazamine, fentin acetate, fentin chloride, fentin hydroxide, ferbam, ferimzone, fluazinam, fludioxonil, flumetover, flumorph, fluopicolide (also known as picobenzamid), fluopyram, fluoroimide, fluoxastrobin, fluquinconazole, flusilazole, flusulfamide, flutianil (2-[[2-fluoro-5-(trifluoromethyl)phenyl]thio]-2-[3-(2-methoxyphenyl)-2-thiazolidinylidene]acetonitrile), flutolanil, flutriafol, fluxapyroxad, folpet, fosetyl-aluminum, fuberidazole, furalaxyl, furametpyr, hexaconazole, hymexazol, guazatine, imazalil, imibenconazole, iminoctadine, iodocarb, ipconazole, iprobenfos, iprodione, iprovalicarb, isoprothiolane, isopyrazam, isotianil, kasugamycin, kresoxim-methyl, mancozeb, mandipropamid, maneb, mepronil, meptyldinocap, metalaxyl, metalaxyl-M, metconazole, methasulfocarb, metiram, metominostrobin, mepanipyrim, metrafenone, myclobutanil, naftifine, neo-asozin (ferric methanearsonate), nuarimol, octhilinone, ofurace, orysastrobin, oxadixyl, oxolinic acid, oxpoconazole, oxycarboxin, oxytetracycline, penconazole, pencycuron, penflufen, penthiopyrad, pefurazoate, phosphorous acid and salts, phthalide, picoxystrobin, piperalin, polyoxin, probenazole, prochloraz, procymidone, propamocarb, propamocarb-hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyrifenone, pyroquilon, pyrrolnitrin, quinomethionate, quinoxyfen, quintozene, sedaxane, silthiofam, simeconazole, spiroxamine, streptomycin, sulfur, tebuconazole, tebufloquin, tecloftalam, tecnazene, terbinafine, tetraconazole, thiabendazole, thifluzamide, thiophanate, thiophanate-methyl, thiram, tiadinil, tolclofos-methyl, tolylfluanid, triadimefon, triadimenol, triazoxide, tricyclazole, tridemorph, triflumizole, tricyclazole, trifloxystrobin, triforine, trimorphamide, triticonazole, uniconazole, validamycin, valifenalate (valiphenal), vinclozolin, zineb, ziram, zoxamide, N'-[4-[4-chloro-3-(trifluoromethyl)phenoxy]-2,5-dimethylphenyl]-N-ethyl-N-methylmethanimidamide, 5-chloro-6-(2,4,6-trifluorophenyl)-7-(4-methylpiperidin-1-yl)[1,2,4]triazolo[1,5-a]pyrimidine (BAS600), penflufen (N-[2-(1,3-dimethylbutyl)phenyl]-5-fluoro-1,3-dimethyl-1H-pyrazole-4-carboxamide), N-[2-[4-[[3-(4-chlorophenyl)-2-propyn-1-yl]oxy]-3-methoxyphenyl]ethyl]-3-methyl-2-[(methylsulfonyl)amino]butanamide, N-[2-[4-[[3-(4-chlorophenyl)-2-propyn-1-yl]oxy]-3-methoxyphenyl]ethyl]-3-methyl-2-[(ethylsulfonyl)amino]butanamide, 2-butoxy-6-iodo-3-propyl-4H-1-benzopyran-4-one, 3-[5-(4-chlorophenyl)-2,3-dimethyl-3-isoxazolidinyl]-pyridine, 4-fluorophenyl N-[1-[[[1-(4-cyanophenyl)ethyl]sulfonyl]methyl]propyl] carbamate, N-[[(cyclopropylmethoxy)amino][6-(difluoromethoxy)-2,3-difluorophenyl]methylene] benzeneacetamide, α-(methoxyimino)-N-methyl-2-[[[1-[3-(trifluoro-methyl)phenyl]ethoxy]imino]methyl] benzeneacetamide, N-[4-[4-chloro-3-(trifluoro-methyl)phenoxy]-2,5-dimethylphenyl]-N-ethyl-N-methylmethanimidamide, N-(4-chloro-2-nitrophenyl)-N-ethyl-4-methylbenzenesulfonamide, 2-[[[[3-(2,6-dichlorophenyl)-1-methyl-2-propen-1-ylidene]amino]oxy]methyl]-α-(methoxyimino)-N-methylbenzeneacetamide, 1-[(2-propenylthio)carbonyl]-2-(1-methylethyl)-4-(2-methylphenyl)-5-amino-1H-pyrazol-3-one, ethyl-6-octyl-[1,2,4]triazolo[1,5-a]pyrimidin-7-ylamine, pentyl N-[4-[[[[(1-methyl-1H-tetrazol-5-yl)phenylmethylene]amino]oxy]methyl]-2-thiazolyl]carbamate and pentyl N-[6-[[[[(1-methyl-1H-tetrazol-5-yl)phenylmethylene]amino]oxy]methyl]-2-pyridinyl]carbamate Of note are combinations of compounds of Formula 1 (or an N-oxide or salt thereof) (i.e. Component (a) in compositions) with azoxystrobin, kresoxim-methyl, trifloxystrobin, pyraclostrobin, picoxystrobin, pyrametostrobin, pyraoxystrobin, dimoxystrobin, metominostrobin/fenominostrobin, carbendazim, chlorothalonil, quinoxyfen, metrafenone, cyflufenamid, fenpropidine, fenpropimorph, bromuconazole, cyproconazole, difenoconazole, epoxiconazole, fenbuconazole, flusilazole, fluxapyroxad, hexaconazole, ipconazole, metconazole, penconazole, propiconazole, proquinazid, prothioconazole, pyriofenone, tebuconazole, triticonazole, famoxadone, prochloraz, penthiopyrad and boscalid (nicobifen) (i.e. as Component (b) in compositions).

Preferred for better control of plant diseases caused by fungal plant pathogens (e.g., lower use rate or broader spectrum of plant pathogens controlled) or resistance management are mixtures of a compound of this invention with a fungicide selected from the group: azoxystrobin, kresoxim-methyl, trifloxystrobin, pyraclostrobin, picoxystrobin, pyrametostrobin, pyraoxystrobin, dimoxystrobin, metominostrobin/fenominostrobin, quinoxyfen, metrafenone, cyflufenamid, fenpropidine, fenpropimorph, cyproconazole, epoxiconazole, flusilazole, metconazole, propiconazole, proquinazid, prothioconazole, pyriofenone, tebuconazole, triticonazole, famoxadone and penthiopyrad.

Tables A1 through A54 list specific combinations of a Component (b) compound with Component (a) (compound numbers refer to compounds in Index Table A) illustrative of the mixtures, compositions and methods of the present invention. In Table A1, each line below the column headings "Component (a)" and "Component (b)" specifically discloses a combination (i.e. mixture) of Component (a), which is Compound 22, with a Component (b) fungicide. The entries under the heading "Illustrative Ratios" disclose three specific weight ratios of Component (b) to Component (a) for the disclosed mixture. For example, the first line of Table A1 discloses a mixture of Compound 22 with acibenzolar-S-methyl and lists weight ratios of acibenzolar-S-methyl to Compound 22 of 1:1, 1:4 or 1:17.

TABLE A1

| Component (a) | Component (b) | Illustrative Ratios(*) | | |
|---|---|---|---|---|
| Compound 22 | acibenzolar-S-methyl | 1:1 | 1:4 | 1:18 |
| Compound 22 | aldimorph | 7:1 | 3:1 | 1:1 |
| Compound 22 | ametoctradin | 3:1 | 1:1 | 1:3 |
| Compound 22 | amisulbrom | 1:1 | 1:2 | 1:6 |
| Compound 22 | anilazine | 22:1 | 8:1 | 4:1 |
| Compound 22 | azaconazole | 2:1 | 1:2 | 1:4 |
| Compound 22 | azoxystrobin | 3:1 | 1:1 | 1:3 |
| Compound 22 | benalaxyl | 1:1 | 1:2 | 1:6 |
| Compound 22 | benalaxyl-M | 1:1 | 1:3 | 1:8 |
| Compound 22 | benodanil | 4:1 | 2:1 | 1:2 |
| Compound 22 | benomyl | 11:1 | 4:1 | 1:1 |
| Compound 22 | benthiavalicarb | 1:1 | 1:4 | 1:12 |
| Compound 22 | benthiavalicarb-isopropyl | 1:1 | 1:4 | 1:12 |
| Compound 22 | bethoxazin | 15:1 | 5:1 | 2:1 |
| Compound 22 | binapacryl | 15:1 | 5:1 | 2:1 |
| Compound 22 | biphenyl | 15:1 | 5:1 | 2:1 |
| Compound 22 | bitertanol | 3:1 | 1:1 | 1:2 |
| Compound 22 | bixafen | 2:1 | 1:1 | 1:3 |
| Compound 22 | blasticidin-S | 1:4 | 1:12 | 1:30 |
| Compound 22 | Bordeaux mixture (tribasic copper sulfate) | 45:1 | 15:1 | 5:1 |
| Compound 22 | boscalid | 4:1 | 2:1 | 1:2 |
| Compound 22 | bromuconazole | 3:1 | 1:1 | 1:3 |
| Compound 22 | bupirimate | 1:3 | 1:10 | 1:30 |
| Compound 22 | captafol | 15:1 | 5:1 | 2:1 |
| Compound 22 | captan | 15:1 | 5:1 | 2:1 |
| Compound 22 | carbendazim | 11:1 | 4:1 | 2:1 |
| Compound 22 | carboxin | 4:1 | 2:1 | 1:2 |
| Compound 22 | carpropamid | 3:1 | 1:1 | 1:3 |
| Compound 22 | chloroneb | 100:1 | 35:1 | 14:1 |
| Compound 22 | chlorothalonil | 15:1 | 5:1 | 2:1 |
| Compound 22 | chlozolinate | 11:1 | 4:1 | 2:1 |
| Compound 22 | clotrimazole | 3:1 | 1:1 | 1:3 |
| Compound 22 | copper hydroxide | 45:1 | 15:1 | 5:1 |
| Compound 22 | copper oxychloride | 45:1 | 15:1 | 5:1 |
| Compound 22 | cyazofamid | 1:1 | 1:2 | 1:6 |
| Compound 22 | cyflufenamid | 1:2 | 1:6 | 1:24 |
| Compound 22 | cymoxanil | 1:1 | 1:2 | 1:5 |
| Compound 22 | cyproconazole | 1:1 | 1:2 | 1:6 |
| Compound 22 | cyprodinil | 4:1 | 2:1 | 1:2 |
| Compound 22 | dichlofluanid | 15:1 | 5:1 | 2:1 |
| Compound 22 | diclocymet | 15:1 | 5:1 | 2:1 |
| Compound 22 | diclomezine | 3:1 | 1:1 | 1:3 |
| Compound 22 | dicloran | 15:1 | 5:1 | 2:1 |
| Compound 22 | diethofencarb | 7:1 | 2:1 | 1:2 |
| Compound 22 | difenoconazole | 1:1 | 1:3 | 1:12 |
| Compound 22 | diflumetorim | 15:1 | 5:1 | 2:1 |
| Compound 22 | dimethirimol | 1:3 | 1:8 | 1:30 |
| Compound 22 | dimethomorph | 3:1 | 1:1 | 1:2 |
| Compound 22 | dimoxystrobin | 2:1 | 1:1 | 1:4 |
| Compound 22 | diniconazole | 1:1 | 1:3 | 1:8 |
| Compound 22 | diniconazole-M | 1:1 | 1:3 | 1:12 |
| Compound 22 | dinocap | 2:1 | 1:1 | 1:3 |
| Compound 22 | dithianon | 5:1 | 2:1 | 1:2 |
| Compound 22 | dodemorph | 7:1 | 3:1 | 1:1 |
| Compound 22 | dodine | 10:1 | 4:1 | 2:1 |
| Compound 22 | edifenphos | 3:1 | 1:1 | 1:3 |
| Compound 22 | enestroburin | 2:1 | 1:1 | 1:4 |

TABLE A1-continued

| Component (a) | Component (b) | Illustrative Ratios(*) | | |
|---|---|---|---|---|
| Compound 22 | epoxiconazole | 1:1 | 1:3 | 1:7 |
| Compound 22 | ethaboxam | 2:1 | 1:1 | 1:3 |
| Compound 22 | ethirimol | 7:1 | 3:1 | 1:1 |
| Compound 22 | etridiazole | 7:1 | 2:1 | 1:2 |
| Compound 22 | famoxadone | 2:1 | 1:1 | 1:4 |
| Compound 22 | fenamidone | 2:1 | 1:1 | 1:4 |
| Compound 22 | fenarimol | 1:2 | 1:7 | 1:24 |
| Compound 22 | fenbuconazole | 1:1 | 1:3 | 1:10 |
| Compound 22 | fenfuram | 4:1 | 1:1 | 1:2 |
| Compound 22 | fenhexamid | 10:1 | 4:1 | 2:1 |
| Compound 22 | fenoxanil | 15:1 | 4:1 | 1:1 |
| Compound 22 | fenpiclonil | 15:1 | 5:1 | 2:1 |
| Compound 22 | fenpropidin | 7:1 | 2:1 | 1:1 |
| Compound 22 | fenpropimorph | 7:1 | 2:1 | 1:1 |
| Compound 22 | fenpyrazamine | 3:1 | 1:1 | 1:3 |
| Compound 22 | fentin salt such as fentin acetate, fentin chloride or fentin hydroxide | 3:1 | 1:1 | 1:3 |
| Compound 22 | ferbam | 30:1 | 10:1 | 4:1 |
| Compound 22 | ferimzone | 7:1 | 2:1 | 1:2 |
| Compound 22 | fluazinam | 3:1 | 1:1 | 1:2 |
| Compound 22 | fludioxonil | 2:1 | 1:1 | 1:4 |
| Compound 22 | flumetover | 3:1 | 1:1 | 1:2 |
| Compound 22 | flumorph | 3:1 | 1:1 | 1:3 |
| Compound 22 | fluopicolide | 1:1 | 1:2 | 1:6 |
| Compound 22 | fluopyram | 3:1 | 1:1 | 1:3 |
| Compound 22 | fluoroimide | 37:1 | 14:1 | 5:1 |
| Compound 22 | fluoxastrobin | 1:1 | 1:2 | 1:6 |
| Compound 22 | fluquinconazole | 1:1 | 1:2 | 1:4 |
| Compound 22 | flusilazole | 3:1 | 1:1 | 1:3 |
| Compound 22 | flusulfamide | 15:1 | 5:1 | 2:1 |
| Compound 22 | flutianil | 1:1 | 1:2 | 1:6 |
| Compound 22 | flutolanil | 4:1 | 1:1 | 1:2 |
| Compound 22 | flutriafol | 1:1 | 1:2 | 1:4 |
| Compound 22 | fluxapyroxad | 2:1 | 1:1 | 1:3 |
| Compound 22 | folpet | 15:1 | 5:1 | 2:1 |
| Compound 22 | fosetyl-aluminum | 30:1 | 12:1 | 5:1 |
| Compound 22 | fuberidazole | 11:1 | 4:1 | 2:1 |
| Compound 22 | furalaxyl | 1:1 | 1:2 | 1:6 |
| Compound 22 | furametpyr | 15:1 | 5:1 | 2:1 |
| Compound 22 | guazatine | 15:1 | 5:1 | 2:1 |
| Compound 22 | hexaconazole | 1:1 | 1:2 | 1:5 |
| Compound 22 | hymexazol | 75:1 | 25:1 | 9:1 |
| Compound 22 | imazalil | 1:1 | 1:2 | 1:5 |
| Compound 22 | imibenconazole | 1:1 | 1:2 | 1:5 |
| Compound 22 | iminoctadine | 15:1 | 4:1 | 1:1 |
| Compound 22 | iodocalb | 15:1 | 5:1 | 2:1 |
| Compound 22 | ipconazole | 1:1 | 1:2 | 1:5 |
| Compound 22 | iprobenfos | 15:1 | 5:1 | 2:1 |
| Compound 22 | iprodione | 15:1 | 5:1 | 2:1 |
| Compound 22 | iprovalicarb | 2:1 | 1:1 | 1:3 |
| Compound 22 | isoprothiolane | 45:1 | 15:1 | 5:1 |
| Compound 22 | isopyrazam | 2:1 | 1:1 | 1:3 |
| Compound 22 | isotianil | 2:1 | 1:1 | 1:3 |
| Compound 22 | kasugamycin | 1:2 | 1:7 | 1:24 |
| Compound 22 | kresoxim-methyl | 2:1 | 1:1 | 1:4 |
| Compound 22 | mancozeb | 22:1 | 7:1 | 3:1 |
| Compound 22 | mandipropamid | 2:1 | 1:1 | 1:4 |
| Compound 22 | maneb | 22:1 | 7:1 | 3:1 |
| Compound 22 | mepanipyrim | 6:1 | 2:1 | 1:1 |
| Compound 22 | mepronil | 1:1 | 1:2 | 1:6 |
| Compound 22 | meptyldinocap | 2:1 | 1:1 | 1:3 |
| Compound 22 | metalaxyl | 1:1 | 1:2 | 1:6 |
| Compound 22 | metalaxyl-M | 1:1 | 1:4 | 1:12 |
| Compound 22 | metconazole | 1:1 | 1:2 | 1:6 |
| Compound 22 | methasulfocalb | 15:1 | 5:1 | 2:1 |
| Compound 22 | metiram | 15:1 | 5:1 | 2:1 |
| Compound 22 | metominostrobin | 3:1 | 1:1 | 1:3 |
| Compound 22 | metrafenone | 2:1 | 1:1 | 1:4 |
| Compound 22 | myclobutanil | 1:1 | 1:3 | 1:8 |
| Compound 22 | naftifine | 15:1 | 5:1 | 2:1 |
| Compound 22 | neo-asozin (ferric methanearsonate) | 15:1 | 5:1 | 2:1 |
| Compound 22 | nuarimol | 3:1 | 1:1 | 1:3 |
| Compound 22 | octhilinone | 15:1 | 4:1 | 1:1 |
| Compound 22 | ofurace | 1:1 | 1:2 | 1:6 |
| Compound 22 | orysastrobin | 3:1 | 1:1 | 1:3 |
| Compound 22 | oxadixyl | 1:1 | 1:2 | 1:6 |
| Compound 22 | oxolinic acid | 7:1 | 2:1 | 1:2 |
| Compound 22 | oxpoconazole | 1:1 | 1:2 | 1:5 |

TABLE A1-continued

| Component (a) | Component (b) | Illustrative Ratios(*) | | |
|---|---|---|---|---|
| Compound 22 | oxycarboxin | 4:1 | 1:1 | 1:2 |
| Compound 22 | oxytetracycline | 3:1 | 1:1 | 1:3 |
| Compound 22 | pefurazoate | 15:1 | 5:1 | 2:1 |
| Compound 22 | penconazole | 1:2 | 1:6 | 1:15 |
| Compound 22 | pencycuron | 11:1 | 4:1 | 2:1 |
| Compound 22 | penthiopyrad | 2:1 | 1:1 | 1:3 |
| Compound 22 | phosphorous acid or a salt thereof | 15:1 | 6:1 | 2:1 |
| Compound 22 | phthalide | 15:1 | 6:1 | 2:1 |
| Compound 22 | picoxystrobin | 1:1 | 1:2 | 1:5 |
| Compound 22 | piperalin | 3:1 | 1:1 | 1:3 |
| Compound 22 | polyoxin | 3:1 | 1:1 | 1:3 |
| Compound 22 | probenazole | 3:1 | 1:1 | 1:3 |
| Compound 22 | prochloraz | 7:1 | 2:1 | 1:2 |
| Compound 22 | procymidone | 11:1 | 4:1 | 2:1 |
| Compound 22 | propamocarb or propamocarb-hydrochloride | 10:1 | 4:1 | 2:1 |
| Compound 22 | propiconazole | 1:1 | 1:2 | 1:5 |
| Compound 22 | propineb | 11:1 | 4:1 | 2:1 |
| Compound 22 | proquinazid | 1:1 | 1:3 | 1:12 |
| Compound 22 | prothiocarb | 3:1 | 1:1 | 1:3 |
| Compound 22 | prothioconazole | 1:1 | 1:2 | 1:5 |
| Compound 22 | pyraclostrobin | 2:1 | 1:1 | 1:4 |
| Compound 22 | pyrametostrobin | 2:1 | 1:1 | 1:4 |
| Compound 22 | pyraoxystrobin | 2:1 | 1:1 | 1:4 |
| Compound 22 | pyrazophos | 15:1 | 4:1 | 1:1 |
| Compound 22 | pyribencarb | 4:1 | 1:1 | 1:2 |
| Compound 22 | pyributicarb | 15:1 | 4:1 | 1:1 |
| Compound 22 | pyrifenox | 3:1 | 1:1 | 1:3 |
| Compound 22 | pyrimethanil | 3:1 | 1:1 | 1:2 |
| Compound 22 | pyriofenone | 2:1 | 1:1 | 1:4 |
| Compound 22 | pyroquilon | 3:1 | 1:1 | 1:3 |
| Compound 22 | pyrrolnitrin | 15:1 | 5:1 | 2:1 |
| Compound 22 | quinomethionate | 15:1 | 5:1 | 2:1 |
| Compound 22 | quinoxyfen | 1:1 | 1:2 | 1:6 |
| Compound 22 | quintozene | 15:1 | 5:1 | 2:1 |
| Compound 22 | silthiofam | 2:1 | 1:1 | 1:4 |
| Compound 22 | simeconazole | 1:1 | 1:2 | 1:5 |
| Compound 22 | spiroxamine | 5:1 | 2:1 | 1:2 |
| Compound 22 | streptomycin | 3:1 | 1:1 | 1:3 |
| Compound 22 | sulfur | 75:1 | 25:1 | 9:1 |
| Compound 22 | tebuconazole | 1:1 | 1:2 | 1:5 |
| Compound 22 | tebufloquin | 3:1 | 1:1 | 1:3 |
| Compound 22 | tecloftalam | 15:1 | 5:1 | 2:1 |
| Compound 22 | tecnazene | 15:1 | 5:1 | 2:1 |
| Compound 22 | terbinafine | 15:1 | 5:1 | 2:1 |
| Compound 22 | tetraconazole | 1:1 | 1:2 | 1:5 |
| Compound 22 | thiabendazole | 11:1 | 4:1 | 2:1 |
| Compound 22 | thifluzamide | 3:1 | 1:1 | 1:3 |
| Compound 22 | thiophanate | 11:1 | 4:1 | 2:1 |
| Compound 22 | thiophanate-methyl | 11:1 | 4:1 | 2:1 |
| Compound 22 | thiram | 37:1 | 14:1 | 5:1 |
| Compound 22 | tiadinil | 2:1 | 1:1 | 1:3 |
| Compound 22 | tolclofos-methyl | 37:1 | 14:1 | 5:1 |
| Compound 22 | tolylfluanid | 15:1 | 5:1 | 2:1 |
| Compound 22 | triadimefon | 1:1 | 1:2 | 1:5 |
| Compound 22 | triadimenol | 1:1 | 1:2 | 1:5 |
| Compound 22 | triazoxide | 15:1 | 5:1 | 2:1 |
| Compound 22 | tricyclazole | 3:1 | 1:1 | 1:3 |
| Compound 22 | tridemorph | 7:1 | 2:1 | 1:1 |
| Compound 22 | trifloxystrobin | 2:1 | 1:1 | 1:4 |
| Compound 22 | triflumizole | 3:1 | 1:1 | 1:3 |
| Compound 22 | triforine | 3:1 | 1:1 | 1:3 |
| Compound 22 | trimorphamide | 7:1 | 2:1 | 1:2 |
| Compound 22 | triticonazole | 1:1 | 1:2 | 1:5 |
| Compound 22 | uniconazole | 1:1 | 1:2 | 1:5 |
| Compound 22 | validamycin | 3:1 | 1:1 | 1:3 |
| Compound 22 | valifenalate (valiphenal) | 2:1 | 1:1 | 1:4 |
| Compound 22 | vinclozolin | 15:1 | 6:1 | 2:1 |
| Compound 22 | zineb | 37:1 | 14:1 | 5:1 |
| Compound 22 | ziram | 37:1 | 14:1 | 5:1 |
| Compound 22 | zoxamide | 2:1 | 1:1 | 1:4 |
| Compound 22 | 5-chloro-6-(2,4,6-trifluorophenyl)-7-(4-methylpiperidin-1-yl)[1,2,4]triazolo[1,5-a]pyrimidine | 1:1 | 1:2 | 1:6 |
| Compound 22 | Penflufen (N-[2-(1,3-dimethylbutyl)phenyl]-5-fluoro-1,3-dimethyl-1H-pyrazole-4-carboxamide) | 2:1 | 1:1 | 1:3 |
| Compound 22 | N-[2-[4-[[3-(4-chlorophenyl)-2-propyn-1-yl]oxy]-3-methoxyphenyl]ethyl]-3-methyl-2-[(methylsulfonyl)amino]butanamide | 2:1 | 1:1 | 1:4 |

TABLE A1-continued

| Component (a) | Component (b) | Illustrative Ratios(*) | | |
|---|---|---|---|---|
| Compound 22 | N-[2-[4-[[3-(4-chlorophenyl)-2-propyn-1-yl]oxy]-3-methoxyphenyl]ethyl]-3-methyl-2-[(ethylsulfonyl)amino]butanamide | 2:1 | 1:1 | 1:4 |
| Compound 22 | 2-butoxy-6-iodo-3-propyl-4H-1-benzopyran-4-one | 1:1 | 1:3 | 1:12 |
| Compound 22 | 3-[5-(4-chlorophenyl)-2,3-dimethyl-3-isoxazolidinyl]pyridine | 3:1 | 1:1 | 1:3 |
| Compound 22 | 4-fluorophenyl N-[1-[[[1-(4-cyanophenyl)ethyl]sulfonyl]methyl]propyl]carbamate | 2:1 | 1:1 | 1:4 |
| Compound 22 | N-[[(cyclopropylmethoxy)amino][6-(difluoromethoxy)-2,3-difluorophenyl]methylene]benzeneacetamide | 1:2 | 1:7 | 1:24 |
| Compound 22 | α-[methoxyimino]-N-methyl-2-[[[1-[3-(trifluoromethyl)phenyl]ethoxy]imino]methyl]-benzeneacetamide | 3:1 | 1:1 | 1:3 |
| Compound 22 | N'-[4-[4-chloro-3-(trifluoromethyl)phenoxy]-2,5-dimethylphenyl]-N-ethyl-N-methylmethanimidamide | 3:1 | 1:1 | 1:3 |
| Compound 22 | N-(4-chloro-2-nitrophenyl)-N-ethyl-4-methyl-benzenesulfonamide | 3:1 | 1:1 | 1:3 |
| Compound 22 | 2-[[[3-(2,6-dichlorophenyl)-1-methyl-2-propen-1-ylidene]amino]oxy]methyl]-α-(methoxyimino)-N-methylbenzeneacetamide | 3:1 | 1:1 | 1:3 |
| Compound 22 | pentyl N-[4-[[[[(1-methyl-1H-tetrazol-5-yl)phenyl-methylene]amino]oxy]methyl]-2-thiazolyl]carbamate | 3:1 | 1:1 | 1:3 |
| Compound 22 | pentyl N-[6-[[[[(1-methyl-1H-tetrazol-5-yl)phenyl-methylene]amino]oxy]methyl]-2-pyridinyl]carbamate | 3:1 | 1:1 | 1:3 |

(*) Ratios of Component (b) relative to Component (a) by weight.

Tables A2 through A54 are each constructed the same as Table A1 above except that entries below the "Component (a)" column heading are replaced with the respective Component (a) Column Entry shown below. Thus, for example, in Table A2 the entries below the "Component (a)" column heading all recite "Compound 18", and the first line below the column headings in Table A2 specifically discloses a mixture of Compound 18 with acibenzolar-S-methyl. Tables A3 through A54 are constructed similarly.

| Table Number | Component (a) Column Entries |
|---|---|
| A2 | Compound 18 |
| A3 | Compound 23 |
| A4 | Compound 24 |
| A5 | Compound 36 |
| A6 | Compound 41 |
| A7 | Compound 45 |
| A8 | Compound 87 |
| A9 | Compound 91 |
| A10 | Compound 118 |
| A11 | Compound 139 |
| A12 | Compound 148 |
| A13 | Compound 172 |
| A14 | Compound 175 |
| A15 | Compound 193 |
| A16 | Compound 232 |
| A17 | Compound 265 |
| A18 | Compound 266 |
| A19 | Compound 284 |
| A20 | Compound 286 |
| A21 | Compound 287 |
| A22 | Compound 292 |
| A23 | Compound 297 |
| A24 | Compound 332 |
| A25 | Compound 336 |
| A26 | Compound 343 |
| A27 | Compound 346 |
| A28 | Compound 349 |
| A29 | Compound 351 |
| A30 | Compound 352 |
| A31 | Compound 357 |
| A32 | Compound 358 |
| A33 | Compound 360 |
| A34 | Compound 361 |
| A35 | Compound 364 |
| A36 | Compound 365 |
| A37 | Compound 367 |
| A38 | Compound 368 |
| A39 | Compound 369 |
| A40 | Compound 372 |
| A41 | Compound 373 |
| A42 | Compound 374 |
| A43 | Compound 375 |
| A44 | Compound 376 |
| A45 | Compound 377 |
| A46 | Compound 378 |
| A47 | Compound 379 |
| A48 | Compound 380 |
| A49 | Compound 381 |
| A50 | Compound 382 |
| A51 | Compound 383 |
| A52 | Compound 384 |
| A53 | Compound 385 |
| A54 | Compound 386 |

Table B1 lists specific combinations of a Component (b) compound with Component (a) illustrative of the mixtures, compositions and methods of the present invention. The first column of Table B1 lists the specific Component (b) compound (e.g., "acibenzolar-S-methyl" in the first line). The second, third and fourth columns of Table B1 lists ranges of weight ratios for rates at which the Component (b) compound is typically applied to a field-grown crop relative to Component (a) (e.g., "2:1 to 1:180" of acibenzolar-S-methyl relative to Component (a) by weight). Thus, for example, the first line of Table B1 specifically discloses the combination of acibenzolar-S-methyl with Component (a) is typically applied in a weight ratio between 2:1 to 1:180. The remaining lines of Table B1 are to be construed similarly. Table B1 thus supplements the specific ratios disclosed in Tables A1 through A54 with ranges of ratios for these combinations.

TABLE B1

| Component (b) | Typical Weight Ratio | More Typical Weight Ratio | Most Typical Weight Ratio |
|---|---|---|---|
| acibenzolar-S-methyl | 2:1 to 1:180 | 1:1 to 1:60 | 1:1 to 1:18 |
| aldimorph | 30:1 to 1:3 | 10:1 to 1:1 | 7:1 to 1:1 |
| ametoctradin | 9:1 to 1:18 | 3:1 to 1:6 | 3:1 to 1:3 |
| amisulbrom | 6:1 to 1:18 | 2:1 to 1:6 | 1:1 to 1:6 |
| anilazine | 90:1 to 2:1 | 30:1 to 4:1 | 22:1 to 4:1 |
| azaconazole | 7:1 to 1:18 | 2:1 to 1:6 | 2:1 to 1:4 |
| azoxystrobin | 9:1 to 1:12 | 3:1 to 1:4 | 3:1 to 1:3 |
| benalaxyl | 4:1 to 1:18 | 1:1 to 1:6 | 1:1 to 1:6 |
| benalaxyl-M | 4:1 to 1:36 | 1:1 to 1:12 | 1:1 to 1:8 |
| benodanil | 18:1 to 1:6 | 6:1 to 1:2 | 4:1 to 1:2 |
| benomyl | 45:1 to 1:4 | 15:1 to 1:1 | 11:1 to 1:1 |
| benthiavalicarb or benthiavalicarb-isopropyl | 2:1 to 1:36 | 1:1 to 1:12 | 1:1 to 1:12 |
| bethoxazin | 150:1 to 1:36 | 50:1 to 1:12 | 15:1 to 2:1 |
| binapacryl | 150:1 to 1:36 | 50:1 to 1:12 | 15:1 to 2:1 |
| biphenyl | 150:1 to 1:36 | 50:1 to 1:12 | 15:1 to 2:1 |
| bitertanol | 15:1 to 1:5 | 5:1 to 1:2 | 3:1 to 1:2 |
| bixafen | 12:1 to 1:9 | 4:1 to 1:3 | 2:1 to 1:3 |
| blasticidin-S | 3:1 to 1:90 | 1:1 to 1:30 | 1:4 to 1:30 |
| boscalid | 18:1 to 1:6 | 6:1 to 1:2 | 4:1 to 1:2 |
| bromuconazole | 15:1 to 1:9 | 5:1 to 1:3 | 3:1 to 1:3 |
| bupirimate | 3:1 to 1:90 | 1:1 to 1:30 | 1:3 to 1:30 |
| captafol | 90:1 to 1:4 | 30:1 to 1:2 | 15:1 to 2:1 |
| captan | 90:1 to 1:4 | 30:1 to 1:2 | 15:1 to 2:1 |
| carbendazim | 45:1 to 1:4 | 15:1 to 1:2 | 11:1 to 2:1 |
| carboxin | 18:1 to 1:6 | 6:1 to 1:2 | 4:1 to 1:2 |
| carpropamid | 15:1 to 1:9 | 5:1 to 1:3 | 3:1 to 1:3 |
| chloroneb | 300:1 to 2:1 | 100:1 to 4:1 | 100:1 to 14:1 |
| chlorothalonil | 90:1 to 1:4 | 30:1 to 1:2 | 15:1 to 2:1 |
| chlozolinate | 45:1 to 1:2 | 15:1 to 2:1 | 11:1 to 2:1 |
| clotrimazole | 15:1 to 1:9 | 5:1 to 1:3 | 3:1 to 1:3 |
| copper salts such as Bordeaux mixture (tribasic copper sulfate), copper oxychloride, copper sulfate and copper hydroxide | 450:1 to 1:1 | 150:1 to 4:1 | 45:1 to 5:1 |
| cyazofamid | 4:1 to 1:18 | 1:1 to 1:6 | 1:1 to 1:6 |
| cyflufenamid | 1:1 to 1:90 | 1:2 to 1:30 | 1:2 to 1:24 |
| cymoxanil | 6:1 to 1:18 | 2:1 to 1:6 | 1:1 to 1:5 |
| cyproconazole | 4:1 to 1:18 | 1:1 to 1:6 | 1:1 to 1:6 |
| cyprodinil | 22:1 to 1:9 | 7:1 to 1:3 | 4:1 to 1:2 |
| dichlofluanid | 150:1 to 1:36 | 50:1 to 1:12 | 15:1 to 2:1 |
| diclocymet | 150:1 to 1:36 | 50:1 to 1:12 | 15:1 to 2:1 |
| diclomezine | 15:1 to 1:9 | 5:1 to 1:3 | 3:1 to 1:3 |
| dicloran | 150:1 to 1:36 | 50:1 to 1:12 | 15:1 to 2:1 |
| diethofencarb | 22:1 to 1:9 | 7:1 to 1:3 | 7:1 to 1:2 |
| difenoconazole | 4:1 to 1:36 | 1:1 to 1:12 | 1:1 to 1:12 |
| diflumetorim | 150:1 to 1:36 | 50:1 to 1:12 | 15:1 to 2:1 |
| dimethirimol | 3:1 to 1:90 | 1:1 to 1:30 | 1:3 to 1:30 |
| dimethomorph | 9:1 to 1:6 | 3:1 to 1:2 | 3:1 to 1:2 |
| dimoxystrobin | 9:1 to 1:18 | 3:1 to 1:6 | 2:1 to 1:4 |
| diniconazole | 3:1 to 1:36 | 1:1 to 1:12 | 1:1 to 1:8 |
| diniconazole M | 3:1 to 1:90 | 1:1 to 1:30 | 1:1 to 1:12 |
| dinocap | 7:1 to 1:9 | 2:1 to 1:3 | 2:1 to 1:3 |
| dithianon | 15:1 to 1:4 | 5:1 to 1:2 | 5:1 to 1:2 |
| dodemorph | 30:1 to 1:3 | 10:1 to 1:1 | 7:1 to 1:1 |
| dodine | 30:1 to 1:2 | 10:1 to 2:1 | 10:1 to 2:1 |
| edifenphos | 30:1 to 1:9 | 10:1 to 1:3 | 3:1 to 1:3 |
| enestroburin | 9:1 to 1:18 | 3:1 to 1:6 | 2:1 to 1:4 |
| epoxiconazole | 3:1 to 1:36 | 1:1 to 1:12 | 1:1 to 1:7 |
| ethaboxam | 7:1 to 1:9 | 2:1 to 1:3 | 2:1 to 1:3 |
| ethirimol | 30:1 to 1:3 | 10:1 to 1:1 | 7:1 to 1:1 |
| etridiazole | 30:1 to 1:9 | 10:1 to 1:3 | 7:1 to 1:2 |
| famoxadone | 9:1 to 1:18 | 3:1 to 1:6 | 2:1 to 1:4 |
| fenamidone | 6:1 to 1:18 | 2:1 to 1:6 | 2:1 to 1:4 |
| fenarimol | 3:1 to 1:90 | 1:1 to 1:30 | 1:2 to 1:24 |
| fenbuconazole | 3:1 to 1:30 | 1:1 to 1:10 | 1:1 to 1:10 |
| fenfuram | 18:1 to 1:6 | 6:1 to 1:2 | 4:1 to 1:2 |
| fenhexamid | 30:1 to 1:2 | 10:1 to 2:1 | 10:1 to 2:1 |
| fenoxanil | 150:1 to 1:36 | 50:1 to 1:12 | 15:1 to 1:1 |
| fenpiclonil | 75:1 to 1:9 | 25:1 to 1:3 | 15:1 to 2:1 |
| fenpropidin | 30:1 to 1:3 | 10:1 to 1:1 | 7:1 to 1:1 |
| fenpropimorph | 30:1 to 1:3 | 10:1 to 1:1 | 7:1 to 1:1 |
| fenpyrazamine | 100:1 to 1:100 | 10:1 to 1:10 | 3:1 to 1:3 |
| fentin salt such as the acetate, chloride or hydroxide | 15:1 to 1:9 | 5:1 to 1:3 | 3:1 to 1:3 |
| ferbam | 300:1 to 1:2 | 100:1 to 2:1 | 30:1 to 4:1 |
| ferimzone | 30:1 to 1:5 | 10:1 to 1:2 | 7:1 to 1:2 |
| fluazinam | 22:1 to 1:5 | 7:1 to 1:2 | 3:1 to 1:2 |
| fludioxonil | 7:1 to 1:12 | 2:1 to 1:4 | 2:1 to 1:4 |
| flumetover | 9:1 to 1:6 | 3:1 to 1:2 | 3:1 to 1:2 |
| flumorph | 9:1 to 1:18 | 3:1 to 1:6 | 3:1 to 1:3 |
| fluopicolide | 3:1 to 1:18 | 1:1 to 1:6 | 1:1 to 1:6 |
| fluopyram | 15:1 to 1:90 | 5:1 to 1:30 | 3:1 to 1:3 |
| fluoromide | 150:1 to 2:1 | 50:1 to 4:1 | 37:1 to 5:1 |
| fluoxastrobin | 4:1 to 1:18 | 1:1 to 1:6 | 1:1 to 1:6 |
| fluquinconazole | 4:1 to 1:12 | 1:1 to 1:4 | 1:1 to 1:4 |
| flusilazole | 15:1 to 1:9 | 5:1 to 1:3 | 3:1 to 1:3 |
| flusulfamide | 90:1 to 1:2 | 30:1 to 2:1 | 15:1 to 2:1 |
| flutianil | 7:1 to 1:36 | 2:1 to 1:12 | 1:1 to 1:6 |
| flutolanil | 18:1 to 1:6 | 6:1 to 1:2 | 4:1 to 1:2 |
| flutriafol | 4:1 to 1:12 | 1:1 to 1:4 | 1:1 to 1:4 |
| fluxapyroxad | 12:1 to 1:9 | 4:1 to 1:3 | 2:1 to 1:3 |
| folpet | 90:1 to 1:4 | 30:1 to 1:2 | 15:1 to 2:1 |
| fosetyl-aluminum | 225:1 to 2:1 | 75:1 to 5:1 | 30:1 to 5:1 |
| fuberidazole | 45:1 to 1:4 | 15:1 to 1:2 | 11:1 to 2:1 |
| furalaxyl | 15:1 to 1:45 | 5:1 to 1:15 | 1:1 to 1:6 |
| furametpyr | 150:1 to 1:36 | 50:1 to 1:12 | 15:1 to 2:1 |
| guazatine or iminoctadine | 150:1 to 1:36 | 50:1 to 1:12 | 15:1 to 2:1 |
| hexaconazole | 15:1 to 1:36 | 5:1 to 1:12 | 1:1 to 1:5 |
| hymexazol | 225:1 to 2:1 | 75:1 to 4:1 | 75:1 to 9:1 |
| imazalil | 7:1 to 1:18 | 2:1 to 1:6 | 1:1 to 1:5 |
| imibenconazole | 15:1 to 1:36 | 5:1 to 1:12 | 1:1 to 1:5 |
| iodocarb | 150:1 to 1:36 | 50:1 to 1:12 | 15:1 to 2:1 |
| ipconazole | 15:1 to 1:36 | 5:1 to 1:12 | 1:1 to 1:5 |
| iprobenfos | 150:1 to 1:36 | 50:1 to 1:12 | 15:1 to 2:1 |
| iprodione | 120:1 to 1:2 | 40:1 to 2:1 | 15:1 to 2:1 |
| iprovalicarb | 9:1 to 1:9 | 3:1 to 1:3 | 2:1 to 1:3 |
| isoprothiolane | 150:1 to 2:1 | 50:1 to 4:1 | 45:1 to 5:1 |
| isopyrazam | 12:1 to 1:9 | 4:1 to 1:3 | 2:1 to 1:3 |
| isotianil | 12:1 to 1:9 | 4:1 to 1:3 | 2:1 to 1:3 |
| kasugamycin | 7:1 to 1:90 | 2:1 to 1:30 | 1:2 to 1:24 |
| kresoxim-methyl | 7:1 to 1:18 | 2:1 to 1:6 | 2:1 to 1:4 |
| mancozeb | 180:1 to 1:3 | 60:1 to 2:1 | 22:1 to 3:1 |
| mandipropamid | 6:1 to 1:18 | 2:1 to 1:6 | 2:1 to 1:4 |
| maneb | 180:1 to 1:3 | 60:1 to 2:1 | 22:1 to 3:1 |
| mepanipyrim | 18:1 to 1:3 | 6:1 to 1:1 | 6:1 to 1:1 |
| mepronil | 7:1 to 1:36 | 2:1 to 1:12 | 1:1 to 1:6 |
| meptyldinocap | 7:1 to 1:9 | 2:1 to 1:3 | 2:1 to 1:3 |
| metalaxyl | 15:1 to 1:45 | 5:1 to 1:15 | 1:1 to 1:6 |
| metalaxyl-M | 7:1 to 1:90 | 2:1 to 1:30 | 1:1 to 1:12 |
| metconazole | 3:1 to 1:18 | 1:1 to 1:6 | 1:1 to 1:6 |
| methasulfocarb | 150:1 to 1:36 | 50:1 to 1:12 | 15:1 to 1:1 |
| metiram | 150:1 to 1:36 | 50:1 to 1:12 | 15:1 to 1:1 |
| metominostrobin | 9:1 to 1:12 | 3:1 to 1:4 | 3:1 to 1:3 |
| metrafenone | 6:1 to 1:12 | 2:1 to 1:4 | 2:1 to 1:4 |
| myclobutanil | 5:1 to 1:26 | 1:1 to 1:9 | 1:1 to 1:8 |
| naftifine | 150:1 to 1:36 | 50:1 to 1:12 | 15:1 to 2:1 |
| neo-asozin (ferric methanearsonate) | 150:1 to 1:36 | 50:1 to 1:12 | 15:1 to 2:1 |
| nuarimol | 15:1 to 1:9 | 5:1 to 1:3 | 3:1 to 1:3 |
| octhilinone | 150:1 to 1:36 | 50:1 to 1:12 | 15:1 to 1:1 |
| ofurace | 15:1 to 1:45 | 5:1 to 1:15 | 1:1 to 1:6 |
| orysastrobin | 9:1 to 1:12 | 3:1 to 1:4 | 3:1 to 1:3 |
| oxadixyl | 15:1 to 1:45 | 5:1 to 1:15 | 1:1 to 1:6 |
| oxolinic acid | 30:1 to 1:9 | 10:1 to 1:3 | 7:1 to 1:2 |
| oxpoconazole | 15:1 to 1:36 | 5:1 to 1:12 | 1:1 to 1:5 |
| oxycarboxin | 18:1 to 1:6 | 6:1 to 1:2 | 4:1 to 1:2 |
| oxytetracycline | 15:1 to 1:9 | 5:1 to 1:3 | 3:1 to 1:3 |
| pefurazoate | 150:1 to 1:36 | 50:1 to 1:12 | 15:1 to 2:1 |
| penconazole | 1:1 to 1:45 | 1:2 to 1:15 | 1:2 to 1:15 |
| pencycuron | 150:1 to 1:2 | 50:1 to 2:1 | 11:1 to 2:1 |
| penthiopyrad | 12:1 to 1:9 | 4:1 to 1:3 | 2:1 to 1:3 |
| phosphorous acid and salts thereof | 150:1 to 1:36 | 50:1 to 1:12 | 15:1 to 2:1 |
| phthalide | 150:1 to 1:36 | 50:1 to 1:12 | 15:1 to 2:1 |

TABLE B1-continued

| Component (b) | Typical Weight Ratio | More Typical Weight Ratio | Most Typical Weight Ratio |
|---|---|---|---|
| picoxystrobin | 7:1 to 1:18 | 2:1 to 1:6 | 1:1 to 1:5 |
| piperalin | 15:1 to 1:9 | 5:1 to 1:3 | 3:1 to 1:3 |
| polyoxin | 15:1 to 1:9 | 5:1 to 1:3 | 3:1 to 1:3 |
| probenazole | 15:1 to 1:9 | 5:1 to 1:3 | 3:1 to 1:3 |
| prochloraz | 22:1 to 1:4 | 7:1 to 1:1 | 7:1 to 1:2 |
| procymidone | 45:1 to 1:3 | 15:1 to 1:1 | 11:1 to 2:1 |
| propamocarb or propamocarb-hydrochloride | 30:1 to 1:2 | 10:1 to 2:1 | 10:1 to 2:1 |
| propiconazole | 4:1 to 1:18 | 1:1 to 1:6 | 1:1 to 1:5 |
| propineb | 45:1 to 1:2 | 15:1 to 2:1 | 11:1 to 2:1 |
| proquinazid | 3:1 to 1:36 | 1:1 to 1:12 | 1:1 to 1:12 |
| prothiocarb | 9:1 to 1:18 | 3:1 to 1:6 | 3:1 to 1:3 |
| prothioconazole | 6:1 to 1:18 | 2:1 to 1:6 | 1:1 to 1:5 |
| pyraclostrobin | 9:1 to 1:18 | 3:1 to 1:6 | 2:1 to 1:4 |
| pyrametostrobin | 9:1 to 1:18 | 3:1 to 1:6 | 2:1 to 1:4 |
| pyraoxystrobin | 9:1 to 1:18 | 3:1 to 1:6 | 2:1 to 1:4 |
| pyrazophos | 150:1 to 1:36 | 50:1 to 1:12 | 15:1 to 1:1 |
| pyribencarb | 15:1 to 1:6 | 5:1 to 1:2 | 4:1 to 1:2 |
| pyrifenox | 15:1 to 1:9 | 5:1 to 1:3 | 3:1 to 1:3 |
| pyrimethanil | 30:1 to 1:6 | 10:1 to 1:2 | 3:1 to 1:2 |
| pyriofenone | 6:1 to 1:12 | 2:1 to 1:4 | 2:1 to 1:4 |
| pyroquilon | 15:1 to 1:9 | 5:1 to 1:3 | 3:1 to 1:3 |
| pyrrolnitrin | 150:1 to 1:36 | 50:1 to 1:12 | 15:1 to 2:1 |
| quinmethionate | 150:1 to 1:36 | 50:1 to 1:12 | 15:1 to 2:1 |
| quinoxyfen | 4:1 to 1:18 | 1:1 to 1:6 | 1:1 to 1:6 |
| quintozene | 150:1 to 1:36 | 50:1 to 1:12 | 15:1 to 2:1 |
| silthiofam | 7:1 to 1:18 | 2:1 to 1:6 | 2:1 to 1:4 |
| simeconazole | 15:1 to 1:36 | 5:1 to 1:12 | 1:1 to 1:5 |
| spiroxamine | 22:1 to 1:4 | 7:1 to 1:2 | 5:1 to 1:2 |
| streptomycin | 15:1 to 1:9 | 5:1 to 1:3 | 3:1 to 1:3 |
| sulfur | 300:1 to 3:1 | 100:1 to 9:1 | 75:1 to 9:1 |
| tebuconazole | 7:1 to 1:18 | 2:1 to 1:6 | 1:1 to 1:5 |
| tebufloquin | 100:1 to 1:100 | 10:1 to 1:10 | 3:1 to 1:3 |
| tecloftalam | 150:1 to 1:36 | 50:1 to 1:12 | 15:1 to 2:1 |
| tecnazene | 150:1 to 1:36 | 50:1 to 1:12 | 15:1 to 2:1 |
| terbinafine | 150:1 to 1:36 | 50:1 to 1:12 | 15:1 to 2:1 |
| tetraconazole | 15:1 to 1:36 | 5:1 to 1:12 | 1:1 to 1:5 |
| thiabendazole | 45:1 to 1:4 | 15:1 to 1:2 | 11:1 to 2:1 |
| thifluzamide | 15:1 to 1:9 | 5:1 to 1:3 | 3:1 to 1:3 |
| thiophanate | 45:1 to 1:3 | 15:1 to 2:1 | 11:1 to 2:1 |
| thiophanate-methyl | 45:1 to 1:3 | 15:1 to 2:1 | 11:1 to 2:1 |
| thiram | 150:1 to 1:2 | 50:1 to 2:1 | 37:1 to 5:1 |
| tiadinil | 12:1 to 1:9 | 4:1 to 1:3 | 2:1 to 1:3 |
| tolclofos-methyl | 150:1 to 1:2 | 50:1 to 2:1 | 37:1 to 5:1 |
| tolylfluanid | 150:1 to 1:36 | 50:1 to 1:12 | 15:1 to 2:1 |
| triadimefon | 15:1 to 1:36 | 5:1 to 1:12 | 1:1 to 1:5 |
| triadimenol | 15:1 to 1:36 | 5:1 to 1:12 | 1:1 to 1:5 |
| triazoxide | 150:1 to 1:36 | 50:1 to 1:12 | 15:1 to 2:1 |
| tricyclazole | 15:1 to 1:9 | 5:1 to 1:3 | 3:1 to 1:3 |
| tridemorph | 30:1 to 1:3 | 10:1 to 1:1 | 7:1 to 1:1 |
| trifloxystrobin | 6:1 to 1:18 | 2:1 to 1:6 | 2:1 to 1:4 |
| triflumizole | 15:1 to 1:9 | 5:1 to 1:3 | 3:1 to 1:3 |
| triforine | 15:1 to 1:9 | 5:1 to 1:3 | 3:1 to 1:3 |
| trimorphamide | 45:1 to 1:9 | 15:1 to 1:3 | 7:1 to 1:2 |
| triticonazole | 15:1 to 1:36 | 5:1 to 1:12 | 1:1 to 1:5 |
| uniconazole | 15:1 to 1:36 | 5:1 to 1:12 | 1:1 to 1:5 |
| validamycin | 150:1 to 1:36 | 50:1 to 1:12 | 3:1 to 1:3 |
| valifenalate (valiphenal) | 6:1 to 1:18 | 2:1 to 1:6 | 2:1 to 1:4 |
| vinclozolin | 120:1 to 1:2 | 40:1 to 2:1 | 15:1 to 2:1 |
| zineb | 150:1 to 1:2 | 50:1 to 2:1 | 37:1 to 5:1 |
| ziram | 150:1 to 1:2 | 50:1 to 2:1 | 37:1 to 5:1 |
| zoxamide | 6:1 to 1:18 | 2:1 to 1:6 | 2:1 to 1:4 |
| 5-chloro-6-(2,4,6-trifluorophenyl)-7-(4-methylpiperidin-1-yl)[1,2,4]triazolo[1,5-a]pyrimidine | 15:1 to 1:36 | 5:1 to 1:12 | 1:1 to 1:6 |
| penflufen (N-[2-(1,3-dimethylbutyl)phenyl]-5-fluoro-1,3-dimethyl-1H-pyrazole-4-carboxamide) | 12:1 to 1:9 | 4:1 to 1:3 | 2:1 to 1:3 |
| N-[2-[4-[[3-(4-chlorophenyl)-2-propyn-1-yl]oxy]-3-methoxyphenyl]ethyl]-3-methyl-2-[methylsulfonyl)amino]butanamide | 6:1 to 1:18 | 2:1 to 1:6 | 2:1 to 1:4 |
| N-[2-[4-[[3-(4-chlorophenyl)-2-propyn-1-yl]oxy]-3-methoxyphenyl]ethyl]-3-methyl-2-[(ethylsulfonyl)amino]butanamide | 6:1 to 1:18 | 2:1 to 1:6 | 2:1 to 1:4 |
| 2-butoxy-6-iodo-3-propyl-4H-1-benzopyran-4-one | 3:1 to 1:36 | 1:1 to 1:12 | 1:1 to 1:12 |
| 3-[5-(4-chlorophenyl)-2,3-dimethyl-3-isoxazolidinyl]pyridine | 15:1 to 1:9 | 5:1 to 1:3 | 3:1 to 1:3 |
| 4-fluorophenyl N-[1-[[[1-(4-cyanophenyl)ethyl]sulfonyl]methyl]propyl]carbamate | 6:1 to 1:18 | 2:1 to 1:6 | 2:1 to 1:4 |
| N-[[(cyclopropylmethoxy)amino][6-(difluoromethoxy)-2,3-difluorophenyl]methylene]benzeneacetamide | 1:1 to 1:90 | 1:2 to 1:30 | 1:2 to 1:24 |
| α-[methoxyimino]-N-methyl-2-[[[1-[3-(trifluoromethyl)phenyl]ethoxy]imino]-methyl]benzeneacetamide | 9:1 to 1:18 | 3:1 to 1:6 | 3:1 to 1:3 |
| N'-[4-[4-chloro-3-(trifluoromethyl)phenoxy]-2,5-dimethylphenyl]-N-ethyl-N-methylmethanimidamide | 15:1 to 1:18 | 5:1 to 1:6 | 3:1 to 1:3 |
| N-(4-chloro-2-nitrophenyl)-N-ethyl-4-methylbenzenesulfonamide | 15:1 to 1:18 | 5:1 to 1:6 | 3:1 to 1:3 |
| 2-[[[3-(2,6-dichlorophenyl)-1-methyl-2-propen-1-ylidene]amino]oxy]methyl]-α-(methoxyimino)-N-methylbenzeneacetamide | 9:1 to 1:18 | 3:1 to 1:6 | 3:1 to 1:3 |
| pentyl N-[4-[[[[(1-methyl-1H-tetrazol-5-yl)phenylmethylene]amino]oxy]methyl]-2-thiazolyl]carbamate | 9:1 to 1:18 | 3:1 to 1:6 | 3:1 to 1:3 |
| pentyl N-[6-[[[[(1-methyl-1H-tetrazol-5-yl)phenylmethylene]amino]oxy]methyl]-2-pyridinyl]carbamate | 9:1 to 1:18 | 3:1 to 1:6 | 3:1 to 1:3 |

As already noted, the present invention includes embodiments wherein in the composition comprising components (a) and (b), component (b) comprises at least one fungicide from each of two groups selected from (b1) through (b46). Tables C1 through C54 list specific mixtures (compound numbers refer to compounds in Index Table A) to illustrate embodiments wherein component (b) includes at least one fungicide from each of two groups selected from (b1) through (b46). In Table C1, each line below the column headings "Component (a)" and "Component (b)" specifically discloses a mixture of Component (a), which is Compound 22, with at least two Component (b) fungicides. The entries under the heading "Illustrative Ratios" disclose three specific weight ratios of Component (a) to each Component (b) fungicide in sequence for the disclosed mixture. For example, the first line discloses a mixture of Compound 22 with cyproconazole and azoxystrobin and lists weight ratios of Compound 22 to cyproconazole to azoxystrobin of 1:1:1, 2:1:1 or 3:1:1.

TABLE C1

| Component (a) | Component (b) | | Illustrative Ratios(*) | | |
|---|---|---|---|---|---|
| Compound 22 | cyproconazole | azoxystrobin | 1:1:1 | 2:1:1 | 3:1:1 |
| Compound 22 | cyproconazole | kresoxim-methyl | 1:1:1 | 2:1:1 | 3:1:1 |
| Compound 22 | cyproconazole | picoxystrobin | 1:1:1 | 2:1:1 | 3:1:1 |
| Compound 22 | cyproconazole | pyraclostrobin | 1:1:1 | 2:1:1 | 3:1:1 |
| Compound 22 | cyproconazole | trifloxystrobin | 1:1:1 | 2:1:1 | 3:1:1 |
| Compound 22 | cyproconazole | bixafen | 1:1:2 | 2:1:2 | 3:1:2 |
| Compound 22 | cyproconazole | boscalid | 1:1:2 | 2:1:2 | 3:1:2 |
| Compound 22 | cyproconazole | cyflufenamid | 1:2:1 | 2:2:1 | 3:2:1 |
| Compound 22 | cyproconazole | fluopyram | 1:1:2 | 2:1:2 | 3:1:2 |
| Compound 22 | cyproconazole | isopyrazam | 1:1:2 | 2:1:2 | 3:1:2 |
| Compound 22 | cyproconazole | metrafenone | 1:1:2 | 2:1:2 | 3:1:2 |
| Compound 22 | cyproconazole | penthiopyrad | 1:1:2 | 2:1:2 | 3:1:2 |
| Compound 22 | cyproconazole | proquinazid | 1:1:1 | 2:1:1 | 3:1:1 |
| Compound 22 | cyproconazole | quinoxyfen | 1:1:1 | 2:1:1 | 3:1:1 |
| Compound 22 | cyproconazole | sedaxane | 1:1:2 | 2:1:2 | 3:1:2 |
| Compound 22 | cyproconazole | picoxystrobin proquinazid | 1:1:1:1 | 2:1:1:1 | 3:1:1:1 |
| Compound 22 | cyproconazole | trifloxystrobin proquinazid | 1:1:1:1 | 2:1:1:1 | 3:1:1:1 |
| Compound 22 | difenconazole | azoxystrobin | 1:1:1 | 2:1:1 | 3:1:1 |
| Compound 22 | difenconazole | kresoxim-methyl | 1:1:1 | 2:1:1 | 3:1:1 |
| Compound 22 | difenconazole | picoxystrobin | 1:1:1 | 2:1:1 | 3:1:1 |
| Compound 22 | difenconazole | pyraclostrobin | 1:1:1 | 2:1:1 | 3:1:1 |
| Compound 22 | difenconazole | trifloxystrobin | 1:1:1 | 2:1:1 | 3:1:1 |
| Compound 22 | difenconazole | bixafen | 1:1:2 | 2:1:2 | 3:1:2 |
| Compound 22 | difenconazole | boscalid | 1:1:2 | 2:1:2 | 3:1:2 |
| Compound 22 | difenconazole | cyflufenamid | 1:2:1 | 2:2:1 | 3:2:1 |
| Compound 22 | difenconazole | fluopyram | 1:1:2 | 2:1:2 | 3:1:2 |
| Compound 22 | difenconazole | isopyrazam | 1:1:2 | 2:1:2 | 3:1:2 |
| Compound 22 | difenconazole | metrafenone | 1:1:2 | 2:1:2 | 3:1:2 |
| Compound 22 | difenconazole | penthiopyrad | 1:1:2 | 2:1:2 | 3:1:2 |
| Compound 22 | difenconazole | proquinazid | 1:1:1 | 2:1:1 | 3:1:1 |
| Compound 22 | difenconazole | quinoxyfen | 1:1:1 | 2:1:1 | 3:1:1 |
| Compound 22 | difenconazole | sedaxane | 1:1:2 | 2:1:2 | 3:1:2 |
| Compound 22 | difenconazole | picoxystrobin proquinazid | 1:1:1:1 | 2:1:1:1 | 3:1:1:1 |
| Compound 22 | difenconazole | trifloxystrobin proquinazid | 1:1:1:1 | 2:1:1:1 | 3:1:1:1 |
| Compound 22 | epoxiconazole | azoxystrobin | 1:1:1 | 2:1:1 | 3:1:1 |
| Compound 22 | epoxiconazole | kresoxim-methyl | 1:1:1 | 2:1:1 | 3:1:1 |
| Compound 22 | epoxiconazole | picoxystrobin | 1:1:1 | 2:1:1 | 3:1:1 |
| Compound 22 | epoxiconazole | pyraclostrobin | 1:1:1 | 2:1:1 | 3:1:1 |
| Compound 22 | epoxiconazole | trifloxystrobin | 1:1:1 | 2:1:1 | 3:1:1 |
| Compound 22 | epoxiconazole | bixafen | 1:1:2 | 2:1:2 | 3:1:2 |
| Compound 22 | epoxiconazole | boscalid | 1:1:2 | 2:1:2 | 3:1:2 |
| Compound 22 | epoxiconazole | cyflufenamid | 1:2:1 | 2:2:1 | 3:2:1 |
| Compound 22 | epoxiconazole | fluopyram | 1:1:2 | 2:1:2 | 3:1:2 |
| Compound 22 | epoxiconazole | isopyrazam | 1:1:2 | 2:1:2 | 3:1:2 |
| Compound 22 | epoxiconazole | metrafenone | 1:1:2 | 2:1:2 | 3:1:2 |
| Compound 22 | epoxiconazole | penthiopyrad | 1:1:2 | 2:1:2 | 3:1:2 |
| Compound 22 | epoxiconazole | proquinazid | 1:1:1 | 2:1:1 | 3:1:1 |
| Compound 22 | epoxiconazole | quinoxyfen | 1:1:1 | 2:1:1 | 3:1:1 |
| Compound 22 | epoxiconazole | sedaxane | 1:1:2 | 2:1:2 | 3:1:2 |
| Compound 22 | epoxiconazole | picoxystrobin proquinazid | 1:1:1:1 | 2:1:1:1 | 3:1:1:1 |
| Compound 22 | epoxiconazole | trifloxystrobin proquinazid | 1:1:1:1 | 2:1:1:1 | 3:1:1:1 |
| Compound 22 | metconazole | azoxystrobin | 1:1:1 | 2:1:1 | 3:1:1 |
| Compound 22 | metconazole | kresoxim-methyl | 1:1:1 | 2:1:1 | 3:1:1 |
| Compound 22 | metconazole | picoxystrobin | 1:1:1 | 2:1:1 | 3:1:1 |
| Compound 22 | metconazole | pyraclostrobin | 1:1:1 | 2:1:1 | 3:1:1 |
| Compound 22 | metconazole | trifloxystrobin | 1:1:1 | 2:1:1 | 3:1:1 |
| Compound 22 | metconazole | bixafen | 1:1:2 | 2:1:2 | 3:1:2 |
| Compound 22 | metconazole | boscalid | 1:1:2 | 2:1:2 | 3:1:2 |
| Compound 22 | metconazole | cyflufenamid | 1:2:1 | 2:2:1 | 3:2:1 |
| Compound 22 | metconazole | fluopyram | 1:1:2 | 2:1:2 | 3:1:2 |
| Compound 22 | metconazole | isopyrazam | 1:1:2 | 2:1:2 | 3:1:2 |
| Compound 22 | metconazole | metrafenone | 1:1:2 | 2:1:2 | 3:1:2 |
| Compound 22 | metconazole | penthiopyrad | 1:1:2 | 2:1:2 | 3:1:2 |
| Compound 22 | metconazole | proquinazid | 1:1:1 | 2:1:1 | 3:1:1 |
| Compound 22 | metconazole | quinoxyfen | 1:1:1 | 2:1:1 | 3:1:1 |
| Compound 22 | metconazole | sedaxane | 1:1:2 | 2:1:2 | 3:1:2 |
| Compound 22 | metconazole | picoxystrobin proquinazid | 1:1:1:1 | 2:1:1:1 | 3:1:1:1 |
| Compound 22 | metconazole | trifloxystrobin proquinazid | 1:1:1:1 | 2:1:1:1 | 3:1:1:1 |
| Compound 22 | myclobutanil | azoxystrobin | 1:1:1 | 2:1:1 | 3:1:1 |
| Compound 22 | myclobutanil | kresoxim-methyl | 1:1:1 | 2:1:1 | 3:1:1 |
| Compound 22 | myclobutanil | picoxystrobin | 1:1:1 | 2:1:1 | 3:1:1 |
| Compound 22 | myclobutanil | pyraclostrobin | 1:1:1 | 2:1:1 | 3:1:1 |
| Compound 22 | myclobutanil | trifloxystrobin | 1:1:1 | 2:1:1 | 3:1:1 |

TABLE C1-continued

| Component (a) | Component (b) | | Illustrative Ratios(*) | | |
|---|---|---|---|---|---|
| Compound 22 | myclobutanil | bixafen | 1:1:2 | 2:1:2 | 3:1:2 |
| Compound 22 | myclobutanil | boscalid | 1:1:2 | 2:1:2 | 3:1:2 |
| Compound 22 | myclobutanil | cyflufenamid | 1:2:1 | 2:2:1 | 3:2:1 |
| Compound 22 | myclobutanil | fluopyram | 1:1:2 | 2:1:2 | 3:1:2 |
| Compound 22 | myclobutanil | isopyrazam | 1:1:2 | 2:1:2 | 3:1:2 |
| Compound 22 | myclobutanil | metrafenone | 1:1:2 | 2:1:2 | 3:1:2 |
| Compound 22 | myclobutanil | penthiopyrad | 1:1:2 | 2:1:2 | 3:1:2 |
| Compound 22 | myclobutanil | proquinazid | 1:1:1 | 2:1:1 | 3:1:1 |
| Compound 22 | myclobutanil | quinoxyfen | 1:1:1 | 2:1:1 | 3:1:1 |
| Compound 22 | myclobutanil | sedaxane | 1:1:2 | 2:1:2 | 3:1:2 |
| Compound 22 | myclobutanil | picoxystrobin proquinazid | 1:1:1:1 | 2:1:1:1 | 3:1:1:1 |
| Compound 22 | myclobutanil | trifloxystrobin proquinazid | 1:1:1:1 | 2:1:1:1 | 3:1:1:1 |
| Compound 22 | prothioconazole | azoxystrobin | 1:1:1 | 2:1:1 | 3:1:1 |
| Compound 22 | prothioconazole | kresoxim-methyl | 1:1:1 | 2:1:1 | 3:1:1 |
| Compound 22 | prothioconazole | picoxystrobin | 1:1:1 | 2:1:1 | 3:1:1 |
| Compound 22 | prothioconazole | pyraclostrobin | 1:1:1 | 2:1:1 | 3:1:1 |
| Compound 22 | prothioconazole | trifloxystrobin | 1:1:1 | 2:1:1 | 3:1:1 |
| Compound 22 | prothioconazole | bixafen | 1:1:2 | 2:1:2 | 3:1:2 |
| Compound 22 | prothioconazole | boscalid | 1:1:2 | 2:1:2 | 3:1:2 |
| Compound 22 | prothioconazole | cyflufenamid | 1:2:1 | 2:2:1 | 3:2:1 |
| Compound 22 | prothioconazole | fluopyram | 1:1:2 | 2:1:2 | 3:1:2 |
| Compound 22 | prothioconazole | isopyrazam | 1:1:2 | 2:1:2 | 3:1:2 |
| Compound 22 | prothioconazole | metrafenone | 1:1:2 | 2:1:2 | 3:1:2 |
| Compound 22 | prothioconazole | penthiopyrad | 1:1:2 | 2:1:2 | 3:1:2 |
| Compound 22 | prothioconazole | proquinazid | 1:1:1 | 2:1:1 | 3:1:1 |
| Compound 22 | prothioconazole | quinoxyfen | 1:1:1 | 2:1:1 | 3:1:1 |
| Compound 22 | prothioconazole | sedaxane | 1:1:2 | 2:1:2 | 3:1:2 |
| Compound 22 | prothioconazole | picoxystrobin proquinazid | 1:1:1:1 | 2:1:1:1 | 3:1:1:1 |
| Compound 22 | prothioconazole | trifloxystrobin proquinazid | 1:1:1:1 | 2:1:1:1 | 3:1:1:1 |
| Compound 22 | tebuconazole | azoxystrobin | 1:1:1 | 2:1:1 | 3:1:1 |
| Compound 22 | tebuconazole | kresoxim-methyl | 1:1:1 | 2:1:1 | 3:1:1 |
| Compound 22 | tebuconazole | picoxystrobin | 1:1:1 | 2:1:1 | 3:1:1 |
| Compound 22 | tebuconazole | pyraclostrobin | 1:1:1 | 2:1:1 | 3:1:1 |
| Compound 22 | tebuconazole | trifloxystrobin | 1:1:1 | 2:1:1 | 3:1:1 |
| Compound 22 | tebuconazole | bixafen | 1:1:2 | 2:1:2 | 3:1:2 |
| Compound 22 | tebuconazole | boscalid | 1:1:2 | 2:1:2 | 3:1:2 |
| Compound 22 | tebuconazole | cyflufenamid | 1:2:1 | 2:2:1 | 3:2:1 |
| Compound 22 | tebuconazole | fluopyram | 1:1:2 | 2:1:2 | 3:1:2 |
| Compound 22 | tebuconazole | isopyrazam | 1:1:2 | 2:1:2 | 3:1:2 |
| Compound 22 | tebuconazole | metrafenone | 1:1:2 | 2:1:2 | 3:1:2 |
| Compound 22 | tebuconazole | penthiopyrad | 1:1:2 | 2:1:2 | 3:1:2 |
| Compound 22 | tebuconazole | proquinazid | 1:1:1 | 2:1:1 | 3:1:1 |
| Compound 22 | tebuconazole | quinoxyfen | 1:1:1 | 2:1:1 | 3:1:1 |
| Compound 22 | tebuconazole | sedaxane | 1:1:2 | 2:1:2 | 3:1:2 |
| Compound 22 | tebuconazole | picoxystrobin proquinazid | 1:1:1:1 | 2:1:1:1 | 3:1:1:1 |
| Compound 22 | tebuconazole | trifloxystrobin proquinazid | 1:1:1:1 | 2:1:1:1 | 3:1:1:1 |

(*) Ratios of Component (a) relative to Component (b) in sequence, by weight.

Tables C2 through C54 are each constructed the same as Table C1 above except that entries below the "Component (a)" column heading are replaced with the respective Component (a) Column Entry shown below. Thus, for example, in Table C2 the entries below the "Component (a)" column heading all recite "Compound 18", and the first line in below the column headings in Table C2 specifically discloses a mixture of Compound 18 with cyproconazole and azoxystrobin, and the illustrative weight ratios of 1:1:1, 2:1:1 and 3:1:1 of Compound 18:cyproconazole:azoxystrobin. Tables C3 through C54 are constructed similarly.

| Table Number | Component (a) Column Entries |
|---|---|
| C2 | Compound 18 |
| C3 | Compound 23 |
| C4 | Compound 24 |
| C5 | Compound 36 |
| C6 | Compound 41 |
| C7 | Compound 45 |
| C8 | Compound 87 |
| C9 | Compound 91 |
| C10 | Compound 118 |
| C11 | Compound 139 |
| C12 | Compound 148 |
| C13 | Compound 172 |
| C14 | Compound 175 |
| C15 | Compound 193 |
| C16 | Compound 232 |
| C17 | Compound 265 |
| C18 | Compound 266 |
| C19 | Compound 284 |
| C20 | Compound 286 |
| C21 | Compound 287 |
| C22 | Compound 292 |
| C23 | Compound 297 |
| C24 | Compound 332 |
| C25 | Compound 336 |
| C26 | Compound 343 |
| C27 | Compound 346 |
| C28 | Compound 349 |
| C29 | Compound 351 |
| C30 | Compound 352 |
| C31 | Compound 357 |
| C32 | Compound 358 |
| C33 | Compound 360 |
| C34 | Compound 361 |

-continued

| Table Number | Component (a) Column Entries |
|---|---|
| C35 | Compound 364 |
| C36 | Compound 365 |
| C37 | Compound 367 |
| C38 | Compound 368 |
| C39 | Compound 369 |
| C40 | Compound 372 |
| C41 | Compound 373 |
| C42 | Compound 374 |
| C43 | Compound 375 |
| C44 | Compound 376 |
| C45 | Compound 377 |
| C46 | Compound 378 |
| C47 | Compound 379 |
| C48 | Compound 380 |
| C49 | Compound 381 |
| C50 | Compound 382 |
| C51 | Compound 383 |
| C52 | Compound 384 |
| C53 | Compound 385 |
| C54 | Compound 386 |

As mentioned in the Summary of the Invention, one aspect of the present invention is a composition comprising (i.e. a mixture or combination of) a compound of Formula 1, an N-oxide, or a salt thereof, and at least one invertebrate pest control compound or agent (e.g., insecticide, acaricide). Of note is a composition comprising component (a) and at least one (i.e. one or more) invertebrate pest control compound or agent, which then can be subsequently combined with component (b) to provide a composition comprising components (a) and (b) and the one or more invertebrate pest control compounds or agents. Alternatively without first mixing with component (b), a biologically effective amount of the composition comprising component (a) with at least one invertebrate pest control agent can be applied to a plant or plant seed (directly or through the environment of the plant or plant seed) to protect the plant or plant seed from diseases caused by fungal pathogens and injury caused by invertebrate pests.

For embodiments where one or more of invertebrate pest control compounds are used, the weight ratio of these compounds (in total) to the component (a) compounds is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity.

Of note is a composition of the present invention which comprises in addition to a component (a) compound, alone or in combination with fungicidal component (b), at least one invertebrate pest control compound or agent selected from the group consisting of abamectin, acephate, acetamiprid, acetoprole, aldicarb, amidoflumet, amitraz, avermectin, azadirachtin, azinphos-methyl, bifenthrin, bifenazate, bistrifluron, buprofezin, carbofuran, cartap, chinomethionat, chlorfenapyr, chlorfluazuron, chlorantraniliprole, chlorpyrifos, chlorpyrifos-methyl, chlorobenzilate, chromafenozide, clothianidin, cyantraniliprole, cyflumetofen, cyfluthrin, beta-cyfluthrin, cyhalothrin, gamma-cyhalothrin, lambda-cyhalothrin, cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, fipronil, flonicamid, flubendiamide, flucythrinate, tau-fluvalinate, flufenerim, flufenoxuron, fonophos, halofenozide, hexaflumuron, hexythiazox, hydramethylnon, imicyafos, imidacloprid, indoxacarb, isofenphos, lufenuron, malathion, meperfluthrin, metaflumizone, metaldehyde, methamidophos, methidathion, methomyl, methoprene, methoxychlor, methoxyfenozide, metofluthrin, monocrotophos, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spiridiclofen, spiromesifen, spirotetramat, sulfoxaflor, sulprofos, tebufenozide, tebufenpyrad, teflubenzuron, tefluthrin, terbufos, tetrachlorvinphos, tetramethylfluthin, thiacloprid, thiamethoxam, thiodicarb, thiosultap-sodium, tolfenpyrad, tralomethrin, triazamate, trichlorfon, triflumuron, *Bacillus thuringiensis* subsp. *aizawai*, *Bacillus thuringiensis* subsp. *kurstaki*, nucleopolyhedro viruses, encapsulated delta-endotoxins of *Bacillus thuringiensis*, baculoviruses, entomopathogenic bacteria, entomopathogenic viruses and entomopathogenic fungi.

In certain instances, combinations of a compound of Formula 1 or an N-oxide or salt thereof (i.e. component (a)), alone or in mixture with fungicidal component (b), with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Table D1 lists specific combinations of invertebrate pest control agents with Compound 22 (identified in Index Table A) as a component (a) compound illustrative of mixtures and compositions comprising these active ingredients and methods using them according to the present invention. The second column of Table D1 lists the specific invertebrate pest control agents (e.g., "Abamectin" in the first line). The third column of Table D1 lists the mode of action (if known) or chemical class of the invertebrate pest control agents. The fourth column of Table D1 lists embodiment(s) of ranges of weight ratios for rates at which the invertebrate pest control agent is typically applied relative to Compound 22 alone or in combination with fungicidal component (b) (e.g., "50:1 to 1:50" of abamectin relative to a Compound 22 by weight). Thus, for example, the first line of Table D1 specifically discloses the combination of Compound 22 with abamectin is typically applied in a weight ratio between 50:1 to 1:50. The remaining lines of Table D1 are to be construed similarly

TABLE D1

| Component (a) | Invertebrate Pest Control Agent | Mode of Action or Chemical Class | Typical Weight Ratio |
|---|---|---|---|
| Compound 22 | Abamectin | macrocyclic lactones | 50:1 to 1:50 |
| Compound 22 | Acetamiprid | neonicotinoids | 150:1 to 1:200 |

TABLE D1-continued

| Component (a) | Invertebrate Pest Control Agent | Mode of Action or Chemical Class | Typical Weight Ratio |
|---|---|---|---|
| Compound 22 | Amitraz | octopamine receptor ligands | 200:1 to 1:100 |
| Compound 22 | Avermectin | macrocyclic lactones | 50:1 to 1:50 |
| Compound 22 | Azadirachtin | ecdysone agonists | 100:1 to 1:120 |
| Compound 22 | Beta-cyfluthrin | sodium channel modulators | 150:1 to 1:200 |
| Compound 22 | Bifenthrin | sodium channel modulators | 100:1 to 1:10 |
| Compound 22 | Buprofezin | chitin synthesis inhibitors | 500:1 to 1:50 |
| Compound 22 | Cartap | nereistoxin analogs | 100:1 to 1:200 |
| Compound 22 | Chlorantraniliprole | ryanodine receptor ligands | 100:1 to 1:120 |
| Compound 22 | Chlorfenapyr | mitochondrial electron transport inhibitors | 300:1 to 1:200 |
| Compound 22 | Chlorpyrifos | cholinesterase inhibitors | 500:1 to 1:200 |
| Compound 22 | Clothianidin | neonicotinoids | 100:1 to 1:400 |
| Compound 22 | Cyantraniliprole | ryanodine receptor ligands | 100:1 to 1:120 |
| Compound 22 | Cyfluthrin | sodium channel modulators | 150:1 to 1:200 |
| Compound 22 | Cyhalothrin | sodium channel modulators | 150:1 to 1:200 |
| Compound 22 | Cypermethrin | sodium channel modulators | 150:1 to 1:200 |
| Compound 22 | Cyromazine | chitin synthesis inhibitors | 400:1 to 1:50 |
| Compound 22 | Deltamethrin | sodium channel modulators | 50:1 to 1:400 |
| Compound 22 | Dieldrin | cyclodiene insecticides | 200:1 to 1:100 |
| Compound 22 | Dinotefuran | neonicotinoids | 150:1 to 1:200 |
| Compound 22 | Diofenolan | molting inhibitor | 150:1 to 1:200 |
| Compound 22 | Emamectin | macrocyclic lactones | 50:1 to 1:10 |
| Compound 22 | Endosulfan | cyclodiene insecticides | 200:1 to 1:100 |
| Compound 22 | Esfenvalerate | sodium channel modulators | 100:1 to 1:400 |
| Compound 22 | Ethiprole | GABA-regulated chloride channel blockers | 200:1 to 1:100 |
| Compound 22 | Fenothiocarb | | 150:1 to 1:200 |
| Compound 22 | Fenoxycarb | juvenile hormone mimics | 500:1 to 1:100 |
| Compound 22 | Fenvalerate | sodium channel modulators | 150:1 to 1:200 |
| Compound 22 | Fipronil | GABA-regulated chloride channel blockers | 150:1 to 1:100 |
| Compound 22 | Flonicamid | | 200:1 to 1:100 |
| Compound 22 | Flubendiamide | ryanodine receptor ligands | 100:1 to 1:120 |
| Compound 22 | Flufenoxuron | chitin synthesis inhibitors | 200:1 to 1:100 |
| Compound 22 | Hexaflumuron | chitin synthesis inhibitors | 300:1 to 1:50 |
| Compound 22 | Hydramethylnon | mitochondrial electron transport inhibitors | 150:1 to 1:250 |
| Compound 22 | Imidacloprid | neonicotinoids | 1000:1 to 1:1000 |
| Compound 22 | Indoxacarb | sodium channel modulators | 200:1 to 1:50 |
| Compound 22 | Lambda-cyhalothrin | sodium channel modulators | 50:1 to 1:250 |
| Compound 22 | Lufenuron | chitin synthesis inhibitors | 500:1 to 1:250 |
| Compound 22 | Meperfluthrin | Sodium channel modulators | 100:1 to 1:400 |
| Compound 22 | Metaflumizone | | 200:1 to 1:200 |
| Compound 22 | Methomyl | cholinesterase inhibitors | 500:1 to 1:100 |
| Compound 22 | Methoprene | juvenile hormone mimics | 500:1 to 1:100 |
| Compound 22 | Methoxyfenozide | ecdysone agonists | 50:1 to 1:50 |
| Compound 22 | Nitenpyram | neonicotinoids | 150:1 to 1:200 |
| Compound 22 | Nithiazine | neonicotinoids | 150:1 to 1:200 |
| Compound 22 | Novaluron | chitin synthesis inhibitors | 500:1 to 1:150 |
| Compound 22 | Oxamyl | cholinesterase inhibitors | 200:1 to 1:200 |
| Compound 22 | Pymetrozine | | 200:1 to 1:100 |
| Compound 22 | Pyrethrin | sodium channel modulators | 100:1 to 1:10 |
| Compound 22 | Pyridaben | mitochondrial electron transport inhibitors | 200:1 to 1:100 |
| Compound 22 | Pyridalyl | | 200:1 to 1:100 |
| Compound 22 | Pyriproxyfen | juvenile hormone mimics | 500:1 to 1:100 |
| Compound 22 | Ryanodine | ryanodine receptor ligands | 100:1 to 1:120 |
| Compound 22 | Spinetoram | macrocyclic lactones | 150:1 to 1:100 |
| Compound 22 | Spinosad | macrocyclic lactones | 500:1 to 1:10 |
| Compound 22 | Spirodiclofen | lipid biosynthesis inhibitors | 200:1 to 1:200 |
| Compound 22 | Spiromesifen | lipid biosynthesis inhibitors | 200:1 to 1:200 |
| Compound 22 | Sulfoxaflor | | 200:1 to 1: 200 |
| Compound 22 | Tebufenozide | ecdysone agonists | 500:1 to 1:250 |
| Compound 22 | Tetramethylfluthrin | Sodium channel modulators | 100:1 to 1:400 |
| Compound 22 | Thiacloprid | neonicotinoids | 100:1 to 1:200 |
| Compound 22 | Thiamethoxam | neonicotinoids | 1250:1 to 1:1000 |
| Compound 22 | Thiodicarb | cholinesterase inhibitors | 500:1 to 1:400 |
| Compound 22 | Thiosultap-sodium | | 150:1 to 1:100 |
| Compound 22 | Tralomethrin | sodium channel modulators | 150:1 to 1:200 |
| Compound 22 | Triazamate | cholinesterase inhibitors | 250:1 to 1:100 |
| Compound 22 | Triflumuron | chitin synthesis inhibitors | 200:1 to 1:100 |
| Compound 22 | *Bacillus thuringiensis* | biological agents | 50:1 to 1:10 |
| Compound 22 | *Bacillus thuringiensis* delta-endotoxin | biological agents | 50:1 to 1:10 |
| Compound 22 | NPV (e.g., Gemstar) | biological agents | 50:1 to 1:10 |

Tables D2 through D54 are each constructed the same as Table D1 above except that entries below the "Component (a)" column heading are replaced with the respective Component (a) Column Entry shown below. Thus, for example, in Table D2 the entries below the "Component (a)" column heading all recite "Compound 18", and the first line in below the column headings in Table D2 specifically discloses a mixture of Compound 18 with abamectin. Tables D3 through D54 are constructed similarly.

| Table Number | Component (a) Column Entries |
|---|---|
| D2 | Compound 18 |
| D3 | Compound 23 |
| D4 | Compound 24 |
| D5 | Compound 36 |
| D6 | Compound 41 |
| D7 | Compound 45 |
| D8 | Compound 87 |
| D9 | Compound 91 |
| D10 | Compound 118 |
| D11 | Compound 139 |
| D12 | Compound 148 |
| D13 | Compound 172 |
| D14 | Compound 175 |
| D15 | Compound 193 |

-continued

| Table Number | Component (a) Column Entries |
|---|---|
| D16 | Compound 232 |
| D17 | Compound 265 |
| D18 | Compound 266 |
| D19 | Compound 284 |
| D20 | Compound 286 |
| D21 | Compound 287 |
| D22 | Compound 292 |
| D23 | Compound 297 |
| D24 | Compound 332 |
| D25 | Compound 336 |
| D26 | Compound 343 |
| D27 | Compound 346 |
| D28 | Compound 349 |
| D29 | Compound 351 |
| D30 | Compound 352 |
| D31 | Compound 357 |
| D32 | Compound 358 |
| D33 | Compound 360 |
| D34 | Compound 361 |
| D35 | Compound 364 |
| D35 | Compound 365 |
| D37 | Compound 367 |
| D38 | Compound 368 |
| D39 | Compound 369 |
| D40 | Compound 372 |
| D41 | Compound 373 |
| D42 | Compound 374 |
| D43 | Compound 375 |
| D44 | Compound 376 |
| D45 | Compound 377 |
| D46 | Compound 378 |
| D47 | Compound 379 |
| D48 | Compound 380 |
| D49 | Compound 381 |
| D50 | Compound 382 |
| D51 | Compound 383 |
| D52 | Compound 384 |
| D53 | Compound 385 |
| D54 | Compound 386 |

One embodiment of invertebrate pest control agents (e.g., insecticides and acaricides) for mixing with compounds of Formula 1 (and N-oxides and salts thereof) include sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-regulated chloride channel blockers such as endosulfan, ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; ecdysone agonists such as azadirachtin, methoxyfenozide and tebufenozide; ryanodine receptor ligands such as ryanodine, anthranilic diamides such as chlorantraniliprole, cyantraniliprole and flubendiamide; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin; cyflumetofen; fenothiocarb; flonicamid; metaflumizone; pyrafluprole; pyridalyl; pyriprole; pymetrozine; spirotetramat; and thiosultap-sodium. One embodiment of biological agents for mixing with compounds of component (a) include nucleopolyhedro virus such as HzNPV and AfNPV; *Bacillus thuringiensis* and encapsulated delta-endotoxins of *Bacillus thuringiensis* such as Cellcap, MPV and MPVII; as well as naturally occurring and genetically modified viral insecticides including members of the family Baculoviridae as well as entomophagous fungi. Of note is a composition comprising component (a) and at least one additional biologically active compound or agent selected from the Invertebrate Pest Control Agents listed in Table D1 above.

The following TESTS demonstrate the control efficacy of compounds of this invention on specific pathogens. The pathogen control protection afforded by the compounds is not limited, however, to these species. See Index Table A for compound descriptions. The following abbreviations are used in the Index Tables which follow: Me is methyl, Ph is phenyl, OMe is methoxy, —CN is cyano, —$NO_2$ is nitro. Also, "pyridin-2-yl" is synonymous with "2-pyridinyl", "pyridin-3-yl" is synonymous with "3-pyridinyl", and "pyrimidin-5-yl" is synonymous with 5-pyrimidinyl". The abbreviation "Ex." stands for "Example" and is followed by a number indicating in which example the compound is prepared. "Cmpd No." means compound number. Mass spectra (M.S.) are reported as the molecular weight of the highest isotopic abundance parent ion (M+1) formed by addition of $H^+$ (molecular weight of 1) to the molecule, observed by mass spectrometry using atmospheric pressure chemical ionization ($AP^+$).

INDEX TABLE A

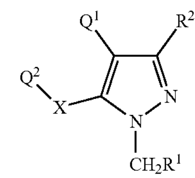

| Cmpd No. | $R^1$ | $R^2$ | $Q^1$ | $Q^2$ | X | M.S |
|---|---|---|---|---|---|---|
| 1 (Ex. 1) | H | Me | 2,4-di-F—Ph | 3-Cl—Ph | NH | ** |
| 2 | H | Me | 2,4-di-F—Ph | 3,5-di-OMe—Ph | NH | 360 |
| 3 | H | Me | 2,4-di-F—Ph | 3-Cl—Ph | NMe | * |
| 4 | H | Me | 4-Cl—Ph | 2,4-di-F—Ph | NH | 334 |
| 5 | H | Me | 4-Cl—Ph | 3,5-di-F—Ph | NH | 334 |
| 6 | H | Me | 4-Cl—Ph | 3,5-di-F—Ph | NMe | 348 |
| 7 | H | Me | 2-Cl-4-F—Ph | 3-Cl-4-F—Ph | NH | 369 |

INDEX TABLE A-continued

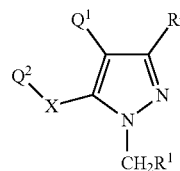

| Cmpd No. | R¹ | R² | Q¹ | Q² | X | M.S |
|---|---|---|---|---|---|---|
| 8 | H | Me | 2-Cl-4-F—Ph | 3-F—Ph | NH | 334 |
| 9 | H | Me | 2-Cl-4-F—Ph | 3,5-di-F—Ph | NH | 352 |
| 10 | H | Me | 4-Cl—Ph | 2,3,5-tri-F—Ph | NH | 352 |
| 11 | H | Me | 2-Cl-4-F—Ph | 4-F—Ph | NH | 334 |
| 12 | H | Me | 2-Cl-4-F—Ph | 2-F—Ph | NH | 334 |
| 13 | H | Me | 2-Cl-4-F—Ph | 2,4-di-F—Ph | NH | 352 |
| 14 | H | Me | 2,4,6-tri-F—Ph | 3-F-4-Cl—Ph | NH | 370 |
| 15 | H | Me | 2-F-4-OMe—Ph | 4-Cl—Ph | O | 347 |
| 16 | H | Me | 3,5-di-OMe—Ph | 4-Cl—Ph | O | 359 |
| 17 (Ex. 2) | H | Me | 2-Cl-4-F—Ph | 2,6-di-F-4-OMe—Ph | NH | ** |
| 18 | H | Me | 2-Cl-4-F—Ph | 2,4,6-tri-F—Ph | NH | 370 |
| 19 | H | Me | 2-Cl-4-F—Ph | 4-Cl—Ph | NH | 350 |
| 20 | H | Me | 2-Cl-4-F—Ph | 2-F-4-NO₂—Ph | O | 380 |
| 21 | H | Me | 2-Cl-4-F—Ph | 2-F-4-OMe—Ph | O | 365 |
| 22 | H | Me | 2,6-di-F-4-OMe—Ph | 4-Cl—Ph | NH | 364 |
| 23 | H | Me | 2,6-di-F-4-OMe—Ph | 2,4-di-F—Ph | NH | 366 |
| 24 (Ex. 3) | H | Me | 2,6-di-F-4-OMe—Ph | 2,4,6-tri-F—Ph | NH | ** |
| 25 | H | Me | 3-Cl—Ph | 2,6-di-F-4-OMe—Ph | NH | 364 |
| 26 | H | Me | 2,4,6-tri-F—Ph | 4-NO₂—Ph | O | 364 |
| 27 | H | Me | 2,4,6-tri-F—Ph | 4-Cl—Ph | O | 353 |
| 28 | H | Me | 4-Cl—Ph | 2,4,6-tri-F—Ph | NH | 352 |
| 29 | H | Me | 4-Cl—Ph | 2,6-di-F-4-OMe—Ph | NH | 364 |
| 30 | H | Me | 2,4,6-tri-F—Ph | 2,6-di-Cl-4-CF₃—Ph | O | 455 |
| 31 | H | Me | 2,4,6-tri-F—Ph | 2,6-di-F-4-CN—Ph | O | 380 |
| 32 | H | Me | 2,4,6-tri-F—Ph | 2-Cl-4-NO₂—Ph | O | 398 |
| 33 | H | Me | 4-Cl—Ph | 2,6-di-F—Ph | NH | 334 |
| 34 | H | Me | 2,6-di-F-4-OMe—Ph | 6-Cl-pyridin-3-yl | NH | 365 |
| 35 | H | Me | 3,4-di-F—Ph | 2,4,6-tri-F—Ph | NH | 354 |
| 36 | H | Me | 3,4-di-F—Ph | 2,6-di-F-4-OMe—Ph | NH | 366 |
| 37 | H | Me | 2,6-di-F—Ph | 3,5-di-OMe—Ph | NH | 360 |
| 38 | H | Me | 2,4,6-tri-F—Ph | 2,4-di-Cl—Ph | O | 387 |
| 39 | H | Me | 2,4,6-tri-F—Ph | 5-Cl-pyridin-2-yl | O | 354 |
| 40 | H | Me | 2,6-di-F-4-OMe—Ph | 2,4-di-Cl—Ph | O | 399 |
| 41 | H | Me | 2,4-di-F—Ph | 2,4,6-tri-F—Ph | NH | 354 |
| 42 | H | Me | 2,4-di-F—Ph | 2,6-di-F-4-OMe—Ph | NH | 366 |
| 43 | H | Me | 3-F—Ph | 2,6-di-F-4-CN—Ph | O | 344 |
| 44 | H | Me | 4-Cl—Ph | 2,6-di-F-4-CN—Ph | O | 360 |
| 45 (Ex. 4) | H | Me | 2-Cl-4-F—Ph | 2,6-di-F-4-CN—Ph | O | ** |
| 46 | H | Me | 2-F-4-OMe—Ph | 2,6-di-F-4-CN—Ph | O | 374 |
| 47 | H | Me | 2,6-di-F-4-OMe—Ph | 5-Cl-pyridin-2-yl | O | 366 |
| 48 | H | Me | 2,6-di-F-4-OMe—Ph | 3,4-di-F—Ph | NH | 366 |
| 49 | H | Me | 2,6-di-F-4-OMe—Ph | 3-F-4-Cl—Ph | NH | 382 |
| 50 | H | Me | 2,6-di-F-4-OMe—Ph | 4-Me—Ph | NH | 344 |
| 51 | H | Me | 2,6-di-F-4-OMe—Ph | 2,4-di-OMe—Ph | NH | 390 |
| 52 | H | Me | 4-Me—Ph | 2-Cl-4-NO₂—Ph | O | 358 |
| 53 | Ph | Me | 2,4,6-tri-F—Ph | 2,6-di-F-4-NO₂—Ph | O | 476 |
| 54 (Ex. 8) | H | Me | 2,4,6-tri-F—Ph | 2,6-di-F-4-NO₂—Ph | O | ** |
| 55 | H | Me | 4-Me—Ph | 2-Cl-4-OMe—Ph | O | 343 |
| 56 | H | Me | 4-Cl—Ph | 4-OMe—Ph | NH | 328 |
| 57 | H | Me | 2,4-di-Cl—Ph | 2,4-di-OMe—Ph | NH | 392 |
| 58 (Ex. 10) | H | Me | 2,6-di-F-4-OMe—Ph | 2,6-di-F-4-Cl—Ph | O | ** |
| 59 | H | Me | 2,6-di-F-4-OMe—Ph | 2,4-di-OMe-6-Cl—Ph | NH | 424 |
| 60 | H | Me | 4-Cl—Ph | 2-Cl-4-OMe—Ph | NH | 362 |
| 61 | Me | Me | 4-Cl—Ph | 2,6-di-F—Ph | NH | 348 |
| 62 | H | Me | 2,4-di-Cl—Ph | 2,6-di-F-4-OMe—Ph | NH | 398 |
| 63 | Me | Me | 2,6-di-F—Ph | 3,5-di-OMe—Ph | NH | 374 |
| 64 | H | Me | 2,4,6-tri-F—Ph | 3,5-di-Cl-pyridin-2-yl | O | 388 |
| 65 | —CO₂Et | Me | 2,4,6-tri-F—Ph | 2,6-di-F, 4-NO₂—Ph | O | 472 |
| 66 | H | Me | 2,6-di-F-4-OMe—Ph | 5-Me-pyridin-2-yl | NH | 345 |
| 67 | H | Me | 2-Cl-4-F—Ph | 5-CN-pyridin-2-yl | NH | 342 |
| 68 | —CO₂H | Me | 2,4,6-tri-F—Ph | 2,6-di-F-4-NO₂—Ph | O | 444 |
| 69 (Ex. 5) | H | Me | 2,4-di-Cl—Ph | 2,4-di-F—Ph | NH | ** |
| 70 | Me | Me | 2,4-di-Cl—Ph | 2,4-di-F—Ph | NH | 382 |
| 71 | H | Me | 2-Cl-4-F—Ph | 2-F-4-(NHC(O)Me)—Ph | O | 392 |
| 72 | H | Me | 2,4-di-F—Ph | 3,4-di-OMe—Ph | NH | 360 |
| 73 | H | Me | 2-Cl-4-F—Ph | 3,5-di-Cl-pyridin-2-yl | NH | 387 |
| 74 | H | Me | 2,4-di-Cl—Ph | 3,4-di-OMe—Ph | NH | 392 |
| 75 | H | Me | 2,4-di-Cl—Ph | 2,4,6-tri-F—Ph | NH | 386 |

INDEX TABLE A-continued

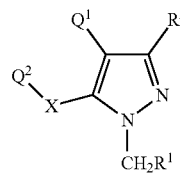

| Cmpd No. | R¹ | R² | Q¹ | Q² | X | M.S |
|---|---|---|---|---|---|---|
| 76 | H | Me | 2,4-di-F—Ph | 6-Cl-pyridin-3-yl | NH | 331 |
| 77 | H | Me | 2,6-di-F-4-OMe—Ph | 2,6-di-F-4-NH₂—Ph | O | 382 |
| 78 | H | Me | 2,4,6-tri-F—Ph | 2,6-di-F-4-OMe—Ph | NH | 384 |
| 79 | H | Me | 4-Me—Ph | 2,4,6-tri-F—Ph | NH | 332 |
| 80 | H | Me | 4-Me—Ph | 2,6-di-F-4-OMe—Ph | NH | 344 |
| 81 | H | Me | 2,6-di-F-4-OMe—Ph | 5-Cl-2,4-di-OMe—Ph | NH | 424 |
| 82 | H | Me | 2,6-di-F-4-OMe—Ph | 2,6-di-F-4-CN—Ph | NH | 391 |
| 83 | H | Me | 2,6-di-F-4-OMe—Ph | 2,6-di-F-4-OMe—Ph | NH | 396 |
| 84 | H | Me | 2,6-di-F—Ph | 2,6-di-F—Ph | O | 367 |
| 85 | H | Me | 3,5-di-OMe—Ph | 2,6-di-F-4-CN—Ph | O | 386 |
| 86 | H | Me | 6-Cl-pyridin-3-yl | 2,6-di-F-4-CN—Ph | O | 361 |
| 87 | H | Me | 2,6-di-F-4-OMe—Ph | 2-Cl-4-F—Ph | NH | 382 |
| 88 | H | Me | 2,6-di-F-4-OMe—Ph | 4-F-2-Me—Ph | NH | 362 |
| 89 | H | Me | 4-F-2-OMe—Ph | 2,6-di-F-4-CN—Ph | O | 374 |
| 90 | H | Me | 2,6-di-F-4-OMe—Ph | 4-Br-2,6-di-F—Ph | O | 447 |
| 91 | H | Me | 2-Cl-4-F—Ph | 2,6-di-F-4-CN—Ph | NH | 377 |
| 92 | H | Me | 2,4,6-tri-F—Ph | 2,6-di-F-4-CN—Ph | NH | 379 |
| 93 | H | Me | 2,4,6-tri-F—Ph | 3,4-di-OMe—Ph | NH | 378 |
| 94 | H | Me | 2,4,6-tri-F—Ph | 6-OMe-pyridin-3-yl | NH | 349 |
| 95 | H | Me | 2,6-di-F-4-OMe—Ph | 6-OMe-pyridin-3-yl | NH | 361 |
| 96 | H | Me | 2,4,6-tri-F—Ph | 2-F-4-CN—Ph | O | 362 |
| 97 | H | Me | 4-F-2-Me—Ph | 2,6-di-F-4-CN—Ph | O | 358 |
| 98 | H | Me | 2,4,6-tri-F—Ph | 2-Cl-4-CN—Ph | O | 378 |
| 99 | H | Me | 2,4,6-tri-F—Ph | 2,5-di-F-4-CN—Ph | O | 380 |
| 100 | H | Me | 2,4,6-tri-F—Ph | 5-Cl-2,4-di-OMe—Ph | NH | 412 |
| 101 | H | Me | 2,4,6-tri-F—Ph | 3,5-di-Cl-pyridin-2-yl | NH | 386 |
| 102 | H | Me | 2,6-di-F-4-OMe—Ph | 3,5-di-Cl-pyridin-2-yl | NH | 398 |
| 103 | H | Me | 2,6-di-F-4-OH—Ph | 2,4-di-F—Ph | NH | 352 |
| 104 | H | Me | 2-Cl-4-OMe—Ph | 2,4,6-tri-F—Ph | NH | 382 |
| 105 | H | Me | 2,6-di-F-4-OS(O)₂CF₃ | 2,4-di-F—Ph | NH | 484 |
| 106 | H | Me | 2,6-di-F-4-CN—Ph | 2,4-di-F—Ph | NH | 361 |
| 107 | H | Me | 2-Cl-4-F—Ph | 2,6-di-Cl-pyridin-3-yl | NH | 386 |
| 108 | H | c-Pr | 2-Cl-4-F—Ph | 2,4-di-F—Ph | NH | 378 |
| 109 | H | Me | 2,4,6-tri-F—Ph | 3,5-di-F-pyridin-2-yl | NH | 355 |
| 110 | H | Me | 2,6-di-F-4-CN—Ph | 4-Cl—Ph | NH | *** |
| 111 | H | Me | 2,6-di-F-4-CN—Ph | 4-F—Ph | NH | *** |
| 112 | H | Me | 2,6-di-F-4-CN—Ph | 2-Cl-4-F—Ph | NH | *** |
| 113 | H | Me | 2,6-di-F-4-CN—Ph | 3-F-4-OMe—Ph | NH | *** |
| 114 | H | Me | 2,6-di-F-4-CN—Ph | 3,4-di-F—Ph | NH | *** |
| 115 | H | Me | 2,6-di-F-4-CN—Ph | 3-Cl—Ph | NH | *** |
| 116 | H | Me | 2-Cl-4-F—Ph | 3-F-5-CN—Ph | O | 360 |
| 117 | H | Me | 2,6-di-F-4-OMe—Ph | 2-Cl-4-CN—Ph | NH | 389 |
| 118 | H | Me | 2-Cl-4-F—Ph | 2-F-4-CN—Ph | O | 360 |
| 119 | H | Me | 2-Cl-4-F—Ph | 2-Cl-4-NO₂—Ph | O | 396 |
| 120 | H | Me | 2,4,6-tri-F—Ph | 2-F-4-CN—Ph | NH | 361 |
| 121 | H | Me | 2-Cl-4-F—Ph | 2,6-di-F-4-NO₂—Ph | O | 398 |
| 122 | H | Me | 2-Cl-4-F—Ph | 4-F-2-NO₂—Ph | O | 380 |
| 123 | H | Me | 2,6-di-F-4-CN—Ph | 3,4-di-Cl—Ph | NH | *** |
| 124 | H | Me | 2,6-di-F-4-CN—Ph | 4-Me—Ph | NH | *** |
| 125 | H | Me | 2,6-di-F-4-CN—Ph | 4-Cl-3-F—Ph | NH | *** |
| 126 | H | Me | 2,6-di-F-4-CN—Ph | 4-OMe—Ph | NH | *** |
| 127 | H | Me | 2,6-di-F-4-CN—Ph | 4-F-3-OMe—Ph | NH | 373 |
| 128 | H | Me | 2,6-di-F-4-OMe—Ph | 3,5-di-F-pyridin-2-yl | NH | 367 |
| 129 | H | Me | 2,4,6-tri-F—Ph | 4-Cl-3-F—Ph | O | *** |
| 130 | H | Me | 2,4,6-tri-F—Ph | 4-Br-3-F—Ph | O | *** |
| 131 | H | Me | 2,4,6-tri-F—Ph | 3-F-4-NO₂—Ph | O | *** |
| 132 | H | Me | 2-Cl-4-F—Ph | 3,4,5-tri-F—Ph | NH | 370 |
| 133 | H | Me | 2,6-di-F-4-CN—Ph | 2,4,6-tri-F—Ph | NH | *** |
| 134 | H | Me | 2,6-di-F-4-CN—Ph | 2,6-di-F-4-OMe—Ph | NH | *** |
| 135 | H | Me | 2,4,6-tri-F—Ph | 3-Me-4-NO₂—Ph | O | *** |
| 136 | H | Me | 2,6-di-F-4-CN—Ph | 3-F—Ph | NH | *** |
| 137 | H | Me | 2,6-di-F-4-CN—Ph | 2,5-di-F—Ph | NH | *** |
| 138 | H | Me | 2,6-di-F-4-CN—Ph | 2,4,5-tri-F—Ph | NH | *** |
| 139 | H | Me | 2-Cl-4-F—Ph | 2-Cl-4-CN—Ph | O | 376 |
| 140 | H | Me | 2,6-di-F-4-OMe—Ph | 2,6-di-F-4-CN—Ph | O | 392 |
| 141 | H | Me | 2,6-di-F-4-OEt—Ph | 2,4-di-F—Ph | NH | 380 |
| 142 | H | Me | 2,6-di-F-4-CN—Ph | 5-Cl-2-F—Ph | NH | *** |
| 143 | H | Me | 2,6-di-F-4-CN—Ph | 4-Cl-2-F—Ph | NH | *** |

INDEX TABLE A-continued

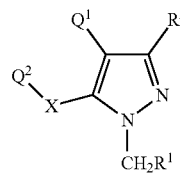

| Cmpd No. | R¹ | R² | Q¹ | Q² | X | M.S |
|---|---|---|---|---|---|---|
| 144 | H | Me | 2,6-di-F-4-CN—Ph | 3-Cl-4-F—Ph | NH | *** |
| 145 | H | Me | 2,6-di-F-4-CN—Ph | 2,3-di-F—Ph | NH | *** |
| 146 | H | Me | 2,6-di-F-4-CN—Ph | 2,5-di-Cl—Ph | NH | *** |
| 147 | H | Me | 2,6-di-F-4-CN—Ph | 2,3-di-Cl—Ph | NH | *** |
| 148 | H | Me | 2-Cl-4-F—Ph | 2,5-di-F-4-CN—Ph | O | 378 |
| 149 | H | Me | 2-Cl-4-F—Ph | 4-F-2-CN—Ph | O | 360 |
| 150 | H | Me | 2-Cl-4-F—Ph | 2-Cl-4,5-di-CN—Ph | O | 401 |
| 151 | H | Me | 2,4,6-tri-F—Ph | 3-OMe-4-NO₂—Ph | O | *** |
| 152 | H | Me | 2,6-di-F-4-OMe—Ph | 4-Cl-3-F—Ph | O | 383 |
| 153 | H | Me | 2,6-di-F-4-OMe—Ph | 4-Br-3-F—Ph | O | 429 |
| 154 | H | Me | 2-Cl-4-F—Ph | 3,5-di-F-pyridin-2-yl | NH | 353 |
| 155 | H | Me | 2-Cl-4-OMe—Ph | 2,6-di-F-4-CN—Ph | O | 390 |
| 156 | H | Me | 2,4,6-tri-F—Ph | 3-CN-4-NO₂—Ph | O | *** |
| 157 | H | Me | 2,4,6-tri-F—Ph | 4-Cl-3-Me—Ph | O | *** |
| 158 | H | Me | 2-Cl-4-F—Ph | 2,6-di-F-4-OMe—Ph | NEt | 410 |
| 159 | H | Me | 2-Cl-4-F—Ph | 2,6-di-F-4-OMe—Ph | NCH₂CH=CH₂ | 422 |
| 160 | H | Me | 2-Cl-4-OMe—Ph | 2,4-di-F—Ph | NH | 364 |
| 161 | H | Me | 2-Cl-4-OMe—Ph | 2,6-di-F—Ph | NH | 364 |
| 162 | H | Me | 2-Cl-4-F—Ph | 2-Cl-4-CN—Ph | NH | 375 |
| 163 | H | Me | 2,4,6-tri-F—Ph | 2-Cl-4,5-di-CN—Ph | O | 403 |
| 164 | H | Me | 2,4,6-tri-F—Ph | 4-Cl-3-OMe—Ph | O | *** |
| 165 | H | Me | 2,4,6-tri-F—Ph | 4-Br-3-Me—Ph | O | *** |
| 166 | H | Me | 2,4,6-tri-F—Ph | 4-Br-3-OMe—Ph | O | 429 |
| 167 | H | Me | 2,4,6-tri-F—Ph | 2,3,5-tri-F—Ph | O | 373 |
| 168 | H | Me | 2-Cl-4-F—Ph | 3,4-di-CN—Ph | O | 367 |
| 169 | H | Me | 2,4,6-tri-F—Ph | 3,4-di-CN—Ph | O | 369 |
| 170 | H | Me | 2,4-di-F—Ph | 2,6-di-F-4-CN—Ph | O | 362 |
| 171 | H | Me | 2-Cl-4-F—Ph | 2,3,6-tri-F—Ph | NH | 370 |
| 172 | H | Me | 2-Cl-4-F—Ph | 2,6-di-F—Ph | NH | 352 |
| 173 | H | Me | 2-Cl-4-F—Ph | 2,5-di-F—Ph | NH | 352 |
| 174 | H | Me | 2-Cl-4-OMe—Ph | 2,3,6-tri-F—Ph | NH | 382 |
| 175 | H | Me | 2-Cl-4-F—Ph | 2-Cl-4-F—Ph | NH | 368 |
| 176 | H | Me | 2-Cl-4-OMe—Ph | 2,5-di-F—Ph | NH | 364 |
| 177 | H | Me | 2-Cl-6-F—Ph | 2,4-di-F—Ph | NH | 352 |
| 178 | H | Me | 2,6-di-F—Ph | 2,4-di-F—Ph | NH | *** |
| 179 | H | Me | 2,6-di-F—Ph | 2,4-di-Cl—Ph | NH | *** |
| 180 | H | Me | 2,6-di-F—Ph | 2-F-4-OMe—Ph | NH | *** |
| 181 | H | Me | 2-F—Ph | 2,4-di-F—Ph | NH | 318 |
| 182 | H | Me | 2-F—Ph | 2,4,6-tri-F—Ph | NH | 336 |
| 183 | H | Me | 2-F—Ph | 2,6-di-F-4-OMe—Ph | NH | 348 |
| 184 | H | Me | 2-F—Ph | 4-F—Ph | NH | 300 |
| 185 | H | Me | 2,6-di-F-4-OMe—Ph | 4-Cl-3-F—Ph | O | 379 |
| 186 | H | Me | 2,6-di-F-4-OMe—Ph | 4-Br-3-Me—Ph | O | *** |
| 187 | H | Me | 2,4,6-tri-F—Ph | 3-F-4-Me—Ph | O | *** |
| 188 | H | Me | 2,6-di-F-4-OMe—Ph | 3-F-4-Me_Ph | O | 363 |
| 189 | H | Me | 2-Cl-4-F—Ph | 3,5-di-F-pyridin-2-yl | O | 354 |
| 190 | H | Me | 2-Cl-6-F—Ph | 2,6-di-F-4-OMe—Ph | NH | 382 |
| 191 | H | Me | 2-Cl-6-F—Ph | 2,4,6-tri-F—Ph | NH | 369 |
| 192 | H | Me | 2-Cl-6-F—Ph | 2,6-di-F-4-CN—Ph | NH | 377 |
| 193 | H | Me | 2-Cl-6-F—Ph | 2-Cl-4-F—Ph | NH | 368 |
| 194 | H | Me | 2,4-di-F—Ph | 4-F—Ph | NH | *** |
| 195 | H | Me | 2,4-di-F—Ph | 4-Cl—Ph | NH | *** |
| 196 | H | Me | 2,6-di-F—Ph | 2-F-4-CN—Ph | NH | 343 |
| 197 | H | Me | 2,6-di-F—Ph | 2,5-di-F—Ph | NH | *** |
| 198 | H | Me | 2,6-di-F—Ph | 2,3-di-F—Ph | NH | *** |
| 199 | H | Me | 2,6-di-F—Ph | 4-F-2-OMe—Ph | NH | *** |
| 200 | H | Me | 2,6-di-F—Ph | 3-OMe—Ph | NH | *** |
| 201 | H | Me | 2,6-di-F—Ph | 2-Cl-4-OMe—Ph | NH | *** |
| 202 | H | Me | 2,3-di-F—Ph | 2,4-di-F—Ph | NH | 336 |
| 203 | H | Me | 2,3-di-F—Ph | 2,4,6-tri-F—Ph | NH | 354 |
| 204 | H | Me | 2,3-di-F—Ph | 2,6-di-F-4-OMe—Ph | NH | 366 |
| 205 | H | Me | 2,3-di-F—Ph | 4-F—Ph | NH | 318 |
| 206 | H | Me | 2,6-di-F-4-OMe—Ph | 4-Cl—Ph | O | 365 |
| 207 | H | Me | 2,4-di-F—Ph | 2-Cl-4-F—Ph | NH | *** |
| 208 | H | Me | 2,6-di-F-4-OMe—Ph | 2,4-di-F—Ph | CHOH | 381 |
| 209 | H | Me | 2,4,6-tri-F—Ph | 3,4-di-Me—Ph | O | *** |
| 210 | H | Me | 2,6-di-F-4-OMe—Ph | 3,4-di-Me—Ph | O | *** |
| 211 | H | Me | 2,6-di-F-4-OMe—Ph | 4-Cl-3-OMe—Ph | O | *** |

INDEX TABLE A-continued

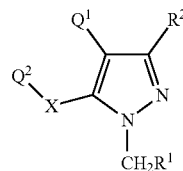

| Cmpd No. | R¹ | R² | Q¹ | Q² | X | M.S |
|---|---|---|---|---|---|---|
| 212 | H | Me | 2,6-di-F-4-OMe—Ph | 4-Br-3-OMe—Ph | O | *** |
| 213 | H | Me | 2,4,6-tri-F—Ph | 3-OMe—Ph | O | 349 |
| 214 | H | Me | 2,4-di-F—Ph | 2,3-di-F—Ph | NH | *** |
| 215 | H | Me | 2,6-di-F—Ph | 2-Cl-5-OMe—Ph | NH | *** |
| 216 | H | Me | 2,6-di-F—Ph | 2-F-5-OMe—Ph | NH | *** |
| 217 | H | Me | 2,4,6-tri-F—Ph | 3-OMe-4-Me—Ph | O | *** |
| 218 | H | Me | 2,6-di-F-4-OMe—Ph | 4-Cl-3-CN—Ph | O | *** |
| 219 | H | Me | 2,4,6-tri-F—Ph | 3-Me—Ph | O | 333 |
| 220 | H | Me | 2,6-di-F-4-OMe—Ph | 3-Me—Ph | O | 345 |
| 221 | H | Me | 2,6-di-F-4-OMe—Ph | 3-OMe—Ph | O | 361 |
| 222 | H | Me | 2,4,6-tri-F—Ph | 3-CN—Ph | O | 344 |
| 223 | H | Me | 2,6-di-F-4-OMe—Ph | 3-CN—Ph | O | 356 |
| 224 | H | Me | 2,4,6-tri-F—Ph | 4-Cl-3-CN—Ph | O | *** |
| 225 | H | Me | 2,4,6-tri-F—Ph | 4-Br-3-CN—Ph | O | *** |
| 226 | H | Me | 2,4-di-F—Ph | 2,5-di-F—Ph | NH | *** |
| 227 | H | Me | 2,4-di-F—Ph | 2-Cl-5-OMe—Ph | NH | *** |
| 228 | H | Me | 2,4-di-F—Ph | 2-F-4-OMe—Ph | NH | *** |
| 229 | H | Me | 2,4-di-F—Ph | 2,4,5-tri-F—Ph | NH | *** |
| 230 | H | Me | 2,4-di-F—Ph | 2,4-di-F—Ph | NH | 336 |
| 231 | H | Me | 2,4-di-F—Ph | 2,3-di-Cl—Ph | NH | *** |
| 232 | H | Me | 2-Br-4-F—Ph | 2,6-di-F-4-CN—Ph | O | 423 |
| 233 | H | Me | 2-Br-4-F—Ph | 2,5-di-F-4-CN—Ph | O | 423 |
| 234 | H | Me | 2-Cl-4-F—Ph | 4-F-3-CN—Ph | NH | 359 |
| 235 | H | Me | 2-Cl-4-F—Ph | 2-Cl-5-CN—Ph | NH | 375 |
| 236 | H | Me | 2-CF₃—Ph | 2-Cl-4-F—Ph | NH | 384 |
| 237 | H | Me | 2-CF₃—Ph | 4-F—Ph | NH | 350 |
| 238 | H | Me | 2-CF₃—Ph | 2,4-di-F—Ph | NH | 368 |
| 239 | H | Me | 2-CF₃—Ph | 2,4,6-tri-F—Ph | NH | 386 |
| 240 | H | Me | 2-CF₃—Ph | 2,6-di-F-4-OMe—Ph | NH | 398 |
| 241 | H | Me | 2,4,6-tri-F—Ph | 3-Cl-pyridin-2-yl | NH | 353 |
| 242 | H | Me | 2,4-di-F—Ph | 2-Cl-4-OMe—Ph | NH | *** |
| 243 | H | Me | 2,4-di-F—Ph | 2,4-di-Cl—Ph | NH | *** |
| 244 | H | Me | 2,4-di-F—Ph | 2-F-5-OMe—Ph | NH | *** |
| 245 | H | Me | 2,4-di-F—Ph | 2,5-di-Cl—Ph | NH | *** |
| 246 | H | Me | 2,4-di-F—Ph | 2-F-4-CN—Ph | NH | *** |
| 247 | H | Me | 2,6-di-F—Ph | 2,6-di-F—Ph | NH | *** |
| 248 | H | Me | 2-Br—Ph | 2,4,6-tri-F—Ph | NH | 398 |
| 249 | H | Me | 2,6-di-F-4-OMe—Ph | 3-OMe-4-F—Ph | O | *** |
| 250 | H | Me | 2,4,6-tri-F—Ph | 3-CN-4-Me—Ph | O | *** |
| 251 | H | Me | 2-CF₃—Ph | 3,5-di-Cl-pyridin-2-yl | NH | 401 |
| 252 | H | Me | 2-Cl-6-F—Ph | 3,5-di-Cl-pyridin-2-yl | NH | 387 |
| 253 | H | Me | 2-F-6-CF₃—Ph | 2-Cl-4-F—Ph | NH | 402 |
| 254 | H | Me | 2-F-6-CF₃—Ph | 4-F—Ph | NH | 368 |
| 255 | H | Me | 2-F-6-CF₃—Ph | 2,4-di-F—Ph | NH | 368 |
| 256 | H | Me | 2,4-di-F—Ph | 2,6-di-F—Ph | NH | *** |
| 257 | H | Me | 2,6-di-F—Ph | 2,6-di-F-4-OMe—Ph | NH | *** |
| 258 | H | Me | 2,6-di-F-4-OMe—Ph | 4-Br-3-CN—Ph | O | *** |
| 259 | H | Me | 2,6-di-F-4-OMe—Ph | 3-CN-4-Me—Ph | O | *** |
| 260 | H | Me | 2-Br-4-F—Ph | 3-F-5-CF₃-pyridin-2-yl | O | 449 |
| 261 | H | Me | 2-Br-4-F—Ph | 3-Cl-5-CF₃-pyridin-2-yl | O | 465 |
| 262 | H | Me | 2-F-6-CF₃—Ph | 2,4,6-tri-F—Ph | NH | 404 |
| 263 | H | Me | 2-F-6-CF₃—Ph | 2,6-di-F-4-OMe—Ph | NH | 416 |
| 264 | H | Me | 2-F-6-CF₃—Ph | 3,5-di-F-pyridin-2-yl | NH | 387 |
| 265 | H | Me | 2-Cl-4-F—Ph | 2-Br-4-F—Ph | NH | 413 |
| 266 | H | Me | 2-Br-4-F—Ph | 2,4,6-tri-F—Ph | NH | 415 |
| 267 | H | Me | 2-Cl-4-OMe—Ph | 3,5-di-Cl-pyridin-2-yl | NH | 399 |
| 268 | H | Me | 2-Cl-4-F—Ph | 2-Cl-pyrimidin-5-yl | NH | *** |
| 269 | H | Me | 2-Cl-4-F—Ph | 2-Me-pyrimidin-5-yl | NH | *** |
| 270 | H | Me | 2-Cl-4-F—Ph | pyrimidin-5-yl | NH | *** |
| 271 | H | Me | 2-Cl—Ph | 2,6-di-F-4-CN—Ph | O | *** |
| 272 | H | Me | 2-Br—Ph | 2,6-di-F-4-CN—Ph | O | *** |
| 273 | H | Me | 2,3-di-Cl—Ph | 2,6-di-F-4-CN—Ph | O | *** |
| 274 | H | Me | 2,3-di-F—Ph | 2,6-di-F-4-CN—Ph | O | *** |
| 275 | H | Me | 2,5-di-Cl—Ph | 2,6-di-F-4-CN—Ph | O | *** |
| 276 | H | Me | 2-Cl-5-F—Ph | 2,6-di-F-4-CN—Ph | O | *** |
| 277 | H | Me | 2-Cl-5-OMe—Ph | 2,6-di-F-4-CN—Ph | O | *** |
| 278 | H | Me | 2-F-5-OMe—Ph | 2,6-di-F-4-CN—Ph | O | *** |
| 279 | H | Me | 2-Cl-6-F—Ph | 3,5-di-F-pyridin-2-yl | NH | 353 |

INDEX TABLE A-continued

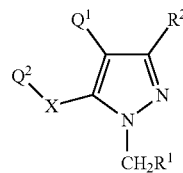

| Cmpd No. | R¹ | R² | Q¹ | Q² | X | M.S |
|---|---|---|---|---|---|---|
| 280 | H | Me | 2-CF₃—Ph | 3,5-di-F-pyridin-2-yl | NH | 369 |
| 281 | H | Me | 2,4-di-F—Ph | 2-Cl-3-OMe—Ph | NH | *** |
| 282 | H | Me | 2-Cl-4-OMe—Ph | 2,4-di-Cl—Ph | NH | 397 |
| 283 | H | Me | 2-Cl-6-F—Ph | 2,4-di-Cl—Ph | NH | 386 |
| 284 | H | Me | 2-Br-4-F—Ph | 2-F-4-CN—Ph | O | 406 |
| 285 | H | Me | 2-Br-4-F—Ph | 2-Cl-4-CN—Ph | O | 422 |
| 286 | H | Me | 2-Cl-4-F—Ph | 4-Cl-2,6-di-F—Ph | NH | 386 |
| 287 | H | Me | 2-Cl-4-F—Ph | 2-Cl-4,6-di-F—Ph | NH | 386 |
| 288 | H | Me | 2-Cl-4-F—Ph | 4-OMe—Ph | NH | 346 |
| 289 | H | Me | 2,6-di-F—Ph | 2-Cl-3-OMe—Ph | NH | *** |
| 290 | H | Me | 2,4-di-F—Ph | 2,6-di-F-4-CN—Ph | NH | *** |
| 291 | H | Me | 2,4-di-F—Ph | 2-Cl-5-CN—Ph | NH | *** |
| 292 | H | Me | 2-Br-4-F—Ph | 2-Cl-4,6-di-F—Ph | NH | 431 |
| 293 | H | Me | 2-Cl-4-F—Ph | 2,4,6-tri-F—Ph | NMe | *** |
| 294 | H | Me | 2-Cl-4-F—Ph | 2,4,6-tri-F—Ph | NEt | *** |
| 295 | H | Me | 2-Br-4-F—Ph | 3,5-di-Cl-pyridin-2-yl | NH | 430 |
| 296 | H | Me | 2-Cl-4-F—Ph | 2,6-di-Cl-4-OMe—Ph | NH | 413 |
| 297 | H | Me | 2,6-di-F—Ph | 2-Cl-4,6-di-F—Ph | NH | 370 |
| 298 | H | Me | 2-Cl-6-F—Ph | 2-Cl-4,6-di-F—Ph | NH | 386 |
| 299 | H | Me | 2-Cl-4-F—Ph | 2,4-di-Cl—Ph | NH | 383 |
| 300 | H | Me | 2,6-di-F—Ph | 2,4,6-tri-F—Ph | NH | *** |
| 301 | H | Me | 2,6-di-F—Ph | 2,6-di-F-4-CN—Ph | NH | *** |
| 302 | H | Me | 2,3-di-Cl—Ph | 2,4-di-F—Ph | NH | 368 |
| 303 | H | Me | 2,3-di-Cl—Ph | 3,5-di-Cl-pyridin-2-yl | NH | 400 |
| 304 | H | Me | 2-Cl-4-F—Ph | 2,4,6-tri-F—Ph | NS(O)₂Me | *** |
| 305 | H | Me | 2-F—Ph | 2,6-di-F-4-CN—Ph | O | *** |
| 306 | H | Me | 2-CF₃—Ph | 2,6-di-F-4-CN—Ph | O | *** |
| 307 | H | Me | 2-Cl-5-CF₃—Ph | 2,6-di-F-4-CN—Ph | O | *** |
| 308 | H | Me | 2-Cl-pyridin-3-yl | 2,6-di-F-4-CN—Ph | O | *** |
| 309 | H | Me | 2-Cl-4-F—Ph | 2,4,6-tri-F—Ph | NCH₂OMe | *** |
| 310 | H | Me | 2-Cl-4-OMe—Ph | 2-F-4-CN—Ph | O | 372 |
| 311 | H | Me | 2-Cl-4-OMe—Ph | 2-Cl-4-CN—Ph | O | 388 |
| 312 | H | Me | 2-Br-4-F—Ph | 2,4-di-F—Ph | NH | 398 |
| 313 | H | Me | 2-Br-4-F—Ph | 2-Br-4-F—Ph | NH | 458 |
| 314 | H | Me | 2-Br-4-F—Ph | 2-Cl-4-F—Ph | NH | 414 |
| 315 | H | Me | 2-Cl—Ph | 2,4-di-F—Ph | NH | 334 |
| 316 | H | Me | 2-Br-4-F—Ph | 2,6-di-Cl-4-F—Ph | NH | 448 |
| 317 | H | Me | 2-Br-4-F—Ph | 4-OMe—Ph | NH | 392 |
| 318 | H | Me | 2-Br-4-OMe—Ph | 2-Cl-4-CN—Ph | O | 433 |
| 319 | H | Me | 2-Br-4-OMe—Ph | 2-F-4-CN—Ph | O | 418 |
| 320 | H | Me | 2-Cl—Ph | 3,5-di-Cl-pyridin-2-yl | NH | 368 |
| 321 | H | Me | 2,6-di-F—Ph | 3,5-di-Cl-pyridin-2-yl | NH | 369 |
| 322 | H | Me | 2-Cl-4-F—Ph | 2-Cl-4-OMe—Ph | NH | 380 |
| 323 | H | Me | 2-Br-4-F—Ph | 2,6-di-Cl-4-OMe—Ph | NH | 459 |
| 324 | H | Me | 2-Br-4-F—Ph | 2-Cl-4-OMe—Ph | NH | 425 |
| 325 | H | Me | 2-Cl-4-F—Ph | 2-Cl-4-OEt—Ph | NH | 394 |
| 326 | H | Me | 2-Cl-4-F—Ph | 2,4,6-tri-F—Ph | NCH₂CN | 409 |
| 327 | H | Me | 2,6-di-Cl—Ph | 2,4-di-Cl—Ph | NH | *** |
| 328 | H | Me | 2,4-di-F—Ph | 3,5-di-Cl-pyridin-2-yl | NH | 369 |
| 329 | H | Me | 2,5-di-F—Ph | 2,6-di-F-4-CN—Ph | O | *** |
| 330 | H | Me | 2-Cl-4,6-di-F—Ph | 2,6-di-F-4-CN—Ph | NH | 395 |
| 331 | H | Me | 2-Cl-4-CN—Ph | 2,4-di-F—Ph | NH | 359 |
| 332 | H | Me | 2-Cl-4-CN—Ph | 2-Cl-4,6-di-F—Ph | NH | 393 |
| 333 | H | Me | 2,6-di-Cl—Ph | 4-OMe—Ph | NH | *** |
| 334 | H | Me | 2,6-di-Cl—Ph | 2-Cl-4-F—Ph | NH | *** |
| 335 | H | Me | 2-Cl-4-CN—Ph | 2,6-di-F—Ph | NH | 359 |
| 336 | H | Me | 2-Cl-4-CN—Ph | 4-Cl-2,6-di-F—Ph | NH | 393 |
| 337 | H | Me | 2,6-di-Cl—Ph | 4-F—Ph | NH | *** |
| 338 | H | Me | 2-Cl-4-CN—Ph | 2-Cl-4-F—Ph | NH | 375 |
| 339 | H | Me | 2,6-di-Cl—Ph | 2,4-di-F—Ph | NH | *** |
| 340 | H | Me | 2,6-di-Cl—Ph | 2-Br-4-F—Ph | NH | *** |
| 341 | H | Me | 2,6-di-Cl—Ph | 2,6-di-Cl-4-F—Ph | NH | *** |
| 342 | H | Me | 2-Cl-6-F—Ph | 2-F-4-CN—Ph | O | 360 |
| 343 | H | Me | 2,4-di-F—Ph | 2-Cl-4,6-di-F—Ph | NH | 369 |
| 344 | H | Me | 2-Cl-4-F—Ph | 2-F-4-NO₂—Ph | NH | 380 |
| 345 | H | Me | 2-Cl-4-F—Ph | 2-F-5-NO₂—Ph | NH | 380 |
| 346 | H | Me | 2,4-di-F—Ph | 2-Br-4-F—Ph | NH | 398 |
| 347 | H | Me | 4-Cl-2-F—Ph | 2-F-4-CN—Ph | O | 360 |

INDEX TABLE A-continued

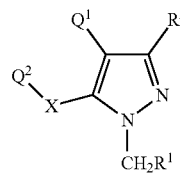

| Cmpd No. | R¹ | R² | Q¹ | Q² | X | M.S |
|---|---|---|---|---|---|---|
| 348 | H | Me | 2,4-di-F—Ph | 2-Br-6-Cl-4-F—Ph | NH | 432 |
| 349 | H | Me | 2,6-di-F—Ph | 4-Cl-2,6-di-F—Ph | NH | 370 |
| 350 | H | Me | 2-Cl-4-F—Ph | 4-F—Ph | CHOH | 349 |
| 351 (Ex. 6) | H | Me | 2-Cl-4-F—Ph | 2,4-di-F—Ph | CHOH | ** |
| 352 | H | Me | 2-Cl-4-F—Ph | 2-Cl-4-F—Ph | CHOH | 383 |
| 353 | H | Me | 2,4-di-Cl—Ph | 2,6-di-F—Ph | NH | *** |
| 354 | H | Me | 2,4-di-Cl—Ph | 2-Cl-4-F Ph | NH | *** |
| 355 | H | Me | 2,4-di-Cl—Ph | 4-OMe—Ph | NH | *** |
| 356 | H | Me | 2-Cl-4-F—Ph | 2,3,6-tri-F—Ph | CHOH | 385 |
| 357 | H | Me | 2,4-di-F—Ph | 4-Cl-2,6-di-F—Ph | NH | 370 |
| 358 | H | Me | 2,6-di-F—Ph | 2-Cl-4-CN—Ph | O | 360 |
| 359 | H | Me | 2,4-di-F—Ph | 2-F-4-CN—Ph | O | 376 |
| 360 | H | Me | 2-Br-4-F—Ph | 4-Cl-2,6-di-F—Ph | NH | 432 |
| 361 | H | Me | 2,6-di-F—Ph | 2-F-4-CN—Ph | O | 344 |
| 362 | H | Me | 2,4-di-Cl—Ph | 2-Cl-4-CN—Ph | O | 394 |
| 363 | H | Me | 2,4-di-Cl—Ph | 2,6-di-Cl-4-F—Ph | NH | *** |
| 364 | H | Me | 2,4-di-F—Ph | 4-Br-2,6-di-F—Ph | NH | 416 |
| 365 | H | Me | 2-Cl-4-F—Ph | 4-Br-2,6-di-F—Ph | NH | 432 |
| 366 | H | Me | 2-Cl-4-F—Ph | 4-Br-2-F—Ph | NH | 414 |
| 367 | H | Me | 2-Cl-4-F—Ph | 2,4-di-Cl-6-F—Ph | NH | 402 |
| 368 | H | Me | 2,4-di-F—Ph | 2,6-di-Cl-4-F—Ph | NH | |
| 369 | H | Me | 2-Cl-4-F—Ph | 2,6-di-Cl-4-F—Ph | NH | |
| 370 (Ex. 7) | H | Me | 2-Cl-4-F—Ph | 2,4-di-F—Ph | C(=O) | ** |
| 371 (Ex. 9) | H | Me | 2,4,6-tri-F—Ph | 2,6-di-F-4-NH₂—Ph | O | ** |
| 372 | H | Me | 2,4-di-F—Ph | 2-Br-4-CN—Ph | O | |
| 373 | H | Me | 2,4-di-F—Ph | 2-Cl-4-CN—Ph | O | |
| 374 | H | Me | 2,4-di-F—Ph | 2,4-di-Cl-6-F—Ph | NH | 386 |
| 375 | H | Me | 2,6-di-F—Ph | 2,6-di-Cl-4-F—Ph | NH | |
| 376 | H | Me | 2,4-di-F—Ph | 2-Br-4,6-di-F—Ph | NH | 416 |
| 377 | H | Me | 2-Cl-4-F—Ph | 2-Br-4,6-di-F—Ph | NH | 432 |
| 378 | H | Me | 2,6-di-F—Ph | 4-Br-2,6-di-F—Ph | NH | |
| 379 | H | Me | 2,6-di-F—Ph | 2-Br-4,6-di-F—Ph | NH | |
| 380 | H | Me | 2-Cl-6-F—Ph | 2-Br-4,6-di-F—Ph | NH | |
| 381 | H | Me | 2-Cl-4-F—Ph | 2,6-di-F-4-Cl—Ph | CHOH | 402 |
| 382 | H | Me | 2-F-4-CN—Ph | 2-Cl-4,6-di-F—Ph | NH | |
| 383 | H | Me | 2-F-4-CN—Ph | 2,6-di-F-4-Cl—Ph | NH | |
| 384 | H | Me | 2-Cl-4-F—Ph | 2-Cl-4,6-di-F—Ph | CHOH | |
| 385 | H | Me | 2,4-di-F—Ph | 2-Br-4-F—Ph | CHOH | |
| 386 | H | Me | 2-Cl-4-F—Ph | 2-Br-4-F—Ph | CHOH | |
| 387 | H | Me | 2-Cl-4-OH—Ph | 2,4-di-F—Ph | NH | 350 |
| 388 | H | Me | 2-Cl-4-OCH₂CN—Ph | 2,4-di-F—Ph | NH | 389 |
| 389 | H | Me | 2,4-di-F—Ph | 4-Br-4-F—Ph | NH | 396 |
| 390 | H | Me | 2,4-di-F—Ph | 4-Br-2,6-di-Cl—Ph | NH | 448 |
| 391 | H | Me | 2,4-di-Cl—Ph | 2-Cl-4,6-di-F—Ph | NH | *** |
| 392 | H | Me | 2,4-di-Cl—Ph | 4-Cl-2,6-di-F—Ph | NH | *** |
| 393 | H | Me | 2-Cl-4-F—Ph | 4-OEt | NH | 360 |
| 394 | H | Me | 2-Cl-4-F—Ph | 4-Cl-2-F | O | 369 |
| 395 | H | Me | 2,4-di-F—Ph | 2-F-4-CN—Ph | O | 344 |
| 396 | H | Me | 2,4-di-F—Ph | 4-Cl-2-F—Ph | NH | 352 |
| 397 | H | Me | 2,4-di-F—Ph | 2,4-di-Cl-6-F—Ph | NH | 386 |
| 398 | H | Me | 2,6-di-F—Ph | 4-Cl-2-F—Ph | NH | 352 |
| 399 | H | Me | 2,6-di-F-4-(OCH₂CH₂CH₂NMe₂)—Ph | 2-F-4-CN—Ph | O | 445 |
| 400 | H | Me | 4-Cl—Ph | 2,6-di-F—Ph | NH | 334 |
| 401 | H | Me | 2-Cl-4-F—Ph | 4-Cl-2,5-di-F—Ph | NH | 386 |
| 402 | H | Me | 2-Br-4-F—Ph | 4-Br-2,6-di-F—Ph | NH | 474 |
| 403 | H | Me | 2-Cl-4-F—Ph | 4-Br-2,6-di-Cl—Ph | NH | 464 |
| 404 | H | Me | 2-Cl-4-F—Ph | 2-Cl-4,5-di-F—Ph | NH | 386 |
| 405 | H | Me | 2,4-di-F—Ph | 2,4,6-tri-Cl—Ph | NH | 404 |
| 406 | H | Me | 2,4-di-F—Ph | 2-Br-4,6-di-F—Ph | NH | 416 |
| 407 | H | Me | 2,4-di-F—Ph | 4-Br-2-Cl—Ph | NH | 414 |
| 408 | H | Me | 2-Br-4-F—Ph | 4-Br-2,6-di-Cl—Ph | NH | 508 |
| 409 | H | Me | 2-Br-2-F—Ph | 4-Br-2-F—Ph | NH | 458 |
| 410 | H | Me | 2-Cl-4-F—Ph | 2,4,6-tri-Cl—Ph | NH | 420 |
| 411 | H | Me | 2-Cl-4-F—Ph | 2-Br-4,6-di-F—Ph | NH | 432 |
| 412 | H | Me | 2-Cl-4-F—Ph | 4-Br-2-Cl—Ph | NH | 430 |
| 413 | H | Me | 2-Br-4-F—Ph | 4-Br-2-Cl—Ph | NH | 474 |
| 414 | H | Me | 2-Br-4-F—Ph | 2,4,6-tri-Cl—Ph | NH | 464 |

INDEX TABLE A-continued

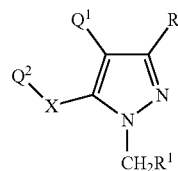

| Cmpd No. | R¹ | R² | Q¹ | Q² | X | M.S |
|---|---|---|---|---|---|---|
| 415 | H | Me | 2,4-di-F—Ph | 4-F-2-I—Ph | NH | 444 |
| 416 | H | Me | 2,4-di-F—Ph | 2,4,6-tri-Me—Ph | NH | 342 |
| 417 | H | Me | 2-Cl-4-F—Ph | 4-Cl-2,5-di-F—Ph | NH | 386 |
| 418 | H | Me | 2-Cl-4-F—Ph | 2-Cl-4,5-di-F—Ph | NH | 386 |
| 419 | H | Me | 2-Cl-4-F—Ph | 2,4-di-F—Ph | CHOAc | 409 |
| 420 | H | Me | 2-Cl-4-F—Ph | pyridin-2-yl | CHOH | 332 |
| 421 | H | Me | 2-Cl-4-F—Ph | 4-Cl-2-F—Ph | CHOH | 384 |
| 422 | H | Me | 2-Cl-4-F—Ph | 2,4,6-tri-F—Ph | CHOH | 385 |
| 423 | H | Me | 2-Cl-4-F—Ph | 2-F-4-CN—Ph | CHOH | 374 |
| 424 | H | Me | 2,4-di-F—Ph | 4-Cl-2-F-6-I—Ph | NH | 478 |
| 425 | H | Me | 2-Cl-4-(OCH₂CH₂CH₂NHMe)—Ph | 2,4-di-F—Ph | NH | 421 |
| 426 | H | Me | 2-Cl-4-(OCH₂CH₂CH₂OMe)—Ph | 2,4-di-F—Ph | NH | 422 |
| 427 | H | Et | 2-Cl-4-F—Ph | 2,4-di-F—Ph | NH | 366 |
| 428 | H | Et | 2-Cl-4-F—Ph | 2,4-di-F—Ph | CHOH | 382 |

*¹H NMR data found in Index Table B
**AP⁺ data or ¹H NMR data found in the Synthesis Examples
***MP data found in Index Table C

INDEX TABLE B

| Cmpd No. | ¹H NMR Data (CDCl₃ solution unless indicated otherwise)ᵃ |
|---|---|
| 3 | δ 7.11 (m, 1H), 6.99 (m, 1H), 6.75-6.85 (m, 3H), 6.58 (m, 1H), 6.40 (m, 1H), 3.58 (s, 3H), 3.07 (s, 3H), 2.21 (s, 3H). |

ᵃ¹H NMR data are in ppm downfield from tetramethylsilane. Couplings are designated by (s)-singlet and (m)-multiplet.

INDEX TABLE C

| Cmpd No. | Melting Point ᵇ |
|---|---|
| 110 | 85-87 |
| 111 | 165-167 |
| 112 | 80-82 |
| 113 | 135-137 |
| 114 | 147-149 |
| 115 | 168-170 |
| 123 | 171-173 |
| 124 | 135-137 |
| 125 | 138-140 |
| 126 | 142-144 |
| 129 | 127-130 |
| 130 | 129-131 |
| 131 | 129-133 |
| 133 | 160-162 |
| 134 | 228-230 |
| 135 | 112-117 |
| 136 | 152-154 |
| 137 | 165-167 |
| 138 | 171-173 |
| 142 | 186-188 |
| 143 | 93-95 |
| 144 | 176-178 |
| 145 | 142-144 |
| 146 | 145-147 |
| 147 | 60-62 |
| 151 | 150-158 |
| 156 | 107-114 |
| 157 | 96-101 |
| 164 | 106-110 |
| 165 | 111-113 |

INDEX TABLE C-continued

| Cmpd No. | Melting Point ᵇ |
|---|---|
| 178 | 110-112 |
| 179 | 105-107 |
| 180 | 130-132 |
| 186 | 78-84 |
| 187 | 107-113 |
| 194 | 133-135 |
| 195 | 98-100 |
| 197 | 115-117 |
| 198 | 106-108 |
| 199 | 134-136 |
| 200 | 139-141 |
| 201 | 109-111 |
| 207 | 57-59 |
| 209 | 92-96 |
| 210 | 73-77 |
| 211 | 110-114 |
| 212 | 130-134 |
| 214 | 105-107 |
| 215 | 90-92 |
| 216 | 152-154 |
| 217 | 72-76 |
| 218 | 112-117 |
| 224 | 132-135 |
| 225 | 123-126 |
| 226 | 139-141 |
| 227 | 99-102 |
| 228 | 133-135 |
| 229 | 144-146 |
| 231 | 108-110 |
| 242 | 91-93 |
| 243 | 82-84 |
| 244 | 95-97 |
| 245 | 73-75 |
| 246 | 182-184 |
| 247 | 156-158 |
| 249 | 83-87 |
| 250 | 126-129 |
| 256 | 171-173 |
| 257 | 172-174 |
| 258 | 121-124 |
| 259 | 97-100 |

INDEX TABLE C-continued

| Cmpd No. | Melting Point [b] |
|---|---|
| 268 | 178-180 |
| 269 | 80-85 |
| 270 | 172-176 |
| 271 | 132-135 |
| 272 | 132-134 |
| 273 | 152-153 |
| 274 | 141-143 |
| 275 | 168-171 |
| 276 | 115-117 |
| 277 | 131-134 |
| 278 | 112-114 |
| 281 | 49-52 |
| 289 | 148-150 |
| 290 | 181-183 |
| 291 | 146-149 |
| 293 | 116-118 |
| 294 | 113-115 |
| 300 | 178-180 |
| 301 | 168-170 |
| 304 | 186-191 |
| 305 | 101-105 |
| 306 | 134-138 |
| 307 | 161-166 |
| 308 | 142-145 |
| 309 | 118-123 |
| 327 | 118-120 |
| 329 | 98-100 |
| 333 | 177-179 |
| 334 | 117-119 |
| 337 | 186-188 |
| 339 | 135-136 |
| 340 | 137-139 |
| 341 | 151-153 |
| 353 | 169-171 |
| 354 | 111-113 |
| 355 | 90-92 |
| 363 | 229-231 |
| 391 | 181-183 |
| 392 | 155-157 |

[b] Melting point data are ° C..

Biological Examples of the Invention

General protocol for preparing test suspensions for Tests A-J: the test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-J. Spraying a 200 ppm test suspension to the point of run-off on the test plants was the equivalent of a rate of 500 g/ha. Unless otherwise indicated, the rating values indicate a 200 ppm test suspension was used. (An asterisk "*" next to the rating value indicates a 40 ppm test suspension was used.)

Test A

Grape seedlings were inoculated with a spore suspension of *Plasmopara viticola* (the causal agent of grape downy mildew) and incubated in a saturated atmosphere at 20° C. for 24 h. After a short drying period, the test suspension was sprayed to the point of run-off on the grape seedlings and then moved to a growth chamber at 20° C. for 4 days, after which time the test units were placed back into a saturated atmosphere at 20° C. for 24 h. Upon removal, visual disease ratings were made.

Test B

The test suspension was sprayed to the point of run-off on tomato seedlings. The following day the seedlings were inoculated with a spore suspension of *Botrytis cinerea* (the causal agent of tomato *Botrytis*) and incubated in saturated atmosphere at 20° C. for 48 h, and then moved to a growth chamber at 24° C. for 3 additional days, after which time visual disease ratings were made.

Test C

The test suspension was sprayed to the point of run-off on tomato seedlings. The following day the seedlings were inoculated with a spore suspension of *Alternaria solani* (the causal agent of tomato early blight) and incubated in a saturated atmosphere at 27° C. for 48 h, and then moved to a growth chamber at 20° C. for 5 days, after which time visual disease ratings were made.

Test D

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 5 days, after which time visual disease ratings were made.

Test E

The test suspension was sprayed to the point of run-off on creeping bent grass (*Agrostis* sp.) seedlings. The following day the seedlings were inoculated with a bran and mycelial slurry of *Rhizoctonia solani* (the causal agent of turf brown patch) and incubated in a saturated atmosphere at 27° C. for 48 h, and then moved to a growth chamber at 27° C. for 3 days, after which time disease ratings were made.

Test F

The test suspension was sprayed to the point of run-off on wheat seedlings. The following day the seedlings were inoculated with a spore suspension of *Septoria nodorum* (the causal agent of *Septoria* glume blotch) and incubated in a saturated atmosphere at 24° C. for 48 h, and then moved to a growth chamber at 20° C. for 6 days, after which time visual disease ratings were made.

Test G

The test suspension was sprayed to the point of run-off on wheat seedlings. The following day the seedlings were inoculated with a spore suspension of *Septoria tritici* (the causal agent of wheat leaf blotch) and incubated in saturated atmosphere at 24° C. for 48 h. and then the seedlings were moved to a growth chamber at 20° C. for 19 additional days, after which time visual disease ratings were made.

Test H

Wheat seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 2 days. At the end of this time the test suspension was sprayed to the point of run-off, and then the seedlings were moved to a growth chamber at 20° C. for 6 days after which time visual disease ratings were made.

Test I

The test suspension was sprayed to the point of run-off on wheat seedlings. The following day the seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 7 days, after which time visual disease ratings were made Test J The test suspension was sprayed to the point of run-off on wheat seedlings. The following day the seedlings were inoculated with a spore dust of *Erysiphe graminis* f sp. *tritici*, (the causal agent of wheat powdery mildew) and incubated in a growth chamber at 20° C. for 8 days, after which time visual disease ratings were made.

Results for Tests A-J are given in Table A. In the Table, a rating of 100 indicates 100% disease control and a rating of 0 indicates no disease control (relative to the controls). A dash (-) indicates no test results.

TABLE A

| Cmpd No. | Test A | Test B | Test C | Test D | Test E | Test F | Test G | Test H | Test I | Test J |
|---|---|---|---|---|---|---|---|---|---|---|
| 1 | 0 | 99 | 0 | 0 | 47 | 0 | 99 | — | 0 | 98 |
| 2 | 8 | 1 | 0 | 0 | 0 | 0 | 0 | — | 0 | 0 |
| 3 | 6 | 0 | 25 | 9 | 0 | 0 | 13 | — | 0 | 99 |
| 4 | 29 | 87 | 46 | 0 | 0 | 0 | 98 | — | 53 | 97 |
| 5 | 36 | 0 | 25 | 0 | 0 | 0 | 0 | — | 0 | 0 |
| 6 | 65 | 10 | 23 | 0 | 0 | 0 | 0 | — | 0 | 93 |
| 7 | 29 | 99 | 0 | 0 | 63 | 0 | 100 | — | 74 | 92 |
| 8 | 55 | 99 | 54 | 0 | 99 | 0 | 100 | — | 97 | 99 |
| 9 | — | 99 | 0 | 0 | 55 | 0 | 100 | — | 98 | 97 |
| 10 | — | 47 | 0 | 0 | 0 | 0 | 0 | — | 0 | 0 |
| 11 | — | 99 | 99 | 0 | 99 | 0 | 100 | — | 99 | 100 |
| 12 | — | 99 | 93 | 0 | 99 | 0 | 100 | — | 99 | 100 |
| 13 | — | 99 | 100 | 0 | 98 | 64 | 100 | — | 100 | 99 |
| 14 | — | 98 | 0 | — | — | 0 | 99 | — | 99 | 98 |
| 15 | — | 99 | 67 | — | — | 73 | 99 | — | 98 | 99 |
| 16 | — | 60 | 0 | — | — | 0 | 47 | 48 | 28 | 0 |
| 17 | — | 100 | 100 | — | — | 93 | 97 | 96 | 100 | 100 |
| 18 | — | 99 | 100 | — | — | 99 | 95 | 99 | 100 | 100 |
| 19 | — | 100 | 85 | — | — | 0 | 96 | 0 | 92 | 98 |
| 20 | — | 100 | 99 | — | — | 100 | 100 | 79 | 100 | 99 |
| 21 | — | 98 | 100 | — | — | 97 | — | — | 100 | 99 |
| 22 | — | 90 | 85 | — | — | 90 | 94 | 9 | 94 | 100 |
| 23 | — | 98 | 100 | — | — | 99 | 93 | 92 | 100 | 100 |
| 24 | — | 98 | 100 | — | — | 0 | 94 | 9 | 97 | 100 |
| 25 | — | 100 | 0 | — | — | 0 | 100 | 0 | 94 | 79 |
| 26 | — | 99 | 83 | — | — | 0 | 100 | 0 | 99 | 100 |
| 27 | — | 99 | 88 | — | — | 0 | 95 | 0 | 25 | 87 |
| 28 | — | 99 | 0 | — | — | 0 | 96 | 7 | 91 | 0 |
| 29 | — | 94 | 0 | — | — | 0 | 98 | 0 | 46 | 0 |
| 30 | — | 7 | 0 | — | — | 0 | 41 | 0 | 79 | 0 |
| 31 | — | 99* | 98* | — | — | 0* | 47* | 15* | 79* | 60* |
| 32 | — | 99 | 0 | — | — | 0 | 96 | 0 | 99 | 97 |
| 33 | — | 0 | 0 | — | — | 0 | 95 | 0 | 18 | 0 |
| 34 | — | 100* | 97* | — | — | 0* | 96* | 0* | 76* | 0* |
| 35 | — | 100 | 0 | — | — | 0 | 95 | 0 | 97 | 100 |
| 36 | — | 100 | 0 | — | — | 0 | 96 | 0 | 96 | 98 |
| 37 | 0 | 0 | 0 | 0 | 0 | 0 | 3 | — | 0 | 0 |
| 38 | — | 99 | 9 | — | — | 0 | 97 | 0 | 99 | 99 |
| 39 | — | 100 | 99 | — | — | 0 | 99 | 99 | 99 | 99 |
| 40 | — | 99 | 0 | — | — | 0 | 94 | 92 | 99 | 99 |
| 41 | — | 100 | 99 | — | — | 90 | 94 | 0 | 100 | 99 |
| 42 | — | 100 | 0 | — | — | 0 | 93 | 0 | 94 | 82 |
| 43 | — | 76 | 0 | — | — | 0 | 97 | 66 | 82 | 99 |
| 44 | — | 82 | 0 | — | — | 0 | 96 | 7 | 9 | 0 |
| 45 | — | 100 | 100 | — | — | 100 | 100 | 7 | 100 | 100 |
| 46 | — | 99 | 100 | — | — | 99 | 100 | 37 | 100 | 99 |
| 47 | — | 100* | 87* | — | — | 0* | 99* | 37* | 96* | 99* |
| 48 | — | 100 | 78 | — | — | 0 | 99 | 0 | 98 | 98 |
| 49 | — | 100 | 17 | — | — | 35 | 99 | 0 | 89 | 79 |
| 50 | — | 99 | 57 | — | — | 0 | 100 | 0 | 98 | 99 |
| 51 | — | 100 | 0 | — | — | 0 | 100 | 0 | 89 | 78 |
| 52 | — | 54 | 0 | — | — | 0 | 97 | 0 | 92 | 64 |
| 53 | — | 0 | 0 | — | — | 0 | 0 | 0 | 0 | 0 |
| 54 | — | 96 | 0 | — | — | 0 | 41 | 0 | 95 | 95 |
| 55 | — | 6 | 0 | — | — | 0 | 98 | 0 | 41 | 73 |
| 56 | — | 43 | 0 | — | — | 0 | 99 | 0 | 28 | 64 |
| 57 | — | 98 | 0 | — | — | 0 | 94 | 85 | 85 | 0 |
| 58 | — | 98 | 100 | — | — | 89 | 98 | 82 | 100 | 100 |
| 59 | — | 94 | 0 | — | — | 0 | 88 | 0 | 68 | 0 |
| 60 | — | 75 | 0 | — | — | 0 | 97 | 59 | 79 | 0 |
| 61 | — | 97 | 0 | — | — | 0 | 99 | 0 | 38 | 73 |

TABLE A-continued

| Cmpd No. | Test A | Test B | Test C | Test D | Test E | Test F | Test G | Test H | Test I | Test J |
|---|---|---|---|---|---|---|---|---|---|---|
| 62 | — | 99 | 98 | — | — | 84 | 98 | 98 | 99 | 99 |
| 63 | — | 0 | 0 | — | — | 0 | 0 | 0 | 0 | 0 |
| 64 | — | 97 | 80 | — | — | 0 | 100 | 0 | 95 | 98 |
| 65 | — | 0 | 0 | — | — | 0 | 1 | 0 | 58 | 0 |
| 66 | — | 100 | 99 | — | — | 0 | 100 | 6 | 100 | 99 |
| 67 | — | 95 | 0 | — | — | 0 | 99 | 24 | 95 | 86 |
| 68 | — | 0 | 0 | — | — | 0 | 0 | 6 | 0 | 0 |
| 69 | — | 100 | 73 | — | — | 60 | 99 | 91 | 99 | 100 |
| 70 | — | 99 | 0 | — | — | 0 | 99 | 41 | 85 | 98 |
| 71 | — | 93 | 0 | — | — | 0 | 96 | 0 | 91 | 67 |
| 72 | — | 0 | 0 | — | — | 0 | 0 | 59 | 0 | 0 |
| 73 | — | 100 | 99 | — | — | 64 | 100 | 88 | 100 | 99 |
| 74 | — | 0 | 0 | — | — | 0 | 25 | 4 | 0 | 0 |
| 75 | — | 100 | 98 | — | — | 98 | 99 | 95 | 99 | 97 |
| 76 | — | 100 | 0 | — | — | 0 | 98 | 6 | 0 | 0 |
| 77 | — | 99 | 0 | — | — | 0 | 95 | 6 | 97 | 0 |
| 78 | — | 99 | 82 | — | — | 0 | 98 | 0 | 89 | 91 |
| 79 | — | 99 | 0 | — | — | 0 | 99 | 0 | 55 | 0 |
| 80 | — | 100 | 0 | — | — | 0 | 99 | 18 | 86 | 89 |
| 81 | — | 97 | 0 | — | — | 0 | 0 | 0 | 27 | 0 |
| 82 | — | 100 | 100 | — | — | 40 | 99 | 0 | 68 | 13 |
| 83 | — | 100 | 100 | — | — | 89 | 99 | 99 | 96 | 94 |
| 84 | — | 100 | 100 | — | — | 78 | 100 | 98 | 100 | 99 |
| 85 | — | 0 | 0 | — | — | 0 | 17 | 0 | 19 | 0 |
| 86 | — | 0 | 0 | — | — | 0 | 48 | 0 | 0 | 0 |
| 87 | — | 100 | 100 | — | — | 95 | 98 | 85 | 99 | 100 |
| 88 | — | 100 | 100 | — | — | 99 | 98 | 95 | 99 | 100 |
| 89 | — | 99 | 0 | — | — | 0 | 99 | 0 | 0 | 97 |
| 90 | — | 99 | 95 | — | — | 84 | 100 | 0 | 98 | 100 |
| 91 | — | 100 | 99 | — | — | 95 | 99 | 0 | 100 | 100 |
| 92 | — | 100 | 100 | — | — | 99 | 100 | 41 | 99 | 100 |
| 93 | — | 41 | 0 | — | — | 0 | 77 | 0 | 9 | 0 |
| 94 | — | 99 | 70 | — | — | 29 | 98 | 0 | 9 | 0 |
| 95 | — | 99 | 16 | — | — | 0 | 97 | 0 | 0 | 0 |
| 96 | — | 99 | 99 | — | — | 99 | 100 | 9 | 99 | 100 |
| 97 | — | 100 | 99 | — | — | 95 | 100 | 0 | 99 | 99 |
| 98 | — | 100 | 17 | — | — | 69 | 100 | 26 | 99 | 99 |
| 99 | — | 100 | 99 | — | — | 100 | 99 | 40 | 100 | 100 |
| 100 | — | 38 | 0 | — | — | 0 | 48 | 0 | 41 | 0 |
| 101 | — | 100 | 99 | — | — | 100 | 100 | 99 | 99 | 100 |
| 102 | — | 100 | 100 | — | — | 98 | 99 | 0 | 100 | 98 |
| 103 | — | 100 | 64 | — | — | 0 | 95 | 0 | 91 | 0 |
| 104 | — | 100 | 99 | — | — | 97 | 99 | 99 | 99 | 100 |
| 105 | — | 23 | 0 | — | — | 0 | 73 | 9 | 0 | 72 |
| 106 | — | 100 | 99 | — | — | 90 | 100 | 82 | 99 | 100 |
| 107 | — | 99* | 0* | — | — | 0* | 99* | 8* | 24* | 0* |
| 108 | — | 97 | 0 | — | — | 0 | 98 | 0 | 16 | 97 |
| 109 | — | 100 | 99 | — | — | 97 | 100 | 99 | 100 | 100 |
| 110 | — | 99 | 66 | — | — | 98 | 99 | 0 | 97 | 94 |
| 111 | — | 99 | 75 | — | — | 90 | 99 | 0 | 97 | 99 |
| 112 | — | 100 | 98 | — | — | 99 | 99 | 53 | 100 | 100 |
| 113 | — | 99 | 47 | — | — | 0 | 100 | 8 | 95 | 48 |
| 114 | — | 99 | 24 | — | — | 69 | 99 | 8 | 99 | 84 |
| 115 | — | 99 | 0 | — | — | 0 | 100 | 0 | 91 | 0 |
| 116 | — | 100 | 94 | — | — | 73 | 100 | 16 | 97 | 99 |
| 117 | — | 99 | 97 | — | — | 82 | 100 | 11 | 98 | 97 |
| 118 | — | 100 | 100 | — | — | 98 | 100 | 99 | 100 | 99 |
| 119 | — | 100 | 0 | — | — | 0 | 100 | 16 | 99 | 96 |
| 120 | — | 100 | 99 | — | — | 94 | 100 | 0 | 99 | 99 |
| 121 | — | 100 | 86 | — | — | 82 | 99 | 83 | 100 | 97 |
| 122 | — | 0 | 0 | — | — | 0 | 0 | 11 | 0 | 0 |
| 123 | — | 99 | 0 | — | — | 40 | 99 | — | 80 | 0 |
| 124 | — | 100 | 78 | — | — | 60 | 99 | — | 96 | 94 |
| 125 | — | 100 | 67 | — | — | 60 | 99 | — | 92 | 0 |
| 126 | — | 99 | 96 | — | — | 60 | 100 | 0 | 94 | 0 |
| 127 | — | 70 | 0 | — | — | 0 | 99 | 0 | 68 | 0 |
| 128 | — | 100 | 100 | — | — | 97 | 99 | 66 | 100 | 100 |
| 129 | — | 99 | 0 | — | — | 0 | 96 | 0 | 0 | 0 |
| 130 | — | 97 | 0 | — | — | 0 | 99 | 0 | 19 | 0 |
| 131 | — | 99 | 0 | — | — | 0 | 98 | 0 | 86 | 94 |
| 132 | — | 99 | 0 | — | — | 0 | 100 | 0 | 94 | 92 |
| 133 | — | 100 | 100 | — | — | 60 | 99 | 0 | 100 | 94 |
| 134 | — | 99 | 0 | — | — | 0 | 99 | 0 | 41 | 0 |
| 135 | — | 0 | 0 | — | — | 0 | 97 | 16 | 74 | 95 |
| 136 | — | 99 | 71 | — | — | 86 | 99 | 0 | 99 | 100 |
| 137 | — | 96 | 97 | — | — | 78 | 99 | 8 | 100 | 100 |
| 138 | — | 99 | 96 | — | — | 84 | 99 | 38 | 100 | 98 |
| 139 | — | 100 | 86 | — | — | 100 | 100 | 69 | 99 | 100 |

TABLE A-continued

| Cmpd No. | Test A | Test B | Test C | Test D | Test E | Test F | Test G | Test H | Test I | Test J |
|---|---|---|---|---|---|---|---|---|---|---|
| 140 | — | 99 | 94 | — | — | 87 | 99 | 0 | 96 | 97 |
| 141 | — | 99 | 99 | — | — | 98 | 100 | 0 | 99 | 100 |
| 142 | — | 33 | 13 | — | — | 20 | 99 | 0 | 95 | 90 |
| 143 | — | 99 | 99 | — | — | 100 | 100 | 63 | 100 | 100 |
| 144 | — | 99 | 9 | — | — | 40 | 99 | 0 | 98 | 91 |
| 145 | — | 96 | 98 | — | — | 100 | 100 | 88 | 100 | 100 |
| 146 | — | 99 | 0 | — | — | 0 | 99 | 0 | 97 | 56 |
| 147 | — | 99 | 88 | — | — | 100 | 100 | 0 | 98 | 92 |
| 148 | — | 99 | 99 | — | — | 100 | 100 | 61 | 100 | 99 |
| 149 | — | 100 | 98 | — | — | 100 | 100 | 99 | 100 | 100 |
| 150 | — | 19 | 0 | — | — | 60 | 7 | 0 | 74 | 50 |
| 151 | — | 99 | 9 | — | — | 0 | 96 | 0 | 54 | 64 |
| 152 | — | 100 | 82 | — | — | 87 | 99 | 9 | 97 | 99 |
| 153 | — | 100 | 0 | — | — | 73 | 100 | 0 | 96 | 98 |
| 154 | — | 99 | 99 | — | — | 97 | 100 | 41 | 100 | 100 |
| 155 | — | 100 | 99 | — | — | 100 | 100 | 92 | 100 | 99 |
| 156 | — | 94 | 0 | — | — | 0 | 73 | 0 | 41 | 47 |
| 157 | — | 0 | 0 | — | — | 0 | 0 | 0 | 54 | 73 |
| 158 | — | 100 | 0 | — | — | 0 | 99 | 18 | 99 | 98 |
| 159 | — | 99 | 0 | — | — | 0 | 100 | 74 | 99 | 100 |
| 160 | — | 98 | 99 | — | — | 0 | 99 | 8 | 100 | 100 |
| 161 | — | 98 | 100 | — | — | 0 | 100 | 95 | 100 | 98 |
| 162 | — | 99 | 0 | — | — | 0 | 99 | 8 | 98 | 94 |
| 163 | — | 0 | 9 | — | — | 0 | 83 | 0 | 88 | 0 |
| 164 | — | 49 | 57 | — | — | 0 | 99 | 15 | 9 | 97 |
| 165 | — | 0 | 0 | — | — | 0 | 52 | 8 | 0 | 99 |
| 166 | — | 0 | 0 | — | — | 0 | 97 | 0 | 68 | 96 |
| 167 | — | 75 | 0 | — | — | 0 | 0 | 0 | 0 | 0 |
| 168 | — | 14 | 0 | — | — | 0 | 33 | 0 | 0 | 0 |
| 169 | — | 24 | 0 | — | — | 0 | 85 | 0 | 0 | 0 |
| 170 | — | 100 | 99 | — | — | 99 | 98 | 0 | 100 | 99 |
| 171 | — | 100 | 97 | — | — | 0 | 97 | 68 | 99 | 100 |
| 172 | — | 100 | 100 | — | — | 87 | 100 | 0 | 99 | 100 |
| 173 | — | 100 | 86 | — | — | 0 | 98 | 0 | 83 | 100 |
| 174 | — | 100 | 99 | — | — | 0 | 96 | 0 | 97 | 99 |
| 175 | — | 100 | 99 | — | — | 82 | 96 | 93 | 99 | 100 |
| 176 | — | 100 | 71 | — | — | 0 | 96 | 0 | 68 | 100 |
| 177 | — | 100 | 100 | — | — | 73 | 98 | 0 | 83 | 100 |
| 178 | — | 100 | 100 | — | — | 80 | 98 | 0 | 83 | 100 |
| 179 | — | 100 | 99 | — | — | 73 | 95 | 0 | 93 | 100 |
| 180 | — | 100 | 99 | — | — | 0 | 98 | 0 | 68 | 100 |
| 181 | — | 94 | 44 | — | — | 0 | 100 | 0 | 60 | 98 |
| 182 | — | 97 | 99 | — | — | 87 | 100 | 0 | 95 | 99 |
| 183 | — | 97 | 100 | — | — | 67 | 99 | 27 | 94 | 99 |
| 184 | — | 97 | 0 | — | — | 0 | 99 | 0 | 82 | 98 |
| 185 | — | 0 | 0 | — | — | 0 | 100 | 0 | 74 | 98 |
| 186 | — | 0 | 0 | — | — | 0 | 99 | 0 | 54 | 93 |
| 187 | — | 33 | 0 | — | — | 0 | 20 | 0 | 9 | 13 |
| 188 | — | 87 | 0 | — | — | 0 | 100 | 0 | 97 | 97 |
| 189 | — | 99 | 100 | — | — | 80 | 100 | 99 | 99 | 98 |
| 190 | — | 99 | 99 | — | — | 80 | 100 | 94 | 100 | 99 |
| 191 | — | 98 | 100 | — | — | 0 | 100 | 0 | 97 | 99 |
| 192 | — | 97 | 100 | — | — | 73 | 100 | 0 | 99 | 99 |
| 193 | — | 99 | 100 | — | — | 0 | 100 | 32 | 99 | 100 |
| 194 | — | 97 | 86 | — | — | 0 | 99 | 0 | 91 | 99 |
| 195 | — | 100 | 97 | — | — | 60 | 100 | 0 | 98 | 97 |
| 196 | — | 99 | 94 | — | — | 73 | 100 | 9 | 98 | 98 |
| 197 | — | 97 | 0 | — | — | 95 | 99 | 0 | 79 | 96 |
| 198 | — | 97 | 68 | — | — | 0 | 100 | 0 | 94 | 97 |
| 199 | — | 99 | 86 | — | — | 0 | 99 | 0 | 68 | 98 |
| 200 | — | 82 | 0 | — | — | 0 | 97 | 0 | 0 | 94 |
| 201 | — | 99 | 97 | — | — | 20 | 100 | 18 | 97 | 99 |
| 202 | — | 99 | 0 | — | — | 0 | 99 | 0 | 28 | 99 |
| 203 | — | 99 | 0 | — | — | 0 | 98 | 0 | 96 | 100 |
| 204 | — | 100* | 77* | — | — | 0* | 99* | 0* | 86* | 99* |
| 205 | — | 100 | 17 | — | — | 0 | 99 | 0 | 91 | 100 |
| 206 | — | 99 | 99 | — | — | 84 | 99 | 41 | 99 | 100 |
| 207 | — | 100 | 93 | — | — | 64 | 100 | 0 | 99 | 100 |
| 208 | — | 100 | 100 | — | — | 99 | 100 | 0 | 99 | 99 |
| 209 | — | 0 | 0 | — | — | 0 | 0 | 0 | 0 | 97 |
| 210 | — | 0 | 0 | — | — | 0 | 100 | 99 | 94 | 99 |
| 211 | — | 77 | 0 | — | — | 0 | 99 | 0 | 17 | 96 |
| 212 | — | 0 | 17 | — | — | — | 98 | 0 | — | — |
| 213 | — | 97 | 30 | — | — | 0 | 85 | 94 | 96 | 100 |
| 214 | — | 98 | 51 | — | — | 0 | 100 | 9 | 99 | 100 |
| 215 | — | 89 | 0 | — | — | 0 | 98 | 0 | 94 | 99 |
| 216 | — | 96 | 0 | — | — | 0 | 76 | 0 | 26 | 99 |
| 217 | — | 75 | 0 | — | — | 0 | 83 | 40 | 79 | 99 |

TABLE A-continued

| Cmpd No. | Test A | Test B | Test C | Test D | Test E | Test F | Test G | Test H | Test I | Test J |
|---|---|---|---|---|---|---|---|---|---|---|
| 218 | — | 94 | 0 | — | — | 0 | 99 | 17 | 92 | 87 |
| 219 | — | 70 | 0 | — | — | 0 | 0 | 17 | 0 | 0 |
| 220 | — | 98 | 97 | — | — | 40 | 98 | 40 | 99 | 100 |
| 221 | — | 98 | 94 | — | — | 82 | 100 | 17 | 99 | 100 |
| 222 | — | 99 | 99 | — | — | 0 | 100 | 88 | 99 | 100 |
| 223 | — | 96 | 9 | — | — | 99 | 100 | 0 | 100 | 100 |
| 224 | — | 99 | 51 | — | — | 0 | 100 | 17 | 91 | 100 |
| 225 | — | 65 | 0 | — | — | 0 | 99 | 0 | 79 | 98 |
| 226 | — | 99 | 0 | — | — | 0 | 96 | 28 | 91 | 100 |
| 227 | — | 87 | 0 | — | — | 0 | 99 | 0 | 74 | 98 |
| 228 | — | 99 | 99 | — | — | 0 | 99 | 0 | 80 | 99 |
| 229 | — | 99 | 17 | — | — | 0 | 99 | 0 | 91 | 98 |
| 230 | — | 99 | 99 | — | — | 0 | 100 | 0 | 97 | 100 |
| 231 | — | 98 | 34 | — | — | 0 | 100 | 0 | 86 | 100 |
| 232 | — | 100 | 99 | — | — | 99 | 100 | 0 | 100 | 100 |
| 233 | — | 100 | 99 | — | — | 99 | 100 | 0 | 100 | 100 |
| 234 | — | 99 | 0 | — | — | 0 | 99 | 0 | 92 | 84 |
| 235 | — | 84 | 0 | — | — | 0 | 17 | 0 | 0 | 79 |
| 236 | — | 97 | 0 | — | — | 0 | 96 | 0 | 68 | 97 |
| 237 | — | 99 | 0 | — | — | 0 | 97 | 0 | 68 | 97 |
| 238 | — | 99 | 0 | — | — | 0 | 0 | 53 | 9 | 43 |
| 239 | — | 99 | 95 | — | — | 0 | 67 | 0 | 68 | 100 |
| 240 | — | 100 | 99 | — | — | 0 | 99 | 0 | 99 | 100 |
| 241 | — | 99 | 99 | — | — | 0 | 100 | 97 | 100 | 100 |
| 242 | — | 99 | 37 | — | — | 0 | 100 | 0 | 91 | 100 |
| 243 | — | 100 | 64 | — | — | 0 | 100 | 0 | 97 | 100 |
| 244 | — | 82 | 0 | — | — | 0 | 91 | 0 | 0 | 96 |
| 245 | — | 90 | 0 | — | — | 0 | 97 | 0 | 68 | 93 |
| 246 | — | 99 | 51 | — | — | 0 | 100 | 0 | 80 | 100 |
| 247 | — | 100 | 99 | — | — | 60 | 100 | 0 | 99 | 100 |
| 248 | — | 99 | 26 | — | — | 73 | 100 | 0 | 99 | 100 |
| 249 | — | 40 | 0 | — | — | 0 | 99 | 0 | 96 | 100 |
| 250 | — | 98 | 0 | — | — | 0 | 77 | 0 | 86 | 100 |
| 251 | — | 99 | 0 | — | — | 0 | 98 | 0 | 86 | 100 |
| 252 | — | 100 | 97 | — | — | 0 | 100 | 0 | 100 | 100 |
| 253 | — | 99 | 0 | — | — | 0 | 0 | 0 | 0 | 76 |
| 254 | — | 100 | 0 | — | — | 0 | 84 | 0 | 0 | 64 |
| 255 | — | 100 | 0 | — | — | 0 | 0 | 0 | 0 | 39 |
| 256 | — | 99 | 99 | — | — | 96 | 100 | 0 | 99 | 100 |
| 257 | — | 100 | 99 | — | — | 0 | 100 | 0 | 97 | 98 |
| 258 | — | 41 | 9 | — | — | 0 | 89 | 0 | 68 | 90 |
| 259 | — | 98 | 9 | — | — | 0 | 100 | 0 | 86 | 97 |
| 260 | — | 0 | 0 | — | — | 0 | 0 | 0 | 0 | 0 |
| 261 | — | 0 | 0 | — | — | 0 | 0 | 0 | 0 | 47 |
| 262 | — | 99 | 51 | — | — | 0 | 0 | 0 | 68 | 99 |
| 263 | — | 100 | 98 | — | — | 0 | 100 | 0 | 98 | 100 |
| 264 | — | 100 | 98 | — | — | 0 | 92 | 0 | 99 | 98 |
| 265 | — | 100 | 99 | — | — | 78 | 100 | 90 | 100 | 100 |
| 266 | — | 100 | 100 | — | — | 98 | 100 | 0 | 100 | 100 |
| 267 | — | 100 | 79 | — | — | 60 | 100 | 0 | 96 | 93 |
| 268 | — | 95 | 93 | — | — | 0 | 99 | 0 | 74 | 0 |
| 269 | — | 80 | 0 | — | — | 0 | 67 | 8 | 0 | 0 |
| 270 | — | 92 | 86 | — | — | 0 | 91 | 8 | 0 | 81 |
| 271 | — | 100 | 99 | — | — | 99 | 100 | 0 | 99 | 98 |
| 272 | — | 100 | 97 | — | — | 99 | 99 | 0 | 99 | 99 |
| 273 | — | 0 | 0 | — | — | 0 | 72 | 0 | 27 | 43 |
| 274 | — | 8 | 0 | — | — | 0 | 96 | 8 | 0 | 69 |
| 275 | — | 97 | 46 | — | — | 0 | 99 | 8 | 97 | 99 |
| 276 | — | 100 | 99 | — | — | 98 | 100 | 31 | 100 | 100 |
| 277 | — | 100 | 0 | — | — | 0 | 100 | 0 | 96 | 98 |
| 278 | — | 99 | 0 | — | — | 0 | 99 | 0 | 82 | 100 |
| 279 | — | 100 | 99 | — | — | 0 | 100 | 8 | 98 | 100 |
| 280 | — | 99 | 0 | — | — | 0 | 96 | 8 | 18 | 87 |
| 281 | — | 98 | 44 | — | — | 0 | — | 0 | 94 | 98 |
| 282 | — | 99 | 98 | — | — | 0 | — | 0 | 99 | 100 |
| 283 | — | 99 | 65 | — | — | 0 | — | 9 | 99 | 100 |
| 284 | — | 99 | 99 | — | — | 100 | — | 28 | 100 | 100 |
| 285 | — | 98 | 0 | — | — | 60 | — | 9 | 99 | 99 |
| 286 | — | 98* | 85* | — | — | 60* | — | 100* | 100* | 100* |
| 288 | 9 | 99 | 52 | 0 | 92 | 0 | — | 0 | 74 | 92 |
| 289 | — | 100 | 0 | — | — | 0 | 99 | 0 | 96 | 97 |
| 290 | — | 100 | 99 | — | — | 87 | 100 | 0 | 100 | 100 |
| 291 | — | 99 | 0 | — | — | 0 | 98 | 0 | 85 | 43 |
| 292 | — | 100 | 99 | — | — | 96 | 100 | 92 | 100 | 100 |
| 293 | 0 | 97 | 47 | 0 | 99 | 0 | — | — | 94 | 99 |
| 294 | 0 | 98 | 0 | 0 | 80 | 0 | — | — | 0 | 84 |
| 296 | — | 99 | 0 | — | — | 0 | 100 | 0 | 99 | — |
| 297 | — | 100 | 99 | — | — | 90 | 100 | 0 | 100 | 100 |

TABLE A-continued

| Cmpd No. | Test A | Test B | Test C | Test D | Test E | Test F | Test G | Test H | Test I | Test J |
|---|---|---|---|---|---|---|---|---|---|---|
| 298 | — | 100 | 93 | — | — | 87 | 100 | 0 | 100 | 100 |
| 299 | — | 100 | 95 | — | — | 51 |  | 41 | 100 | 100 |
| 300 | — | 100 | 99 | — | — | 82 | 100 | 9 | 99 | 100 |
| 301 | — | 99 | 87 | — | — | 87 | 100 | 0 | 98 | 99 |
| 302 | — | 99* | 0* | — | — | 0* | 99* | 0* | 18* | 97* |
| 303 | — | 99 | 0 | — | — | 0 | 98 | 0 | 92 | 71 |
| 304 | — | 0 | 0 | — | 0 | 0 | 16 | — | 0 | 0 |
| 305 | — | 99 | 99 | — | — | 94 | 100 | 0 | 99 | 99 |
| 306 | — | 7 | 0 | — | — | 0 | 93 | 0 | 28 | 64 |
| 307 | — | 0 | 0 | — | — | 0 | 0 | 0 | 0 | 0 |
| 308 | — | 81 | 0 | — | — | 0 | 98 | 9 | 100 | 0 |
| 309 | — | 97 | 61 | — | 92 | 60 | 100 | — | 0 | 99 |
| 310 | — | 100 | 99 | — | — | 99 | 100 | 0 | 99 | 96 |
| 311 | — | 100 | 0 | — | — | 60 | 100 | 0 | 99 | 91 |
| 313 | — | 100 | 97 | — | — | 51 | 100 | 91 | 100 | 100 |
| 314 | — | 100 | 95 | — | — | 0 | 100 | 94 | 100 | 100 |
| 315 | — | 99 | 99 | — | — | 0 | 100 | 0 | 96 | 100 |
| 316 | — | 99 | 0 | — | — | 0 | — | 9 | 99 | 96 |
| 318 | — | 99 | 0 | — | — | 0 | 100 | 0 | 97 | 89 |
| 319 | — | 92 | 88 | — | — | 100 | 100 | 0 | 99 | 95 |
| 320 | — | 99 | 67 | — | — | 0 | 100 | 0 | 99 | 98 |
| 321 | — | 100 | 99 | — | — | 78 | 100 | 9 | 99 | 100 |
| 322 | — | 100 | 93 | — | — | 0 | 100 | 99 | 100 | 100 |
| 323 | — | 98 | 0 | — | — | 0 | 98 | 0 | 94 | — |
| 324 | — | 99 | 83 | — | — | 0 | 100 | 63 | 99 | 99 |
| 325 | — | 100 | 0 | — | — | 0 | 100 | 0 | 97 | 99 |
| 326 | 8 | 99 | 99 | 0 | 99 | 73 | 100 | — | 99 | 94 |
| 327 | — | 99 | 0 | — | — | 0 | 100 | 0 | 96 | 99 |
| 328 | — | 100 | 86 | — | — | 0 | 100 | 0 | 98 | 100 |
| 329 | — | 100 | 99 | — | — | 69 | 100 | 0 | 100 | 100 |
| 331 | — | 100 | 80 | — | — | 73 | 100 | 8 | 100 | 97 |
| 333 | — | 100 | 0 | — | — | 0 | 100 | 9 | 74 | 0 |
| 334 | — | 100 | 0 | — | — | 0 | 100 | 0 | 97 | 100 |
| 336 | — | 100 | 97 | — | — | 95 | 100 | 94 | 100 | 99 |
| 337 | — | 99 | 0 | — | — | 0 | 99 | 9 | 41 | 98 |
| 338 | — | 100 | 37 | — | — | 40 | 100 | 8 | 100 | 99 |
| 339 | — | 100 | 0 | — | — | 0 | 100 | 0 | 98 | 100 |
| 340 | — | 99 | 0 | — | — | 0 | 100 | 0 | 91 | 100 |
| 341 | — | 99 | 0 | — | — | 0 | 99 | 0 | 99 | 93 |
| 342 | — | 100 | 33 | — | — | 99 | 100 | 0 | 100 | 100 |
| 343 | — | 100 | 100 | — | — | 97 | 100 | 91 | 100 | 100 |
| 344 | — | 100 | 40 | — | — | 87 | 100 | 62 | 100 | 100 |
| 345 | — | 0 | 0 | — | — | 0 | 67 | 0 | 9 | 0 |
| 348 | — | 100 | 80 | — | — | 94 | 100 | 19 | 100 | 100 |
| 350 | — | 99 | 9 | — | — | 0 | — | 9 | 96 | 0 |
| 351 | — | 100 | 99 | — | — | 92 | — | 96 | 100 | 99 |
| 353 | — | 97 | 17 | — | — | 0 | 99 | 3 | 99 | 99 |
| 354 | — | 99 | 0 | — | — | 0 | 100 | 82 | 98 | 100 |
| 355 | — | 99 | 0 | — | — | 0 | 100 | 3 | 91 | 0 |
| 356 | — | 100 | 0 | — | — | 0 | — | 100 | 100 | 0 |
| 357 | — | 100 | 86 | — | — | 87 | 100 | 0 | 99 | 100 |
| 358 | — | 99 | 0 | — | — | 0 | 100 | 0 | 97 | 97 |
| 359 | — | 100 | 99 | — | — | 97 | 100 | 0 | 100 | 99 |
| 360 | — | 100 | 97 | — | — | 95 | 100 | 79 | 100 | 100 |
| 361 | — | 100 | 90 | — | — | 0 | 100 | 0 | 100 | 100 |
| 362 | — | 100 | 0 | — | — | 0 | 100 | 0 | 96 | 96 |
| 363 | — | 65 | 0 | — | — | 0 | 99 | 0 | 96 | 43 |
| 364 | — | 99 | 97 | — | — | 88 | 100 | 0 | 99 | 100 |
| 365 | — | 100 | 99 | — | — | 64 | 100 | 74 | 100 | 100 |
| 366 | — | 100 | 58 | — | — | 0 | 100 | 9 | 99 | 100 |
| 367 | — | 100 | 100 | — | — | 100 | — | 100 | 100 | 100 |
| 369 | — | 100 | 66 | — | — | 0 | — | 17 | 100 | 99 |
| 389 | — | 100 | 9 | — | — | 0 | — | 68 | 98 | 99 |
| 391 | — | 100 | 99 | — | — | 73 | — | 31 | 99 | 99 |
| 403 | — | 99 | 0 | — | — | 0 | — | 99 | 100 | 99 |

"Cmpd No." means compound number and refers to the same compound number as in Index Table A.

What is claimed is:

1. A compound selected from Formula 18, N-oxides and salts thereof,

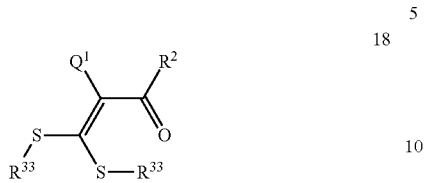

18 wherein
 $Q^1$ is 2-Br-4-F-phenyl, 2-Cl-4-F-phenyl, 2-F-4-Cl-phenyl, 2,4-di-Cl-phenyl, 2,4-di-F-phenyl, 2-Br-6-F-phenyl, 2-Cl-6-F-phenyl, 2,6-di-Cl-phenyl or 2,6-di-F-phenyl;
 $R^2$ is $CH_3$; and
 $R^{33}$ is $CH_3$, $CH_2CH_3$ or $CH_2CH_2CH_3$.

2. A compound of claim 1 wherein
 $Q^1$ is 2-Br-4-F-phenyl or 2-Cl-4-F-phenyl;
 $R^{33}$ is $CH_3$ and $CH_2CH_3$.

3. A compound of claim 2 wherein
 $Q^1$ is 2-Br-4-F-phenyl; and
 $R^{33}$ is $CH_3$.

* * * * *